United States Patent [19]

Shapiro

[11] Patent Number: 4,806,142

[45] Date of Patent: Feb. 21, 1989

[54] HERBICIDAL PYRIMIDINE SULFONYLUREAS

[75] Inventor: Rafael Shapiro, Wilmington, Del.

[73] Assignee: E. I. DuPont De Nemours and Company, Wilmington, Del.

[21] Appl. No.: 896,091

[22] Filed: Aug. 13, 1986

Related U.S. Application Data

[60] Division of Ser. No. 723,450, Apr. 15, 1985, Pat. No. 4,629,494, which is a continuation of Ser. No. 543,835, Oct. 20, 1983, abandoned, which is a continuation-in-part of Ser. No. 434,038, Oct. 20, 1982, abandoned, which is a continuation-in-part of Ser. No. 328,018, Dec. 7, 1981, abandoned.

[51] Int. Cl.[4] ................ A01N 43/54; A01N 43/66; C07D 251/46; C07D 239/28

[52] U.S. Cl. ........................................ 71/92; 71/93; 544/211; 544/212; 544/332

[58] Field of Search ...................... 544/332; 71/92

[56] References Cited

U.S. PATENT DOCUMENTS

| | | | |
|---|---|---|---|
| 4,169,719 | 10/1979 | Levitt | 71/92 |
| 4,191,553 | 3/1980 | Reap | 541/332 |
| 4,310,346 | 1/1982 | Levitt et al. | 71/92 |
| 4,332,611 | 1/1982 | Petersen | 71/92 |
| 4,348,220 | 9/1982 | Schwing | 71/92 |
| 4,370,479 | 1/1983 | Levitt | 71/92 |
| 4,394,506 | 7/1983 | Levitt | 71/92 |
| 4,398,939 | 8/1983 | Levitt | 544/332 |

Primary Examiner—Donald G. Daus
Assistant Examiner—Cecilia Shen

[57] ABSTRACT

Certain substituted pyrimidine sulfonylureas, such as 3-[[[-(4-dimethoxymethyl)-6-methylpyrimidin-2-yl]aminocarbonyl]aminosulfonyl]-2-thiophenecarboxylic acid, methyl ester, are selective pre-emergence and-/or post-emergence herbicides.

3 Claims, No Drawings

HERBICIDAL PYRIMIDINE SULFONYLUREAS

RELATED APPLICATION

This application is a divisional of my copending application Ser. No. 723,450, filed Apr. 15, 1985, now U.S. Pat. No. 4,629,494, which is a continuation of my application Ser. No. 543,835, filed Oct. 20, 1983, now abandoned, which is a continuation-in-part of my application Ser. No. 434,038, filed Oct. 20, 1982, now abandoned, which is a continuation-in-part of Ser. No. 328,018, filed Dec. 7, 1981, now abandoned.

BACKGROUND OF THE INVENTION

This invention relates to herbicidal sulfonamides, and, more particularly, to (dimethoxymethyl)pyrimidinyl sulfonylurea compounds which are selective pre-emergence and/or post-emergence herbicides.

DESCRIPTION OF THE PRIOR ART

U.S. Pat. Nos. 4,127,405 and 4,169,719 disclose herbicidal methoxymethylpyrimidine sulfonylurea compounds of the type which contain a —$CH_2OCH_3$ heterocyclic substituent.

European Pat. No. 7687 discloses herbicidal sulfonylurea compounds such as, among others,

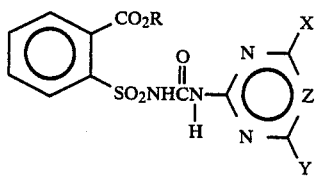

where
X is $CH_3$ or $OCH_3$;
Z is CH or N; and
Y is $C_1$–$C_4$ alkyl substituted with $OCH_3$, $OC_2H_5$, CN, C(O)L, or 1–3 atoms of F, Cl, or Br, where L is $NH_2$, OH, $N(OCH_3)CH_3$, $NH(CH_1$–$C_4$ alkyl), $N(C_1$–$C_4$ alkyl) or $C_1$–$C_6$ alkoxy.

U.S. application Ser. No. 116,920, discloses herbicidal substituted benzenesulfonylureas which contain as the heterocyclic substituent

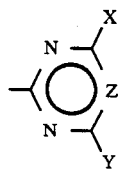

where
X is $CH_3$ or $OCH_3$;
Z is CH or N; and
Y is (among others) $C_1$–$C_4$ alkyl substituted with $OC_2H_5$, CN, $CO_2H$, $CO_2H_3$ or $CO_2C_2H_5$.

*J. Am. Chem. Soc.*, 69, 3072 (1947) teaches compounds of the formula:

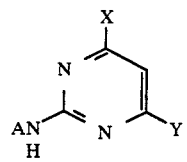

where
A is H or

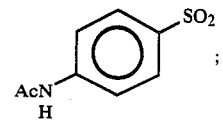

X is Cl, $CH_3$, $CH_3O$, $CH_2OCH_3$, or H; and
Y is $CH(OCH_3)_2$ or $CH(OC_2H_5)$;
and their use as antibacterial agents.

SUMMARY OF THE INVENTION

This invention relates to novel compounds of Formula I, suitable agricultural compositions containing them, and their method of use as general and/or selective pre-emergence and/or post-emergence herbicides or plant growth regulants.

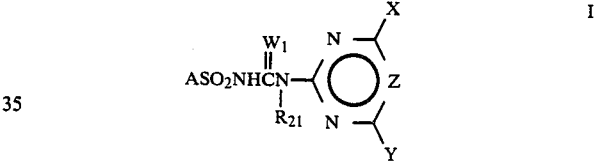

wherein
X is $CH_3$, $OCH_3$, Cl, $C_2H_5$ or $OC_2H_5$;
Z is CH or N;
Y is $CH_2OR$, $CH_2S(O)_mR_1$, $CH(QR_1)_2$, $R_1CHS(O)_mR_1$,

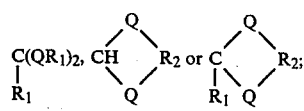

R is H, $C(O)R_3$, $CO_2R_4$,

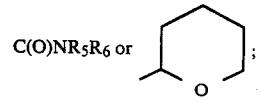

$R_1$ is $C_1$–$C_2$ alkyl;
$R_2$ is —$CH_2CH_2$—, —$CH(CH_3)CH_2$— or —$CH_2CH_2CH_2$—,
$R_3$ is $C_1$–$C_3$ alkyl;
$R_4$ is $C_1$–$C_4$ alkyl;
$R_5$ is H or $CH_3$;
$R_6$ is $C_1$–$C_3$ alkyl;
Q is O or S;
m is 0, 1 or 2;
A is

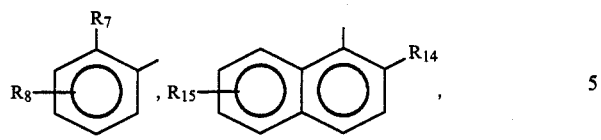

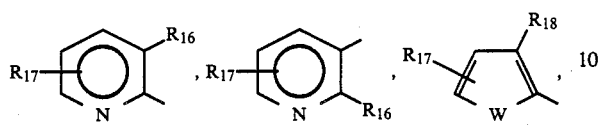

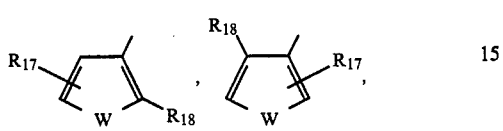

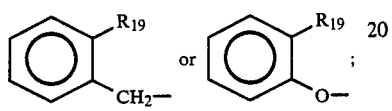

$R_7$ is H, $C_1$-$C_4$ alkyl, $C_1$-$C_4$ alkoxy, F, Cl, I, Br, $NO_2$, $CF_3$, $CO_2R_9$, $SO_2NR_{10}R_{11}$, $SO_2N(OCH_3)CH_3$, $OSO_2R_{12}$, $S(O)_nR_{13}$, $LCF_3$, $LCHF_2$, $LCF_2CF_2H$, $CH_2Cl$, $CHCl_2$, $CH_2OCH_3$ or $CH_2OCH_2CH_3$;

$R_8$ is H, F, Cl, Br, $CF_3$, $NO_2$, $C_1$-$C_3$ alkyl $C_1$-$C_3$ alkoxy, $OCF_2H$ or $SCF_2H$;

$R_9$ is $C_1$-$C_4$ alkyl, $CH_2CH_2OCH_3$, $CH_2CH_2Cl$ or $CH_2CH=CH_2$;

$R_{10}$ and $R_{11}$ are independently $C_1$-$C_3$ alkyl;

$R_{12}$ is $C_1$-$C_4$ alkyl, $CH_2CH_2OCH_3$, $CH_2CH_2CH_2OCH_3$ or $C_1$-$C_4$ alkyl substituted with 1-3 atoms of F, Cl or Br;

$R_{13}$ is $C_1$-$C_4$ alkyl or $CH_2CH=CH_2$; n is 0 or 2;

L is O, S or $SO_2$;

$R_{14}$ is H, $CH_3$, $OCH_3$, F, Cl, Br, $NO_2$, $SO_2N(CH_3)_2$, $OSO_2R_1$ or $S(O)_nR_1$;

$R_{15}$ is H, Cl, Br, $CH_3$, $OCH_3$ or $NO_2$;

$R_{16}$ is H, $C_1$-$C_4$ alkyl, $C_1$-$C_4$ alkoxy, F, Cl, Br, $CF_3$, $CO_2R_9$, $SO_2NR_{10}R_{11}$, $SO_2N(OCH_3)CH_3$ or $S(O)_nR_{13}$;

$R_{17}$ is H, F, Cl, Br, $CH_3$ or $OCH_3$;

W is O or S;

$W_1$ is O or S;

$R_{18}$ is H, $C_1$-$C_4$ alkyl, $C_1$-$C_4$ alkoxy, F, Cl, Br, $NO_2$, $CO_2R_9$, $SO_2NR_{10}R_{11}$, $SO_2N(OCH_3)CH_3$ or $S(O)_nR_{13}$;

$R_{19}$ is Cl, $NO_2$, $CF_3$, $CO_2R_9$, $SO_2N(OCH_3)CH_3$, $SO_2NR_{10}R_{11}$, $OSO_2R_{12}$, $S(O)_nR_{13}$, $C_1$-$C_3$ alkyl, or $C_1$-$C_3$ alkoxy optionally substituted with 1-5 atoms of Cl or F;

$R_{20}$ is Cl, $NO_2$, $CF_3$, $CO_2R_9$, $SO_2N(OCH_3)CH_3$, $C_1$-$C_3$ alkyl, $OSO_2R_{12}$ or $C_1$-$C_3$ alkoxy optionally substituted with 1-5 atoms of Cl or F;

$R_{21}$ is H or $CH_3$;

and their agriculturally suitable salts; provided that (1) the total number of carbon atoms of $R_{10}$ and $R_{11}$ is less than or equal to 4;

(2) when X is Cl, then Z is CH;

(3) when W is O, then $R_{18}$ is H, Cl, Br, $CH_3$ or $CO_2R_9$;

(4) when W is O and $R_{18}$ is H, Cl, Br, or $CH_3$, then A is

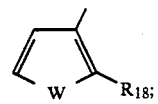

and (5) when $W_1$ is S, then $R_{21}$ is H and A is

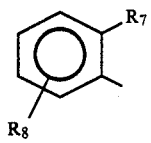

Preferred for their higher herbicidal activity and/or more favorable ease of synthesis are:

(1) Compounds of Formula I where $W_1$ is O, X is $CH_3$, $OCH_2CH_3$ or $OCH_3$ and $R_{21}$ is H;

(2) Compounds of Preferred 1 where Y is $CH(QR_1)_2$, $CH_2SR_1$, $CR_1(QR_1)_2$,

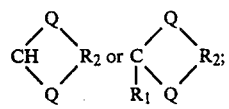

(3) Compounds of Preferred 2 where Y is $CH(QR_1)_2$, $CH_2SR_1$ or

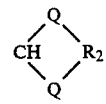

and Q is 0;

(4) Compounds of Preferred (3) wherein A is

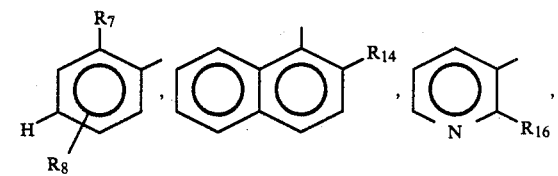

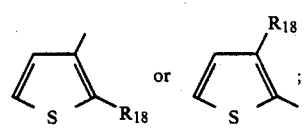

$R_7$ is $C_1$-$C_3$ alkyl, $C_1$-$C_3$ alkoxy, Cl, $NO_2$, $CO_2R_9$, $SO_2(C_1$-$C_3$ alkyl), $SO_2NR_{10}R_{11}$, $SO_2N(OCH_3)CH_3$, $OSO_2R_{13}$, $CH_2OCH_3$ or $LCF_2H$;

$R_{14}$ is $CH_3$, $OCH_3$, Cl, $OSO_2CH_3$ or $SO_2(C_1$-$C_3$ alkyl);

$R_{16}$ is $CH_3$, $OCH_3$, Cl, $SO_2CH_3$ or $SO_2N(CH_3)_2$;

$R_{18}$ is $CH_3$, Cl, Br, $CO_2R_9$ or $SO_2CH_3$;

(5) Compounds of Preferred (4) where A is

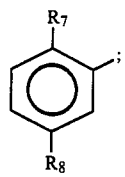

(6) Compounds of Preferred (5) where
$R_7$ is $CO_2CH_3$, $CO_2H_2CH_3$, $SO_2CH_3$, $SO_2CH_2CH_3$, $SO_2N(CH_3)_2$, $OSO_2CH_3$, $OSO_2CH_2CH_3$; and
$R_8$ is H, F, Cl, $CF_3$, $CH_3$ or $OCH_3$.
Specifically preferred are:

3-[[(4-dimethoxymethyl-6-methylpyrimidin-2-yl)aminocarbonyl]aminosulfonyl]-2-thiophenecarboxylic acid, methyl ester;

2-chloro-N-[(4-dimethoxymethyl-6-methylpyrimidin-2-yl)aminocarbonyl]benzenesulfonamide;

2-[[(4-dimethoxymethyl-6-methylpyrimidin-2-yl)aminocarbonyl]aminosulfonyl]benzoic acid, methyl ester;

N-[(4-dimethoxymethyl-6-methylpyrimidin-2-yl)aminocarbonyl]-2-methylsulfonylbenzenesulfonamide;

N-[(4-dimethoxymethyl-6-methylpyrimidin-2-yl)aminocarbonyl]-2-nitrobenzenesulfonamide;

2-[[(4-dimethoxymethyl-6-methylpyrimidin-2-yl)aminocarbonyl]aminosulfonyl]benzoic acid, 2-propyl ester;

2-[[[4-methyl-6-(tetrahydropyran-2-yloxymethyl)-pyrimidin-2-yl]aminocarbonyl]aminosulfonyl]benzoic acid, methyl ester;

2-[[[4-(hydroxymethyl)-6-methylpyrimidin-2-yl]aminocarbonyl]aminosulfonyl]benzoic acid, methyl ester;

2-[[[4-(acetyloxymethyl)-6-methylpyrimidin-2-yl]aminocarbonyl]aminosulfonyl]benzoic acid, methyl ester;

2-[[(4-dimethoxymethyl-6-methoxypyrimidin-2-yl)aminocarbonyl]aminosulfonyl]benzoic acid, methyl ester;

5-chloro-2-[[(4-dimethoxymethyl-6-methylpyrimidin-2-yl)aminocarbonyl]aminosulfonyl]benzoic acid, methyl ester;

5-chloro-2-[[(4-dimethoxymethyl-6-methoxypyrimidin-2-yl)aminocarbonyl]aminosulfonyl]benzoic acid, methyl ester;

2-[[(4-(1,3-dioxan-2-yl)-6-methoxypyrimidin-2-yl)aminocarbonyl]aminosulfonyl]benzoic acid, methyl ester; and 2-[[(4-(1,3-dioxolan-2-yl)-6-methoxypyrimidin-2-yl)aminocarbonyl]aminosulfonyl]benzoic acid, methyl ester.

The compounds of this invention are highly active pre-emergence and/or post-emergence herbicides. Certain compounds of this invention are useful for selective weed control in crops such as cotton, soybeans, wheat or corn.

DETAILED DESCRIPTION OF THE INVENTION

Synthesis

The compounds of Formula I may be prepared by the reaction of an appropriately substituted sulfonyl isocyanate of Formula II with an appropriate 2-aminoheterocycle of Formula III according to Equation 1:

Equation 1

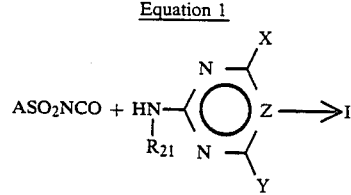

wherein

A, X, $R_{21}$ and $Z(O)_m$ are as previously defined;

Y is $CH_2OR$, $CH_2SR_1$, $CH(QR_1)_2$ $CH(QR_2Q)$, $CH(R_1)S(O)_mR_1$, $C(R_1)(QR_1)_2$ or $C(R_1)(QR_2Q)$; R is

[structure] = THP;

and m, $R_1$ and $R_2$ are as previously defined.

The reaction of Equation 1 is best carried out in an inert aprotic solvent such as methylene chloride, tetrahydrofuran, acetonitrile at a temperature between 20° and 80°. A catalytic amount of DABCO (1,4-diazabicyclo[2.2.2]octane) may be used to accelerate the reaction. In the cases in which the products are insoluble in the reaction solvent, they may be isolated by simple filtration. When the products are soluble in the reaction solvent they are isolated by evaporation of the solvent and trituration of the residue with solvents such as 1-chlorobutane, ethyl ether or methanol and filtration.

Preparation of isocyanates (II) is described in the following: U.S. Pat. No. 4,127,405, U.S. Pat. No. 4,169,719, Eur. Pat. No. 7,687, Eur. Pat. No. 13,480, Eur. Pat. No. 23,141, Eur. Pat. No. 23,422, Eur. Pat. No. 30,141, and Brit. Pat. No. 2,065 116-A, the disclosures of which are herein incorporated by reference. Furthermore, the sulfonyl isocyanates of Formula IIa, which are disclosed in European Patent Pub. 44,212, may be prepared analogously to the teachings of U.S. Pat. No. 4,127,405.

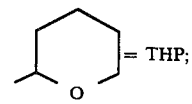

(IIa)

wherein $R_8$ and $R_{12}$ are as previously defined.

Certain compounds of Formula III are known in the art. For example, the compounds IIIa shown below:

[structure (IIIa)]

wherein

X=$CH_3$, Cl or $OCH_3$; and $R_1$=$CH_3$ or $C_2H_5$;

are described by W. Braker, et al., *J. Amer. Chem. Soc.*, 69, 3072 (19747), the disclosures of which are herein incorporated by reference.

Triazines of Formula IIIb may be prepared according to the methods outlined in Equations 2 and 3.

Equation 2

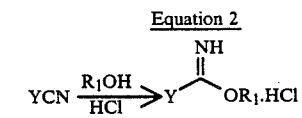
(2a)

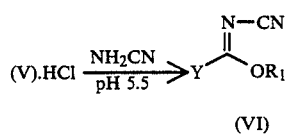
(2b)

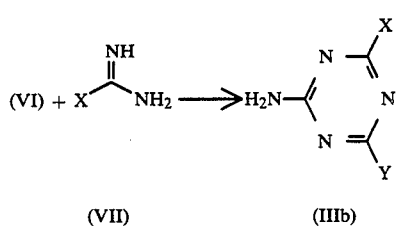
(2c)

wherein
$R_1$ and $R_2$ are as previously defined; and
Y is as defined in Equation 1, with m=0 or 2.

The reaction of Equation 2a is carried out according to the teachings of J. M. McElvain and R. L. Clarke, *J. Amer. Chem. Soc.*, 69, 2657 (1947), in which the preparation of ethyl diethoxyiminoacetate is described. The intermediate N-cyanoimidates of Formula VI may be prepared according to the teaching of D. Lwowski in *Synthesis*, 1971, 263, by reacting V with cyanamide at pH 5.5, and these may be condensed according to reaction 2c with the appropriate compound of Formula VII in an alcoholic solvent at 25° to 80° C. to provide the appropriate triazines. Alternatively, the reaction of Equation 3a, described for substituted acetonitriles by F. C. Schaefer and G. A. Peters in *J. Org. Chem.*, 26, 412 (1961), may be used to convert nitriles of Formula IV to the corresponding iminoesters. The free base may be carried on through reactions 2b and 2c, or, alternatively, converted to the amidinium hydrochloride salts (VIII) as described in the aforementioned reference. The compounds of Formula VIII may be converted to the compounds IIIb by the reaction of Equation 3c, in which VIII is contacted with a compound of Formula IX at 0° to 30° C. in the presence of 3–4 equivalents of the appropriate sodium alkoxide in the appropriate alcohol. The product may be isolated by evaporation of solvent, neutralization with aqueous acetic acid, and filtration.

Equation 3

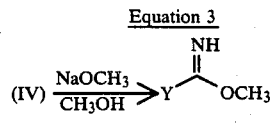
(3a)

-continued
Equation 3

(3b)

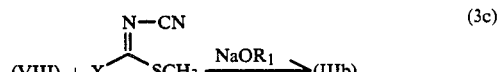
(3c)

wherein
Y is as defined in Equation 1 with m=0;
X is $R_1$ or $SCH_3$; and
$R_1$ and $R_2$ are as previously defined.

The compounds of Formula IIIc may be prepared by the sequence of reactions outlined in Equation 4.

Equation 4

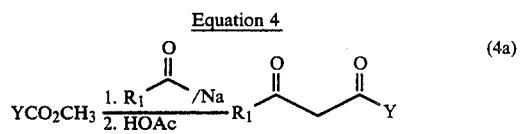
(4a)

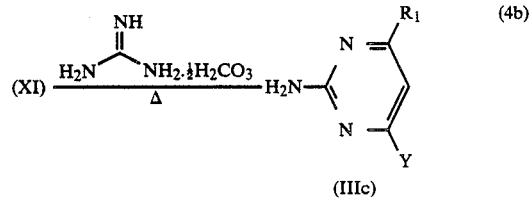
(4b)

wherein
Y, m, $R_1$ and $R_2$ are as defined in Equation 3.

The reactions of Equations 4a and 4b are carried out as described by W. Braker, et al., loc. cit.

The compounds of Formula IIId may be prepared by similar methods shown in Equation 5.

Equation 5

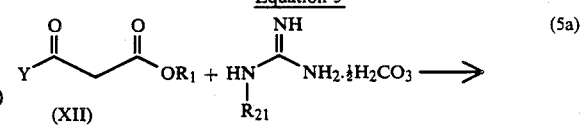
(5a)

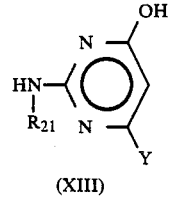
(XIII)

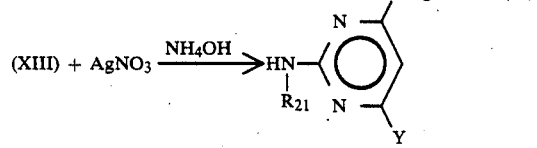
(5b)

(XIV)

-continued
Equation 5

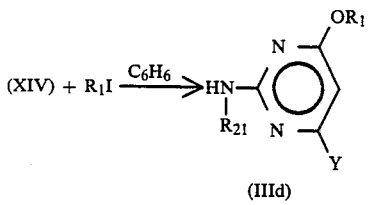

(IIId)

wherein $R_{21}$, $R_1$ and Y are as defined in Equation 1.

The reactions of Equations 5a and 5b are conducted as described for 2-amino-4-hydroxy-6-dimethoxymethylpyrimidine (J. I. De Graw and V. H. Brown, *J. Het. Chem.*, 13, 439 (1976)). The silver salt of XIII may be prepared by addition of ammonia to an aqueous solution of XIII and an equivalent amount of silver nitrate. The dried silver salt may be contacted with one equivalent of methyl or ethyl iodide in a non-polar solvent such as benzene at 25° to 80° C. to provide pyrimidines of Formula IIId after purification by column chromatography or recrystallization.

Alternatively, the compounds of Formula IIId may be prepared via the corresponding chloropyrimidines (IIIe). These may be obtained by the reaction of Equation 6a, in which a compound of Formula XIII is contacted with 2-5 equivalents of phosphorous oxychloride at 20°-90° C. for 3-30 hours. The product is isolated by removal of excess POCl$_3$ in vacuo, treatment of the residue with ice-water, extraction into an organic solvent, concentration, crystallization or column chromatography. The chloropyrimidines may then be converted to the compounds of Formula IIId by contacting with one equivalent of the appropriate sodium alkoxide in alcohol at 0°-30° C. followed by concentration and precipitation with ice-water.

Equation 6

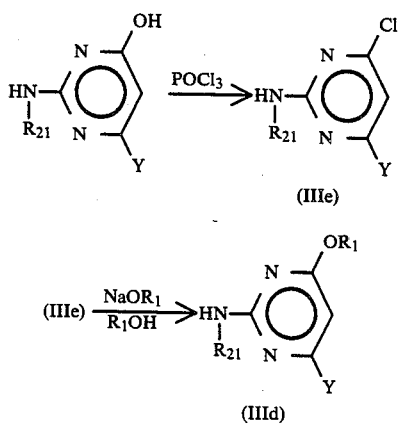

wherein

Y is $CH(QR_1)_2$, $CH_2SR_1$, $CH(QR_2Q)$, $C(R_1)(QR_1)_2$, $CH(R_1)S(O)_mR_1$ or $C(R_1)(QR_2Q)$;

$R_1$, $R_2$ and $R_{21}$ are as defined in Equation 1; and m=0 or 2.

The ketoesters of Formula XII may be prepared by the methods of Equation 7.

Equation 7

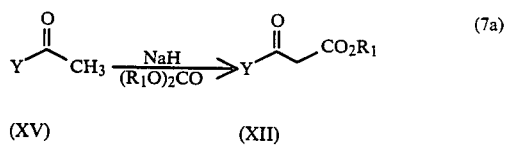

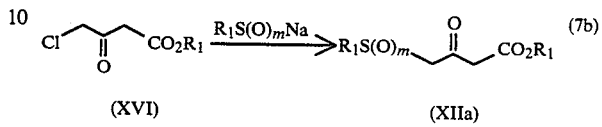

wherein m, Y and $R_1$ are as defined in Equation 3.

The reaction of Equation 7a is carried out by the slow addition of the appropriate dialkyl carbonate to a solution of the appropriate methyl ketone of Formula XV in an inert solvent (such as toluene) at 30°-110° in the presence of 1-2 equivalent of sodium hydride. The product may be isolated by concentration, neutralization, and extraction from water into an organic solvent, such as diethyl ether. The product may then be purified by distillation. Compounds of Formula XIIa may be obtained by the well-known reaction of a γ-chloroacetoacetic ester (XVI) with the appropriate sodium mercaptide or alkylsulfinate in a hydroxylic or dipolar aprotic solvent.

Cyclic acetals of Formula IIIe may be prepared from compounds of Formula IIIa according to Equation 8 by acetal exchange.

Equation 8

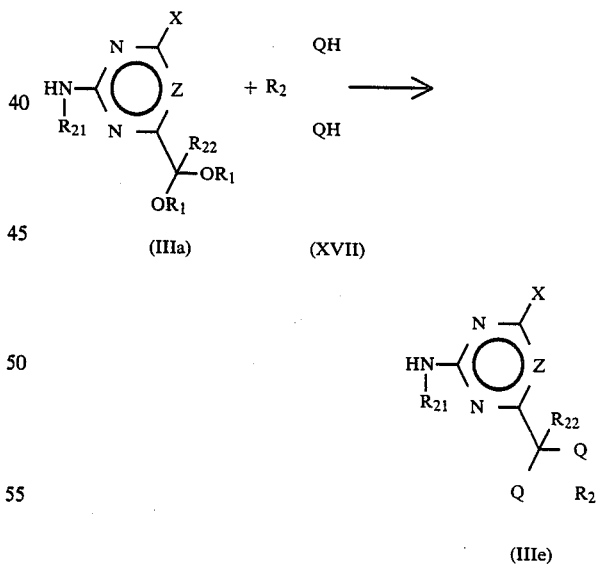

wherein

X, Q, Z, $R_1$ and $R_2$ are defined in Equation 1; and $R_{22}$ is H, $CH_3$ or $C_2H_5$.

The reaction of Equation 8 is carried out by heating the acyclic acetal in an inert solvent in the presence of one equivalent of a compound of Formula XVII and slightly more than one equivalent of an acidic catalyst, such as p-toluenesulfonic acid or boron trifluoride etherate with distillation of the by-product alcohol. The compound of Formula IIIe may be isolated by extraction with an organic solvent, and purified by crystallization or column chromatography.

The synthesis of N-methyl compounds of Formula IIIg may be accomplished by the procedure shown in Equation 9.

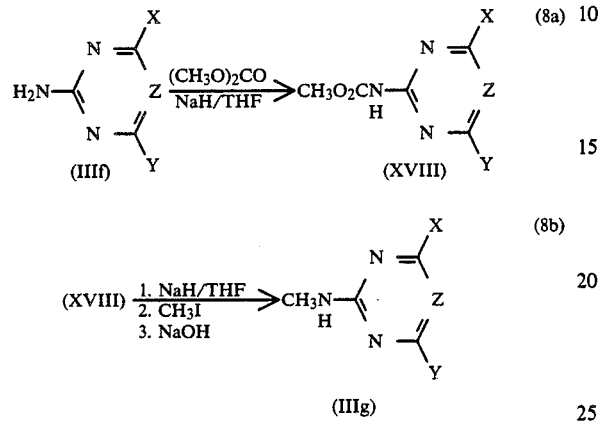

wherein
Z, $R_1$ and Q are as previously defined;
Y is as defined in Equation 1; and
X is $CH_3$, $C_2H_5$, $OCH_3$ or $OC_2H_5$.

The reaction of Equation 9a may be carried out by stirring a mixture of IIIf with one equivalent each of sodium hydride and dimethyl carbonate for 1–3 days in an inert solvent such as tetrahydrofuran or dimethylformamide. The product of Formula XVIII may be isolated by evaporation of solvent, neutralization with aqueous acetic acid, and filtration of the product. The reaction of Equation 8b is performed by adding XVI to a slurry of one equivalent of sodium hydride in tetrahydrofuran at 0°–30°, stirring for ½ hour, and adding methyl iodide, heating to reflux for 1–20 hours, and stirring with water and aqueous sodium hydroxide for 1–20 hours at 20°–30°. The product is isolated by evaporating the solvent, adding ice-water, and filtering.

The acetals and ketals of Formula IIIi may be prepared from the corresponding thioethers of Formula IIIh by the reaction of Equation 10.

Equation 10

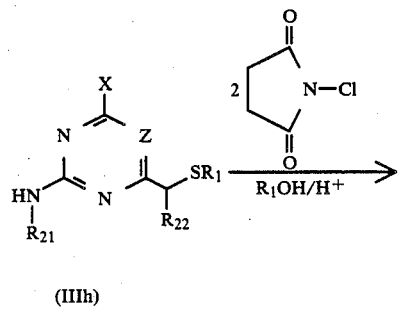

-continued
Equation 10

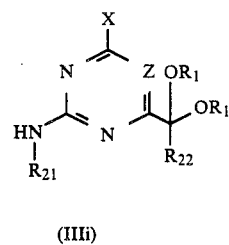

wherein
X, $R_1$, $R_{21}$ and Z are as previously defined; and
$R_{22}$ is H, $CH_3$ or $C_2H_5$.

The reaction of Equation 10 may be carried out by adding 2 to 2.3 equivalents of N-chlorosuccinimide to an alcoholic solution of a sulfide of Formula IIIh in the presence of 0.01 to 0.2 equivalents of a strong acid, such as $H_2SO_4$, at $-20°$ to $20°$ C. After 10 to 100 minutes, the reaction mixture is concentrated, diluted with water, and the reaction product is isolated by crystallization or extraction into an organic solvent.

Thioacetals and thioketals of Formul IIIj may be prepared by the reaction of Equation 11.

Equation 11

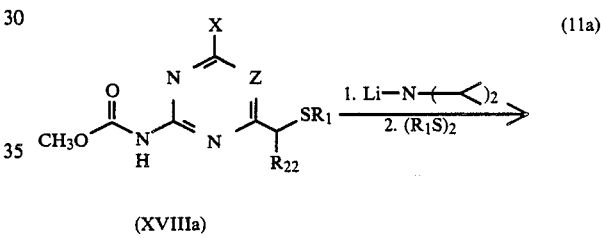

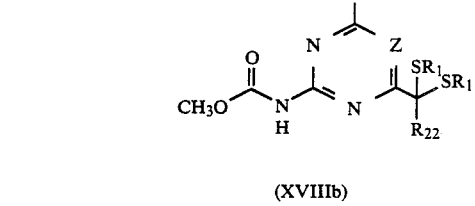

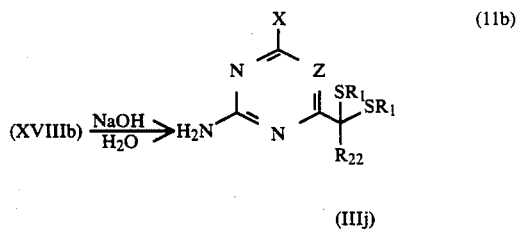

wherein
X is $CH_3$, $C_2H_5$, $OCH_3$ or $OC_2H_5$; and
Z, $R_1$, $R_{21}$ and $R_{22}$ are as defined in Equation 10.

The reaction of Equation 11a may be carried out by contacting a carbamate of Formula XVIIIa with 2–2.5 equivalents of lithium diisopropylamide in a solvent such as tetrahydrofuran at $-78°$ and then with 1 to 2 equivalents of the appropriate dialkyl disulfide and allowing the mixture to warm to 20°. The product of Formula XVIIIb may be isolated by concentration, neutralization, and extraction into an organic solvent.

Purification may be accomplished by column chromatography or recrystallization. The reaction of Equation IIb is carried out by contacting with aqueous alkali for 10–100 minutes at 20°–80° and extracting the product into an organic solvent. The product may be isolated by concentration and crystallization.

The preparation of compounds of Formula IIIk is shown in Equation 12.

Equation 12

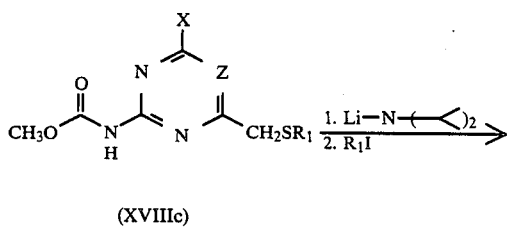

(XVIIIc)

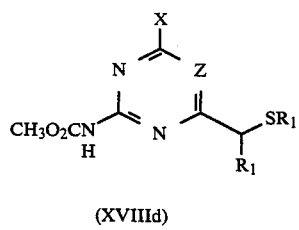

(XVIIId)

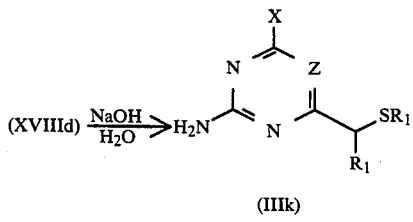

(IIIk)

wherein

Z, $R_1$ and X are as defined in Equation 11.

The reaction of Equation 12a is carried out as described for Equation 11a, only using one equivalent of the appropriate alkyl iodide, rather than a disulfide. The reaction of Equation 12b is carried out as described for Equation 11b.

Sulfoxides and sulfones of Formula IIIl and IIIo, respectively, may be prepared from the corresponding sulfides of Formula IIIh as shown in Equation 13.

Equation 13

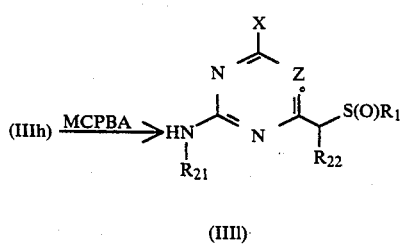

(IIIl)

-continued
Equation 13

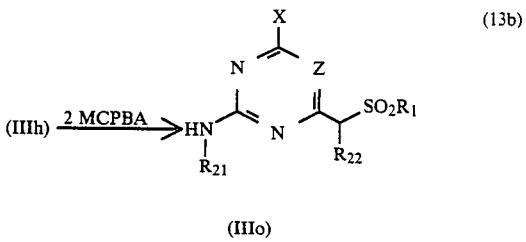

(IIIo)

wherein

Z, X, $R_1$, $R_{21}$ and $R_{22}$ are as defined in Equation 10.

The reaction of Equation 13a is carried out by contacting IIIh with 0.9 to 1.1 equivalents of m-chloroperbenzoic acid in an inert solvent at $-20°$ to $0°$ for 1 to 2 hours, concentration, and trituration with ether. If the product is ether-soluble, it is isolated by washing an ether solution with aqueous bicarbonate and concentration of the dried ether phase. The preparation of the corresponding sulfones is accomplished in the same way except that 2 to 2.2 equivalents of MCPBA are used to $0°$–$30°$ for 1–24 hours.

Compounds of Formula Ib may be prepared by acidic hydrolysis of compounds of Formula Ia according to Equation 14:

Equation 14

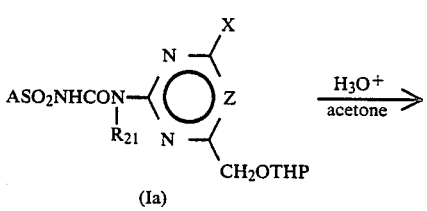

wherein

A, X, $R_{21}$ and Z are as defined in Equation 1.

The reaction of Equation 14 is carried out by stirring a solution or suspension of Ia in aqueous acetone containing a catalytic amount of a strong mineral acid, such as hydrochloric or sulfuric acid, at $0°$ to $30°$ C., followed by concentration and filtration of the product.

The compounds of Formula Ib may be in turn converted to compounds of Formulae Ic, Id, or Ie according to Equation 15:

Equation 15

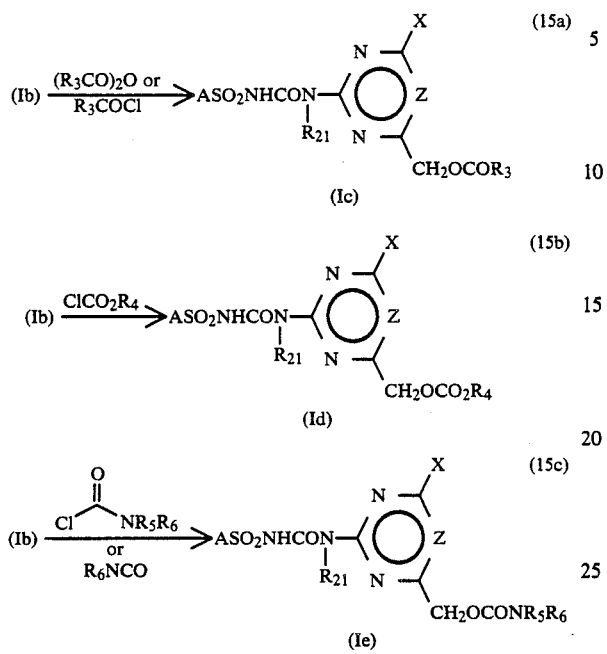

wherein
A, X, Z, $R_3$, $R_4$, $R_5$, $R_6$ and $R_{21}$ are as previously defined.

The reactions of Equation 15 are carried out by contacting a compound of Formula Ib with at least one equivalent of an alkyl carboxylic anhydride, carbonyl chloride, chloroformate or carbamoyl chloride in an inert solvent in the presence of an excess of an acid acceptor such as pyridine, triethylamine, or aqueous sodium carbonate, followed by isolation of the product by acidification and crystallization or extraction into an organic solvent. Alternatively, compounds of Formula Ie wherein $R_5$=H may be prepared by contacting the appropriate compound of Formula Ib with one equivalent of an appropriate alkyl isocyanate in an inert solvent and filtration of the product.

Certain compounds of Formula I may also be prepared by the reactions of Equation 16.

Equation 16

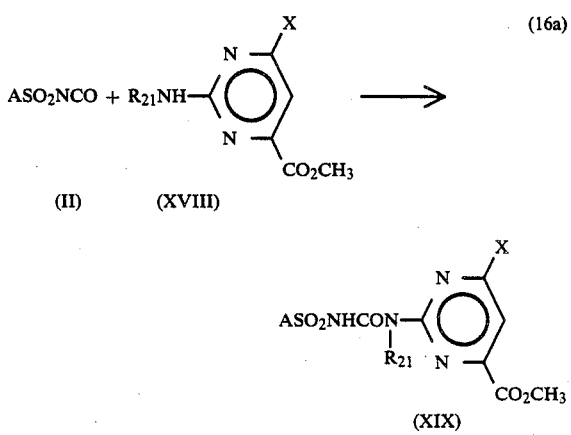

-continued
Equation 16

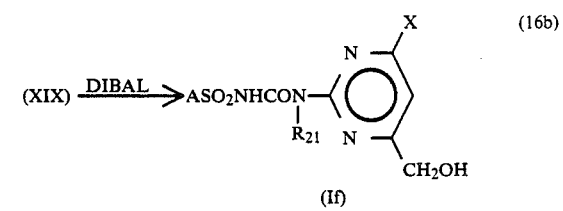

wherein
$R_{21}$, X and A are as previously defined, provided that $R_7$, $R_{16}$, $R_{18}$ and $R_{19}$ are not $CO_2R_9$.

The reaction of Equation 16a is conducted in the same manner as described for Equation 1. The resulting compounds of Formula XIX may be converted to compounds of Formula If by contacting them with 3-5 equivalents of diisobutyl aluminum hydride in an ethereal solvent at $-20°$ to $20°$, after which the reaction mixture is quenched with aqueous mineral acid and extracted with an organic solvent. The product may be isolated by evaporation of solvent and crystallization.

Equation 17 outlines the preparation of the compounds of Formula XX.

Equation 17

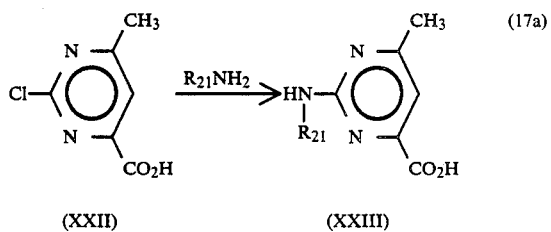

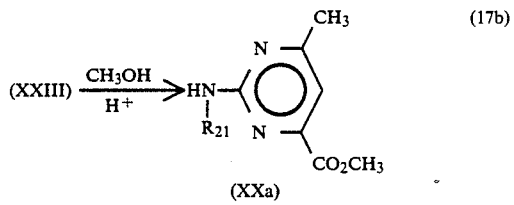

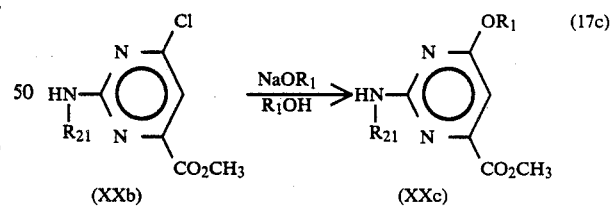

wherein
$R_1$ and $R_{21}$ are as previously defined.

The pyrimidine of Formula XXII is described by Z. Budésinsky and F. Roubínek, in *Coll. Czech. Chem. Comm.*, 26, 2871 (1961). This may be heated in an autoclave at 80° to 140° with ammonia or methyl amine to afford the amino acids of Formula XXIII. These may be esterified in the usual manner with methanol and acid, followed by evaporation of solvent, neutralization and filtration to afford the compounds of Formula XXa.

The preparation of XXb ($R_{21}$=H) is reported in *J. Org. Chem.*, 26, 2755, by G. Davies, et al., and the N-methyl compounds ($R_{21}$=$CH_3$) may be prepared in an analogous fashion. The reaction of Equation 17c is conducted according to the procedure described for Equation 6b.

EXAMPLE 1

2-Amino-4-(dimethoxymethyl)-6-methylpyrimidine

To 6.9 g of sodium pellets in 120 ml of toluene containing 50 g of methyl dimethoxyacetate was added 20 g of acetone dropwise over 30 minutes at 0°–20°. The mixture was stirred overnight at room temperature, concentrated at reduced pressure, and the product was precipitated with ether and filtered. Ten ml of acetic acid in ice-water was added, and the β-diketone was extracted with methylene chloride. The residue from concentration of the organic extract was heated with 25 g of guanidine carbonate at 80°–90° for 30 minutes, cooled, digested with methylene chloride, filtered, dried with sodium sulfate, filtered, concentrated at reduced pressure, and triturated with petroleum ether to provide 11 g of 2-amino-4-dimethoxymethyl-6-methylpyrimidine, m.p. 69°–71° (lit, m.p. 71°–74°).

NMR (CDCl$_3$)δ: 2.3 (s, 3), 3.3 (s, 6), 5.0 (s, 1), 5.9 (br s, 2), 6.7 (s, 1).

EXAMPLE 2

2-Chloro-N-[[4-(dimethoxymethyl)-6-methylpyrimidin-2-yl]aminocarbonyl]benzenesulfonamide A solution of 0.3 g of 2-amino-4-dimethoxymethyl-6-methylpyrimidine in 50 ml of ether was stirred overnight at room temperature with 0.46 g of o-chlorobenzenesulfonyl isocyanate. The product was filtered and washed with hexane to provide 0.5 g of the title compound, m.p. 150°–153°.

NMR (CDCl$_3$)δ: 2.5 (s, 3), 3.4 (s, 6), 5.2 (s, 1), 7.1 (s, 1), 7.4 (m, 3), 7.9 (br s, 1), 8.3 (m, 1).

EXAMPLE 3

2-Amino-4-methyl-6-(tetrahydropyran-2-yloxymethyl)-pyrimidine

A solution containing 30 g of methyl glycolate, 33 g of dihydropyran, and 0.2 g of p-toluenesulfonic acid in 100 ml of toluene was stirred at room temperature overnight. After cooling to −5°, 6.8 g of sodium pellets was added, followed by 24 ml of acetone at −5° to 8°. Stirring was continued for 20 hours at room temperature, after which time hexane was added, and the solution was poured into ice-water and partitioned. The aqueous phase was washed with ether and acidified with 20 ml of acetic acid, extracted with 600 ml of methylene chloride, the organic layer was dried (MgSO$_4$) and concentrated, and the residue was heated at 80°–90° with 28 g of guanidine carbonate for 1 hour. Addition of ice-water to the cooled reaction mixture precipitated the product, which was filtered and dried to afford the title compound, m.p. 109°–110.5°.

NMR (CDCl$_3$)δ: 1.7 (br s, 6), 2.3 (s, 3), 3.6 (br m, 2), 4.5 (d, 2), 4.7 (m, 1), 5.4 (br s, 2), 6.6 (br s, 1).

EXAMPLE 4

Methyl 2-[[[4-methyl-6-(tetrahydropyran-2-yloxymethyl)-pyrimidin-2-yl]aminocarbonyl]aminosulfonyl]benzoate To a solution of 3.25 g of the product from Example 3 in 50 ml of ether was added 3.75 g of 2-methoxycarbonylbenzenesulfonyl isocyanate and the mixture was stirred for 3 hours under nitrogen. The precipitated product was filtered and washed with ether to afford 6.0 g of the title compound, m.p. 126°–128°(d).

EXAMPLE 5

Methyl [[[4-(hydroxymethyl)-6-methylpyrimidin-2-yl]aminocarbonyl]aminosulfonyl]benzoate A solution of 6 g of the product prepared in Example 4 in 50 ml of acetone was stirred with 3 ml of 1N aqueous HCl for 3 days at room temperature, concentrated at reduced pressure, and the residue was thoroughly washed with water to provide 4 g of the title compound, m.p. 140°–141°.

NMR (CDCl$_3$+DMSO-d$_6$)δ: 2.5 (s, 3), 3.9 (s, 3), 4.6 (br s, 2), 7.0 (br s, 1), 7.6 (m, 3), 8.3 (m, 1), 9.6 (br s, 1).

EXAMPLE 6

Methyl [[[4-(acetoxymethyl)-6-methylpyrimidin-2-yl]aminocarbonyl]aminosulfonyl]benzoate To 0.5 g of the compound from Example 5 was added 1 ml of acetic anhydride and 1 ml of pyridine. After 1 hour at room temperature, ice-water was added, the precipitated oil was triturated, filtered, and washed with water to afford 0.4 g of the title compound, m.p. 145°–150°.

NMR (CDCl$_3$)δ: 2.2 (s, 3), 2.6 (s, 3), 3.9 (s, 3), 5.2 (s, 2), 6.9 (s, 1), 7.7 (m, 3), 8.3 (br s, 1), 8.4 (m, 1), 13.1 (br s, 1).

TABLE 1a

| R$_7$ | R$_8$ | R$_{21}$ | X | Y | m.p. (°C.) |
|---|---|---|---|---|---|
| Cl | H | H | CH$_3$ | CH(OCH$_3$)$_2$ | 150–153° |
| CO$_2$CH$_3$ | H | H | CH$_3$ | CH(OCH$_3$)$_2$ | 121–125° |
| SO$_2$CH$_3$ | H | H | CH$_3$ | CH(OCH$_3$)$_2$ | 152–155° |
| NO$_2$ | H | H | CH$_3$ | CH(OCH$_3$)$_2$ | 144–152° |
| CO$_2$CH(CH$_3$)$_2$ | H | H | CH$_3$ | CH(OCH$_3$)$_2$ | 73–79° |
| CO$_2$C$_2$H$_5$ | H | H | CH$_3$ | CH(OCH$_3$)$_2$ | |
| CF$_3$ | H | H | CH$_3$ | CH(OCH$_3$)$_2$ | |
| Br | H | H | CH$_3$ | CH(OCH$_3$)$_2$ | |
| CH$_3$ | H | H | CH$_3$ | CH(OCH$_3$)$_2$ | |
| C$_2$H$_5$ | H | H | CH$_3$ | CH(OCH$_3$)$_2$ | |

TABLE 1a-continued

| $R_7$ | $R_8$ | $R_{21}$ | X | Y | m.p. (°C.) |
|---|---|---|---|---|---|
| $SO_2$—n-$C_3H_7$ | H | H | $CH_3$ | $CH(OCH_3)_2$ | 135–145° d |
| $SO_2N(CH_3)_2$ | H | H | $CH_2CH_3$ | $CH(OCH_3)_2$ | 146–157° |
| $OCH_3$ | 6-$OCHF_2$ | H | $CH_3$ | $CH(OCH_3)_2$ | |
| $CO_2CH_2CH=CH_2$ | H | H | $CH_3$ | $CH(OCH_3)_2$ | |
| $OCF_2CF_2H$ | H | H | $CH_3$ | $CH(OCH_3)_2$ | |
| $CH_2OCH_3$ | H | H | $CH_2CH_3$ | $CH(OCH_3)_2$ | |
| $OSO_2CHCl_2$ | H | H | $CH_3$ | $CH(OCH_3)_2$ | |
| $SC_2H_5$ | H | H | $CH_2CH_3$ | $CH(OCH_3)_2$ | |
| $OSO_2CH_3$ | H | H | $CH_3$ | $CH(OCH_3)_2$ | |
| $OSO_2C_2H_5$ | H | H | $CH_3$ | $CH(OCH_3)_2$ | |
| $CO_2CH_2CH_2OCH_3$ | H | H | $CH_3$ | $CH(OCH_3)_2$ | |
| $SO_2C_2H_5$ | H | H | $CH_3$ | $CH(OCH_3)_2$ | |
| $NO_2$ | 5-$CF_3$ | H | $CH_2CH_3$ | $CH(OCH_3)_2$ | |
| $SO_2$—n-$C_3H_7$ | 3-Cl | H | $CH_3$ | $CH(OCH_3)_2$ | |
| $OC_2H_5$ | 5-$NO_2$ | H | $CH_3$ | $CH(OCH_3)_2$ | |
| $CO_2C_2H_5$ | H | H | $CH_3$ | $CH(OCH_3)_2$ | 98–100° d |
| I | H | H | $CH_3$ | $CH(OCH_3)_2$ | |
| $SO_2N(CH_3)C_2H_5$ | 6-$NO_2$ | H | $CH_3$ | $CH(OCH_3)_2$ | |
| Cl | 5-Cl | H | $CH_3$ | $CH(OCH_3)_2$ | |
| $SO_2CH_3$ | 5-Cl | H | $CH_3$ | $CH(OCH_3)_2$ | |
| $CO_2CH_3$ | 4-F | H | $CH_3$ | $CH(OCH_3)_2$ | |
| $OCH_2CH=CH_2$ | H | H | $CH_3$ | $CH(OCH_3)_2$ | |
| $CH(OCH_3)CH_3$ | H | H | $CH_3$ | $CH(OCH_3)_2$ | |
| $SO_2CF_3$ | H | H | $CH_3$ | $CH(OCH_3)_2$ | |
| $SCHF_2$ | H | H | $CH_3$ | $CH(OCH_3)_2$ | |
| $OCH_2CH=CHCH_3$ | H | H | $CH_3$ | $CH(OCH_3)_2$ | |
| Cl | H | $CH_3$ | $CH_3$ | $CH(OCH_3)_2$ | |
| $CO_2CH_3$ | H | $CH_3$ | $CH_3$ | $CH(OCH_3)_2$ | |
| $CO_2CH_2CH_3$ | H | $CH_3$ | $CH_3$ | $CH(OCH_3)_2$ | |
| $SO_2CH_3$ | H | $CH_3$ | $CH_3$ | $CH(OCH_3)_2$ | |
| $SO_2N(CH_3)_2$ | H | $CH_3$ | $CH_3$ | $CH(OCH_3)_2$ | |
| $CH(CH_3)_2$ | H | $CH_3$ | $CH_3$ | $CH(OCH_3)_2$ | |
| $OCH_3$ | H | $CH_3$ | $CH_3$ | $CH(OCH_3)_2$ | |
| $SCH_3$ | H | $CH_3$ | $CH_3$ | $CH(OCH_3)_2$ | |
| $SO_2$—n-$C_3H_7$ | H | $CH_3$ | $CH_3$ | $CH(OCH_3)_2$ | |
| n-$C_4H_9$ | H | $CH_3$ | $CH_3$ | $CH(OCH_3)_2$ | |
| O—n-$C_4H_9$ | H | $CH_3$ | $CH_3$ | $CH(OCH_3)_2$ | |
| $NO_2$ | H | $CH_3$ | $CH_3$ | $CH(OCH_3)_2$ | |
| $CO_2$—n-$C_4H_9$ | H | $CH_3$ | $CH_3$ | $CH(OCH_3)_2$ | |
| Cl | H | H | $CH_3$ | $C(CH_3)(OCH_3)_2$ | |
| $CH_2OCH_3$ | H | H | $CH_3$ | $C(CH_3)(OCH_3)_2$ | |
| $SO_2C_2H_5$ | H | H | $CH_3$ | $C(CH_3)(OCH_3)_2$ | |
| $OCH_3$ | H | H | $CH_3$ | $C(CH_3)(OCH_3)_2$ | |
| $SC_2H_5$ | H | H | $CH_3$ | $C(CH_3)(OCH_3)_2$ | |
| $CO_2C_2H_5$ | H | H | $CH_3$ | $C(CH_3)(OCH_3)_2$ | |
| $CO_2CH_3$ | 5-Cl | H | $CH_3$ | $C(CH_3)(OCH_3)_2$ | |
| Cl | H | H | $CH_3$ | $CH(SCH_3)_2$ | |
| $CO_2CH_3$ | H | H | $CH_3$ | $CH(SCH_3)_2$ | |
| $SO_2CH_3$ | H | H | $CH_3$ | $CH(SCH_3)_2$ | |
| $NO_2$ | H | H | $CH_3$ | $CH(SCH_3)_2$ | |

TABLE 1b

| $R_7$ | $R_8$ | $R_{21}$ | X | Y | m.p. (°C.) |
|---|---|---|---|---|---|
| $NO_2$ | H | H | $CH_3$ | $CH_2OTHP$ | 129–132° |
| Br | H | H | $CH_3$ | $CH_2OTHP$ | |
| Cl | H | H | $CH_3$ | $CH_2OTHP$ | 148–150° |
| $SO_2CH_3$ | H | H | $CH_3$ | $CH_2OTHP$ | 161–165° |
| F | H | H | $CH_3$ | $CH_2OTHP$ | |
| H | H | H | $CH_3$ | $CH_2OTHP$ | |

TABLE 1b-continued

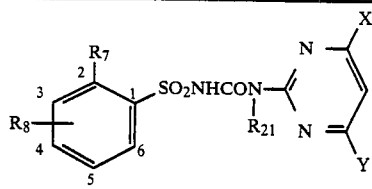

| R7 | R8 | R21 | X | Y | m.p. (°C.) |
|---|---|---|---|---|---|
| $CO_2CH_3$ | H | H | $CH_3$ | $CH_2OTHP$ | 126–128° |
| $CH_3$ | 5-$SCHF_2$ | H | $CH_3$ | $CH_2OTHP$ | |
| $SO_2N(CH_3)_2$ | H | H | $CH_3$ | $CH_2OTHP$ | |
| $SO_2$—n-$C_3H_7$ | H | H | $CH_3$ | $CH_2OTHP$ | |
| $OCH_3$ | H | H | $CH_2CH_3$ | $CH_2OTHP$ | |
| O—n-$C_3H_7$ | H | H | $CH_3$ | $CH_2OTHP$ | |
| $CH_2OCH_3$ | H | H | $CH_2CH_3$ | $CH_2OTHP$ | |
| $CO_2CH_2CH=CH_2$ | H | H | $CH_3$ | $CH_2OTHP$ | |
| $SO_2N(CH_3)_2$ | H | $CH_3$ | $CH_3$ | $CH_2OTHP$ | |
| $OC_2H_5$ | H | $CH_3$ | $CH_3$ | $CH_2OTHP$ | |
| $CO_2Et$ | H | $CH_3$ | $CH_3$ | $CH_2OTHP$ | |
| $OCF_2CF_2H$ | H | $CH_3$ | $CH_3$ | $CH_2OTHP$ | |
| $CH_2OCH_3$ | H | $CH_3$ | $CH_3$ | $CH_2OTHP$ | |
| Cl | H | $CH_3$ | $CH_3$ | $CH_2OTHP$ | |
| $SC_2H_5$ | H | $CH_3$ | $CH_3$ | $CH_2OTHP$ | |
| $SO_2CH_2CH=CH_2$ | H | H | $CH_3$ | $CH_2OTHP$ | |
| $SCF_3$ | H | H | $CH_3$ | $CH_2OTHP$ | |
| $CH(OCH_3)CH_3$ | H | H | $CH_3$ | $CH_2OTHP$ | |

TABLE 1c

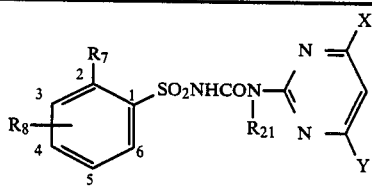

| R7 | R8 | R21 | X | Y | m.p. (°C.) |
|---|---|---|---|---|---|
| Cl | H | H | $CH_3$ | $CH_2OH$ | 130–132° |
| $CO_2CH_3$ | H | H | $CH_3$ | $CH_2OH$ | 140–141° |
| $SO_2CH_3$ | H | H | $CH_3$ | $CH_2OH$ | 155° d |
| $NO_2$ | H | H | $CH_3$ | $CH_2OH$ | 112–116° |
| $CO_2CH(CH_3)_2$ | H | H | $CH_3$ | $CH_2OH$ | 154–157° |
| $CO_2C_2H_5$ | H | H | $CH_3$ | $CH_2OH$ | |
| $CF_3$ | H | H | $CH_2CH_3$ | $CH_2OH$ | |
| Br | H | H | $CH_3$ | $CH_2OH$ | |
| $CH_3$ | H | H | $CH_3$ | $CH_2OH$ | |
| $C_2H_5$ | H | H | $CH_3$ | $CH_2OH$ | |
| $SO_2$—n-$C_3H_7$ | H | H | $CH_3$ | $CH_2OH$ | 128° d |
| $SO_2N(CH_3)_2$ | H | H | $CH_3$ | $CH_2OH$ | 163–169° d |
| $OCH_3$ | H | H | $CH_3$ | $CH_2OH$ | |
| $CO_2CH_2CH=CH_2$ | H | H | $CH_3$ | $CH_2OH$ | |
| $OCF_2CF_2H$ | H | H | $CH_3$ | $CH_2OH$ | |
| $CH_2OCH_3$ | H | H | $CH_3$ | $CH_2OH$ | |
| $OSO_2CHCl_2$ | H | H | $CH_3$ | $CH_2OH$ | |
| $SC_2H_5$ | H | H | $CH_3$ | $CH_2OH$ | |
| $OSO_2CH_3$ | 3-$OCHF_2$ | H | $CH_3$ | $CH_2OH$ | |
| $OSO_2C_2H_5$ | H | H | $CH_3$ | $CH_2OH$ | |
| $CO_2CH_2CH_2OCH_3$ | H | H | $CH_3$ | $CH_2OH$ | |
| $SO_2C_2H_5$ | H | H | $CH_2CH_3$ | $CH_2OH$ | |
| $NO_2$ | 5-$CF_3$ | H | $CH_3$ | $CH_2OH$ | |
| $SO_2$—n-$C_3H_7$ | 3-Cl | H | $CH_3$ | $CH_2OH$ | |
| $OC_2H_5$ | 5-$NO_2$ | H | $CH_3$ | $CH_2OH$ | |
| $SO_2N(CH_3)C_2H_5$ | 6-$NO_2$ | H | $CH_3$ | $CH_2OH$ | |
| Cl | 5-Cl | H | $CH_3$ | $CH_2OH$ | |
| $SO_2CH_3$ | 5-Cl | H | $CH_2CH_3$ | $CH_2OH$ | |
| $CO_2CH_3$ | 4-F | H | $CH_3$ | $CH_2OH$ | |
| $NO_2$ | H | $CH_3$ | $CH_3$ | $CH_2OH$ | |
| Br | H | $CH_3$ | $CH_3$ | $CH_2OH$ | |
| Cl | H | $CH_3$ | $CH_3$ | $CH_2OH$ | |
| $SO_2CH_3$ | H | $CH_3$ | $CH_3$ | $CH_2OH$ | |
| F | H | $CH_3$ | $CH_3$ | $CH_2OH$ | |
| H | H | $CH_3$ | $CH_3$ | $CH_2OH$ | |
| $CO_2CH_3$ | H | $CH_3$ | $CH_3$ | $CH_2OH$ | |
| $CH_3$ | H | $CH_3$ | $CH_3$ | $CH_2OH$ | |
| $SO_2$—i-$C_3H_7$ | H | $CH_3$ | $CH_3$ | $CH_2OH$ | |

TABLE 1c-continued

| R7 | R8 | R21 | X | Y | m.p. (°C.) |
|---|---|---|---|---|---|
| SCF$_3$ | H | CH$_3$ | CH$_3$ | CH$_2$OH | |
| SO$_2$CH$_2$CH=CH$_2$ | H | CH$_3$ | CH$_3$ | CH$_2$OH | |
| SCH$_2$CH$_3$ | H | CH$_3$ | CH$_3$ | CH$_2$OH | |
| OCH$_2$CH=CH$_2$ | H | CH$_3$ | CH$_3$ | CH$_2$OH | |
| OCH$_2$C(CH$_3$)=CH$_2$ | H | CH$_3$ | CH$_3$ | CH$_2$OH | |
| CH$_2$OEt | H | CH$_3$ | CH$_3$ | CH$_2$OH | |
| CH(OCH$_3$)CH$_3$ | H | CH$_3$ | CH$_3$ | CH$_2$OH | |
| CO$_2$CH$_2$CH$_2$Cl | H | CH$_3$ | CH$_3$ | CH$_2$OH | |
| O—i-C$_3$H$_7$ | H | CH$_3$ | CH$_3$ | CH$_2$OH | |
| i-C$_4$H$_9$ | H | CH$_3$ | CH$_3$ | CH$_2$OH | |
| SO$_2$Et | H | H | CH$_3$ | CH$_2$OH | |
| n-C$_4$H$_9$ | H | H | CH$_3$ | CH$_2$OH | |
| O—n-C$_4$H$_9$ | H | H | CH$_3$ | CH$_2$OH | |
| O—t-C$_4$H$_9$ | H | H | CH$_3$ | CH$_2$OH | |
| SO$_2$N(CH$_3$)C$_2$H$_5$ | H | H | CH$_3$ | CH$_2$OH | |
| I | H | H | CH$_3$ | CH$_2$OH | |
| OCF$_2$H | H | H | CH$_3$ | CH$_2$OH | |
| SCF$_2$CF$_2$H | H | H | CH$_3$ | CH$_2$OH | |
| CH$_2$Cl | H | H | CH$_3$ | CH$_2$OH | |

TABLE 1d

| R7 | R8 | R21 | X | Y | m.p. (°C.) |
|---|---|---|---|---|---|
| H | H | H | CH$_3$ | CH(OCH$_2$CH$_2$O) | |
| H | H | H | CH$_3$ | CH(OEt)$_2$ | |
| H | H | H | C$_2$H$_5$ | CH$_2$OCOCH$_3$ | |
| H | H | H | CH$_3$ | CH$_2$SCH$_3$ | |
| H | H | H | CH$_3$ | CH(OCH$_2$CH$_2$O) | |
| Cl | H | H | CH$_3$ | CH(OCH$_2$CH$_2$O) | 158–163° |
| Cl | H | CH$_3$ | CH$_3$ | CH(OCH$_2$CH$_2$O) | |
| Cl | H | H | C$_2$H$_5$ | CH(OCH$_2$CH$_2$O) | |
| Cl | H | H | CH$_3$ | CH(OCH$_2$CH$_2$O) | |
| Cl | 6-Cl | H | CH$_3$ | CH(OCH$_2$CH$_2$CH$_2$O) | |
| Cl | H | CH$_3$ | CH$_3$ | CH(OCH$_2$CH$_2$CH$_2$O) | |
| Cl | 4-F | H | CH$_3$ | CH(OEt)$_2$ | |
| Cl | H | H | CH$_3$ | CH(OEt)$_2$ | |
| CH$_3$ | H | H | CH$_3$ | CH(OEt)$_2$ | |
| CH$_3$ | H | H | C$_2$H$_5$ | CH(OEt)$_2$ | |
| CH$_3$ | H | H | CH$_3$ | CH$_2$SCH$_3$ | |
| C$_2$H$_5$ | H | H | CH$_3$ | CH$_2$OCOCH$_3$ | |
| C$_2$H$_5$ | H | CH$_3$ | CH$_3$ | CH$_2$OCOCH$_3$ | |
| C$_2$H$_5$ | 5-Cl | H | CH$_3$ | CH$_2$OCOCH$_3$ | |
| n-C$_4$H$_9$ | H | H | CH$_3$ | CH(OCH(CH$_3$)CH$_2$O) | |
| OCH$_3$ | H | H | CH$_3$ | CH(OCH(CH$_3$)CH$_2$O) | |
| OCH$_3$ | 3-NO$_2$ | H | CH$_3$ | CH(OCH(CH$_3$)CH$_2$O) | |
| OCH$_3$ | H | H | CH$_3$ | CH(OCH$_2$CH$_2$O) | |
| OCH$_3$ | H | H | CH$_3$ | CH(OEt)$_2$ | |
| OSO$_2$CH$_3$ | H | H | CH$_3$ | CH(CH$_3$)SCH$_3$ | 151–155° |
| CO$_2$CH$_3$ | H | H | CH$_3$ | CH(CH$_3$)SCH$_3$ | 153–157° |
| SO$_2$N(CH$_3$)$_2$ | H | H | CH$_3$ | CH(CH$_3$)SCH$_3$ | 104–107° |
| NO$_2$ | H | H | CH$_3$ | CH(CH$_3$)SCH$_3$ | 133–138° |
| CO$_2$CH$_3$ | H | H | CH$_3$ | CH$_2$OCOCH$_3$ | 145–150° |
| CO$_2$CH$_3$ | H | H | CH$_3$ | CH(SCH$_2$CH$_2$S) | |
| CO$_2$CH$_3$ | H | H | C$_2$H$_5$ | CH(OEt)$_2$ | |
| CO$_2$CH$_3$ | H | H | CH$_3$ | CH$_2$SEt | |
| CO$_2$CH$_3$ | H | H | CH$_3$ | CH(OCH$_2$CH$_2$O) | 151–156° |
| CO$_2$CH$_3$ | H | CH$_3$ | CH$_3$ | CH(OCH$_2$CH$_2$O) | |
| CO$_2$CH$_3$ | 6-CH$_3$ | H | CH$_3$ | CH(OCH$_2$CH$_2$O) | |
| CO$_2$CH$_3$ | 5-OEt | H | CH$_3$ | CH(OCH$_2$CH$_2$O) | |
| CO$_2$CH$_3$ | 4-CF$_3$ | H | CH$_3$ | CH(OCH$_2$CH$_2$O) | |

TABLE 1d-continued

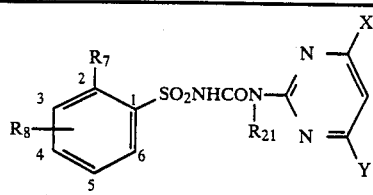

| R7 | R8 | R21 | X | Y | m.p. (°C.) |
|---|---|---|---|---|---|
| SO2CH3 | H | H | CH3 | CH2OCOEt | |
| SO2CH3 | H | H | CH3 | CH2OCOEt | |
| SO2CH3 | 3-F | H | CH3 | CH2SCH3 | |
| SO2CH3 | H | H | CH3 | CH(OCH2CH2O) | 193–195° d |
| SO2CH3 | H | CH3 | CH3 | CH(OCH2CH2O) | |
| SO2CH3 | 6-O—n-C3H7 | H | CH3 | CH(OCH2CH2O) | |
| SO2CH3 | 3-i-C3H7 | H | CH3 | CH(OCH2CH2O) | |
| SO2N(CH3)2 | H | H | CH3 | CH2OCO—n-C3H7 | |
| SO2N(CH3)2 | H | H | CH3 | CH2OCOCH3 | |
| SO2N(CH3)2 | H | H | CH3 | CH(SCH(CH3)CH2S) | |
| SO2N(CH3)2 | H | H | CH3 | CH(OCH2CH2O) | 185–187° |
| SO2N(CH3)2 | H | CH3 | CH3 | CH(OCH2CH2O) | |
| SO2N(CH3)2 | 6-NO2 | H | CH3 | CH(OCH2CH2O) | |
| NO2 | 3-Br | H | CH3 | CH(OCH2CH2O) | |
| NO2 | 6-Cl | CH3 | CH3 | CH(OCH2CH2O) | |
| NO2 | H | H | C2H5 | CH(OCH2CH2O) | |
| NO2 | H | H | CH3 | CH(OCH2CH2O) | 179–182° d |
| NO2 | 3-F | H | CH3 | CH(OCH2CH2O) | |
| CO2CH2CH=CH2 | H | H | CH3 | CH(OCH2CH2O) | |
| CO2CH2CH=CH2 | H | H | CH3 | CH(OCH2CH2CH2O) | |
| Br | H | H | CH3 | CH(SCH2CH2S) | |
| Br | H | H | CH3 | CH2OCO2CH3 | |
| CO2CH2CH3 | H | H | CH3 | CH(OCH2CH2O) | 119–121° |
| I | H | H | CH3 | CH(OCH2CH2O) | |
| CH2Cl | H | H | CH3 | CH(OCH2CH2O) | |
| OCHF2 | H | H | CH3 | CH(OCH2CH2O) | |
| Br | H | CH3 | CH3 | CH2OCONHCH3 | |
| CF3 | H | H | CH3 | CH(OCH2CH2O) | |
| CF3 | H | H | CH3 | CH2SEt | |
| SO2N(Et)2 | H | H | CH3 | CH(OCH2CH2O) | |
| OCH2CH3 | H | H | C2H5 | CH(OCH2CH2O) | |
| O—n-C4H9 | H | H | CH3 | CH(OCH2CH2O) | |
| O—i-C3H7 | H | H | CH3 | CH(OCH2CH2O) | |
| O—CH2CH=CH2 | H | H | CH3 | CH(OCH2CH2O) | |
| SO2CF3 | H | H | CH3 | CH(OCH2CH2O) | |
| SO2CF3 | 5-CF3 | H | CH3 | CH(OEt)2 | |
| SO2CF3 | H | H | CH3 | CH(OEt)2 | |
| SO2—n-C3H7 | H | H | CH3 | CH(OEt)2 | |
| SO2—n-C3H7 | H | CH3 | CH3 | CH(OEt)2 | |
| SO2—n-C3H7 | H | H | CH3 | CH(OCH2CH2O) | 144° d |
| OCF2CF2H | H | H | CH3 | CH2OCOCH3 | |
| OCF2CF2H | H | H | C2H5 | CH2OCOCH3 | |
| OCF2CF2H | H | H | CH3 | CH2OCOCH3 | |
| OSO2C2H5 | H | H | CH3 | CH2OCOCH3 | |
| CH2OEt | 6-F | H | CH3 | CH2OCOCH3 | |
| CH2CH2CH2Cl | H | H | CH3 | CH(OCH(CH3)CH2O) | |
| SO2N(CH3)Et | H | H | CH3 | CH2OCO2Et | |
| SO2N(CH3)Et | H | H | CH3 | CH2OCON(CH3)2 | |
| SO2N(CH3)Et | H | H | CH3 | CH(OCH2CH2O) | |
| Cl | H | H | CH3 | CH(SEt)2 | |
| CO2CH3 | H | H | CH3 | C(CH3)(SCH3)2 | |
| CO2C2H5 | H | H | CH3 | C(CH3)(OCH2CH2O) | |
| NO2 | H | H | CH3 | C(C2H5)(SCH2CH2CH2S) | |
| SO2CH3 | H | H | CH3 | CH(CH3)SO2CH3 | |
| SO2—n-C3H7 | H | H | CH3 | CH2SCH3 | 179–185° |
| CO2CH3 | H | H | CH3 | CH2SCH3 | 133–138° |
| Cl | H | H | CH3 | CH2SCH3 | 133–135° |
| NO2 | H | H | CH3 | CH2SCH3 | 148–154° |
| SO2N(CH3)2 | H | H | CH3 | CH2SCH3 | 127–133° |
| Cl | H | H | CH3 | CH2SO2CH3 | 182–187° |
| Cl | H | H | CH3 | CH2S(O)CH3 | |
| SO2N(CH3)2 | H | H | CH3 | CH(CH3)(S(O)CH3) | |
| NO2 | H | H | CH3 | CH(CH3)(SO2CH3) | |
| Cl | H | H | CH3 | CH2S(O)CH2CH3 | |
| CO2CH3 | H | H | CH3 | CH2SO2CH2CH3 | |
| SO2CH2CH3 | H | H | CH3 | CH2S(O)CH3 | |

TABLE 1e

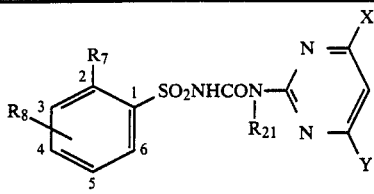

| R7 | R8 | R21 | X | Y | m.p. (°C.) |
|---|---|---|---|---|---|
| Cl | H | H | OCH3 | CH(OCH3)2 | 179–182° |
| CO2CH3 | H | H | OCH3 | CH(OCH3)2 | 121–133° |
| SO2CH3 | H | H | OCH3 | CH(OCH3)2 | 162° d |
| NO2 | H | H | OCH3 | CH(OCH3)2 | 150° d |
| CO2CH(CH3)2 | H | H | OCH3 | CH(OCH3)2 | |
| CO2C2H5 | H | H | OCH3 | CH(OCH3)2 | |
| CF3 | H | H | OCH3 | CH(OCH3)2 | |
| Br | H | CH3 | OCH3 | CH(OCH3)2 | |
| CH3 | H | H | OCH3 | CH(OCH3)2 | |
| C2H5 | H | H | OCH2CH3 | CH(OCH3)2 | |
| SO2—n-C3H7 | H | H | OCH3 | CH(OCH3)2 | 161–167° d |
| SO2N(CH3)2 | H | H | OCH3 | CH(OCH3)2 | 93–102° d |
| OCH3 | H | H | OCH3 | CH(OCH3)2 | |
| CO2CH2CH=CH2 | H | H | OCH3 | CH(OCH3)2 | |
| OCF2CF2H | H | H | OCH3 | CH(OCH3)2 | |
| CH2OCH3 | H | H | OCH2CH3 | CH(OCH3)2 | |
| OSO2CHCl2 | H | H | OCH3 | CH(OCH3)2 | |
| SC2H5 | H | CH3 | OCH3 | CH(OCH3)2 | |
| OSO2CH3 | H | H | OCH3 | CH(OCH3)2 | |
| OSO2C2H5 | H | H | OCH3 | CH(OCH3)2 | |
| CO2CH2CH2OCH3 | H | H | OCH3 | CH(OCH3)2 | |
| SO2C2H5 | H | H | OCH3 | CH(OCH3)2 | |
| NO2 | 5-CF3 | H | OCH3 | CH(OCH3)2 | |
| SO2—n-C3H7 | 3-Cl | H | OCH3 | CH(OCH3)2 | |
| OC2H5 | 5-NO2 | H | OCH2CH3 | CH(OCH3)2 | |
| OSO2CH3 | H | H | OCH3 | C(CH3)(OCH3)2 | |
| CO2CH3 | H | H | OCH3 | C(CH3)(OCH3)2 | |
| CO2CH2CH3 | H | H | OCH3 | C(CH3)(OCH3)2 | |
| SO2N(CH3)C2H5 | 6-NO2 | H | OCH3 | CH(OCH3)2 | |
| Cl | 5-Cl | H | OCH3 | CH(OCH3)2 | |
| SO2CH3 | 5-Cl | H | OCH3 | CH(OCH3)2 | |
| CO2CH3 | 4-F | H | OCH3 | CH(OCH3)2 | |

TABLE 1f

| R7 | R8 | R21 | X | Y | m.p. (°C.) |
|---|---|---|---|---|---|
| NO2 | H | H | OCH3 | CH2OTHP | |
| Br | H | H | OCH3 | CH2OTHP | |
| Cl | H | H | OCH3 | CH2OTHP | |
| SO2CH3 | H | H | OCH3 | CH2OTHP | |
| F | H | H | OCH3 | CH2OTHP | |
| H | H | H | OCH3 | CH2OTHP | |
| CO2CH3 | H | H | OCH3 | CH2OTHP | |
| CH3 | H | H | OCH3 | CH2OTHP | |
| SO2N(CH3)2 | H | H | OCH3 | CH2OTHP | |
| SO2—n-C3H7 | H | H | OCH3 | CH2OTHP | |
| OCH3 | H | H | OCH3 | CH2OTHP | |
| O—n-C3H7 | H | CH3 | OCH3 | CH2OTHP | |
| CH2OCH3 | H | CH3 | OCH3 | CH2OTHP | |
| CO2CH2CH=CH2 | H | H | OCH3 | CH2OTHP | |
| Cl | 6-Cl | H | OCH3 | CH2OTHP | |
| I | H | H | OCH3 | CH2OTHP | |

TABLE 1g

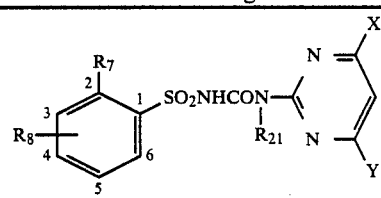

| R7 | R8 | R21 | X | Y | m.p. (°C.) |
|---|---|---|---|---|---|
| Cl | H | H | OCH3 | CH2OH | |
| CO2CH3 | H | H | OCH3 | CH2OH | |
| SO2CH3 | H | H | OCH3 | CH2OH | 170° d |
| NO2 | H | H | OCH3 | CH2OH | |
| CO2CH(CH3)2 | H | H | OCH3 | CH2OH | |
| CO2C2H5 | H | H | OCH3 | CH2OH | |
| CF3 | H | H | OCH3 | CH2OH | |
| Br | H | H | OCH3 | CH2OH | |
| CH3 | H | CH3 | OCH3 | CH2OH | |
| C2H5 | H | H | OCH3 | CH2OH | |
| SO2—n-C3H7 | H | H | OCH3 | CH2OH | |
| SO2N(CH3)2 | H | H | OCH3 | CH2OH | |
| OCH3 | H | H | OCH3 | CH2OH | |
| CO2CH2CH=CH2 | H | H | OCH2CH3 | CH2OH | |
| OCF2CF2H | H | H | OCH3 | CH2OH | |
| CH2OCH3 | H | H | OCH3 | CH2OH | |
| OSO2CHCl2 | H | H | OCH3 | CH2OH | |
| SC2H5 | H | CH3 | OCH3 | CH2OH | |
| OSO2CH3 | H | H | OCH2CH3 | CH2OH | |
| OSO2C2H5 | H | H | OCH3 | CH2OH | |
| CO2CH2CH2OCH3 | H | H | OCH3 | CH2OH | |
| SO2C2H5 | H | H | OCH3 | CH2OH | |
| NO2 | 5-CF3 | H | OCH3 | CH2OH | |

TABLE 1g-continued

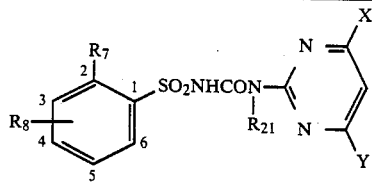

| R7 | R8 | R21 | X | Y | m.p. (°C.) |
|---|---|---|---|---|---|
| SO2—n-C3H7 | 3-Cl | H | OCH3 | CH2OH | |
| OC2H5 | 5-NO2 | H | OCH3 | CH2OH | |
| I | H | H | OCH3 | CH2OH | |
| SO2N(CH3)C2H5 | 6-NO2 | H | OCH3 | CH2OH | |
| Cl | 5-Cl | H | OCH3 | CH2OH | |
| SO2CH3 | 5-Cl | H | OCH3 | CH2OH | |
| CO2CH3 | 4-F | H | OCH3 | CH2OH | |

TABLE 1h

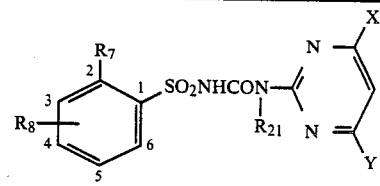

| R7 | R8 | R21 | X | Y | m.p. (° C.) |
|---|---|---|---|---|---|
| H | H | H | OCH3 | CH(OCH2CH2O) | |
| H | H | H | OCH3 | CH(OEt)2 | |
| H | H | H | OC2H5 | CH2OCOCH3 | |
| H | H | H | OCH3 | CH2SCH3 | |
| H | H | H | OCH3 | CH(OCH2CH2CH2O) | |
| Cl | H | H | OCH3 | CH(OCH2CH2O) | 105–112° d |
| Cl | H | CH3 | OCH3 | CH(OCH2CH2O) | |
| Cl | H | H | OC2H5 | CH(OCH2CH2O) | |
| Cl | H | H | OCH3 | CH(OCH2CH2CH2O) | |
| Cl | 6-Cl | H | OCH3 | OCH(OCH2CH2CH2O) | |
| Cl | H | CH3 | OCH3 | CH(OCH2CH2CH2O) | |
| Cl | 4-F | H | OCH3 | CH(OEt)2 | |
| Cl | H | H | OCH3 | CH(OEt)2 | 143–145° |
| CH3 | H | H | OCH3 | CH(OET)2 | |
| CH3 | H | H | OC2H5 | CH(OEt)2 | |
| CH3 | H | H | OCH3 | CH2SCH3 | |
| C2H5 | H | H | OCH3 | CH2OCOCH3 | |
| C2H5 | H | CH3 | OCH3 | CH2OCOCH3 | |
| C2H5 | 5-Cl | H | OCH3 | CH2OCOCH3 | |
| n-C4H9 | H | H | OCH3 | CH(OCH(CH3)CH2O) | |
| OCH3 | H | H | OCH3 | CH(OCH(CH3)CH2O) | |
| OCH3 | 3-NO2 | H | OCH3 | CH(OCH(CH3)CH2O) | |
| OCH3 | H | H | OCH3 | CH(OCH2CH2O) | |
| OCH3 | H | H | OCH3 | CH(OEt)2 | |
| CO2CH2CH3 | H | H | OCH3 | CH(OCH2CH2O) | 145–149° |
| Cl | H | H | OCH3 | C(CH3)(OCH2CH2O) | |
| CO2CH3 | H | H | OCH3 | C(CH3)(OCH2CH2O) | |
| C2H5 | H | H | OCH3 | C(CH3)(OCH2CH2O) | |
| SO2CH3 | H | H | OCH3 | C(CH3)(OCH2CH2O) | |
| CO2CH3 | H | H | OCH3 | CH2OCOCH3 | |
| CO2CH3 | H | H | OCH3 | CH(SCH2CH2S) | |
| CO2CH3 | H | H | OCH3 | CH(OEt)2 | 127–144° |
| CO2CH3 | H | H | OCH3 | CH2SEt | |
| CO2CH3 | H | H | OCH3 | CH(OCH2CH2O) | 161–163° |
| CO2CH3 | H | CH3 | OCH3 | CH(OCH2CH2O) | |
| CO2CH3 | 6-CH3 | H | OCH3 | CH(OCH2CH2O) | |
| CO2CH3 | 5-OEt | H | OCH3 | CH(OCH2CH2O) | |
| CO2CH3 | 4-CF3 | H | OCH3 | CH(OCH2CH2O) | |
| SO2CH3 | H | H | OCH3 | CH2OCOEt | |
| SO2CH3 | H | H | OCH3 | CH(OEt)2 | 210–213° |
| SO2CH3 | 3-F | H | OCH3 | CH2SCH3 | |
| SO2CH3 | H | H | OCH3 | CH(OCH2CH2O) | |
| SO2CH3 | H | CH3 | OCH3 | CH(OCH2CH2O) | |
| SO2CH3 | 6-O—n-C3H7 | H | OCH3 | CH(OCH2CH2O) | |
| SO2CH3 | 3-i-C3H7 | H | OCH3 | CH(OCH2CH2O) | |
| SO2N(CH3)2 | H | H | OCH3 | CH2OCO—n-C3H7 | |
| SO2N(CH3)2 | H | H | OCH3 | CH(OEt)2 | 138–141° |
| SO2N(CH3)2 | H | H | OCH3 | CH(SCH(CH3)CH2S) | |
| SO2N(CH3)2 | H | H | OCH3 | CH(OCH2CH2O) | |
| SO2N(CH3)2 | H | CH3 | OCH3 | CH(OCH2CH2O) | |
| SO2N(CH3)2 | 6-NO2 | H | OCH3 | CH(OCH2CH2O) | |
| NO2 | 3-Br | H | OCH3 | CH(OCH2CH2O) | |
| NO2 | 6-Cl | CH3 | OCH3 | CH(OCH2CH2O) | |
| NO2 | H | H | OC2H5 | CH(OCH2CH2O) | |
| NO2 | H | H | OCH3 | CH(OCH2CH2O) | |
| NO2 | 3-F | H | OCH3 | CH(OCH2CH2O) | |
| CO2CH2CH=CH2 | H | H | OCH3 | CH(OCH2CH2O) | |
| CO2CH2CH=CH2 | H | H | OCH3 | CH(OCH2CH2CH2O) | |
| Br | H | H | OCH3 | CH(SCH2CH2S) | |

TABLE 1h-continued

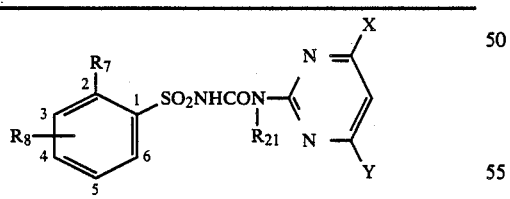

| R7 | R8 | R21 | X | Y | m.p. (° C.) |
|---|---|---|---|---|---|
| Br | H | H | OCH3 | CH2OCO2CH3 | |
| CO2C2H5 | H | H | OCH3 | CH(CH3)SC2H5 | |
| Br | H | H | OCH3 | CH(CH2CH3)SCH3 | |
| SO2N(CH3)2 | H | H | OCH3 | C(CH3)(SCH2CH2S) | |
| CO2CH3 | H | H | OCH3 | CH(SCH3)2 | |
| Br | H | CH3 | OCH3 | CH2OCONHCH3 | |
| CF3 | H | H | OCH3 | CH(OCH2CH2O) | |
| CF3 | H | H | OCH3 | CH2SEt | |
| SO2N(Et)2 | H | H | OCH3 | CH(OCH2CH2O) | |
| OCH2CH3 | H | H | OC2H5 | CH(OCH2CH2O) | |
| O—n-C4H9 | H | H | OCH3 | CH(OCH2CH2O) | |
| O—i-C3H7 | H | H | OCH3 | CH(OCH2CH2O) | |
| O—CH2CH=CH2 | H | H | OCH3 | CH(OCH2CH2O) | |
| SO2CF3 | H | H | OCH3 | CH(OCH2CH2O) | |
| SO2CF3 | 5-CF3 | H | OCH3 | CH(OEt)2 | |
| SO2CF3 | H | H | OCH3 | CH(OEt)2 | |
| SO2—n-C3H7 | H | H | OCH3 | CH(OEt)2 | |
| SO2—n-C3H7 | H | CH3 | OCH3 | CH(OEt)2 | |
| SO2—n-C3H7 | H | H | OCH3 | CH(OCH2CH2O) | |
| OCF2CF2H | H | H | OCH3 | CH2OCOCH3 | |
| OCF2CF2H | H | H | OC2H5 | CH2OCOCH3 | |
| OCF2CF2H | H | H | OCH3 | CH2OCOCH3 | |
| OSO2C2H5 | H | H | OCH3 | CH2OCOCH3 | |
| CH2OEt | 6-F | H | OCH3 | CH2OCOCH3 | |
| CH2CH2CH2Cl | H | H | OCH3 | CH(OCH(CH3)CH2O) | |
| SO2N(CH3)Et | H | H | OCH3 | CH2OCO2Et | |
| SO2N(CH3)Et | H | H | OCH3 | CH2OCON(CH3)2 | |
| SO2N(CH3)Et | H | H | OCH3 | CH(OCH2CH2CH2O) | |
| Cl | H | H | OCH3 | CH2SCH3 | 149–152° |
| CO2CH3 | H | H | OCH3 | CH2SCH3 | 146–149° |
| CO2CH2CH3 | H | H | OCH3 | CH2SCH3 | 146–149° |
| SO2N(CH3)2 | H | H | OCH3 | CH2SCH3 | 136–146° d |
| NO2 | H | H | OCH3 | CH2SCH3 | 152–156° d |
| SO2CH3 | H | H | OCH3 | CH2SCH3 | 185–188° |
| Cl | H | H | OCH3 | CH2SO2CH3 | 158–158.5° |
| CO2CH3 | H | H | OCH3 | CH2SO2CH3 | |
| Cl | H | H | OCH3 | CH(CH3)(S(O)CH3) | 58° d |
| CO2CH3 | H | H | OCH3 | CH(CH3)(SO2CH3) | |
| CO2CH2CH3 | H | H | OCH3 | CH2S(O)CH3 | |
| SO2N(CH3)2 | H | H | OCH3 | CH2S(O)CH2CH3 | |
| NO2 | 6-Cl | H | OCH3 | CH2S(O)CH3 | |
| SO2CH3 | H | H | OCH3 | CH2S(O)CH3 | |
| Cl | H | H | OCH3 | CH(CH3)(S(O)CH2CH3) | |

TABLE 1i

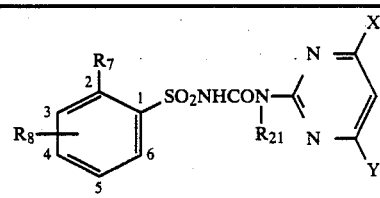

| R7 | R8 | R21 | X | Y | m.p. (°C.) |
|---|---|---|---|---|---|
| Cl | H | H | Cl | CH(OCH3)2 | 164–166° |
| CO2CH3 | H | H | Cl | CH(OCH3)2 | 149–152° |
| SO2CH3 | H | H | Cl | CH(OCH3)2 | |
| NO2 | H | H | Cl | CH(OC2H5)2 | |
| CO2CH(CH3)2 | H | H | Cl | CH2SCH3 | |
| CO2C2H5 | H | CH3 | Cl | CH2SC2H5 | |
| CF3 | H | H | Cl | CH(OCH2CH2CH2O) | |
| Br | H | H | Cl | CH(OCH3)2 | |
| CH3 | H | H | Cl | CH(OCH3)2 | |
| C2H5 | H | H | Cl | CH(OCH3)2 | |

TABLE 1i-continued

| R7 | R8 | R21 | X | Y | m.p. (°C.) |
|---|---|---|---|---|---|
| SO2—n-C3H7 | H | H | Cl | CH(OCH3)2 | |
| SO2N(CH3)2 | H | H | Cl | CH(OCH3)2 | |
| OCH3 | H | CH3 | Cl | CH(OCH3)2 | |
| CO2CH2CH=CH2 | H | H | Cl | CH(OCH3)2 | |
| OCF2CF2H | H | H | Cl | CH(OCH3)2 | |
| CH2OCH3 | H | H | Cl | CH(OCH3)2 | |
| OSO2CHCl2 | H | H | Cl | CH(OCH3)2 | |
| SC2H5 | H | H | Cl | CH(OCH3)2 | |
| OSO2CH3 | H | H | Cl | CH(OCH3)2 | |
| OSO2C2H5 | H | H | Cl | CH(OCH3)2 | |
| CO2CH2CH2OCH3 | H | H | Cl | CH(OCH3)2 | |
| SO2C2H5 | H | H | Cl | CH(OCH3)2 | |

TABLE 1i-continued

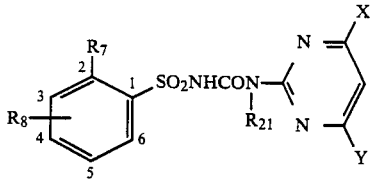

| R7 | R8 | R21 | X | Y | m.p. (°C.) |
|---|---|---|---|---|---|
| NO2 | 5-CF3 | H | Cl | CH(OCH3)2 | |
| SO2—n-C3H7 | 3-Cl | H | Cl | CH(OCH3)2 | |
| OC2H5 | 5-NO2 | H | Cl | CH(OCH3)2 | |
| I | H | H | Cl | CH(OCH3)2 | |
| CO2CH3 | H | H | Cl | CH(OCH3)2 | |
| SO2N(CH3)C2H5 | 6-NO2 | H | Cl | C(CH3)(OCH3)2 | |
| Cl | 5-Cl | H | Cl | CH(OCH3)2 | |
| SO2CH3 | 5-Cl | H | Cl | CH(OCH3)2 | |
| CO2CH3 | 4-F | H | Cl | CH(OCH3)2 | |

TABLE 1j

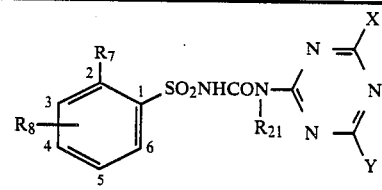

| R7 | R8 | R21 | X | Y | m.p. (°C.) |
|---|---|---|---|---|---|
| Cl | H | H | CH3 | CH(OCH3)2 | |
| CO2CH3 | H | H | CH3 | CH(OCH3)2 | 113–121° |
| SO2CH3 | H | H | CH2CH3 | CH(OCH3)2 | |
| NO2 | H | H | CH3 | CH(OCH3)2 | |
| CO2CH(CH3)2 | H | H | CH3 | CH(OCH3)2 | |
| CO2C2H5 | H | H | CH3 | CH(OCH3)2 | |
| CF3 | H | H | CH3 | CH(OCH3)2 | |
| Br | H | H | CH2CH3 | CH(OCH3)2 | |
| CH(CH3)2 | H | H | CH3 | CH(OCH3)2 | |
| C2H5 | H | H | CH3 | CH(OCH3)2 | |
| SO2—n-C3H7 | H | H | CH3 | CH(OCH3)2 | |
| SO2N(CH3)2 | H | H | CH3 | CH(OCH3)2 | |
| OCH2CH=CHCH3 | H | H | CH3 | CH(OCH3)2 | |
| CO2CH2CH=CH2 | H | CH3 | CH3 | CH(OCH3)2 | |
| OCF2CF2H | H | H | CH3 | CH(OCH3)2 | |
| CH2OCH3 | H | H | CH2CH3 | CH(OCH3)2 | |
| OSO2CHCl2 | H | H | CH3 | CH(OCH3)2 | |
| SC2H5 | H | H | CH3 | CH(OCH3)2 | |
| OSO2CH3 | H | H | CH3 | CH(OCH3)2 | |
| OSO2C2H5 | H | H | CH3 | CH(OCH3)2 | |
| CO2CH2CH2OCH3 | H | H | CH3 | CH(OCH3)2 | |
| SO2C2H5 | H | H | CH3 | CH(OCH3)2 | |
| NO2 | 5-CF3 | H | CH3 | CH(OCH3)2 | |
| SO2—n-C3H7 | 3-Cl | H | CH3 | CH(OCH3)2 | |
| OC2H5 | 5-NO2 | H | CH3 | CH(OCH3)2 | |
| CO2CH2CH3 | H | H | CH3 | CH(OCH3)2 | |
| I | H | H | CH3 | CH(OCH3)2 | |
| SO2N(CH3)C2H5 | 6-NO2 | H | CH3 | CH(OCH3)2 | |
| Cl | 5-Cl | H | CH3 | CH(OCH3)2 | |
| SO2CH3 | 5-Cl | H | CH3 | CH(OCH3)2 | |
| CO2CH3 | 4-F | H | CH3 | CH(OCH3)2 | |
| OCH2CH=CH2 | H | H | CH3 | CH(OCH3)2 | |
| CH(OCH3)CH3 | H | H | CH3 | CH(OCH3)2 | |
| SO2CF3 | H | H | CH3 | CH(OCH3)2 | |
| SCHF2 | H | H | CH3 | CH(OCH3)2 | |
| OCH2CH=CHCH3 | H | H | CH3 | CH(OCH3)2 | |
| Cl | H | CH3 | CH3 | CH(OCH3)2 | |
| CO2CH3 | H | CH3 | CH3 | CH(OCH3)2 | |
| CO2CH2CH3 | H | CH3 | CH3 | CH(OCH3)2 | |
| SO2CH3 | H | CH3 | CH3 | CH(OCH3)2 | |
| SO2N(CH3)2 | H | CH3 | CH3 | CH(OCH3)2 | |
| CH(CH3)2 | H | CH3 | CH3 | CH(OCH3)2 | |
| OCH3 | H | CH3 | CH3 | CH(OCH3)2 | |
| SCH3 | H | CH3 | CH3 | CH(OCH3)2 | |
| SO2—n-C3H7 | H | CH3 | CH3 | CH(OCH3)2 | |
| n-C4H9 | H | CH3 | CH3 | CH(OCH3)2 | |
| O—n-C4H9 | H | CH3 | CH3 | CH(OCH3)2 | |
| NO2 | H | CH3 | CH3 | CH(OCH3)2 | |
| CO2—n-C4H9 | H | CH3 | CH3 | CH(OCH3)2 | |
| Cl | H | H | CH3 | C(CH3)(OCH3)2 | |
| CH2OCH3 | H | H | CH3 | C(CH3)(OCH3)2 | |
| SO2C2H5 | H | H | CH3 | C(CH3)(OCH3)2 | |
| OCH3 | H | H | CH3 | C(CH3)(OCH3)2 | |
| SC2H5 | H | H | CH3 | C(CH3)(OCH3)2 | |
| CO2C2H5 | H | H | CH3 | C(CH3)(OCH3)2 | |
| CO2CH3 | 5-Cl | H | CH3 | C(CH3)(OCH3)2 | |
| Cl | H | H | CH3 | CH(SCH3)2 | |
| CO2CH3 | H | H | CH3 | CH(SCH3)2 | |

TABLE 1j-continued

| R7 | R8 | R21 | X | Y | m.p. (°C.) |
|---|---|---|---|---|---|
| SO2CH3 | H | H | CH3 | CH(SCH3)2 | |
| NO2 | H | H | CH3 | CH(SCH3)2 | |

TABLE 1k

| R7 | R8 | R21 | X | Y | m.p. (°C.) |
|---|---|---|---|---|---|
| NO2 | H | H | CH3 | CH2OTHP | |
| Br | H | H | CH3 | CH2OTHP | |
| Cl | H | H | CH3 | CH2OTHP | |
| F | H | H | CH3 | CH2OTHP | |
| SO2CH3 | H | CH3 | CH3 | CH2OTHP | |
| H | H | H | CH3 | CH2OTHP | |
| CO2CH3 | H | H | CH3 | CH2OTHP | |
| CH3 | H | H | CH3 | CH2OTHP | |
| SO2N(CH3)2 | H | H | CH3 | CH2OTHP | |
| SO2—n-C3H7 | H | H | CH3 | CH2OTHP | |
| OCH3 | H | H | CH2CH3 | CH2OTHP | |
| O—n-C3H7 | H | H | CH3 | CH2OTHP | |
| CH2OCH3 | H | H | CH3 | CH2OTHP | |
| CO2CH2CH=CH2 | H | H | CH3 | CH2OTHP | |

TABLE 1l

| R7 | R8 | R21 | X | Y | m.p. (°C.) |
|---|---|---|---|---|---|
| Cl | H | H | CH3 | CH2OH | |
| CO2CH3 | H | CH3 | CH3 | CH2OH | |
| SO2CH3 | H | H | CH3 | CH2OH | |
| NO2 | H | H | CH3 | CH2OH | |
| CO2CH(CH3)2 | H | H | CH3 | CH2OH | |
| CO2C2H5 | H | H | CH2CH3 | CH2OH | |
| CF3 | H | H | CH3 | CH2OH | |
| Br | H | H | CH3 | CH2OH | |
| CH3 | H | H | CH3 | CH2OH | |
| C2H5 | H | H | CH3 | CH2OH | |
| SO2—n-C3H7 | H | H | CH3 | CH2OH | |
| SO2N(CH3)2 | H | H | CH3 | CH2OH | |
| OCH3 | H | H | CH3 | CH2OH | |
| CO2CH2CH=CH2 | H | CH3 | CH3 | CH2OH | |
| OCF2CF2H | H | H | CH3 | CH2OH | |
| CH2OCH3 | H | H | CH3 | CH2OH | |
| OSO2CHCl2 | H | H | CH3 | CH2OH | |
| SC2H5 | H | H | CH3 | CH2OH | |
| OSO2CH3 | H | H | CH2CH3 | CH2OH | |
| OSO2C2H5 | H | H | CH3 | CH2OH | |
| CO2CH2CH2OCH3 | H | H | CH3 | CH2OH | |
| SO2C2H5 | H | H | CH3 | CH2OH | |
| NO2 | 5-CF3 | H | CH3 | CH2OH | |
| SO2—n-C3H7 | 3-Cl | H | CH3 | CH2OH | |
| OC2H5 | 5-NO2 | H | CH3 | CH2OH | |
| SO2N(CH3)C2H5 | 6-NO2 | H | CH3 | CH2OH | |
| Cl | 5-Cl | H | CH3 | CH2OH | |
| SO2CH3 | 5-Cl | H | CH3 | CH2OH | |
| CO2CH3 | 4-F | H | CH3 | CH2OH | |

TABLE 1m

| R7 | R8 | R21 | X | Y | m.p. (°C.) |
|---|---|---|---|---|---|
| NO2 | H | H | CH3 | CH(OC2H5)2 | |
| NO2 | H | CH3 | CH3 | CH2OCOCH3 | |
| NO2 | H | H | CH3 | CH2SCH3 | |
| Br | H | H | CH3 | CH2OCONHCH3 | |
| Cl | H | H | CH3 | CH2OCO2CH3 | |
| F | H | H | CH3 | CH2SC2H5 | |
| F | H | H | CH3 | CH(OCH2CH2O) | |
| SO2CH3 | H | H | CH2CH3 | CH2OCOC2H5 | |

TABLE 1m-continued

| $R_7$ | $R_8$ | $R_{21}$ | X | Y | m.p. (°C.) |
|---|---|---|---|---|---|
| $SO_2CH_3$ | H | H | $CH_3$ | $CH(OCH(CH_3)CH_2O)$ | |
| $SO_2CH_3$ | H | H | $CH_3$ | $CH(OCH_2CH_2CH_2O)$ | |
| $SO_2CH_3$ | H | H | $CH_3$ | $CH_2SCH_2CH_3$ | |
| H | H | H | $CH_3$ | $CH_2OCOCH_3$ | |
| $CO_2CH_3$ | H | H | $CH_3$ | $CH_2OCON(CH_3)_2$ | |
| $CO_2CH_3$ | H | H | $CH_3$ | $CH(OCH_2CH_2O)$ | |
| $CO_2CH_3$ | H | $CH_3$ | $CH_3$ | $CH_2OCOCH_3$ | |
| $CO_2CH_3$ | H | H | $CH_3$ | $CH_2SC_2H_5$ | |
| $CH_3$ | H | H | $CH_2CH_3$ | $CH(OC_2H_5)_2$ | |
| $CH_3$ | H | H | $CH_3$ | $CH_2OCO_2C_2H_5$ | |
| $SO_2N(CH_3)_2$ | H | H | $CH_3$ | $CH_2OCON(C_2H_5)_2$ | |
| $SO_2N(CH_3)_2$ | H | H | $CH_3$ | $CH_2OCO-i-C_3H_7$ | |
| $SO_2-n-C_3H_7$ | H | H | $CH_3$ | $CH_2OCONH-n-C_3H_7$ | |
| $SO_2-n-C_3H_7$ | H | H | $CH_3$ | $CH(OC_2H_5)_2$ | |
| $OCH_3$ | H | H | $CH_3$ | $CH(SCH_2CH_2S)$ | |
| $OCH_3$ | H | H | $CH_3$ | $CH_2SCH_3$ | |
| $O-n-C_3H_7$ | H | H | $CH_3$ | $CH_2OCO_2CH_3$ | |
| Cl | H | H | $CH_3$ | $C(CH_3)(SCH_3)_2$ | |
| $CO_2CH_3$ | H | H | $CH_3$ | $CH(C_2H_5)SCH_3$ | |
| $SO_2N(CH_3)_2$ | H | H | $CH_3$ | $C(CH_3)(OCH_2CH_2O)$ | |
| I | H | H | $CH_3$ | $C(CH_3)(OCH_2CH_2CH_2O)$ | |
| Br | H | $CH_3$ | $OCH_3$ | $CH_2OCONHCH_3$ | |
| $CF_3$ | H | H | $OCH_3$ | $CH(OCH_2CH_2O)$ | |
| $CF_3$ | H | H | $OCH_3$ | $CH_2SEt$ | |
| $SO_2N(Et)_2$ | H | H | $OCH_3$ | $CH(OCH_2CH_2O)$ | |
| $OCH_2CH_3$ | H | H | $OC_2H_5$ | $CH(OCH_2CH_2O)$ | |
| $O-n-C_4H_9$ | H | H | $OCH_3$ | $CH(OCH_2CH_2O)$ | |
| $O-i-C_3H_7$ | H | H | $OCH_3$ | $CH(OCH_2CH_2O)$ | |
| $O-CH_2CH=CH_2$ | H | H | $OCH_3$ | $CH(OCH_2CH_2O)$ | |
| $SO_2CF_3$ | H | H | $OCH_3$ | $CH(OCH_2CH_2O)$ | |
| $SO_2CF_3$ | $5-CF_3$ | H | $OCH_3$ | $CH(OEt)_2$ | |
| $SO_2CF_3$ | H | H | $OCH_3$ | $CH(OEt)_2$ | |
| $SO_2-n-C_3H_7$ | H | H | $OCH_3$ | $CH(OEt)_2$ | |
| $SO_2-n-C_3H_7$ | H | $CH_3$ | $OCH_3$ | $CH(OEt)_2$ | |
| $SO_2-n-C_3H_7$ | H | H | $OCH_3$ | $CH(OCH_2CH_2O)$ | |
| $OCF_2CF_2H$ | H | H | $OCH_3$ | $CH_2OCOCH_3$ | |
| $OCF_2CF_2H$ | H | H | $OC_2H_5$ | $CH_2OCOCH_3$ | |
| $OCF_2CF_2H$ | H | H | $OCH_3$ | $CH_2OCOCH_3$ | |
| $OSO_2C_2H_5$ | H | H | $OCH_3$ | $CH_2OCOCH_3$ | |
| $CH_2OEt$ | 6-F | H | $OCH_3$ | $CH_2OCOCH_3$ | |
| $CH_2CH_2CH_2Cl$ | H | H | $OCH_3$ | $CH(OCH(CH_3)CH_2O)$ | |
| $SO_2N(CH_3)Et$ | H | H | $OCH_3$ | $CH_2OCO_2Et$ | |
| $SO_2N(CH_3)Et$ | H | H | $OCH_3$ | $CH_2OCON(CH_3)_2$ | |
| $SO_2N(CH_3)Et$ | H | H | $OCH_3$ | $CH(OCH_2CH_2CH_2O)$ | |
| Cl | H | H | $OCH_3$ | $CH_2SCH_3$ | |
| $CO_2CH_3$ | H | H | $OCH_3$ | $CH_2SCH_3$ | |
| $CO_2CH_2CH_3$ | H | H | $OCH_3$ | $CH_2SCH_3$ | |
| $SO_2N(CH_3)_2$ | H | H | $OCH_3$ | $CH_2SCH_3$ | |
| $NO_2$ | H | H | $OCH_3$ | $CH_2SCH_3$ | |
| $SO_2CH_3$ | H | H | $OCH_3$ | $CH_2SCH_3$ | |
| Cl | H | H | $OCH_3$ | $CH_2SO_2CH_3$ | |
| $CO_2CH_3$ | H | H | $OCH_3$ | $CH_2SO_2CH_3$ | |
| $O-n-C_3H_7$ | H | H | $CH_3$ | $CH_2OCON(C_2H_5)_2$ | |
| $CH_2OCH_3$ | H | H | $CH_3$ | $CH_2OCOCH_3$ | |
| $CH_2OCH_3$ | H | H | $CH_3$ | $CH_2OCO_2CH_3$ | |
| $CO_2CH_2CH=CH_2$ | H | H | $CH_3$ | $CH(OC_2H_5)_2$ | |
| $SO_2CH_3$ | H | H | $CH_3$ | $CH_2S(O)CH_3$ | |
| Cl | H | H | $CH_3$ | $CH_2S(O)CH_3$ | |
| $CO_2CH_3$ | H | H | $CH_3$ | $CH_2S(O)CH_3$ | |
| $OCH_3$ | H | H | $OCH_3$ | $CH(CH_3)(S(O)CH_3)$ | |
| $CH_2OCH_3$ | H | H | $OCH_3$ | $CH(CH_3)(S(O)CH_3)$ | |

TABLE 1n

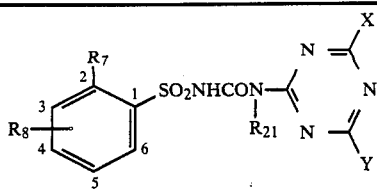

| R7 | R8 | R21 | X | Y | m.p. (°C.) |
|---|---|---|---|---|---|
| Cl | H | H | OCH3 | CH(OCH3)2 | 117–121° |
| CO2CH3 | H | H | OCH3 | CH(OCH3)2 | 135–158° |
| SO2CH3 | H | H | OCH3 | CH(OCH3)2 | |
| NO2 | H | H | OCH3 | CH(OCH3)2 | |
| CO2CH(CH3)2 | H | H | OCH3 | CH(OCH3)2 | |
| CO2C2H5 | H | H | OCH3 | CH(OCH3)2 | |
| CF3 | H | H | OCH2CH3 | CH(OCH3)2 | |
| Br | H | H | OCH3 | CH(OCH3)2 | |
| CH3 | H | H | OCH3 | CH(OCH3)2 | |
| C2H5 | H | H | OCH3 | CH(OCH3)2 | |
| SO2—n-C3H7 | H | H | OCH3 | CH(OCH3)2 | |
| SO2N(CH3)2 | H | H | OCH3 | CH(OCH3)2 | |
| OCH3 | H | H | OCH2CH3 | CH(OCH3)2 | |
| CO2CH2CH=CH2 | H | CH3 | OCH3 | CH(OCH3)2 | |
| OCF2CF2H | H | H | OCH3 | CH(OCH3)2 | |
| CH2OCH3 | H | H | OCH3 | CH(OCH3)2 | |
| OSO2CHCl2 | H | H | OCH3 | CH(OCH3)2 | |
| SC2H5 | H | H | OCH3 | CH(OCH3)2 | |
| OSO2CH3 | H | H | OCH3 | CH(OCH3)2 | |
| OSO2C2H5 | H | H | OCH3 | CH(OCH3)2 | |
| CO2CH2CH2OCH3 | H | H | OCH3 | CH(OCH3)2 | |
| SO2C2H5 | H | H | OCH3 | CH(OCH3)2 | |
| NO2 | 5-CF3 | H | OCH3 | CH(OCH3)2 | |
| SO2—n-C3H7 | 3-Cl | H | OCH3 | CH(OCH3)2 | |
| OC2H5 | 5-NO2 | H | OCH3 | CH(OCH3)2 | |
| CH2CH3 | H | H | OCH3 | C(CH3)(OCH3)2 | |
| CO2CH3 | H | H | OCH3 | C(CH3)(OCH3)2 | |
| CH2Cl | H | H | OCH3 | C(CH3)(OCH3)2 | |
| SO2N(CH3)C2H5 | 6-NO2 | H | OCH3 | CH(OCH3)2 | |
| Cl | 5-Cl | H | OCH3 | CH(OCH3)2 | |
| SO2CH3 | 5-Cl | H | OCH3 | CH(OCH3)2 | |
| CO2CH3 | 4-F | H | OCH3 | CH(OCH3)2 | |
| CO2CH2CH3 | H | H | OCH3 | C(C2H5)(OCH3)2 | |
| I | H | H | OCH3 | C(C2H5)(OCH3)2 | |
| Cl | H | H | OCH3 | C(C2H5)(OCH3)2 | |

TABLE 1o

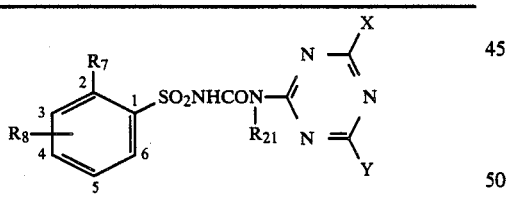

| R7 | R8 | R21 | X | Y | m.p. (°C.) |
|---|---|---|---|---|---|
| NO2 | H | H | OCH3 | CH2OTHP | |
| Br | H | H | OCH3 | CH2OTHP | |
| Cl | H | H | OCH3 | CH2OTHP | 136–139° |
| SO2CH3 | H | H | OCH3 | CH2OTHP | |
| F | H | H | OCH3 | CH2OTHP | |
| H | H | H | OCH3 | CH2OTHP | |
| CO2CH3 | H | H | OCH3 | CH2OTHP | |
| CH3 | H | H | OCH3 | CH2OTHP | |
| SO2N(CH3)2 | H | H | OCH3 | CH2OTHP | |
| SO2—n-C3H7 | H | H | OCH3 | CH2OTHP | |
| OCH3 | H | CH3 | OCH3 | CH2OTHP | |
| O—n-C3H7 | H | H | OCH2CH3 | CH2OTHP | |
| CH2OCH3 | H | H | OCH3 | CH2OTHP | |
| CO2CH2CH=CH2 | H | H | OCH3 | CH2OTHP | |
| I | H | H | OCH3 | CH2OTHP | |
| CH2Cl | H | H | OCH3 | CH2OTHP | |

TABLE 1p

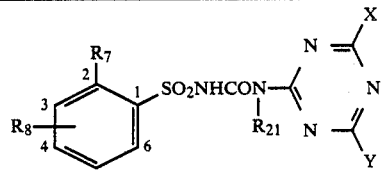

| R7 | R8 | R21 | X | Y | m.p. (°C.) |
|---|---|---|---|---|---|
| Cl | H | H | OCH3 | CH2OH | 133–135° |
| CO2CH3 | H | H | OCH3 | CH2OH | 115° d |
| SO2CH3 | H | H | OCH3 | CH2OH | |
| NO2 | H | H | OCH3 | CH2OH | |
| CO2CH(CH3)2 | H | H | OCH3 | CH2OH | |
| CO2C2H5 | H | H | OCH3 | CH2OH | |
| CF3 | H | H | OCH3 | CH2OH | |
| Br | H | H | OCH2CH3 | CH2OH | |
| CH3 | H | H | OCH3 | CH2OH | |
| C2H5 | H | H | OCH3 | CH2OH | |
| SO2—n-C3H7 | H | H | OCH3 | CH2OH | 152° d |
| SO2N(CH3)2 | H | H | OCH3 | CH2OH | |
| OCH3 | H | H | OCH3 | CH2OH | |
| CO2CH2CH=CH2 | H | H | OCH3 | CH2OH | |
| OCF2CF2H | H | H | OCH3 | CH2OH | |
| CH2OCH3 | H | H | OCH3 | CH2OH | |
| OSO2CHCl2 | H | H | OCH3 | CH2OH | |

TABLE 1p-continued

| R7 | R8 | R21 | X | Y | m.p. (°C.) |
|---|---|---|---|---|---|
| SC2H5 | H | CH3 | OCH3 | CH2OH | |
| OSO2CH3 | H | H | OCH3 | CH2OH | |
| OSO2C2H5 | H | H | OCH3 | CH2OH | |
| CO2CH2CH2OCH3 | H | H | OCH3 | CH2OH | |
| SO2C2H5 | H | H | OCH3 | CH2OH | |
| NO2 | 5-CF3 | H | OCH2CH3 | CH2OH | |
| SO2—n-C3H7 | 3-Cl | H | OCH3 | CH2OH | |
| OC2H5 | 5-NO2 | H | OCH3 | CH2OH | |

TABLE 1p-continued

| R7 | R8 | R21 | X | Y | m.p. (°C.) |
|---|---|---|---|---|---|
| I | H | H | OCH3 | CH2OH | |
| CH2Cl | H | H | OCH3 | CH2OH | |
| SO2N(CH3)C2H5 | 6-NO2 | H | OCH3 | CH2OH | |
| Cl | 5-Cl | H | OCH3 | CH2OH | |
| SO2CH3 | 5-Cl | H | OCH3 | CH2OH | |
| CO2CH3 | 4-F | H | OCH3 | CH2OH | |

TABLE 1q

| R7 | R8 | R21 | X | Y | m.p. (°C.) |
|---|---|---|---|---|---|
| NO2 | H | H | OCH3 | CH(OC2H5)2 | |
| NO2 | H | H | OCH3 | CH2OCOCH3 | |
| NO2 | H | H | OCH3 | CH2SCH3 | |
| Br | H | H | OCH3 | CH2OCONHCH3 | |
| Cl | H | H | OCH3 | CH2OCO2CH3 | |
| F | H | H | OCH3 | CH2SC2H5 | |
| F | H | H | OCH3 | CH(OCH2CH2O) | |
| SO2CH3 | H | H | OCH3 | CH2OCOC2H5 | |
| SO2CH3 | H | H | OCH3 | CH(OCH(CH3)CH2O) | |
| SO2CH3 | H | H | OCH3 | CH(OCH2CH2CH2O) | |
| SO2CH3 | H | H | OCH2CH3 | CH2SCH3 | |
| H | H | H | OCH3 | CH2OCOCH3 | |
| CO2CH3 | H | H | OCH3 | CH2OCON(CH3)2 | |
| CO2CH3 | H | H | OCH3 | CH(OCH2CH2O) | |
| CO2CH3 | H | H | OCH3 | CH2OCOCH3 | |
| CO2CH3 | H | CH3 | OCH3 | CH2SC2H5 | |
| CH3 | H | H | OCH3 | CH(OC2H5)2 | |
| CH3 | H | H | OCH3 | CH2OCO2C2H5 | |
| SO2N(CH3)2 | H | H | OCH3 | CH2OCON(C2H5)2 | |
| SO2N(CH3)2 | H | H | OCH3 | CH2OCO—i-C3H7 | |
| SO2—n-C3H7 | H | H | OCH3 | CH2OCONH—n-C3H7 | |
| SO2—n-C3H7 | H | H | OCH3 | CH(OC2H5)2 | |
| OCH3 | H | H | OCH2CH3 | CH(OCH2CH2O) | |
| OCH3 | H | H | OCH3 | CH2SCH3 | |
| O—n-C3H7 | H | H | OCH3 | CH2OCO2CH3 | |
| NO2 | H | H | OCH3 | CH2SO2CH3 | |
| SO2CH3 | H | H | OCH3 | CH2SO2CH3 | |
| CO2CH3 | H | H | OCH3 | CH2SO2CH3 | |
| CO2CH2CH3 | H | H | OCH3 | CH2SO2CH3 | |
| O—n-C3H7 | H | H | OCH3 | CH2OCON(C2H5)2 | |
| CH2OCH3 | H | H | OCH3 | CH2OCOCH3 | |
| CH2OCH3 | H | H | OCH3 | CH2OCO2CH3 | |
| CO2CH2CH=CH2 | H | H | OCH3 | CH(OC2H5)2 | |
| I | H | H | OCH3 | CH(CH3)SCH3 | |
| CH2Cl | H | H | OCH3 | CH(C2H5)SO2CH3 | |
| CO2CH2CH3 | H | H | OCH3 | C(CH3)(SCH2CH2S) | |
| NO2 | H | H | OCH3 | C(C2H5)(SCH3)2 | |
| SO2N(CH3)2 | H | H | OCH3 | CH(SC2H5)2 | |
| OCHF2 | H | H | OCH3 | CH(SCH3)2 | |
| Cl | H | H | OCH3 | CH2SO2CH2CH3 | |
| Br | H | H | OCH3 | CH2SO2CH3 | |
| CH2OCH3 | H | H | OCH3 | C(CH3)(SCH3)2 | |
| SO2N(CH3)2 | H | H | OCH3 | CH2S(O)CH3 | |
| NO2 | H | H | OCH3 | CH2S(O)CH2CH3 | |
| CH2OCH3 | H | H | OCH3 | CH2S(O)CH3 | |
| SO2CH3 | H | H | OCH3 | CH(CH3)(S(O)CH3) | |
| CO2CH3 | H | H | OCH3 | CH(CH3)(S(O)CH3) | |

TABLE 1r

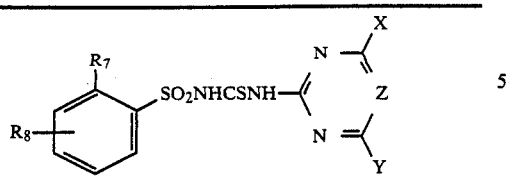

| R7 | R8 | X | Y | Z | m.p. (°C.) |
|---|---|---|---|---|---|
| H | H | CH3 | CH(OCH3)2 | CH | |
| H | H | OCH3 | CH2SCH3 | CH | |
| Cl | H | CH3 | CH2SO2CH3 | CH | |
| Cl | H | OCH3 | C(CH3)(OCH2CH2O) | CH | |
| Cl | H | CH3 | CH(OCH3)2 | CH | |
| Cl | 5-Cl | OCH3 | CH(OCH3)2 | N | |
| NO2 | H | CH3 | CH(OCH3)2 | N | |
| NO2 | H | OCH3 | CH(OCH3)2 | CH | |
| CO2CH3 | H | CH3 | CH(OCH3)2 | CH | |
| CO2CH3 | H | OCH3 | CH(OEt)2 | CH | |
| CO2CH3 | H | OC2H5 | CH(OEt)2 | CH | |
| CO2CH2CH3 | H | CH3 | CH2OTHP | N | |
| CO2CH2CH3 | H | C2H5 | CH2OH | N | |
| CO2CH2CH3 | H | Cl | CH2SCH3 | N | |
| SO2CH3 | H | CH3 | CH(CH3)SC2H5 | CH | |
| SO2CH3 | H | OC2H5 | CH(CH3)SC2H5 | CH | |
| SO2CH3 | H | CH3 | CH(OCH2CH2CH2O) | CH | |
| SC2H5 | H | OCH3 | CH(OCH2CH2CH2O) | N | |
| SC2H5 | H | CH3 | CH(OCH2CH2CH2O) | N | |
| SC2H5 | H | OCH3 | CH(OCH3)2 | CH | |
| SO2N(CH3)2 | H | C2H5 | CH(OCH3)2 | CH | |
| SO2N(CH3)2 | 3-CH3 | OCH3 | CH(OCH3)2 | CH | |
| SO2N(CH3)2 | H | CH3 | CH(OCH3)2 | CH | |
| C2H5 | H | OCH3 | CH(OCH3)2 | CH | |
| C2H5 | H | CH3 | CH(CH3)SO2CH3 | N | |
| C2H5 | H | OCH3 | CH(CH3)SO2CH3 | N | |
| C2H5 | H | OCH3 | CH(CH3)SO2CH3 | CH | |
| O—i-C3H7 | H | CH3 | CH(OCH2CH2O) | CH | |
| O—i-C3H7 | H | OCH3 | CH(OCH2CH2O) | CH | |
| F | H | CH3 | CH(OCH2CH2O) | CH | |
| Br | H | OCH3 | CH(OCH(CH3)CH2O) | N | |
| CH2OCH3 | H | CH3 | CH(SCH2CH2S) | CH | |
| CH2OCH3 | H | OCH3 | CH(SCH3)2 | CH | |
| CH2OCH3 | 6-Cl | OCH3 | CH(OC2H5)2 | CH | |
| SO2—n-C3H7 | H | CH3 | CH(CH3)SCH3 | CH | |
| CO2CH3 | H | OCH3 | CH2S(O)CH3 | CH | |
| CO2CH3 | H | OCH3 | CH2S(O)CH3 | N | |

TABLE 2a

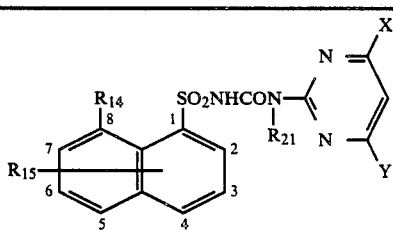

| R14 | R15 | R21 | X | Y | m.p. (°C.) |
|---|---|---|---|---|---|
| Cl | H | H | CH3 | CH(OCH3)2 | |
| Br | H | H | CH3 | CH(OCH3)2 | |
| F | H | H | OCH3 | CH(OCH3)2 | |
| H | H | H | OCH3 | CH(OCH3)2 | |
| Cl | H | H | Cl | CH(OCH3)2 | |
| Cl | 3-Cl | H | CH3 | CH(OCH3)2 | |
| Cl | H | H | OCH3 | CH(OCH3)2 | |
| OCH3 | H | H | CH3 | CH(OCH3)2 | |
| CH3 | H | H | OCH2CH3 | CH(OCH3)2 | |
| Br | H | H | Cl | CH(OCH3)2 | |
| CH3 | H | H | CH3 | CH(OCH3)2 | |
| NO2 | H | CH3 | OCH3 | CH(OCH3)2 | |
| CH3 | 4-F | H | OCH3 | CH(OCH3)2 | |
| Cl | 6-NO2 | H | OCH3 | CH(OCH3)2 | |
| NO2 | H | H | CH3 | CH(OCH3)2 | |
| NO2 | H | H | Cl | CH(OCH3)2 | |

TABLE 2a-continued

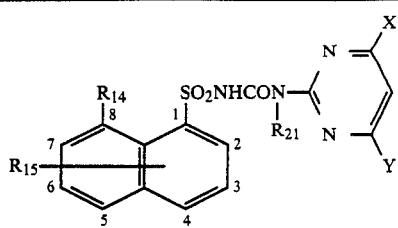

| R14 | R15 | R21 | X | Y | m.p. (°C.) |
|---|---|---|---|---|---|
| Cl | 6-F | H | CH2CH3 | CH(OCH3)2 | |
| NO2 | 4-Cl | H | CH3 | CH(OCH3)2 | |
| Cl | 5-OCH3 | H | OCH3 | CH(OCH3)2 | |
| F | H | H | CH3 | CH(OCH3)2 | |
| H | H | H | CH3 | CH(OCH3)2 | |
| SO2N(CH3)2 | H | H | OCH3 | CH(OCH3)2 | |
| SO2N(CH3)2 | H | H | OCH2CH3 | CH(OCH3)2 | |
| OCH3 | H | CH3 | CH3 | CH(OCH3)2 | |
| OSO2CH3 | H | H | CH3 | CH(OCH3)2 | |
| Cl | H | H | CH3 | C(CH3)(OCH3)2 | |
| Br | H | H | CH3 | C(C2H5)(OCH3)2 | |
| OCH3 | H | H | CH3 | C(CH3)(OCH3)2 | |
| NO2 | H | H | CH3 | C(CH3)(OCH3)2 | |

TABLE 2b

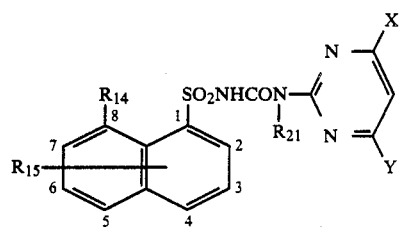

| R14 | R15 | R21 | X | Y | m.p. (°C.) |
|---|---|---|---|---|---|
| Cl | H | H | CH3 | CH2OTHP | |
| Br | H | H | CH3 | CH2OTHP | |
| F | H | H | OCH3 | CH2OTHP | |
| H | H | H | OCH3 | CH2OTHP | |
| Cl | 3-Cl | H | CH3 | CH2OTHP | |
| Cl | H | H | OCH2CH3 | CH2OTHP | |
| OCH3 | H | H | CH3 | CH2OTHP | |
| CH3 | H | CH3 | OCH3 | CH2OTHP | |
| CH3 | H | H | CH3 | CH2OTHP | |
| NO2 | H | H | OCH3 | CH2OTHP | |
| CH3 | 4-F | H | OCH3 | CH2OTHP | |
| Cl | 6-NO2 | H | OCH3 | CH2OTHP | |
| NO2 | H | H | CH2CH3 | CH2OTHP | |
| Cl | 6-F | H | CH3 | CH2OTHP | |
| NO2 | 4-Cl | H | CH3 | CH2OTHP | |
| Cl | 5-OCH3 | H | OCH3 | CH2OTHP | |
| F | H | H | CH3 | CH2OTHP | |
| H | H | H | CH3 | CH2OTHP | |
| SO2N(CH3)2 | H | H | OCH3 | CH2OTHP | |
| SO2N(CH3)2 | H | H | OCH3 | CH2OTHP | |
| OCH3 | H | H | CH3 | CH2OTHP | |
| OSO2CH3 | H | H | CH3 | CH2OTHP | |

TABLE 2c

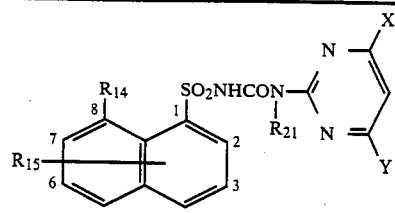

| R14 | R15 | R21 | X | Y | m.p. (°C.) |
|---|---|---|---|---|---|
| Cl | H | H | CH3 | CH2OH | |
| Br | H | H | CH3 | CH2OH | |
| F | H | H | OCH3 | CH2OH | |
| H | H | H | OCH3 | CH2OH | |
| Cl | 3-Cl | H | CH3 | CH2OH | |
| Cl | H | H | OCH3 | CH2OH | |
| OCH3 | H | H | CH2CH3 | CH2OH | |
| CH3 | H | H | OCH3 | CH2OH | |
| CH3 | H | H | CH3 | CH2OH | |
| NO2 | H | CH3 | OCH3 | CH2OH | |
| CH3 | 4-F | H | OCH3 | CH2OH | |
| Cl | 6-NO2 | H | OCH2CH3 | CH2OH | |

TABLE 2c-continued

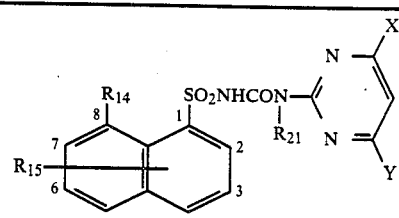

| R14 | R15 | R21 | X | Y | m.p. (°C.) |
|---|---|---|---|---|---|
| NO2 | H | H | CH3 | CH2OH | |
| Cl | 6-F | H | CH3 | CH2OH | |
| NO2 | 4-Cl | H | CH3 | CH2OH | |
| Cl | 5-OCH3 | H | OCH3 | CH2OH | |
| F | H | H | CH3 | CH2OH | |
| H | H | H | CH3 | CH2OH | |
| SO2N(CH3)2 | H | H | OCH3 | CH2OH | |
| SO2N(CH3)2 | H | H | OCH3 | CH2OH | |
| OCH3 | H | H | CH3 | CH2OH | |
| OSO2CH3 | H | CH3 | CH3 | CH2OH | |
| SO2—n-C3H7 | H | H | OCH2CH3 | CH2OH | |

TABLE 2d

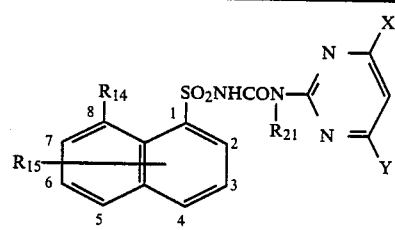

| R14 | R15 | R21 | X | Y | m.p. (°C.) |
|---|---|---|---|---|---|
| Cl | H | H | CH3 | CH(OCH2CH2O) | |
| Br | H | H | CH3 | CH2OCOCH3 | |
| F | H | H | OCH3 | CH2SC2H5 | |
| H | H | H | OCH3 | CH2OCO2CH3 | |
| Cl | 3-Cl | H | CH3 | CH2SCH3 | |
| Cl | H | H | OCH3 | CH(OC2H5) | |
| OCH3 | H | H | CH3 | CH(OCH2CH2CH2O) | |
| CH3 | H | H | OCH3 | CH2OCO—i-C3H7 | |
| CH3 | H | H | CH3 | CH2OCO2C2H5 | |
| NO2 | H | H | OCH3 | CH(OC2H5)2 | |
| CH3 | 4-F | CH3 | OCH3 | CH(OCH2CH2O) | |
| Cl | 6-NO2 | H | OCH3 | CH2OCOCH3 | |
| NO2 | H | H | CH3 | CH2OCOC2H5 | |
| Cl | 6-F | H | CH3 | CH2OCO2—n-C3H7 | |
| NO2 | 4-Cl | H | CH3 | CH2SCH3 | |
| Cl | 5-OCH3 | H | OCH3 | CH2SC2H5 | |
| F | H | H | CH3 | CH(SCH(CH3)CH2S) | |
| H | H | H | CH3 | CH(OC2H5)2 | |
| SO2N(CH3)2 | H | H | OCH3 | CH(OCH2CH2O) | |
| SO2N(CH3)2 | H | H | OCH3 | CH2OCONHCH3 | |
| OCH3 | H | H | CH3 | CH2OCONH—n-C3H7 | |
| OSO2CH3 | H | H | CH3 | CH2OCOCH3 | |
| SO2—n-C3H7 | H | H | OCH3 | CH(OC2H5)2 | |
| Cl | H | H | OCH3 | CH(SCH3)2 | |
| NO2 | H | H | OCH3 | CH2SO2CH2CH3 | |
| OSO2CH3 | H | H | OCH3 | CH(CH3)SCH3 | |
| CH3 | H | H | OCH3 | CH2SO2CH3 | |
| SO2CH3 | H | H | OCH3 | C(CH3)(SCH2CH2CH2S) | |

TABLE 2e

Structure: naphthalene with R14 at position 8, R15 at positions 5-7, SO2NHCON(R21)-C(=N-C(X)=N-C(Y)=N-) at position 1

| R14 | R15 | R21 | X | Y | m.p. (°C) |
|---|---|---|---|---|---|
| Cl | H | H | CH3 | CH(OCH3)2 | |
| Br | H | H | CH2CH3 | CH(OCH3)2 | |
| F | H | H | OCH3 | CH(OCH3)2 | |
| H | H | H | OCH3 | CH(OCH3)2 | |
| Cl | 3-Cl | H | CH3 | CH(OCH3)2 | |
| Cl | H | H | OCH2CH3 | CH(OCH3)2 | |
| OCH3 | H | H | CH3 | CH(OCH3)2 | |
| CH3 | H | H | OCH3 | CH(OCH3)2 | |
| CH3 | H | CH3 | CH3 | CH(OCH3)2 | |
| NO2 | H | H | OCH3 | CH(OCH3)2 | |
| CH3 | 4-F | H | OCH3 | CH(OCH3)2 | |
| Cl | 6-NO2 | H | OCH3 | CH(OCH3)2 | |
| NO2 | H | H | CH2 | CH(OCH3)2 | |
| Cl | 6-F | H | CH3 | CH(OCH3)2 | |
| NO2 | 4-Cl | H | CH2CH3 | CH(OCH3)2 | |
| Cl | 5-OCH3 | H | OCH3 | CH(OCH3)2 | |
| F | H | H | CH3 | CH(OCH3)2 | |
| H | H | H | CH3 | CH(OCH3)2 | |
| SO2N(CH3)2 | H | H | OCH3 | CH(OCH3)2 | |
| SO2N(CH3)2 | H | H | OCH2CH3 | CH(OCH3)2 | |
| OCH3 | H | H | CH3 | CH(OCH3)2 | |
| OSO2CH3 | H | H | CH3 | CH(OCH3)2 | |
| SO2—n-C3H7 | H | H | OCH3 | CH(OCH3)2 | |
| OCH3 | H | H | OCH3 | C(CH3)(OCH3)2 | |
| Cl | H | H | OCH3 | C(CH3)(OCH3)2 | |
| F | H | H | OCH3 | C(CH3)(OCH3)2 | |
| SO2CH2CH3 | H | H | CH3 | C(CH3)(OCH3)2 | |
| NO2 | H | H | OCH3 | C(CH2CH3)(OCH3)2 | |

TABLE 2f

| R14 | R15 | R21 | X | Y | m.p. (°C) |
|---|---|---|---|---|---|
| Cl | H | CH3 | CH2CH3 | CH2OTHP | |
| Br | H | H | CH3 | CH2OTHP | |
| F | H | H | OCH3 | CH2OTHP | |
| H | H | H | OCH3 | CH2OTHP | |
| Cl | 3-Cl | H | CH3 | CH2OTHP | |
| Cl | H | H | OCH2CH3 | CH2OTHP | |
| OCH3 | H | H | CH3 | CH2OTHP | |
| CH3 | H | H | CH3 | CH2OTHP | |
| CH3 | H | H | CH3 | CH2OTHP | |
| NO2 | H | H | OCH3 | CH2OTHP | |
| CH3 | 4-F | H | OCH3 | CH2OTHP | |
| Cl | 6-NO2 | H | OCH3 | CH2OTHP | |
| NO2 | H | H | CH3 | CH2OTHP | |
| Cl | 6-F | H | CH3 | CH2OTHP | |
| NO2 | 4-Cl | H | CH3 | CH2OTHP | |
| Cl | 5-OCH3 | H | OCH3 | CH2OTHP | |
| F | H | H | CH3 | CH2OTHP | |
| H | H | H | CH3 | CH2OTHP | |
| SO2N(CH3)2 | H | CH3 | OCH3 | CH2OTHP | |
| SO2N(CH3)2 | H | H | CH3 | CH2OTHP | |
| OCH3 | H | H | CH2CH3 | CH2OTHP | |
| OSO2CH3 | H | H | CH3 | CH2OTHP | |

TABLE 2f-continued

| R14 | R15 | R21 | X | Y | m.p. (°C) |
|---|---|---|---|---|---|
| SO2—n-C3H7 | H | H | OCH3 | CH2OTHP | |

TABLE 2g

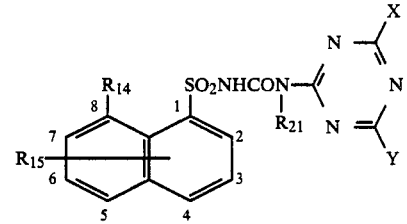

| R14 | R15 | R21 | X | Y | m.p. (°C) |
|---|---|---|---|---|---|
| Cl | H | H | CH3 | CH2OH | |
| Br | H | H | CH3 | CH2OH | |
| F | H | H | OCH2CH3 | CH2OH | |
| H | H | H | OCH3 | CH2OH | |
| Cl | 3-Cl | H | CH3 | CH2OH | |

TABLE 2g-continued

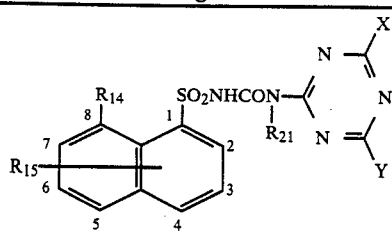

| R14 | R15 | R21 | X | Y | m.p. (°C.) |
|---|---|---|---|---|---|
| Cl | H | H | OCH3 | CH2OH | |
| OCH3 | H | H | CH3 | CH2OH | |
| CH3 | H | H | OCH3 | CH2OH | |
| CH3 | H | H | CH3 | CH2OH | |
| NO2 | H | H | OCH3 | CH2OH | |
| CH3 | 4-F | H | OCH3 | CH2OH | |
| Cl | 6-NO2 | H | OCH3 | CH2OH | |
| NO2 | H | H | CH3 | CH2OH | |
| Cl | 6-F | H | CH3 | CH2OH | |

TABLE 2g-continued

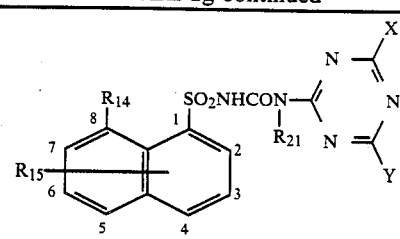

| R14 | R15 | R21 | X | Y | m.p. (°C.) |
|---|---|---|---|---|---|
| NO2 | 4-Cl | H | CH3 | CH2OH | |
| Cl | 5-OCH3 | H | OCH3 | CH2OH | |
| F | H | H | CH3 | CH2OH | |
| H | H | H | CH3 | CH2OH | |
| SO2N(CH3)2 | H | CH3 | OCH3 | CH2OH | |
| SO2N(CH3)2 | H | H | OCH3 | CH2OH | |
| OCH3 | H | H | CH3 | CH2OH | |
| OSO2CH3 | H | H | CH2CH3 | CH2OH | |
| SO2—n-C3H7 | H | H | OCH3 | CH2OH | |

TABLE 2h

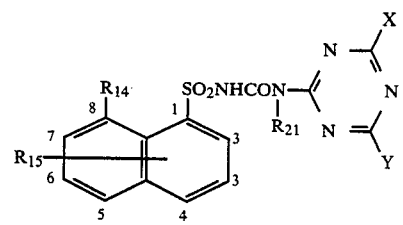

| R14 | R15 | R21 | X | Y | m.p. (°C.) |
|---|---|---|---|---|---|
| Cl | H | H | CH3 | CH(OCH2CH2O) | |
| Br | H | H | CH3 | CH2OCOCH3 | |
| F | H | H | OCH3 | CH2SC2H5 | |
| H | H | H | OCH3 | CH2OCO2CH3 | |
| Cl | 3-Cl | H | CH3 | CH2SCH3 | |
| Cl | H | H | OCH3 | CH(OC2H5)2 | |
| OCH3 | H | H | CH3 | CH(OCH2CH2CH2O) | |
| CH3 | H | H | OCH3 | CH2OCO—i-C3H7 | |
| CH3 | H | H | CH3 | CH2OCO2C2H5 | |
| NO2 | H | H | OCH3 | CH(OC2H5)2 | |
| CH3 | 4-F | H | OCH3 | CH(OCH2CH2O) | |
| Cl | 6-NO2 | H | OCH3 | CH2OCOCH3 | |
| NO2 | H | CH3 | CH3 | CH2OCOC2H5 | |
| Cl | 6-F | H | CH3 | CH2OCO2—n-C3H7 | |
| NO2 | 4-Cl | CH3 | CH3 | CH2SCH3 | |
| Cl | 5-OCH3 | H | OCH3 | CH2SC2H5 | |
| F | H | H | CH3 | CH(SCH(CH3)CH2S) | |
| H | H | H | CH3 | CH(OC2H5)2 | |
| SO2N(CH3)2 | H | H | OCH3 | CH(OCH2CH2O) | |
| SO2N(CH3)2 | H | H | OCH3 | CH2OCONHCH3 | |
| OCH3 | H | H | CH3 | CH2OCONH—n-C3H7 | |
| OSO2CH3 | H | H | CH3 | CH2OCOCH3 | |
| SO2—n-C3H7 | H | H | OCH3 | CH(OC2H5)2 | |
| Cl | H | H | OCH3 | CH2SO2CH3 | |
| H | H | H | OCH3 | CH(SCH3)2 | |
| OCH3 | H | H | CH3 | C(CH3)(OCH2CH2O) | |
| SO2CH3 | H | H | CH3 | CH(C2H5)SO2CH3 | |
| NO2 | H | H | CH3 | CH2SO2CH2CH3 | |
| NO2 | H | H | CH3 | CH2S(O)CH3 | |

TABLE 3a

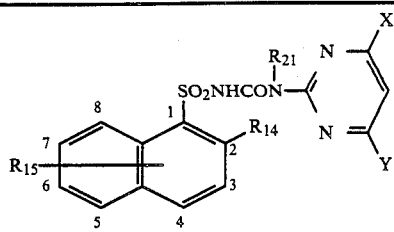

| R14 | R15 | R21 | X | Y | m.p. (°C.) |
|---|---|---|---|---|---|
| Cl | H | H | CH3 | CH(OCH3)2 | 177–178° d. |
| Br | H | H | CH3 | CH(OCH3)2 | |
| F | H | H | OCH3 | CH(OCH3)2 | |
| H | H | H | OCH3 | CH(OCH3)2 | |
| Cl | H | H | Cl | CH(OCH3)2 | |
| Cl | 3-Cl | H | CH3 | CH(OCH3)2 | |
| Cl | H | H | OCH3 | CH(OCH3)2 | 156–175° d. |
| OCH3 | H | H | CH2CH3 | CH(OCH3)2 | |
| CH3 | H | H | OCH3 | CH(OCH3)2 | |
| Br | H | H | Cl | CH(OCH3)2 | |
| CH3 | H | H | CH3 | CH(OCH3)2 | |
| NO2 | H | H | OCH3 | CH(OCH3)2 | |
| CH3 | 4-F | H | OCH3 | CH(OCH3)2 | |
| Cl | 6-NO2 | H | OCH3 | CH(OCH3)2 | |
| NO2 | H | H | CH3 | CH(OCH3)2 | |
| NO2 | H | H | Cl | CH(OCH3)2 | |
| Cl | 6-F | CH3 | CH3 | CH(OCH3)2 | |
| NO2 | 4-Cl | H | CH3 | CH(OCH3)2 | |
| Cl | 5-OCH3 | H | OCH3 | CH(OCH3)2 | |
| F | H | H | CH3 | CH(OCH3)2 | |
| H | H | H | CH3 | CH(OCH3)2 | |
| SO2N(CH3)2 | H | H | OCH3 | CH(OCH3)2 | |
| SO2N(CH3)2 | H | H | OCH2CH3 | CH(OCH3)2 | |
| OCH3 | H | H | CH3 | CH(OCH3)2 | |
| OSO2CH3 | H | H | CH3 | CH(OCH3)2 | |
| Cl | H | H | CH3 | C(CH3)(OCH3)2 | |
| NO2 | H | H | CH3 | C(C2H5)(OCH3)2 | |
| OCH3 | H | H | CH3 | C(C2H5)(OCH3)2 | |
| Br | H | H | OCH3 | C(C2H5)(OCH3)2 | |

TABLE 3b

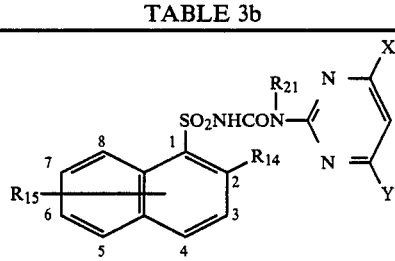

| R14 | R15 | R21 | X | Y | m.p. (°C.) |
|---|---|---|---|---|---|
| Cl | H | H | CH2CH3 | CH2OTHP | |
| Br | H | H | CH3 | CH2OTHP | |
| F | H | H | OCH3 | CH2OTHP | |
| H | H | H | OCH3 | CH2OTHP | |
| Cl | 3-Cl | H | CH3 | CH2OTHP | |
| Cl | H | H | OCH2CH3 | CH2OTHP | |
| OCH3 | H | H | CH3 | CH2OTHP | |
| CH3 | H | H | OCH3 | CH2OTHP | |
| CH3 | H | H | CH3 | CH2OTHP | |
| NO2 | H | H | OCH3 | CH2OTHP | |
| CH3 | 4-F | H | OCH3 | CH2OTHP | |
| Cl | 6-NO2 | H | OCH3 | CH2OTHP | |
| NO2 | H | H | CH3 | CH2OTHP | |
| Cl | 6-F | H | OCH3 | CH2OTHP | |
| NO2 | 4-Cl | H | CH3 | CH2OTHP | |
| Cl | 5-OCH3 | H | OCH3 | CH2OTHP | |
| F | H | CH3 | CH3 | CH2OTHP | |
| H | H | CH3 | CH3 | CH2OTHP | |
| SO2N(CH3)2 | H | H | OCH2CH3 | CH2OTHP | |
| SO2N(CH3)2 | H | H | OCH3 | CH2OTHP | |
| OCH3 | H | H | CH3 | CH2OTHP | |
| OSO2CH3 | H | H | CH3 | CH2OTHP | |

TABLE 3b-continued

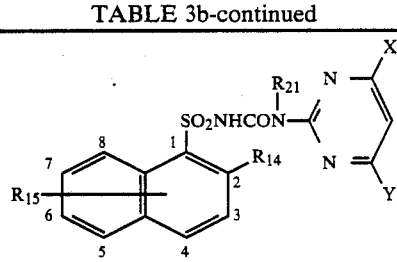

| R14 | R15 | R21 | X | Y | m.p. (°C.) |
|---|---|---|---|---|---|
| SO2—n-C3H7 | H | H | OCH3 | CH2OTHP | |
| SO2N(OCH3)CH3 | H | H | CH3 | CH2OTHP | |
| O—n-C3H7 | H | H | CH3 | CH2OTHP | |

TABLE 3c

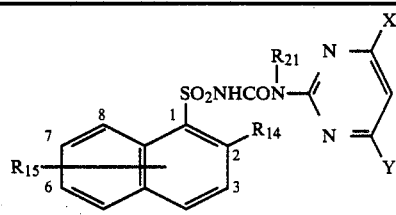

| R14 | R15 | R21 | X | Y | m.p.(°C.) |
|---|---|---|---|---|---|
| Cl | H | CH3 | CH3 | CH2OH | |
| Br | H | H | CH3 | CH2OH | |

TABLE 3c-continued

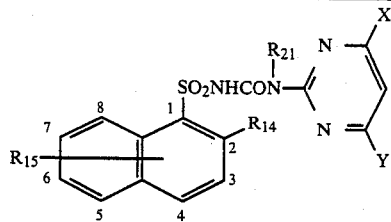

| R14 | R15 | R21 | X | Y | m.p.(°C.) |
|---|---|---|---|---|---|
| F | H | H | OCH3 | CH2OH | |
| H | H | H | OCH3 | CH2OH | |
| Cl | 3-Cl | H | CH3 | CH2OH | |
| Cl | H | H | CH3 | CH2OH | |
| OCH3 | H | H | CH3 | CH2OH | |
| CH3 | H | H | OCH3 | CH2OH | |
| CH3 | H | H | CH2CH3 | CH2OH | |
| NO2 | H | H | OCH3 | CH2OH | |
| CH3 | 4-F | H | OCH3 | CH2OH | |
| Cl | 6-NO2 | H | OCH3 | CH2OH | |
| NO2 | H | H | CH3 | CH2OH | |

TABLE 3c-continued

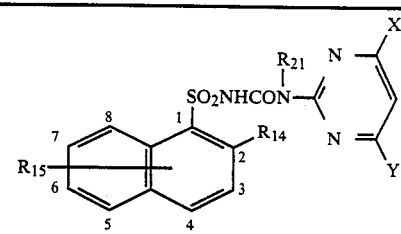

| R14 | R15 | R21 | X | Y | m.p.(°C.) |
|---|---|---|---|---|---|
| Cl | 6-F | H | CH3 | CH2OH | |
| NO2 | 4-Cl | H | CH3 | CH2OH | |
| Cl | 5-OCH3 | H | OCH2CH3 | CH2OH | |
| F | H | H | CH3 | CH2OH | |
| H | H | H | CH3 | CH2OH | |
| SO2N(CH3)2 | H | CH3 | OCH3 | CH2OH | |
| SO2N(CH3)2 | H | H | OCH3 | CH2OH | |
| OCH3 | H | H | CH3 | CH2OH | |
| OSO2CH3 | H | H | CH2CH3 | CH2OH | |
| SO2—n-C3H7 | H | H | OCH3 | CH2OH | |

TABLE 3d

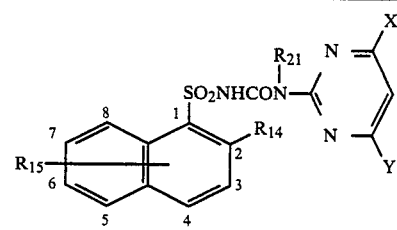

| R14 | R15 | R21 | X | Y | m.p.(°C.) |
|---|---|---|---|---|---|
| Cl | H | H | OCH3 | CH(OCH2CH2O) | 180–182° d |
| Br | H | H | CH3 | CH2OCOCH3 | |
| F | H | H | OCH3 | CH2SC2H5 | |
| H | H | CH3 | OCH3 | CH2OCO2CH3 | |
| Cl | 3-Cl | H | CH3 | CH2SCH3 | |
| Cl | H | H | OCH3 | CH(OC2H5)2 | |
| OCH3 | H | H | CH2CH3 | CH(SCH2CH2CH2S) | |
| CH3 | H | H | OCH3 | CH2OCO—i-C3H7 | |
| CH3 | H | H | CH3 | CH2OCO2C2H5 | |
| NO2 | H | H | OCH3 | CH(OC2H5)2 | |
| CH3 | 4-F | H | OCH3 | CH(OCH2CH2O) | |
| Cl | 6-NO2 | H | OCH3 | CH2OCOCH3 | |
| NO2 | H | H | CH3 | CH2OCOC2H5 | |
| Cl | 6-F | H | CH3 | CH2OCO2—n-C3H7 | |
| NO2 | 4-Cl | H | CH3 | CH2SCH3 | |
| Cl | 5-OCH3 | H | OCH3 | CH2SC2H5 | |
| F | H | CH3 | CH3 | CH(OCH(CH3)CH2O) | |
| H | H | H | CH3 | CH(OC2H5)2 | |
| SO2N(CH3)2 | H | H | OCH3 | CH(OCH2CH2O) | |
| SO2N(CH3)2 | H | H | OCH2CH3 | CH2OCONHCH3 | |
| OCH3 | H | H | CH3 | CH2OCONH—n-C3H7 | |
| OSO2CH3 | H | H | CH3 | CH2OCOCH3 | |
| SO2—n-C3H7 | H | H | OCH3 | CH(OC2H5)2 | |
| Cl | H | H | OCH3 | CH(CH3)SCH3 | |
| Br | H | H | OCH3 | C(CH3)(OCH2CH2O) | |
| F | H | H | OCH3 | CH2SO2CH3 | |
| OCH3 | H | H | CH3 | CH2SO2CH2CH3 | |
| OCH3 | H | H | CH3 | CH2S(O)CH2CH3 | |

TABLE 3e

| R14 | R15 | R21 | X | Y | m.p.(°C.) |
|---|---|---|---|---|---|
| Cl | H | H | $CH_3$ | $CH(OCH_3)_2$ | |
| Br | H | H | $CH_3$ | $CH(OCH_3)_2$ | |
| F | H | H | $OCH_3$ | $CH(OCH_3)_2$ | |
| H | H | H | $OCH_3$ | $CH(OCH_3)_2$ | |
| Cl | 3-Cl | H | $CH_3$ | $CH(OCH_3)_2$ | |
| Cl | H | H | $OCH_2CH_3$ | $CH(OCH_3)_2$ | |
| $OCH_3$ | H | H | $CH_3$ | $CH(OCH_3)_2$ | |
| $CH_3$ | H | H | $OCH_3$ | $CH(OCH_3)_2$ | |
| $CH_3$ | H | H | $CH_3$ | $CH(OCH_3)_2$ | |
| $NO_2$ | H | H | $OCH_2CH_3$ | $CH(OCH_3)_2$ | |
| $CH_3$ | 4-F | H | $OCH_3$ | $CH(OCH_3)_2$ | |
| Cl | 6-$NO_2$ | H | $OCH_3$ | $CH(OCH_3)_2$ | |
| $NO_2$ | H | H | $CH_3$ | $CH(OCH_3)_2$ | |
| Cl | 6-F | H | $CH_3$ | $CH(OCH_3)_2$ | |
| $NO_2$ | 4-Cl | H | $CH_3$ | $CH(OCH_3)_2$ | |
| Cl | 5-$OCH_3$ | H | $OCH_3$ | $CH(OCH_3)_2$ | |
| F | H | H | $CH_3$ | $CH(OCH_3)_2$ | |
| H | H | H | $CH_3$ | $CH(OCH_3)_2$ | |
| $SO_2N(CH_3)_2$ | H | H | $OCH_3$ | $CH(OCH_3)_2$ | |
| $SO_2N(CH_3)_2$ | H | H | $OCH_3$ | $CH(OCH_3)_2$ | |
| $OCH_3$ | H | H | $CH_2CH_3$ | $CH(OCH_3)_2$ | |
| $OSO_2CH_3$ | H | H | $CH_3$ | $CH(OCH_3)_2$ | |
| $SO_2-\underline{n}-C_3H_7$ | H | H | $OCH_3$ | $CH(OCH_3)_2$ | |
| $SO_2N(CH_3)_2$ | H | H | $OCH_3$ | $C(CH_3)(OCH_3)_2$ | |
| Cl | H | H | $OCH_3$ | $C(CH_3)(OCH_3)_2$ | |
| $NO_2$ | H | H | $OCH_3$ | $C(CH_3)(OCH_3)_2$ | |
| $OCH_3$ | H | H | $OCH_3$ | $C(CH_3)(OCH_3)_2$ | |
| F | H | H | $CH_3$ | $C(CH_2CH_3)(OCH_3)_2$ | |

TABLE 3f

| R14 | R15 | R21 | X | Y | m.p. (°C.) |
|---|---|---|---|---|---|
| Cl | H | $CH_3$ | $CH_2CH_3$ | $CH_2OTHP$ | |
| Br | H | H | $CH_3$ | $CH_2OTHP$ | |
| F | H | H | $OCH_3$ | $CH_2OTHP$ | |
| H | H | H | $OCH_3$ | $CH_2OTHP$ | |
| Cl | 3-Cl | H | $CH_3$ | $CH_2OTHP$ | |
| Cl | H | H | $OCH_3$ | $CH_2OTHP$ | |
| $OCH_3$ | H | H | $CH_3$ | $CH_2OTHP$ | |
| $CH_3$ | H | H | $OCH_3$ | $CH_2OTHP$ | |
| $CH_3$ | H | H | $CH_3$ | $CH_2OTHP$ | |
| $NO_2$ | H | H | $OCH_2CH_3$ | $CH_2OTHP$ | |
| $CH_3$ | 4-F | H | $OCH_3$ | $CH_2OTHP$ | |
| Cl | 6-$NO_2$ | H | $OCH_3$ | $CH_2OTHP$ | |
| $NO_2$ | H | H | $CH_3$ | $CH_2OTHP$ | |
| Cl | 6-F | H | $CH_3$ | $CH_2OTHP$ | |
| $NO_2$ | 4-Cl | H | $CH_3$ | $CH_2OTHP$ | |
| Cl | 5-$OCH_3$ | H | $OCH_3$ | $CH_2OTHP$ | |
| F | H | H | $CH_3$ | $CH_2OTHP$ | |
| H | H | H | $CH_3$ | $CH_2OTHP$ | |
| $SO_2N(CH_3)_2$ | H | $CH_3$ | $OCH_3$ | $CH_2OTHP$ | |
| $SO_2N(CH_3)_2$ | H | H | $OCH_3$ | $CH_2OTHP$ | |
| $OCH_3$ | H | H | $OCH_3$ | $CH_2OTHP$ | |
| $OSO_2CH_3$ | H | H | $CH_3$ | $CH_2OTHP$ | |
| $SO_2-\underline{n}-C_3H_7$ | H | H | $OCH_2CH_3$ | $CH_2OTHP$ | |

TABLE 3g

| R14 | R15 | R21 | X | Y | m.p.(°C.) |
|---|---|---|---|---|---|
| Cl | H | H | $CH_3$ | $CH_2OH$ | |
| Br | H | H | $CH_3$ | $CH_2OH$ | |
| F | H | H | $OCH_3$ | $CH_2OH$ | |
| H | H | H | $OCH_2CH_3$ | $CH_2OH$ | |
| Cl | 3-Cl | H | $CH_3$ | $CH_2OH$ | |

TABLE 3g-continued

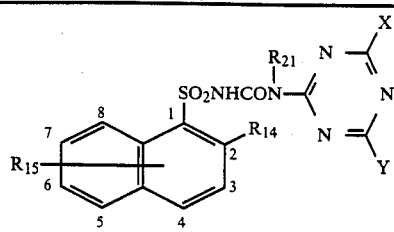

| R14 | R15 | R21 | X | Y | m.p.(°C.) |
|---|---|---|---|---|---|
| Cl | H | H | OCH3 | CH2OH | |
| OCH3 | H | H | CH3 | CH2OH | |
| CH3 | H | H | OCH3 | CH2OH | |
| CH3 | H | H | CH3 | CH2OH | |
| NO2 | H | H | OCH3 | CH2OH | |
| CH3 | 4-F | H | OCH3 | CH2OH | |
| Cl | 6-NO2 | H | OCH3 | Ch2OH | |
| NO2 | H | H | CH3 | CH2OH | |
| Cl | 6-F | H | CH3 | CH2OH | |

TABLE 3g-continued

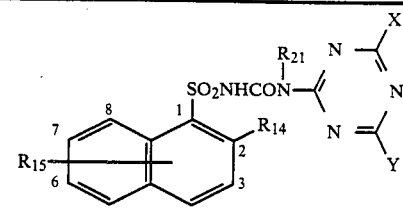

| R14 | R15 | R21 | X | Y | m.p.(°C.) |
|---|---|---|---|---|---|
| NO2 | 4-Cl | H | CH3 | CH2OH | |
| Cl | 5-OCH3 | H | OCH3 | CH2OH | |
| F | H | H | CH3 | CH2OH | |
| H | H | H | CH3 | CH2OH | |
| SO2N(CH3)2 | H | H | OCH3 | CH2OH | |
| SO2N(CH3)2 | H | CH3 | OCH3 | CH2OH | |
| OCH3 | H | H | CH2CH3 | CH2OH | |
| OSO2CH3 | H | H | CH3 | CH2OH | |
| SO2—n-C3H7 | H | H | OCH3 | CH2OH | |

TABLE 3h

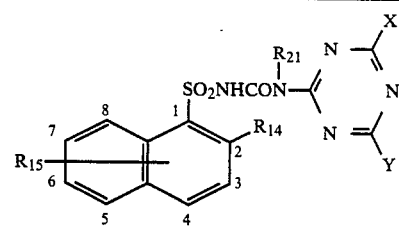

| R14 | R15 | R21 | X | Y | m.p.(°C.) |
|---|---|---|---|---|---|
| Cl | H | CH3 | CH3 | CH(OCH2CH2O) | |
| Br | H | H | CH3 | CH2OCOCH3 | |
| F | H | H | OCH2CH3 | CH2SC2H5 | |
| H | H | H | OCH3 | CH2OCO2CH3 | |
| Cl | 3-Cl | H | CH3 | CH2SCH3 | |
| Cl | H | H | OCH3 | CH(OC2H5)2 | |
| OCH3 | H | H | CH3 | CH(OCH2CH2CH2O) | |
| CH3 | H | H | OCH3 | CH2OCO—i-C3H7 | |
| CH3 | H | H | CH3 | CH2OCO2C2H5 | |
| NO2 | H | H | OCH3 | CH(OC2H5)2 | |
| CH3 | 4-F | H | OCH3 | CH(OCH2CH2O) | |
| Cl | 6-NO2 | H | OCH3 | CH2OCOCH3 | |
| NO2 | H | H | CH2CH3 | CH2OCOC2H5 | |
| Cl | 6-F | H | CH3 | CH2OCO2—n-C3H7 | |
| NO2 | 4-Cl | H | CH3 | CH2SCH3 | |
| Cl | 5-OCH3 | H | OCH3 | CH2SC2H5 | |
| F | H | H | CH3 | CH(SCH(CH3)CH2S) | |
| H | H | H | CH3 | CH(OC2H5)2 | |
| SO2N(CH3)2 | H | CH3 | OCH3 | CH(OCH2CH2O) | |
| SO2N(CH3)2 | H | H | OCH3 | CH2OCONHCH3 | |
| OCH3 | H | H | CH3 | CH2OCONH—n-C3H7 | |
| OSO2CH3 | H | H | CH3 | CH2OCOCH3 | |
| SO2—n-C3H7 | H | H | OCH3 | CH(OC2H5)2 | |
| NO2 | H | H | OCH3 | C(CH3)(OCH2CH2O) | |
| Cl | H | H | OCH3 | C(CH3)(SCH2CH2S) | |
| OSO2CH3 | H | H | OCH3 | CH2SO2CH3 | |
| SO2—n-C3H7 | H | H | CH3 | CH2SO2CH3 | |
| CH3 | H | H | CH3 | CH2SO2CH3 | |
| Br | H | H | CH3 | CH2SO2CH3 | |
| Br | H | H | CH3 | CH(CH3)(S(O)CH3) | |

TABLE 4a

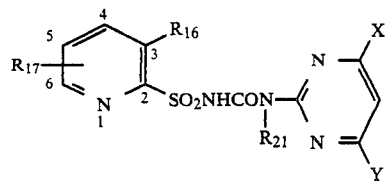

| R16 | R17 | R21 | X | Y | m.p.(°C.) |
|---|---|---|---|---|---|
| $CO_2CH_3$ | H | H | $CH_3$ | $CH(OCH_3)_2$ | |
| Cl | H | H | $CH_2CH_3$ | $CH(OCH_3)_2$ | |
| $CO_2CH_3$ | H | H | Cl | $CH(OCH_3)_2$ | |
| Cl | H | $CH_3$ | $OCH_3$ | $CH(OCH_3)_2$ | |
| H | H | H | $OCH_3$ | $CH(OCH_3)_2$ | |
| $CO_2CH(CH_3)_2$ | 5-F | H | $CH_3$ | $CH(OCH_3)_2$ | |
| $CO_2CH(CH_3)_2$ | H | H | $CH_3$ | $CH(OCH_3)_2$ | |
| $NO_2$ | H | H | $CH_3$ | $CH(OCH_3)_2$ | |
| $NO_2$ | 6-Br | H | $CH_3$ | $CH(OCH_3)_2$ | |
| Cl | 4-Cl | H | Cl | $CH(OCH_3)_2$ | |
| $CF_3$ | H | H | $OCH_3$ | $CH(OCH_3)_2$ | |
| Cl | 6-$CH_3$ | $CH_3$ | $OCH_3$ | $CH(OCH_3)_2$ | |
| $C_2H_5$ | H | H | $CH_3$ | $CH(OCH_3)_2$ | |
| $CH(CH_3)_2$ | H | H | $CH_3$ | $CH(OCH_3)_2$ | |
| $SO_2CH_3$ | H | H | $CH_3$ | $CH(OCH_3)_2$ | |
| $SO_2CH_3$ | 4-$OCH_3$ | H | $OCH_3$ | $CH(OCH_3)_2$ | |
| $SO_2CH_3$ | 6-F | H | $OCH_3$ | $CH(OCH_3)_2$ | |
| $SO_2$—n-$C_4H_9$ | H | H | $CH_3$ | $CH(OCH_3)_2$ | |
| $SO_2N(CH_3)_2$ | H | H | $OCH_2CH_3$ | $CH(OCH_3)_2$ | |
| $SO_2N(C_2H_5)_2$ | H | H | $CH_3$ | $CH(OCH_3)_2$ | |
| $SO_2N(OCH_3)CH_3$ | H | H | $CH_3$ | $CH(OCH_3)_2$ | |
| $SO_2$—n-$C_3H_7$ | H | H | $CH_3$ | $CH(OCH_3)_2$ | |
| $SO_2$—i-$C_3H_7$ | H | H | $OCH_3$ | $CH(OCH_3)_2$ | |
| $SCH_3$ | H | H | $CH_3$ | $CH(OCH_3)_2$ | |
| $S(O)_2CH_3$ | H | H | $CH_3$ | $CH(OCH_3)_2$ | |
| $SCH_2CH_3$ | H | H | $OCH_3$ | $CH(OCH_3)_2$ | |
| $S(O)_2(CH_2)_3CH_3$ | H | H | $OCH_3$ | $CH(OCH_3)_2$ | |
| Cl | H | H | $CH_3$ | $C(CH_3)(OCH_3)_2$ | |
| $NO_2$ | H | H | $OCH_3$ | $C(CH_3)(OCH_3)_2$ | |
| $CO_2C_2H_5$ | H | H | $OCH_3$ | $C(CH_3)(OCH_3)_2$ | |
| $SO_2N(OCH_3)CH_3$ | H | H | $OCH_3$ | $C(CH_3)(OCH_3)_2$ | |

TABLE 4b

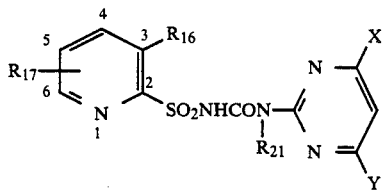

| R16 | R17 | R21 | X | Y | m.p.(°C.) |
|---|---|---|---|---|---|
| $CO_2CH_3$ | H | H | $CH_3$ | $CH_2OTHP$ | |
| Cl | H | H | $CH_2CH_3$ | $CH_2OTHP$ | |
| Cl | H | H | $OCH_3$ | $CH_2OTHP$ | |
| H | H | H | $OCH_3$ | $CH_2OTHP$ | |
| $CO_2CH(CH_3)_2$ | 5-F | H | $CH_3$ | $CH_2OTHP$ | |
| $CO_2CH(CH_3)_2$ | H | H | $CH_3$ | $CH_2OTHP$ | |
| $NO_2$ | H | H | $CH_3$ | $CH_2OTHP$ | |
| $NO_2$ | 6-Br | H | $CH_3$ | $CH_2OTHP$ | |
| Cl | 4-Cl | H | $OCH_3$ | $CH_2OTHP$ | |
| $CF_3$ | H | H | $OCH_3$ | $CH_2OTHP$ | |
| Cl | 6-$CH_3$ | H | $OCH_3$ | $CH_2OTHP$ | |
| $C_2H_5$ | H | H | $CH_3$ | $CH_2OTHP$ | |
| $CH(CH_3)_2$ | H | H | $CH_3$ | $CH_2OTHP$ | |
| $SO_2CH_3$ | H | H | $CH_3$ | $CH_2OTHP$ | |
| $SO_2CH_3$ | 4-$OCH_3$ | H | $OCH_3$ | $CH_2OTHP$ | |
| $SO_2CH_3$ | 6-F | H | $OCH_3$ | $CH_2OTHP$ | |
| $SO_2$—n-$C_4H_9$ | H | H | $CH_3$ | $CH_2OTHP$ | |
| $SO_2N(CH_3)_2$ | H | $CH_3$ | $OCH_3$ | $CH_2OTHP$ | |
| $SO_2N(C_2H_5)_2$ | H | H | $CH_3$ | $CH_2OTHP$ | |
| $SO_2N(OCH_3)CH_3$ | H | H | $CH_3$ | $CH_2OTHP$ | |
| $SO_2$—n-$C_3H_7$ | H | H | $CH_3$ | $CH_2OTHP$ | |
| $SO_2$—i-$C_3H_7$ | H | H | $OCH_2CH_3$ | $CH_2OTHP$ | |
| $SCH_3$ | H | H | $CH_3$ | $CH_2OTHP$ | |
| $S(O)_2CH_3$ | H | H | $CH_3$ | $CH_2OTHP$ | |
| $SCH_2CH_3$ | H | H | $OCH_3$ | $CH_2OTHP$ | |
| $S(O)_2$—n-$C_4H_9$ | H | H | $OCH_3$ | $CH_2OTHP$ | |

TABLE 4c

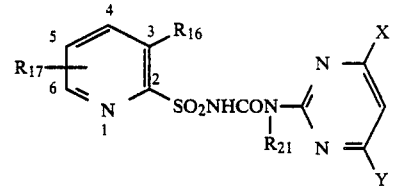

| R16 | R17 | R21 | X | Y | m.p.(°C.) |
|---|---|---|---|---|---|
| $CO_2CH_3$ | H | H | $CH_3$ | $CH_2OH$ | |
| Cl | H | H | $CH_3$ | $CH_2OH$ | |
| Cl | H | $CH_3$ | $OCH_3$ | $CH_2OH$ | |
| H | H | H | $OCH_3$ | $CH_2OH$ | |

TABLE 4c-continued

Structure: Pyridine (positions 3-R16, 4, 5, 6, N1, R17 at 5/6) with 2-SO2NHCON(R21)-pyrimidine (X, Y substituents)

| R16 | R17 | R21 | X | Y | m.p. (°C.) |
|---|---|---|---|---|---|
| CO2CH(CH3)2 | 5-F | H | CH3 | CH2OH | |
| CO2CH(CH3)2 | H | H | CH2CH3 | CH2OH | |
| NO2 | H | H | CH3 | CH2OH | |
| NO2 | 6-Br | H | CH3 | CH2OH | |
| Cl | 4-Cl | H | OCH3 | CH2OH | |
| CF3 | H | H | OCH3 | CH2OH | |
| Cl | 6-CH3 | CH3 | OCH3 | CH2OH | |
| C2H5 | H | H | CH3 | CH2OH | |
| CH(CH3)2 | H | H | CH3 | CH2OH | |
| SO2CH3 | H | H | CH3 | CH2OH | |
| SO2CH3 | 4-OCH3 | H | OCH2CH3 | CH2OH | |
| SO2CH3 | 6-F | H | OCH3 | CH2OH | |
| SO2—n-C4H9 | H | H | CH3 | CH2OH | |
| SO2N(CH3)2 | H | H | OCH3 | CH2OH | |
| SO2N(C2H5)2 | H | H | CH3 | CH2OH | |
| SO2N(OCH3)CH3 | H | H | CH3 | CH2OH | |
| SO2—n-C3H7 | H | H | CH3 | CH2OH | |
| SO2—i-C3H7 | H | H | OCH3 | CH2OH | |
| SCH3 | H | H | CH2CH3 | CH2OH | |
| S(O)2CH3 | H | H | CH3 | CH2OH | |
| SCH2CH3 | H | H | OCH3 | CH2OH | |
| S(O)2—n-C4H9 | H | H | OCH3 | CH2OH | |

TABLE 4d

| R16 | R17 | R21 | X | Y | m.p. (°C.) |
|---|---|---|---|---|---|
| CO2CH3 | H | CH3 | CH3 | CH2OCOCH3 | |
| Cl | H | H | CH2CH3 | CH(OC2H5)2 | |
| Cl | H | H | OCH3 | CH2SCH3 | |
| H | H | H | OCH3 | CH2OCONHCH3 | |
| CO2CH(CH3)2 | 5-F | H | CH3 | CH2OCO2CH3 | |
| CO2CH(CH3)2 | H | H | CH3 | CH2SC2H5 | |
| NO2 | H | H | CH3 | CH(SCH2CH2S) | |
| NO2 | 6-Br | H | CH3 | CH2OCOC2H5 | |
| Cl | 4-Cl | H | OCH3 | CH(OCH2CH2CH2O) | |
| CF3 | H | CH3 | OCH3 | CH(OCH(CH3)CH2) | |
| Cl | 6-CH3 | H | OCH3 | CH2SCH3 | |
| C2H5 | H | H | CH3 | CH2OCOCH3 | |
| CH(CH3)2 | H | H | CH3 | CH2OCON(CH3)2 | |
| SO2CH3 | H | H | CH3 | CH(OCH2CH2O) | |
| SO2CH3 | 4-OCH3 | H | OCH3 | CH2OCOCH3 | |
| SO2CH3 | 6-F | H | OCH3 | CH2SC2H5 | |
| SO2—n-C4H9 | H | H | CH3 | CH(OC2H5)2 | |
| SO2N(CH3)2 | H | H | OCH2CH3 | CH2OCO2—n-C3H7 | |
| SO2N(C2H5)2 | H | H | CH3 | CH2OCON(C2H5)2 | |
| SO2N(OCH3)CH3 | H | H | CH3 | CH2OCON(CH3)(n-C3H7) | |
| SO2—n-C3H7 | H | H | CH3 | CH2OCO—i-C3H7 | |
| SO2—i-C3H7 | H | H | OCH3 | CH2OCONH(n-C3H7) | |
| SCH3 | H | H | CH3 | CH(OC2H5)2 | |
| S(O)2CH3 | H | H | CH3 | CH(OC2H5)2 | |
| SCH2CH3 | H | H | OCH3 | CH2OCO2—i-C3H7 | |
| S(O)2—n-C4H9 | H | CH3 | OCH3 | CH2SCH3 | |
| Cl | H | H | OCH3 | CH(SCH2CH3)2 | |
| CH3 | H | H | OCH3 | C(CH3)(OCH2CH2O) | |
| SO2N(CH3)2 | H | H | OCH3 | CH2SO2CH3 | |
| SCH3 | H | H | CH3 | CH2SO2CH2CH3 | |
| SCH3 | H | H | OCH3 | CH2S(O)CH3 | |

TABLE 4e

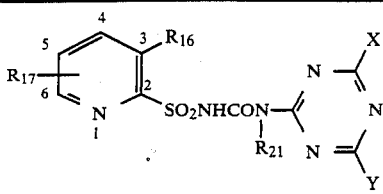

| R16 | R17 | R21 | X | Y | m.p. (°C.) |
|---|---|---|---|---|---|
| CO2CH3 | H | H | CH3 | CH(OCH3)2 | |
| Cl | H | H | CH2CH3 | CH(OCH3)2 | |
| Cl | H | CH3 | OCH3 | CH(OCH3)2 | |
| H | H | H | OCH3 | CH(OCH3)2 | |
| CO2CH(CH3)2 | 5-F | H | CH3 | CH(OCH3)2 | |
| CO2CH(CH3)2 | H | H | CH3 | CH(OCH3)2 | |
| NO2 | H | H | CH3 | CH(OCH3)2 | |
| NO2 | 6-Br | H | CH3 | CH(OCH3)2 | |
| CF3 | H | H | OCH3 | CH(OCH3)2 | |
| Cl | 6-CH3 | H | OCH3 | CH(OCH3)2 | |
| C2H5 | H | H | CH3 | CH(OCH3)2 | |
| CH(CH3)2 | H | H | CH3 | CH(OCH3)2 | |
| SO2CH3 | H | H | CH3 | CH(OCH3)2 | |
| SO2CH3 | 4-OCH3 | H | OCH2CH3 | CH(OCH3)2 | |
| SO2CH3 | 6-F | H | OCH3 | CH(OCH3)2 | |
| SO2—n-C4H9 | H | H | CH3 | CH(OCH3)2 | |
| SO2N(CH3)2 | H | H | OCH3 | CH(OCH3)2 | |
| SO2N(C2H5)2 | H | H | CH3 | CH(OCH3)2 | |
| SO2N(OCH3)CH3 | H | H | CH3 | CH(OCH3)2 | |
| SO2—n-C3H7 | H | H | CH3 | CH(OCH3)2 | |
| SO2—i-C3H7 | H | H | OCH2CH3 | CH(OCH3)2 | |
| SCH3 | H | CH3 | CH3 | CH(OCH3)2 | |
| S(O)2CH3 | H | H | CH3 | CH(OCH3)2 | |
| SCH2CH3 | H | H | OCH3 | CH(OCH3)2 | |
| S(O)2(CH2)3CH3 | H | H | OCH3 | CH(OCH3)2 | |
| CF3 | H | H | CH3 | C(CH3)(OCH3)2 | |
| Cl | H | H | OCH3 | C(CH3)(OCH3)2 | |
| NO2 | H | H | OCH3 | C(CH3)(OCH3)2 | |
| SO2CH2CH3 | H | H | OCH3 | C(CH3)(OCH3)2 | |

TABLE 4f

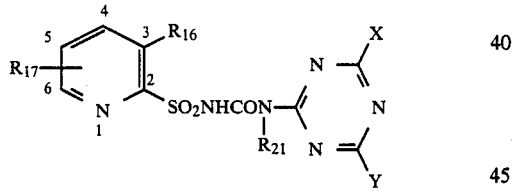

| R16 | R17 | R21 | X | Y | m.p. (°C.) |
|---|---|---|---|---|---|
| CO2CH3 | H | H | CH3 | CH2OTHP | |
| Cl | H | H | CH3 | CH2OTHP | |
| Cl | H | H | OCH3 | CH2OTHP | |
| H | H | H | OCH2CH3 | CH2OTHP | |
| CO2CH(CH3)2 | 5-F | H | CH3 | CH2OTHP | |
| CO2CH(CH3)2 | H | H | CH3 | CH2OTHP | |
| NO2 | H | H | CH3 | CH2OTHP | |
| NO2 | 6-Br | H | CH3 | CH2OTHP | |
| Cl | 4-Cl | H | OCH3 | CH2OTHP | |
| CF3 | H | CH3 | OCH3 | CH2OTHP | |
| Cl | 6-CH3 | H | OCH2CH3 | CH2OTHP | |
| C2H5 | H | H | CH3 | CH2OTHP | |
| CH(CH3)2 | H | H | CH3 | CH2OTHP | |
| SO2CH3 | H | H | CH3 | CH2OTHP | |
| SO2CH3 | 4-OCH3 | H | OCH3 | CH2OTHP | |
| SO2CH3 | 6-F | H | OCH3 | CH2OTHP | |
| SO2—n-C4H9 | H | H | CH3 | CH2OTHP | |
| SO2N(CH3)2 | H | H | OCH3 | CH2OTHP | |
| SO2N(C2H5)2 | H | H | CH3 | CH2OTHP | |
| SO2N(OCH3)CH3 | H | H | CH3 | CH2OTHP | |
| SO2—n-C3H7 | H | H | CH3 | CH2OTHP | |
| SO2—i-C3H7 | H | H | OCH3 | CH2OTHP | |
| SCH3 | H | H | CH2CH3 | CH2OTHP | |
| S(O)2CH3 | H | H | OCH3 | CH2OTHP | |
| SCH2CH3 | H | H | OCH3 | CH2OTHP | |

TABLE 4f-continued

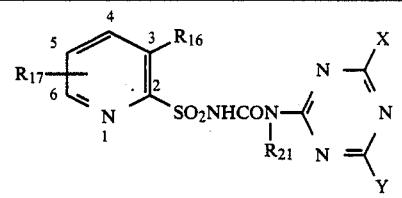

| R16 | R17 | R21 | X | Y | m.p. (°C.) |
|---|---|---|---|---|---|
| S(O)2—n-C4H9 | H | H | OCH3 | CH2OTHP | |

TABLE 4g

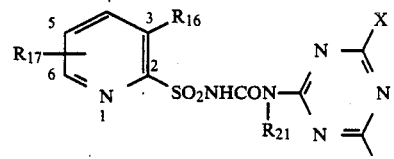

| R16 | R17 | R21 | X | Y | m.p. (°C.) |
|---|---|---|---|---|---|
| CO2CH3 | H | CH3 | CH3 | CH2OH | |
| Cl | H | H | CH3 | CH2OH | |
| Cl | H | H | OCH3 | CH2OH | |
| H | H | H | OCH3 | CH2OH | |
| CO2CH(CH3)2 | 5-F | H | CH2CH3 | CH2OH | |
| CO2CH(CH3)2 | H | H | CH3 | CH2OH | |
| NO2 | H | H | CH3 | CH2OH | |
| NO2 | 6-Br | H | CH3 | CH2OH | |

TABLE 4g-continued

| R16 | R17 | R21 | X | Y | m.p. (°C.) |
|---|---|---|---|---|---|
| Cl | 4-Cl | H | OCH3 | CH2OH | |
| CF3 | H | H | OCH3 | CH2OH | |
| Cl | 6-CH3 | H | OCH3 | CH2OH | |
| C2H5 | H | H | CH3 | CH2OH | |
| CH(CH3)2 | H | H | CH3 | CH2OH | |
| SO2CH3 | H | H | CH3 | CH2OH | |
| SO2CH3 | 4-OCH3 | H | OCH3 | CH2OH | |
| SO2CH3 | 6-F | H | OCH3 | CH2OH | |
| SO2—n-C4H9 | H | H | CH3 | CH2OH | |
| SO2N(CH3)2 | H | H | OCH3 | CH2OH | |
| SO2N(C2H5)2 | H | CH3 | CH3 | CH2OH | |
| SO2N(OCH3)CH3 | H | H | CH3 | CH2OH | |
| SO2—n-C3H7 | H | H | CH3 | CH2OH | |
| SO2—i-C3H7 | H | H | OCH3 | CH2OH | |
| SCH3 | H | H | CH3 | CH2OH | |
| S(O)2CH3 | H | H | CH3 | CH2OH | |
| SCH2CH3 | H | H | OCH2CH3 | CH2OH | |
| S(O)2—n-C4H9 | H | H | OCH3 | CH2OH | |

TABLE 4h

| R16 | R17 | R21 | X | Y | m.p. (°C.) |
|---|---|---|---|---|---|
| CO2CH3 | H | H | CH2CH3 | CH2OCOCH3 | |
| Cl | H | H | CH3 | CH(OC2H5)2 | |
| Cl | H | H | OCH3 | CH2SCH3 | |
| H | H | H | OCH3 | CH2OCONHCH3 | |
| CO2CH(CH3)2 | 5-F | H | CH3 | CH2OCO2CH3 | |
| CO2CH(CH3)2 | H | H | CH3 | CH2SC2H5 | |
| NO2 | H | H | CH3 | CH(OCH2CH2O) | |
| NO2 | 6-Br | CH3 | CH3 | CH2OCOC2H5 | |
| Cl | 4-Cl | H | OCH3 | CH(OCH2CH2CH2O) | |
| CF3 | H | H | OCH2CH3 | CH(OCH(CH3)CH2) | |
| Cl | 6-CH3 | H | OCH3 | CH2SCH3 | |
| C2H5 | H | H | CH3 | CH2OCOCH3 | |
| CH(CH3)2 | H | H | CH3 | CH2OCON(CH3)2 | |
| SO2CH3 | H | H | CH3 | CH(OCH2CH2O) | |
| SO2CH3 | 4-OCH3 | H | OCH3 | CH2OCOCH3 | |
| SO2CH3 | 6-F | H | OCH3 | CH2SC2H5 | |
| SO2—n-C4H9 | H | H | CH3 | CH(OC2H5)2 | |
| SO2N(CH3)2 | H | H | OCH3 | CH2OCO2—n-C3H7 | |
| SO2N(C2H5)2 | H | H | CH3 | CH2OCON(C2H5)2 | |
| SO2N(OCH3)CH3 | H | CH3 | CH3 | CH2OCON(CH3)(n-C3H7) | |
| SO2—n-C3H7 | H | H | CH3 | CH2OCO—i-C3H7 | |
| SO2—i-C3H7 | H | H | OCH3 | CH2OCONH(n-C3H7) | |
| SCH3 | H | H | CH3 | CH(OC2H5)2 | |
| S(O)2CH3 | H | H | CH3 | CH(OC2H5)2 | |
| SCH2CH3 | H | H | OCH3 | CH2OCO2—i-C3H7 | |
| S(O)2—n-C4H9 | H | H | OCH3 | CH2SCH3 | |
| NO2 | H | H | CH3 | CH(CH3)(SCH3)2 | |
| Cl | H | H | CH3 | CH(CH3)(SO2CH3) | |
| CF3 | H | H | CH3 | CH2SO2CH3 | |
| CO2CH2CH3 | H | H | CH3 | CH(SCH3)2 | |
| CO2CH2CH3 | H | H | OCH3 | CH2S(O)CH2CH3 | |
| CO2CH2CH3 | H | H | CH3 | CH2S(O)CH3 | |

TABLE 5a

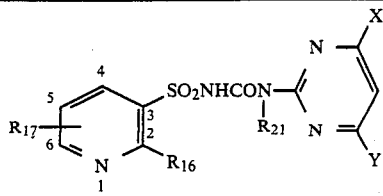

| $R_{16}$ | $R_{17}$ | $R_{21}$ | X | Y | m.p. (°C.) |
|---|---|---|---|---|---|
| $CO_2CH_3$ | H | H | $CH_3$ | $CH(OCH_3)_2$ | |
| Cl | H | H | $CH_3$ | $CH(OCH_3)_2$ | |
| $CO_2CH_3$ | H | $CH_3$ | Cl | $CH(OCH_3)_2$ | |
| Cl | H | H | $OCH_2CH_3$ | $CH(OCH_3)_2$ | |
| H | H | H | $OCH_3$ | $CH(OCH_3)_2$ | |
| $CO_2CH(CH_3)_2$ | 5-F | H | $CH_3$ | $CH(OCH_3)_2$ | |
| $CO_2CH(CH_3)_2$ | H | H | $CH_3$ | $CH(OCH_3)_2$ | |
| $NO_2$ | H | H | $CH_2CH_3$ | $CH(OCH_3)_2$ | |
| $NO_2$ | 6-Br | H | $CH_3$ | $CH(OCH_3)_2$ | |
| Cl | 4-Cl | H | Cl | $CH(OCH_3)_2$ | |
| $CF_3$ | H | H | $OCH_3$ | $CH(OCH_3)_2$ | |
| Cl | 6-$CH_3$ | H | $OCH_3$ | $CH(OCH_3)_2$ | |
| $C_2H_5$ | H | H | $CH_3$ | $CH(OCH_3)_2$ | |
| $CH(CH_3)_2$ | H | H | $CH_2CH_3$ | $CH(OCH_3)_2$ | |
| $SO_2CH_3$ | H | H | $CH_3$ | $CH(OCH_3)_2$ | |
| $SO_2CH_3$ | 4-$OCH_3$ | H | $OCH_3$ | $CH(OCH_3)_2$ | |
| $SO_2CH_3$ | 6-F | H | $OCH_3$ | $CH(OCH_3)_2$ | |
| $SO_2$—n-$C_4H_9$ | H | $CH_3$ | $CH_3$ | $CH(OCH_3)_2$ | |
| $SO_2N(CH_3)_2$ | H | H | $OCH_3$ | $CH(OCH_3)_2$ | |
| $SO_2N(C_2H_5)_2$ | H | H | $CH_3$ | $CH(OCH_3)_2$ | |
| $SO_2N(OCH_3)CH_3$ | H | H | $CH_3$ | $CH(OCH_3)_2$ | |
| $SO_2$—n-$C_3H_7$ | H | H | $CH_3$ | $CH(OCH_3)_2$ | |
| $SO_2$—i-$C_3H_7$ | H | H | $OCH_3$ | $CH(OCH_3)_2$ | |
| $SCH_3$ | H | H | $CH_3$ | $CH(OCH_3)_2$ | |
| $S(O)_2CH_3$ | H | H | $CH_3$ | $CH(OCH_3)_2$ | |
| $CH_2CH_3$ | H | H | $CH_3$ | $C(CH_2CH_3)(OCH_3)_2$ | |
| $SCH_3$ | H | H | $OCH_3$ | $C(CH_3)(OCH_3)_2$ | |
| $NO_2$ | H | H | $OCH_3$ | $C(CH_3)(OCH_3)_2$ | |
| $CO_2CH_3$ | H | H | $OCH_3$ | $C(CH_3)(OCH_3)_2$ | |
| $SCH_2CH_3$ | H | H | $OCH_3$ | $CH(OCH_3)_2$ | |
| $S(O)_2(CH_2)_3CH_3$ | H | H | $OCH_3$ | $CH(OCH_3)_2$ | |

TABLE 5b

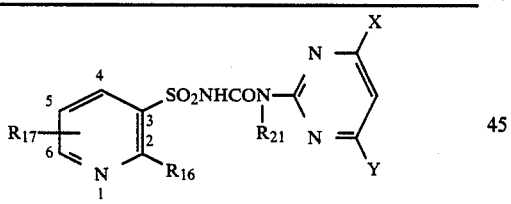

| $R_{16}$ | $R_{17}$ | $R_{21}$ | X | Y | m.p. (°C.) |
|---|---|---|---|---|---|
| $CO_2CH_3$ | H | H | $CH_3$ | $CH_2OTHP$ | |
| Cl | H | H | $CH_3$ | $CH_2OTHP$ | |
| Cl | H | H | $OCH_3$ | $CH_2OTHP$ | |
| H | H | H | $OCH_3$ | $CH_2OTHP$ | |
| $CO_2CH(CH_3)_2$ | 5-F | H | $CH_3$ | $CH_2OTHP$ | |
| $CO_2CH(CH_3)_2$ | H | H | $CH_2CH_3$ | $CH_2OTHP$ | |
| $NO_2$ | H | H | $CH_3$ | $CH_2OTHP$ | |
| $NO_2$ | 6-Br | H | $CH_3$ | $CH_2OTHP$ | |
| Cl | 4-Cl | H | $OCH_3$ | $CH_2OTHP$ | |
| $CF_3$ | H | H | $OCH_3$ | $CH_2OTHP$ | |
| Cl | 6-$CH_3$ | H | $OCH_3$ | $CH_2OTHP$ | |
| $C_2H_5$ | H | H | $CH_3$ | $CH_2OTHP$ | |
| $CH(CH_3)_2$ | H | $CH_3$ | $CH_3$ | $CH_2OTHP$ | |
| $SO_2CH_3$ | H | H | $CH_3$ | $CH_2OTHP$ | |
| $SO_2CH_3$ | 4-$OCH_3$ | H | $OCH_2CH_3$ | $CH_2OTHP$ | |
| $SO_2CH_3$ | 6-F | H | $OCH_3$ | $CH_2OTHP$ | |
| $SO_2$—n-$C_4H_9$ | H | H | $CH_3$ | $CH_2OTHP$ | |
| $SO_2N(CH_3)_2$ | H | H | $OCH_3$ | $CH_2OTHP$ | |
| $SO_2N(C_2H_5)_2$ | H | H | $CH_3$ | $CH_2OTHP$ | |
| $SO_2N(OCH_3)CH_3$ | H | H | $CH_3$ | $CH_2OTHP$ | |
| $SO_2$—n-$C_3H_7$ | H | H | $CH_3$ | $CH_2OTHP$ | |

TABLE 5b-continued

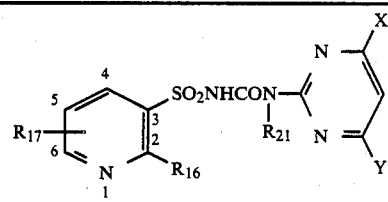

| $R_{16}$ | $R_{17}$ | $R_{21}$ | X | Y | m.p. (°C.) |
|---|---|---|---|---|---|
| $SO_2$—i-$C_3H_7$ | H | H | $OCH_3$ | $CH_2OTHP$ | |
| $SCH_3$ | H | H | $CH_3$ | $CH_2OTHP$ | |
| $S(O)_2CH_3$ | H | H | $CH_3$ | $CH_2OTHP$ | |
| $SCH_2CH_3$ | H | H | $OCH_3$ | $CH_2OTHP$ | |
| $S(O)_2$—n-$C_4H_9$ | H | H | $OCH_3$ | $CH_2OTHP$ | |

TABLE 5c

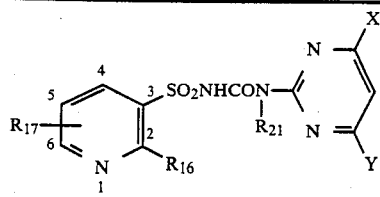

| R16 | R17 | R21 | X | Y | m.p. (°C.) |
|---|---|---|---|---|---|
| CO2CH3 | H | H | CH3 | CH2OH | |
| Cl | H | H | CH3 | CH2OH | |
| Cl | H | H | OCH2CH3 | CH2OH | |
| H | H | H | OCH3 | CH2OH | |
| CO2CH(CH3)2 | 5-F | H | CH3 | CH2OH | |
| CO2CH(CH3)2 | H | CH3 | CH3 | CH2OH | |
| NO2 | H | H | CH3 | CH2OH | |
| NO2 | 6-Br | H | CH3 | CH2OH | |
| Cl | 4-Cl | H | OCH3 | CH2OH | |
| CF3 | H | H | OCH3 | CH2OH | |
| Cl | 6-CH3 | H | OCH2CH3 | CH2OH | |
| C2H5 | H | H | CH3 | CH2OH | |
| CH(CH3)2 | H | H | CH3 | CH2OH | |
| SO2CH3 | H | H | CH3 | CH2OH | |

TABLE 5c-continued

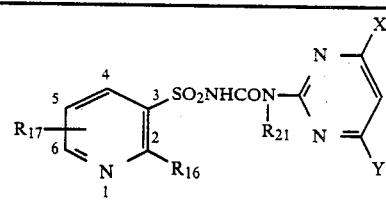

| R16 | R17 | R21 | X | Y | m.p. (°C.) |
|---|---|---|---|---|---|
| SO2CH3 | 4-OCH3 | H | OCH3 | CH2OH | |
| SO2CH3 | 6-F | H | OCH3 | CH2OH | |
| SO2—n-C4H9 | H | H | CH3 | CH2OH | |
| SO2N(CH3)2 | H | H | OCH3 | CH2OH | |
| SO2N(C2H5)2 | H | H | CH3 | CH2OH | |
| SO2N(OCH3)CH3 | H | H | CH3 | CH2OH | |
| SO2—n-C3H7 | H | H | CH3 | CH2OH | |
| SO2—i-C3H7 | H | H | OCH3 | CH2OH | |
| SCH3 | H | H | CH3 | CH2OH | |
| S(O)2CH3 | H | H | CH3 | CH2OH | |
| SCH2CH3 | H | H | OCH3 | CH2OH | |
| S(O)2—n-C4H9 | H | H | OCH3 | CH2OH | |

TABLE 5d

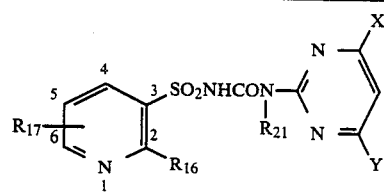

| R16 | R17 | R21 | X | Y | m.p. (°C.) |
|---|---|---|---|---|---|
| CO2CH3 | H | H | CH3 | CH2OCOCH3 | |
| Cl | H | CH3 | CH3 | CH(OC2H5)2 | |
| Cl | H | H | OCH2CH3 | CH2SCH3 | |
| H | H | H | OCH3 | CH2OCONHCH3 | |
| CO2CH(CH3)2 | 5-F | H | CH3 | CH2OCO2CH3 | |
| CO2CH(CH3)2 | H | H | CH3 | CH2SC2H5 | |
| NO2 | H | H | CH3 | CH(OCH2CH2O) | |
| NO2 | 6-Br | H | CH3 | CH2OCOC2H5 | |
| Cl | 4-Cl | H | OCH3 | CH(OCH2CH2CH2O) | |
| CF3 | H | H | OCH3 | CH(OCH(CH3)CH2) | |
| Cl | 6-CH3 | H | OCH3 | CH2SCH3 | |
| C2H5 | H | H | CH2CH3 | CH2OCOCH3 | |
| CH(CH3)2 | H | H | CH3 | CH2OCON(CH3)2 | |
| SO2CH3 | H | H | CH3 | CH(OCH2CH2O) | |
| SO2CH3 | 4-OCH3 | H | OCH3 | CH2OCOCH3 | |
| SO2CH3 | 6-F | H | OCH3 | CH2SC2H5 | |
| SO2—n-C4H9 | H | H | CH3 | CH(OC2H5)2 | |
| SO2N(CH3)2 | H | H | OCH3 | CH2OCO2—n-C3H7 | |
| SO2N(C2H5)2 | H | H | CH3 | CH2OCON(C2H5)2 | |
| SO2N(OCH3)CH3 | H | H | CH3 | CH2OCON(CH3)(n-C3H7) | |
| SO2—n-C3H7 | H | H | CH3 | CH2OCO—i-C3H7 | |
| SO2—i-C3H7 | H | H | OCH3 | CH2OCONH(n-C3H7) | |
| SCH3 | H | CH3 | CH3 | CH(OC2H5)2 | |
| S(O)2CH3 | H | H | CH3 | CH(OC2H5)2 | |
| SCH2CH3 | H | H | OCH3 | CH2OCO2—i-C3H7 | |
| S(O)2—n-C4H9 | H | H | OCH3 | CH2SCH3 | |
| CO2CH2CH3 | H | H | CH3 | C(CH3)(OC2H5)2 | |
| CF3 | H | H | CH3 | CH(CH3)SC2H5 | |
| SO2CH3 | H | H | CH3 | CH2SO2CH3 | |
| SO2CH3 | H | H | CH3 | CH2S(O)CH3 | |
| SO2CH3 | H | H | CH3 | CH(CH3)(S(O)CH3) | |

TABLE 5e

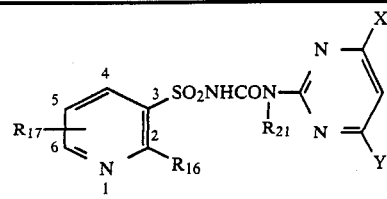

| R16 | R17 | R21 | X | Y | m.p. (°C.) |
|---|---|---|---|---|---|
| CO2CH3 | H | H | CH3 | CH(OCH3)2 | |
| Cl | H | H | CH3 | CH(OCH3)2 | |
| Cl | H | H | OCH3 | CH(OCH3)2 | |
| H | H | CH3 | OCH3 | CH(OCH3)2 | |
| CO2CH(CH3)2 | 5-F | H | CH3 | CH(OCH3)2 | |
| CO2CH(CH3)2 | H | H | CH3 | CH(OCH3)2 | |
| NO2 | H | H | CH3 | CH(OCH3)2 | |
| NO2 | 6-Br | H | CH3 | CH(OCH3)2 | |
| CF3 | H | H | OCH3 | CH(OCH3)2 | |
| Cl | 6-CH3 | H | OCH3 | CH(OCH3)2 | |
| C2H5 | H | H | CH3 | CH(OCH3)2 | |
| CH(CH3)2 | H | H | CH3 | CH(OCH3)2 | |
| SO2CH3 | H | H | CH3 | CH(OCH3)2 | |
| SO2CH3 | 4-OCH3 | H | OCH3 | CH(OCH3)2 | |
| SO2CH3 | 6-F | H | OCH3 | CH(OCH3)2 | |
| SO2—n-C4H9 | H | H | CH3 | CH(OCH3)2 | |
| SO2N(CH3)2 | H | H | OCH3 | CH(OCH3)2 | |
| SO2N(C2H5)2 | H | H | CH3 | CH(OCH3)2 | |
| SO2N(OCH3)CH3 | H | H | CH2CH3 | CH(OCH3)2 | |
| SO2—n-C3H7 | H | H | CH3 | CH(OCH3)2 | |
| SO2—i-C3H7 | H | H | OCH3 | CH(OCH3)2 | |
| SCH3 | H | H | CH3 | CH(OCH3)2 | |
| S(O)2CH3 | H | H | CH3 | CH(OCH3)2 | |
| SCH2CH3 | H | H | OCH2CH3 | CH(OCH3)2 | |
| S(O)2(CH2)3CH3 | H | CH3 | OCH3 | CH(OCH3)2 | |
| SO2CH2CH3 | H | H | OCH3 | C(CH3)(OCH3)2 | |
| CH3 | H | H | OCH3 | C(CH3)(OCH3)2 | |
| CO2CH3 | H | H | OCH3 | C(CH3)(OCH3)2 | |

TABLE 5f

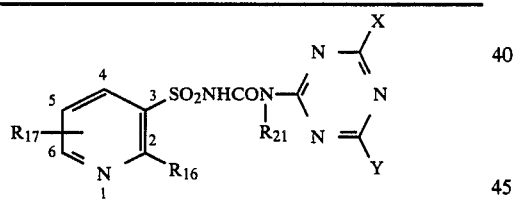

| R16 | R17 | R21 | X | Y | m.p. (°C.) |
|---|---|---|---|---|---|
| CO2CH3 | H | H | CH3 | CH2OTHP | |
| Cl | H | H | CH3 | CH2OTHP | |
| Cl | H | H | OCH2CH3 | CH2OTHP | |
| H | H | H | OCH3 | CH2OTHP | |
| CO2CH(CH3)2 | 5-F | H | CH3 | CH2OTHP | |
| CO2CH(CH3)2 | H | H | CH3 | CH2OTHP | |
| NO2 | H | H | CH3 | CH2OTHP | |
| NO2 | 6-Br | H | CH3 | CH2OTHP | |
| Cl | 4-Cl | H | OCH3 | CH2OTHP | |
| CF3 | H | CH3 | OCH3 | CH2OTHP | |
| Cl | 6-CH3 | H | OCH3 | CH2OTHP | |
| C2H5 | H | H | CH3 | CH2OTHP | |
| CH(CH3)2 | H | H | CH3 | CH2OTHP | |
| SO2CH3 | H | H | CH3 | CH2OTHP | |
| SO2CH3 | 4-OCH3 | H | OCH3 | CH2OTHP | |
| SO2CH3 | 6-F | H | OCH3 | CH2OTHP | |
| SO2—n-C4H9 | H | H | CH2CH3 | CH2OTHP | |
| SO2N(CH3)2 | H | H | OCH3 | CH2OTHP | |
| SO2N(C2H5)2 | H | H | CH3 | CH2OTHP | |
| SO2N(OCH3)CH3 | H | H | CH3 | CH2OTHP | |
| SO2—n-C3H7 | H | H | CH3 | CH2OTHP | |
| SO2—i-C3H7 | H | H | OCH3 | CH2OTHP | |
| SCH3 | H | H | CH3 | CH2OTHP | |
| S(O)2CH3 | H | H | CH3 | CH2OTHP | |
| SCH2CH3 | H | H | OCH3 | CH2OTHP | |
| S(O)2—n-C4H9 | H | H | OCH3 | CH2OTHP | |

TABLE 5g

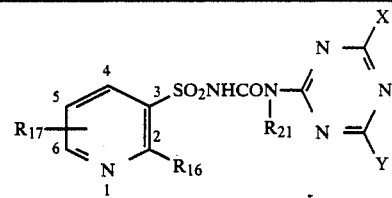

| R16 | R17 | R21 | X | Y | m.p. (°C.) |
|---|---|---|---|---|---|
| CO2CH3 | H | H | CH3 | CH2OH | |
| Cl | H | CH3 | CH3 | CH2OH | |
| Cl | H | H | OCH3 | CH2OH | |
| H | H | H | OCH3 | CH2OH | |
| CO2CH(CH3)2 | 5-F | H | CH3 | CH2OH | |
| CO2CH(CH3)2 | H | H | Ch2CH3 | CH2OH | |

TABLE 5g-continued

| R16 | R17 | R21 | X | Y | m.p. (°C.) |
|---|---|---|---|---|---|
| NO2 | H | H | CH3 | CH2OH | |
| NO2 | 6-Br | H | CH3 | CH2OH | |
| Cl | 4-Cl | H | OCH3 | CH2OH | |
| CF3 | H | H | OCH3 | CH2OH | |
| Cl | 6-CH3 | H | OCH3 | CH2OH | |
| C2H5 | H | H | CH3 | CH2OH | |
| CH(CH3)2 | H | H | CH3 | CH2OH | |
| SO2CH3 | H | H | CH3 | CH2OH | |
| SO2CH3 | 4-OCH3 | H | OCH3 | CH2OH | |
| SO2CH3 | 6-F | H | OCH3 | CH2OH | |
| SO2—n-C4H9 | H | H | CH3 | CH2OH | |
| SO2N(CH3)2 | H | H | OCH3 | CH2OH | |
| SO2N(C2H5)2 | H | H | CH3 | CH2OH | |
| SO2N(OCH3)CH3 | H | H | CH3 | CH2OH | |
| SO2—n-C3H7 | H | H | CH3 | CH2OH | |
| SO2—i-C3H7 | H | CH3 | OCH3 | CH2OH | |
| SCH3 | H | H | CH3 | CH2OH | |
| S(O)2CH3 | H | H | CH3 | CH2OH | |
| SCH2CH3 | H | H | OCH3 | CH2OH | |
| S(O)2—n-C4H9 | H | H | OCH2CH3 | CH2OH | |

TABLE 5h

| R16 | R17 | R21 | X | Y | m.p. (°C.) |
|---|---|---|---|---|---|
| CO2CH3 | H | H | CH3 | CH2OCOCH3 | |
| Cl | H | H | CH3 | CH(OC2H5)2 | |
| Cl | H | H | OCH3 | CH2SCH3 | |
| H | H | H | OCH3 | CH2OCONHCH3 | |
| CO2CH(CH3)2 | 5-F | H | CH3 | CH2OCO2CH3 | |
| CO2CH(CH3)2 | H | CH3 | CH3 | CH2SC2H5 | |
| NO2 | H | H | CH3 | CH(OCH2CH2O) | |
| NO2 | 6-Br | H | CH3 | CH2OCOC2H5 | |
| Cl | 4-Cl | H | OCH3 | CH(OCH2CH2CH2O) | |
| CF3 | H | H | OCH3 | CH(OCH(CH3)CH2) | |
| Cl | 6-CH3 | H | OCH3 | CH2SCH3 | |
| C2H5 | H | H | CH2CH3 | CH2OCOCH3 | |
| CH(CH3)2 | H | H | CH3 | CH2OCON(CH3)2 | |
| SO2CH3 | H | H | CH3 | CH(OCH2CH2O) | |
| SO2CH3 | 4-OCH3 | H | OCH3 | CH2OCOCH3 | |
| SO2CH3 | 6-F | H | OCH3 | CH2SC2H5 | |
| SO2—n-C4H9 | H | H | CH3 | CH(OC2H5)2 | |
| SO2N(CH3)2 | H | H | OCH2CH3 | CH2OCO2—n-C3H7 | |
| SO2N(C2H5)2 | H | H | CH3 | CH2OCON(C2H5)2 | |
| SO2N(OCH3)CH3 | H | H | CH3 | CH2OCON(CH3)(n-C3H7) | |
| SO2—n-C3H7 | H | H | CH3 | CH2OCO—i-C3H7 | |
| SO2—i-C3H7 | H | H | OCH3 | CH2OCONH(n-C3H7) | |
| SCH3 | H | H | CH3 | CH(OC2H5)2 | |
| S(O)2CH3 | H | H | CH3 | CH(OC2H5)2 | |
| SCH2CH3 | H | CH3 | OCH3 | CH2OCO2—i-C3H7 | |
| S(O)2—n-C4H9 | H | H | OCH3 | CH2SCH3 | |
| SO2CH2CH3 | H | H | OCH3 | CH2SO2CH2CH3 | |
| Cl | H | H | OCH3 | C(C2H5)(OCH2CH2O) | |
| NO2 | H | H | OCH3 | C(CH3)(SCH3)2 | |
| NO2 | H | H | OCH3 | CH2S(O)CH3 | |

TABLE 6a

| R16 | R17 | R21 | X | Y | m.p. (°C.) |
|---|---|---|---|---|---|
| CO2CH3 | H | H | CH3 | CH(OCH3)2 | |
| Cl | H | H | CH3 | CH(OCH3)2 | |
| CO2CH3 | H | H | Cl | CH(OCH3)2 | |
| Cl | H | H | OCH3 | CH(OCH3)2 | |
| H | H | H | OCH3 | CH(OCH3)2 | |
| CO2CH(CH3)2 | 5-F | H | CH3 | CH(OCH3)2 | |
| CO2CH(CH3)2 | H | H | CH3 | CH(OCH3)2 | |
| NO2 | H | H | CH3 | CH(OCH3)2 | |
| NO2 | 6-Br | H | CH3 | CH(OCH3)2 | |
| CF3 | H | H | OCH2CH3 | CH(OCH3)2 | |
| Cl | 6-CH3 | H | OCH3 | CH(OCH3)2 | |
| C2H5 | H | H | CH3 | CH(OCH3)2 | |
| CH(CH3)2 | H | H | CH3 | CH(OCH3)2 | |
| SO2CH3 | H | H | H3 | CH(OCH3)2 | |
| SO2CH3 | 6-F | H | OCH3 | CH(OCH3)2 | |
| SO2—n-C4H9 | H | CH3 | CH3 | CH(OCH3)2 | |
| SO2N(CH3)2 | H | H | OCH3 | CH(OCH3)2 | |
| SO2N(C2H5) | H | H | CH3 | CH(OCH3)2 | |
| SO2N(OCH3)CH3 | H | H | CH3 | CH(OCH3)2 | |
| SO2—n-C3H7 | H | H | CH3 | CH(OCH3)2 | |
| SO2—i-C3H7 | H | H | OCH3 | Ch(OCH3)2 | |
| SCH3 | H | H | CH3 | CH(OCH3)2 | |
| S(O)2CH3 | H | H | CH2CH3 | CH(OCH3)2 | |
| SCH2CH3 | H | H | OCH3 | CH(OCH3)2 | |
| S(O)2(CH2)3CH3 | H | H | OCH3 | CH(OCH3)2 | |
| CH3 | H | H | CH3 | C(CH3)(OCH3)2 | |
| CO2CH2CH3 | H | H | CH3 | C(CH3)(OCH3)2 | |
| SCH3 | H | H | OCH3 | C(CH3)(OCH3)2 | |
| Cl | H | H | OCH3 | C(CH3)(OCH3)2 | |

TABLE 6b

| R16 | R17 | R21 | X | Y | m.p. (°C.) |
|---|---|---|---|---|---|
| CO2CH3 | H | H | CH3 | CH2OTHP | |
| Cl | H | CH3 | CH3 | CH2OTHP | |
| Cl | H | H | OCH3 | CH2OTHP | |
| H | H | H | OCH2CH3 | CH2OTHP | |
| CO2CH(CH3)2 | 5-F | H | CH3 | CH2OTHP | |
| CO2CH(CH3)2 | H | H | CH3 | CH2OTHP | |
| NO2 | H | H | CH3 | CH2OTHP | |
| NO2 | 6-Br | H | CH3 | CH2OTHP | |
| Cl | 2-Cl | H | OCH3 | CH2OTHP | |
| CF3 | H | H | OCH3 | CH2OTHP | |
| Cl | 6-CH3 | H | OCH3 | CH2OTHP | |
| C2H5 | H | H | CH2CH3 | CH2OTHP | |
| CH(CH3)2 | H | H | CH3 | CH2OTHP | |
| SO2CH3 | H | H | CH3 | CH2OTHP | |
| SO2CH3 | 5-OCH3 | H | OCH3 | CH2OTHP | |
| SO2CH3 | 6-F | H | OCH3 | CH2OTHP | |
| SO2—n-C4H9 | H | H | CH3 | CH2OTHP | |
| SO2N(CH3)2 | H | CH3 | OCH3 | CH2OTHP | |
| SO2N(C2H5)2 | H | CH3 | CH3 | CH2OTHP | |
| SO2N(OCH3)CH3 | H | H | CH3 | CH2OTHP | |
| SO2—n-C3H7 | H | H | CH3 | CH2OTHP | |
| SO2—i-C3H7 | H | H | OCH3 | CH2OTHP | |
| SCH3 | H | H | CH3 | CH2OTHP | |
| S(O)2CH3 | H | H | CH3 | CH2OTHP | |
| SCH2CH3 | H | H | OCH3 | CH2OTHP | |

TABLE 6b-continued

| R16 | R17 | R21 | X | Y | m.p. (°C.) |
|---|---|---|---|---|---|
| S(O)$_2$—n-C$_4$H$_9$ | H | H | OCH$_3$ | CH$_2$OTHP | |

TABLE 6c

| R16 | R17 | R21 | X | Y | m.p. (°C.) |
|---|---|---|---|---|---|
| CO$_2$CH$_3$ | H | H | CH$_3$ | CH$_2$OH | |
| Cl | H | H | CH$_2$CH$_3$ | CH$_2$OH | |
| Cl | H | H | OCH$_3$ | CH$_2$OH | |
| H | H | H | OCH$_3$ | CH$_2$OH | |
| CO$_2$CH(CH$_3$)$_2$ | 5-F | H | CH$_3$ | CH$_2$OH | |
| CO$_2$CH(CH$_3$)$_2$ | H | H | CH$_3$ | CH$_2$OH | |
| NO$_2$ | H | H | CH$_3$ | CH$_2$OH | |
| NO$_2$ | 6-Br | H | CH$_3$ | CH$_2$OH | |
| Cl | 2-Cl | H | OCH$_2$CH$_3$ | CH$_2$OH | |
| CF$_3$ | H | H | OCH$_3$ | CH$_2$OH | |
| Cl | 6-CH$_3$ | H | OCH$_3$ | CH$_2$OH | |
| C$_2$H$_5$ | H | H | CH$_3$ | CH$_2$OH | |
| CH(CH$_3$)$_2$ | H | H | CH$_3$ | CH$_2$OH | |
| SO$_2$CH$_3$ | H | H | CH$_3$ | CH$_2$OH | |
| SO$_2$CH$_3$ | 5-OCH$_3$ | H | OCH$_3$ | CH$_2$OH | |
| SO$_2$CH$_3$ | 6-F | H | OCH$_3$ | CH$_2$OH | |
| SO$_2$—n-C$_4$H$_9$ | H | H | CH$_3$ | CH$_2$OH | |
| SO$_2$N(CH$_3$)$_2$ | H | H | OCH$_3$ | CH$_2$OH | |
| SO$_2$N(C$_2$H$_5$)$_2$ | H | H | CH$_3$ | CH$_2$OH | |
| SO$_2$N(OCH$_3$)CH$_3$ | H | H | CH$_3$ | CH$_2$OH | |
| SO$_2$—n-C$_3$H$_7$ | H | H | CH$_3$ | CH$_2$OH | |
| SO$_2$—i-C$_3$H$_7$ | H | CH$_3$ | OCH$_3$ | CH$_2$OH | |
| SCH$_3$ | H | CH$_3$ | CH$_3$ | CH$_2$OH | |
| S(O)$_2$CH$_3$ | H | H | CH$_3$ | CH$_2$OH | |
| SCH$_2$CH$_3$ | H | H | OCH$_3$ | CH$_2$OH | |
| S(O)$_2$—n-C$_4$H$_9$ | H | H | OCH$_3$ | CH$_2$OH | |

TABLE 6d

| R16 | R17 | R21 | X | Y | m.p. (°C.) |
|---|---|---|---|---|---|
| CO$_2$CH$_3$ | H | H | CH$_3$ | CH$_2$OCOCH$_3$ | |
| Cl | H | H | CH$_3$ | CH(OC$_2$H$_5$)$_2$ | |
| Cl | H | H | OCH$_3$ | CH$_2$SCH$_3$ | |
| H | H | H | OCH$_3$ | CH$_2$OCONHCH$_3$ | |
| CO$_2$CH(CH$_3$)$_2$ | 5-F | H | CH$_3$ | CH$_2$OCO$_2$CH$_3$ | |
| CO$_2$CH(CH$_3$)$_2$ | H | H | CH$_3$ | CH$_2$SC$_2$H$_5$ | |
| NO$_2$ | H | H | CH$_3$ | CH(OCH$_2$CH$_2$O) | |
| NO$_2$ | 6-Br | H | CH$_3$ | CH$_2$OCOC$_2$H$_5$ | |
| Cl | 2-Cl | H | OCH$_3$ | CH(OCH$_2$CH$_2$CH$_2$O) | |
| CF$_3$ | H | H | OCH$_3$ | CH(OCH(CH$_3$)CH$_2$) | |
| Cl | 6-CH$_3$ | CH$_3$ | OCH$_3$ | CH$_2$SCH$_3$ | |
| C$_2$H$_5$ | H | CH$_3$ | CH$_3$ | CH$_2$OCOCH$_3$ | |
| CH(CH$_3$)$_2$ | H | H | CH$_2$CH$_3$ | CH$_2$OCON(CH$_3$)$_2$ | |
| SO$_2$CH$_3$ | H | H | CH$_3$ | CH(OCH$_2$CH$_2$O) | |
| SO$_2$CH$_3$ | 5-OCH$_3$ | H | OCH$_3$ | CH$_2$OCOCH$_3$ | |
| SO$_2$CH$_3$ | 6-F | H | CH$_3$ | CH$_2$SC$_2$H$_5$ | |
| SO$_2$—n-C$_4$H$_9$ | H | H | CH$_3$ | CH(OC$_2$H$_5$)$_2$ | |
| SO$_2$N(CH$_3$)$_2$ | H | H | OCH$_3$ | CH$_2$OCO$_2$—n-C$_3$H$_7$ | |
| SO$_2$N(C$_2$H$_5$)$_2$ | H | H | CH$_3$ | CH$_2$OCON(C$_2$H$_5$)$_2$ | |
| SO$_2$N(OCH$_3$)CH$_3$ | H | H | CH$_3$ | CH$_2$OCON(CH$_3$)(n-C$_3$H$_7$) | |
| SO$_2$—n-C$_3$H$_7$ | H | H | CH$_3$ | CH$_2$OCO—i-C$_3$H$_7$ | |
| SO$_2$—i-C$_3$H$_7$ | H | H | OCH$_3$ | CH$_2$OCONH(n-C$_3$H$_7$) | |
| SCH$_3$ | H | H | CH$_3$ | CH(OC$_2$H$_5$)$_2$ | |
| S(O)$_2$CH$_3$ | H | H | CH$_3$ | CH(OC$_2$H$_5$)$_2$ | |
| SCH$_2$CH$_3$ | H | H | OCH$_3$ | CH$_2$OCO$_2$—i-C$_3$H$_7$ | |
| S(O)$_2$—n-C$_4$H$_9$ | H | H | OCH$_2$CH$_3$ | CH$_2$SCH$_3$ | |

TABLE 6d-continued

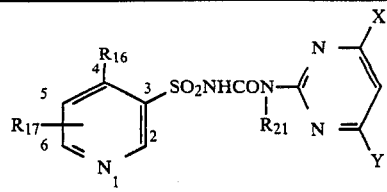

| R16 | R17 | R21 | X | Y | m.p. (°C.) |
|---|---|---|---|---|---|
| CH3 | H | H | OCH3 | CH(SCH2CH3)2 | |
| NO2 | H | H | OCH3 | CH(SCH3)2 | |
| SO2N(CH3)2 | H | H | C2H5 | CH2SO2CH3 | |
| SO2N(CH3)2 | H | H | OCH3 | CH2S(O)CH3 | |
| SO2N(CH3)2 | H | H | CH3 | CH2S(O)CH2CH3 | |

TABLE 6e

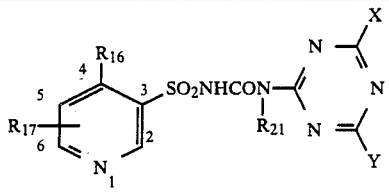

| R16 | R17 | R21 | X | Y | m.p. (°C.) |
|---|---|---|---|---|---|
| CO2CH3 | H | CH3 | CH3 | CH(OCH3)2 | |
| Cl | H | H | CH3 | CH(OCH3)2 | |
| Cl | H | H | OCH3 | CH(OCH3)2 | |
| H | H | H | OCH3 | CH(OCH3)2 | |
| CO2CH(CH3)2 | 5-F | H | CH3 | CH(OCH3)2 | |
| CO2CH(CH3)2 | H | H | CH3 | CH(OCH3)2 | |
| NO2 | H | H | CH3 | CH(OCH3)2 | |
| NO2 | 6-Br | H | CH3 | CH(OCH3)2 | |
| CF3 | H | H | OCH3 | CH(OCH3)2 | |
| Cl | 6-CH3 | H | OCH3 | CH(OCH3)2 | |
| C2H5 | H | H | CH3 | CH(OCH3)2 | |
| CH(CH3)2 | H | H | CH3 | CH(OCH3)2 | |
| SO2CH3 | H | H | CH3 | CH(OCH3)2 | |
| SO2CH3 | 5-OCH3 | H | OCH3 | CH(OCH3)2 | |
| SO2CH3 | 6-F | H | OCH3 | CH(OCH3)2 | |
| SO2—n-C4H9 | H | H | CH3 | CH(OCH3)2 | |
| SO2N(CH3)2 | H | H | OCH3 | CH(OCH3)2 | |
| SO2N(C2H5)2 | H | H | CH3 | CH(OCH3)2 | |
| SO2N(OCH3)CH3 | H | CH3 | CH2CH3 | CH(OCH3)2 | |
| SO2—n-C3H7 | H | H | CH3 | CH(OCH3)2 | |
| SO2—i-C3H7 | H | H | OCH2CH3 | CH(OCH3)2 | |
| SCH3 | H | H | CH3 | CH(OCH3)2 | |
| S(O)2CH3 | H | H | CH3 | CH(OCH3)2 | |
| SCH2CH3 | H | H | OCH3 | CH(OCH3)2 | |
| S(O)2(CH2)3CH3 | H | H | OCH3 | CH(OCH3)2 | |
| CH(CH3)2 | H | H | OCH3 | C(CH2CH3)(OCH3)2 | |
| CO2CH(CH3)2 | H | H | OCH3 | C(CH2CH3)(OCH3)2 | |
| CF3 | H | H | OCH3 | C(CH2CH3)(OCH3)2 | |

TABLE 6f

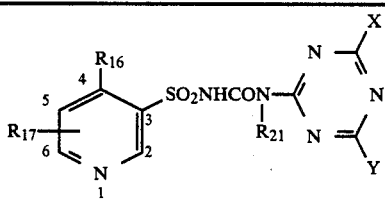

| R16 | R17 | R21 | X | Y | m.p. (°C.) |
|---|---|---|---|---|---|
| CO2CH3 | H | H | CH3 | CH2OTHP | |
| Cl | H | H | CH3 | CH2OTHP | |
| Cl | H | H | OCH3 | CH2OTHP | |
| H | H | H | OCH3 | CH2OTHP | |
| CO2CH(CH3)2 | 5-F | CH3 | CH3 | CH2OTHP | |
| CO2CH(CH3)2 | H | CH3 | CH3 | CH2OTHP | |

TABLE 6f-continued

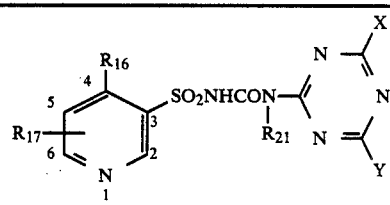

| R16 | R17 | R21 | X | Y | m.p. (°C.) |
|---|---|---|---|---|---|
| NO2 | H | H | CH3 | CH2OTHP | |
| NO2 | 6-Br | H | CH3 | CH2OTHP | |
| Cl | 2-Cl | H | OCH2CH3 | CH2OTHP | |
| CF3 | H | H | OCH3 | CH2OTHP | |
| Cl | 6-CH3 | H | OCH3 | CH2OTHP | |
| C2H5 | H | H | CH3 | CH2OTHP | |

TABLE 6f-continued

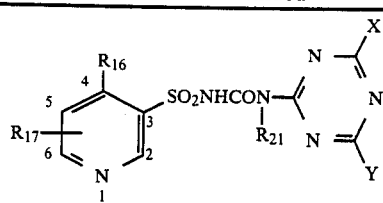

| R16 | R17 | R21 | X | Y | m.p. (°C.) |
|---|---|---|---|---|---|
| CH(CH3)2 | H | H | CH3 | CH2OTHP | |
| SO2CH3 | H | H | CH3 | CH2OTHP | |
| SO2CH3 | 5-OCH3 | H | OCH3 | CH2OTHP | |
| SO2CH3 | 6-F | H | OCH3 | CH2OTHP | |
| SO2—n-C4H9 | H | H | CH3 | CH2OTHP | |
| SO2N(CH3)2 | H | H | OCH3 | CH2OTHP | |
| SO2N(C2H5)2 | H | H | CH2CH3 | CH2OTHP | |
| SO2N(OCH3)CH3 | H | H | CH3 | CH2OTHP | |
| SO2—n-C3H7 | H | H | CH3 | CH2OTHP | |
| SO2—i-C3H7 | H | H | OCH3 | CH2OTHP | |
| SCH3 | H | H | CH3 | CH2OTHP | |
| S(O)2CH3 | H | H | CH3 | CH2OTHP | |
| SCH2CH3 | H | H | OCH3 | CH2OTHP | |
| S(O)2—n-C4H9 | H | H | OCH3 | CH2OTHP | |

TABLE 6g

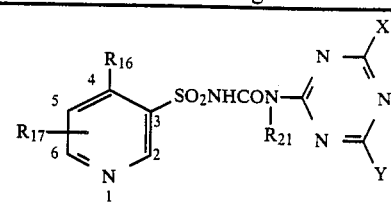

| R16 | R17 | R21 | X | Y | m.p. (°C.) |
|---|---|---|---|---|---|
| CO2CH3 | H | H | CH3 | CH2OH | |
| Cl | H | H | CH3 | CH2OH | |
| Cl | H | H | OCH3 | CH2OH | |
| H | H | H | OCH3 | CH2OH | |
| CO2CH(CH3)2 | 5-F | H | CH2CH3 | CH2OH | |
| CO2CH(CH3)2 | H | H | CH3 | CH2OH | |
| NO2 | H | H | CH3 | CH2OH | |
| NO2 | 6-Br | H | CH3 | CH2OH | |
| Cl | 2-Cl | H | OCH3 | CH2OH | |
| CF3 | H | H | OCH3 | CH2OH | |
| Cl | 6-CH3 | H | OCH3 | CH2OH | |
| C2H5 | H | H | CH3 | CH2OH | |
| CH(CH3)2 | H | H | CH3 | CH2OH | |
| SO2CH3 | H | H | CH3 | CH2OH | |
| SO2CH3 | 5-OCH3 | H | OCH3 | CH2OH | |
| SO2CH3 | 6-F | H | OCH3 | CH2OH | |
| SO2—n-C4H9 | H | CH3 | CH3 | CH2OH | |
| SO2N(CH3)2 | H | H | OCH3 | CH2OH | |
| SO2N(C2H5)2 | H | H | CH3 | CH2OH | |
| SO2N(OCH3)CH3 | H | H | CH3 | CH2OH | |
| SO2—n-C3H7 | H | H | CH3 | CH2OH | |
| SO2—i-C3H7 | H | H | OCH3 | CH2OH | |
| SCH3 | H | H | CH3 | CH2OH | |
| S(O)2CH3 | H | H | CH3 | CH2OH | |
| SCH2CH3 | H | H | OCH2CH3 | CH2OH | |
| S(O)2—n-C4H9 | H | H | OCH3 | CH2OH | |

TABLE 6h

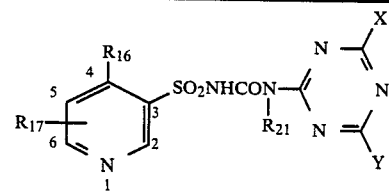

| R16 | R17 | R21 | X | Y | m.p. (°C.) |
|---|---|---|---|---|---|
| CO2CH3 | H | H | CH3 | CH2OCOCH3 | |
| Cl | H | H | CH3 | CH(OC2H5)2 | |
| Cl | H | H | OCH3 | CH2SCH3 | |
| H | H | H | OCH3 | CH2OCONHCH3 | |
| CO2CH(CH3)2 | 5-F | H | CH3 | CH2OCO2CH3 | |
| CO2CH(CH3)2 | H | H | CH3 | CH2SC2H5 | |
| NO2 | H | H | CH3 | CH(OCH2CH2O) | |
| NO2 | 6-Br | H | CH3 | CH2OCOC2H5 | |
| Cl | 2-Cl | H | OCH3 | CH(OCH2CH2CH2O) | |
| CF3 | H | H | OCH3 | CH(OCH(CH3)CH2) | |
| Cl | 6-CH3 | H | OCH3 | CH2SCH3 | |
| C2H5 | H | H | CH3 | CH2OCOCH3 | |
| CH(CH3)2 | H | CH3 | CH3 | CH2OCON(CH3)2 | |
| SO2CH3 | H | H | CH3 | CH(OCH2CH2O) | |
| SO2CH3 | 5-OCH3 | H | OCH3 | CH2OCOCH3 | |
| SO2CH3 | 6-F | H | OCH3 | CH2SC2H5 | |
| SO2—n-C4H9 | H | H | CH3 | CH(OC2H5)2 | |
| SO2N(CH3)2 | H | H | OCH2CH3 | CH2OCO2—n-C3H7 | |
| SO2N(C2H5)2 | H | H | CH3 | CH2OCON(C2H5)2 | |
| SO2N(OCH3)CH3 | H | H | CH3 | CH2OCON(CH3)(n-C3H7) | |
| SO2—n-C3H7 | H | H | CH3 | CH2OCO—i-C3H7 | |
| SO2—i-C3H7 | H | H | OCH3 | CH2OCONH(n-C3H7) | |
| SCH3 | H | H | CH3 | CH(OC2H5)2 | |
| S(O)2CH3 | H | H | CH3 | CH(OC2H5)2 | |
| SCH2CH3 | H | H | OCH2CH3 | CH2OCO2—i-C3H7 | |
| S(O)2—n-C4H9 | H | CH3 | OCH3 | CH2SCH3 | |
| SCH2CH3 | H | H | OC2H5 | C(CH3)(OCH2CH2CH2O) | |
| Cl | H | H | CH3 | CH2SO2CH3 | |

TABLE 6h-continued

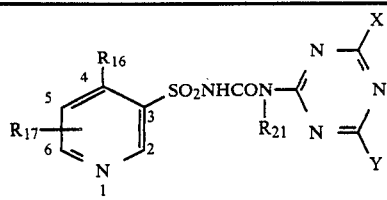

| R16 | R17 | R21 | X | Y | m.p. (°C.) |
|---|---|---|---|---|---|
| CH3 | H | H | OCH3 | CH(SCH2CH3)2 | |

TABLE 7a

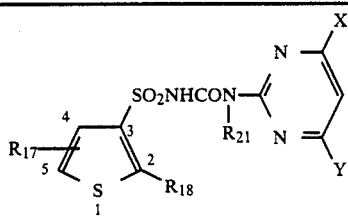

| R17 | R18 | R21 | X | Y | m.p. (°C.) |
|---|---|---|---|---|---|
| H | CO2CH3 | H | CH3 | CH(OCH3)2 | |
| 4-CH3 | CO2CH3 | H | CH3 | CH(OCH3)2 | |
| H | CO2CH3 | H | OCH3 | CH(OCH3)2 | |
| H | CO2CH2CH=CH2 | H | CH3 | CH(OCH3)2 | |
| H | H | H | CH3 | CH(OCH3)2 | |
| H | SCH2CH2CH3 | H | OCH3 | CH(OCH3)2 | |
| H | SCH3 | H | CH3 | CH(OCH3)2 | |
| H | CH(CH3)2 | H | OCH2CH3 | CH(OCH3)2 | |
| H | CH2CH3 | H | CH3 | CH(OCH3)2 | |
| H | F | H | OCH3 | CH(OCH3)2 | |
| H | Cl | H | OCH3 | CH(OCH3)2 | |
| 5-Cl | Cl | H | CH3 | CH(OCH3)2 | |
| H | Br | CH3 | OCH3 | CH(OCH3)2 | |
| H | NO2 | H | CH3 | CH(OCH3)2 | |
| H | SO2N(CH3)CH2CH3 | H | CH3 | CH(OCH3)2 | |
| H | SO2N(CH3)2 | H | OCH3 | CH(OCH3)2 | |
| H | SO2N(OCH3)CH3 | H | OCH3 | CH(OCH3)2 | |
| H | OCH3 | CH3 | CH3 | CH(OCH3)2 | |
| 5-OCH3 | OCH3 | H | CH2CH3 | CH(OCH3)2 | |
| 5-F | O(CH2)3CH3 | H | OCH3 | CH(OCH3)2 | |
| H | SO2CH2CH2CH3 | H | OCH3 | CH(OCH3)2 | |
| H | SO2CH3 | H | CH3 | CH(OCH3)2 | |
| 4-Br | SO2CH3 | H | CH3 | CH(OCH3)2 | |
| H | CO2CH3 | H | Cl | CH(OCH3)2 | |
| H | NO2 | H | Cl | CH(OCH3)2 | |
| H | Cl | H | OCH3 | C(CH3)(OCH3)2 | |
| H | CO2CH3 | H | OCH3 | C(CH3)(OCH3)2 | |
| H | CO2CH3 | H | OCH3 | C(CH2CH3)(OCH3)2 | |
| H | SO2CH2CH2CH3 | H | Cl | CH(OCH3)2 | |
| H | SO2CH3 | H | Cl | CH(OCH3)2 | |
| H | SCH3 | H | Cl | CH(OCH3)2 | |

TABLE 7b

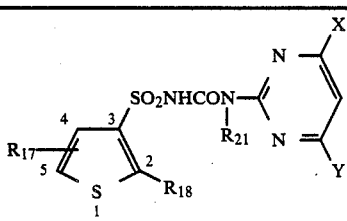

TABLE 7b-continued

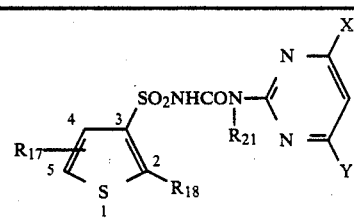

| R17 | R18 | R21 | X | Y | m.p. (°C.) |
|---|---|---|---|---|---|
| H | CO2CH3 | H | CH3 | CH2OTHP | |
| 4-CH3 | CO2CH3 | H | CH2CH3 | CH2OTHP | |
| H | CO2CH2CH3 | H | OCH3 | CH2OTHP | |
| H | CO2CH2CH=CH2 | H | CH3 | CH2OTHP | |
| H | H | H | CH3 | CH2OTHP | |
| H | SCH2CH2CH3 | H | OCH3 | CH2OTHP | |
| H | SCH3 | H | CH3 | CH2OTHP | |
| H | CH(CH3)2 | H | OCH3 | CH2OTHP | |
| H | CH2CH3 | H | CH3 | CH2OTHP | |
| H | F | H | OCH3 | CH2OTHP | |

TABLE 7b-continued

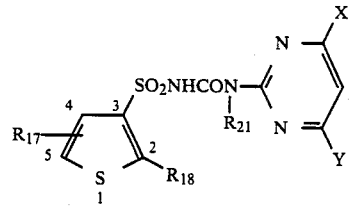

| $R_{17}$ | $R_{18}$ | $R_{21}$ | X | Y | m.p. (°C.) |
|---|---|---|---|---|---|
| H | Cl | H | OCH$_3$ | CH$_2$OTHP | |
| 5-Cl | Cl | H | CH$_3$ | CH$_2$OTHP | |
| H | Br | CH$_3$ | OCH$_3$ | CH$_2$OTHP | |
| H | NO$_2$ | CH$_3$ | CH$_3$ | CH$_2$OTHP | |
| H | SO$_2$N(CH$_3$)CH$_2$CH$_3$ | H | CH$_3$ | CH$_2$OTHP | |
| H | SO$_2$N(CH$_3$)$_2$ | H | OCH$_3$ | CH$_2$OTHP | |
| H | SO$_2$N(OCH$_3$)CH$_3$ | H | OCH$_2$CH$_3$ | CH$_2$OTHP | |
| H | OCH$_3$ | H | CH$_3$ | CH$_2$OTHP | |
| 5-OCH$_3$ | OCH$_3$ | H | CH$_3$ | CH$_2$OTHP | |
| 5-F | O(CH$_2$)$_3$CH$_3$ | H | OCH$_3$ | CH$_2$OTHP | |
| H | SO$_2$CH$_2$CH$_2$CH$_3$ | H | OCH$_3$ | CH$_2$OTHP | |
| H | SO$_2$CH$_3$ | H | CH$_3$ | CH$_2$OTHP | |
| 4-Br | SO$_2$CH$_3$ | H | CH$_3$ | CH$_2$OTHP | |

TABLE 7c

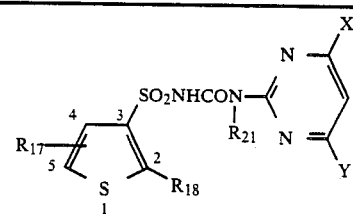

| $R_{17}$ | $R_{18}$ | $R_{21}$ | X | Y | m.p. (°C.) |
|---|---|---|---|---|---|
| H | CO$_2$CH$_3$ | H | CH$_3$ | CH$_2$OH | 143–147° |
| 4-CH$_3$ | CO$_2$CH$_3$ | H | CH$_3$ | CH$_2$OH | |
| H | CO$_2$CH$_2$CH$_3$ | H | OCH$_3$ | CH$_2$OH | |
| H | CO$_2$CH$_2$CH=CH$_2$ | H | CH$_3$ | CH$_2$OH | |
| H | H | H | CH$_3$ | CH$_2$OH | |
| H | SCH$_2$CH$_2$CH$_3$ | H | OCH$_3$ | CH$_2$OH | |
| H | SCH$_3$ | H | CH$_3$ | CH$_2$OH | |
| H | CH(CH$_3$)$_2$ | H | OCH$_3$ | CH$_2$OH | |
| H | CH$_2$CH$_3$ | CH$_3$ | CH$_3$ | CH$_2$OH | |
| H | F | H | OCH$_2$CH$_3$ | CH$_2$OH | |
| H | Cl | CH$_3$ | OCH$_3$ | CH$_2$OH | |
| 5-Cl | Cl | H | CH$_2$CH$_3$ | CH$_2$OH | |
| H | Br | H | OCH$_3$ | CH$_2$OH | |
| H | NO$_2$ | H | CH$_3$ | CH$_2$OH | |
| H | SO$_2$N(CH$_3$)CH$_2$CH$_3$ | H | CH$_3$ | CH$_2$OH | |
| H | SO$_2$N(CH$_3$)$_2$ | H | OCH$_3$ | CH$_2$OH | |
| H | SO$_2$N(OCH$_3$)CH$_3$ | H | OCH$_3$ | CH$_2$OH | |
| H | OCH$_3$ | H | CH$_3$ | CH$_2$OH | |
| 5-OCH$_3$ | OCH$_3$ | H | CH$_3$ | CH$_2$OH | |
| 5-F | O(CH$_2$)$_3$CH$_3$ | H | OCH$_3$ | CH$_2$OH | |
| H | SO$_2$CH$_2$CH$_2$CH$_3$ | H | OCH$_3$ | CH$_2$OH | |
| H | SO$_2$CH$_3$ | H | CH$_3$ | CH$_2$OH | |
| 4-Br | SO$_2$CH$_3$ | H | CH$_3$ | CH$_2$OH | |

TABLE 7d

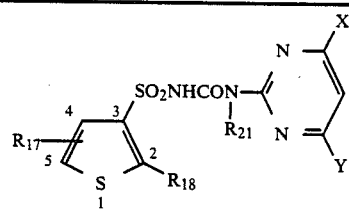

| $R_{17}$ | $R_{18}$ | $R_{21}$ | X | Y | m.p. (°C.) |
|---|---|---|---|---|---|
| H | CO$_2$CH$_3$ | H | CH$_3$ | CH(OC$_2$H$_5$)$_2$ | |
| 4-CH$_3$ | CO$_2$CH$_3$ | H | CH$_3$ | CH$_2$OCOCH$_3$ | |
| H | CO$_2$CH$_3$ | H | OCH$_3$ | CH$_2$SCH$_3$ | |
| H | CO$_2$CH$_2$CH=CH$_2$ | H | CH$_3$ | CH$_2$OCONHCH$_3$ | |
| H | H | H | CH$_3$ | CH$_2$OCO$_2$CH$_3$ | |
| H | SCH$_2$CH$_2$CH$_3$ | H | OCH$_3$ | CH$_2$SC$_2$H$_5$ | |
| H | SCH$_3$ | H | CH$_3$ | CH(OCH$_2$CH$_2$O) | |
| H | CH(CH$_3$)$_2$ | H | OCH$_3$ | CH$_2$OCOC$_2$H$_5$ | |
| H | CH$_2$CH$_3$ | H | CH$_3$ | CH(OCH(CH$_3$)CH$_2$O) | |
| H | F | H | OCH$_3$ | CH(OCH$_2$CH$_2$CH$_2$O) | |
| H | Cl | H | OCH$_3$ | CH$_2$SCH$_3$ | |
| 5-Cl | Cl | H | CH$_3$ | CH$_2$OCOCH$_3$ | |
| H | Br | CH$_3$ | OCH$_3$ | CH$_2$OCON(CH$_3$)$_2$ | |
| H | NO$_2$ | CH$_3$ | CH$_3$ | CH(OCH$_2$CH$_2$O) | |
| H | SO$_2$N(CH$_3$)C$_2$H$_5$ | H | CH$_3$ | CH$_2$OCOCH$_3$ | |

TABLE 7d-continued

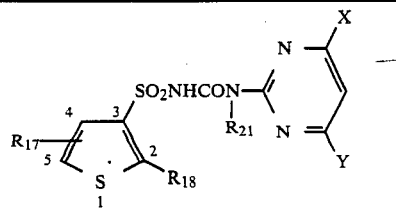

| R17 | R18 | R21 | X | Y | m.p. (°C.) |
|---|---|---|---|---|---|
| H | SO2N(CH3)2 | H | OCH2CH3 | CH2SCH2CH3 | |
| H | SO2N(OCH3)CH3 | H | CH3 | CH(OC2H5)2 | |
| H | OCH3 | H | CH3 | CH2OCO2C2H5 | |
| 5-OCH3 | OCH3 | H | CH3 | CH2OCON(C2H5)2 | |
| 5-F | O(CH2)3CH3 | H | OCH3 | CH2OCON(C2H5)2 | |
| H | SO2CH2CH2CH3 | H | CH3 | CH2OCO(i-C3H7) | |
| H | SO2CH3 | H | CH2CH3 | CH2OCONH(n-C3H7) | |
| H | SCH3 | H | CH3 | CH2SO2CH3 | |
| H | CH3 | H | CH3 | CH2SO2CH2CH3 | |
| H | CO2CH3 | H | CH3 | CH2SO2CH3 | |

TABLE 7e

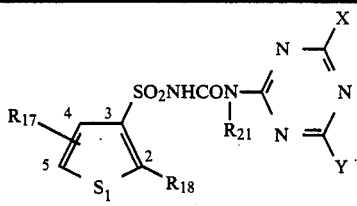

| R17 | R18 | R21 | X | Y | m.p. (°C.) |
|---|---|---|---|---|---|
| H | CO2CH3 | H | CH3 | CH(OCH3)2 | |
| 4-CH3 | CO2CH3 | H | CH3 | CH(OCH3)2 | |
| H | CO2CH3 | H | OCH2CH3 | CH(OCH3)2 | |
| H | CO2CH2CH=CH2 | H | CH3 | CH(OCH3)2 | |
| H | H | CH3 | CH3 | CH(OCH3)2 | |
| H | SCH2CH2CH3 | H | OCH3 | CH(OCH3)2 | |
| H | SCH3 | H | CH3 | CH(OCH3)2 | |
| H | CH(CH3)2 | H | OCH3 | CH(OCH3)2 | |
| H | CH2CH3 | H | CH3 | CH(OCH3)2 | |
| H | F | H | OCH3 | CH(OCH3)2 | |
| H | Cl | H | OCH3 | CH(OCH3)2 | |
| 5-Cl | Cl | H | CH3 | CH(OCH3)2 | |
| H | Br | H | OCH3 | CH(OCH3)2 | |
| H | NO2 | H | CH3 | CH(OCH3)2 | |
| H | SO2N(CH3)CH2CH3 | H | CH3 | CH(OCH3)2 | |
| H | SO2N(CH3)2 | CH3 | OCH3 | CH(OCH3)2 | |
| H | SO2N(OCH3)CH3 | H | OCH3 | CH(OCH3)2 | |
| H | OCH3 | H | CH2CH3 | CH(OCH3)2 | |
| 5-OCH3 | OCH3 | H | CH3 | CH(OCH3)2 | |
| 5-F | O(CH2)3CH3 | H | OCH3 | CH(OCH3)2 | |
| H | SO2CH2CH2CH3 | H | OCH3 | CH(OCH3)2 | |
| H | SO2CH3 | H | CH3 | CH(OCH3)2 | |
| 4-Br | SO2CH3 | H | CH3 | CH(OCH3)2 | |
| H | Cl | H | CH3 | C(CH3)(OCH3)2 | |
| H | Br | H | OCH3 | C(CH3)(OCH3)2 | |
| H | SO2CH3 | H | OCH3 | C(CH3)(OCH3)2 | |
| H | CO2CH3 | H | OCH3 | C(CH3)(OCH3)2 | |

TABLE 7f

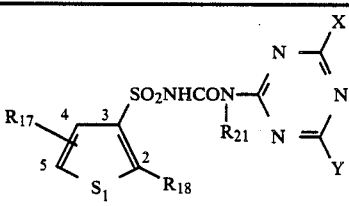

| R17 | R18 | R21 | X | Y | m.p. (°C.) |
|---|---|---|---|---|---|
| H | CO2CH3 | H | CH3 | CH2OTHP | |

TABLE 7f-continued

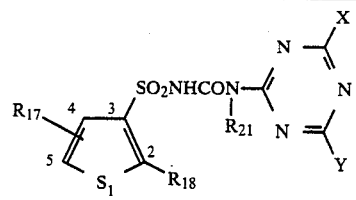

| $R_{17}$ | $R_{18}$ | $R_{21}$ | X | Y | m.p. (°C.) |
|---|---|---|---|---|---|
| 4-CH₃ | CO₂CH₃ | H | CH₃ | CH₂OTHP | |
| H | CO₂CH₂CH₃ | H | OCH₃ | CH₂OTHP | |
| H | CO₂CH₂CH=CH₂ | H | CH₂CH₃ | CH₂OTHP | |
| H | H | H | CH₃ | CH₂OTHP | |
| H | SCH₂CH₂CH₃ | H | OCH₃ | CH₂OTHP | |
| H | SCH₃ | H | CH₃ | CH₂OTHP | |
| H | CH(CH₃)₂ | H | OCH₃ | CH₂OTHP | |
| H | CH₂CH₃ | H | CH₃ | CH₂OTHP | |
| H | F | H | OCH₂CH₃ | CH₂OTHP | |
| H | Cl | H | OCH₃ | CH₂OTHP | |
| 5-Cl | Cl | H | CH₃ | CH₂OTHP | |
| H | Br | CH₃ | OCH₃ | CH₂OTHP | |
| H | NO₂ | H | CH₃ | CH₂OTHP | |
| H | SO₂N(CH₃)CH₂CH₃ | CH₃ | CH₃ | CH₂OTHP | |
| H | SO₂N(CH₃)₂ | H | OCH₃ | CH₂OTHP | |
| H | SO₂N(OCH₃)CH₃ | H | OCH₃ | CH₂OTHP | |
| H | OCH₃ | H | CH₃ | CH₂OTHP | |
| 5-OCH₃ | OCH₃ | H | CH₃ | CH₂OTHP | |
| 5-F | O(CH₂)₃CH₃ | H | OCH₃ | CH₂OTHP | |
| H | SO₂CH₂CH₂CH₃ | H | OCH₃ | CH₂OTHP | |
| H | SO₂CH₃ | H | CH₃ | CH₂OTHP | |
| 4-Br | SO₂CH₃ | H | CH₃ | CH₂OTHP | |

TABLE 7g

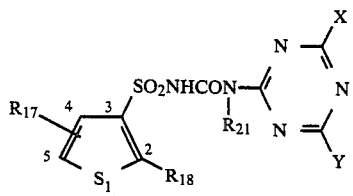

| $R_{17}$ | $R_{18}$ | $R_{21}$ | X | Y | m.p. (°C.) |
|---|---|---|---|---|---|
| H | CO₂CH₃ | H | CH₃ | CH₂OH | |
| 4-CH₃ | CO₂CH₃ | H | CH₃ | CH₂OH | |
| H | CO₂CH₂CH₃ | CH₃ | OCH₃ | CH₂OH | |
| H | CO₂CH₂CH=CH₂ | H | CH₃ | CH₂OH | |
| H | H | H | CH₃ | CH₂OH | |
| H | SCH₂CH₂CH₃ | H | OCH₃ | CH₂OH | |
| H | SCH₃ | H | CH₃ | CH₂OH | |
| H | CH(CH₃)₂ | H | OCH₃ | CH₂OH | |
| H | CH₂CH₃ | H | CH₃ | CH₂OH | |
| H | F | H | OCH₃ | CH₂OH | |
| H | Cl | H | OCH₂CH₃ | CH₂OH | |
| 5-Cl | Cl | H | CH₂CH₃ | CH₂OH | |
| H | Br | H | OCH₃ | CH₂OH | |
| H | NO₂ | H | CH₃ | CH₂OH | |
| H | SO₂N(CH₃)CH₂CH₃ | H | CH₃ | CH₂OH | |
| H | SO₂N(CH₃)₂ | H | OCH₃ | CH₂OH | |
| H | SO₂N(OCH₃)CH₃ | H | OCH₃ | CH₂OH | |
| H | OCH₃ | H | CH₃ | CH₂OH | |
| 5-OCH₃ | OCH₃ | H | CH₃ | CH₂OH | |
| 5-F | O(CH₂)₃CH₃ | H | OCH₃ | CH₂OH | |
| H | SO₂CH₂CH₂CH₃ | H | OCH₃ | CH₂OH | |
| H | SO₂CH₃ | H | CH₃ | CH₂OH | |
| 4-Br | SO₂CH₃ | H | CH₃ | CH₂OH | |

TABLE 7h

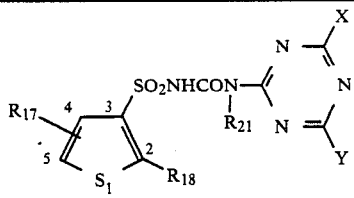

| R17 | R18 | R21 | X | Y | m.p. (°C.) |
|---|---|---|---|---|---|
| H | $CO_2CH_3$ | H | $CH_3$ | $CH(OC_2H_5)_2$ | |
| 4-$CH_3$ | $CO_2CH_3$ | H | $CH_3$ | $CH_2OCOCH_3$ | |
| H | $CO_2CH_3$ | H | $OCH_3$ | $CH_2SCH_3$ | |
| H | $CO_2CH_2CH=CH_2$ | H | $CH_3$ | $CH_2OCONHCH_3$ | |
| H | H | H | $CH_3$ | $CH_2OCO_2CH_3$ | |
| H | $SCH_2CH_2CH_3$ | H | $OCH_3$ | $CH_2SC_2H_5$ | |
| H | $SCH_3$ | H | $CH_3$ | $CH(OCH_2CH_2O)$ | |
| H | $CH(CH_3)_2$ | H | $OCH_3$ | $CH_2OCOC_2H_5$ | |
| H | $CH_2CH_3$ | $CH_3$ | $CH_3$ | $CH(OCH(CH_3)CH_2O)$ | |
| H | F | H | $OCH_3$ | $CH(OCH_2CH_2CH_2O)$ | |
| H | Cl | H | $OCH_3$ | $CH_2SCH_3$ | |
| 5-Cl | Cl | H | $CH_2CH_3$ | $CH_2OCOCH_3$ | |
| H | Br | H | $OCH_2CH_3$ | $CH_2OCON(CH_3)_2$ | |
| H | $NO_2$ | H | $CH_3$ | $CH(OCH_2CH_2O)$ | |
| H | $SO_2N(CH_3)C_2H_5$ | H | $CH_3$ | $CH_2OCOCH_3$ | |
| H | $SO_2N(CH_3)_2$ | H | $OCH_3$ | $CH_2SCH_2CH_3$ | |
| H | $SO_2N(OCH_3)CH_3$ | H | $CH_3$ | $CH(OC_2H_5)_2$ | |
| H | $OCH_3$ | H | $CH_3$ | $CH_2OCO_2C_2H_5$ | |
| 5-$OCH_3$ | $OCH_3$ | H | $CH_3$ | $CH_2OCON(C_2H_5)_2$ | |
| 5-F | $O(CH_2)_3CH_3$ | H | $OCH_3$ | $CH_2OCON(C_2H_5)_2$ | |
| H | $SO_2CH_2CH_2CH_3$ | H | $CH_3$ | $CH_2OCO(i-C_3H_7)$ | |
| H | $SO_2CH_3$ | H | $CH_3$ | $CH_2OCONH(n-C_3H_7)$ | |
| H | $CO_2CH_3$ | H | $CH_3$ | $C(CH_3)(OCH_2CH_2CH_2O)$ | |
| H | $CO_2CH_3$ | H | $OCH_3$ | $C(CH_3)(SCH_3)_2$ | |
| H | $CO_2CH_3$ | H | $OCH_3$ | $CH(SCH_3)_2$ | |
| H | Cl | H | $OCH_3$ | $CH_2SO_2CH_2CH_3$ | |

TABLE 8a

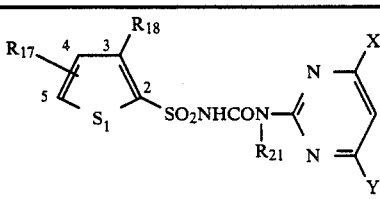

| R17 | R18 | R21 | X | Y | m.p. (°C.) |
|---|---|---|---|---|---|
| H | $CO_2CH_3$ | H | $CH_3$ | $CH(OCH_3)_2$ | |
| 4-$CH_3$ | $CO_2CH_3$ | H | $CH_3$ | $CH(OCH_3)_2$ | |
| H | $CO_2CH_3$ | H | $OCH_3$ | $CH(OCH_3)_2$ | |
| H | $CO_2CH_2CH=CH_2$ | H | $CH_3$ | $CH(OCH_3)_2$ | |
| H | H | H | $CH_2CH_3$ | $CH(OCH_3)_2$ | |
| H | $SCH_2CH_2CH_3$ | H | $OCH_2CH_3$ | $CH(OCH_3)_2$ | |
| H | $SCH_3$ | H | $CH_3$ | $CH(OCH_3)_2$ | |
| H | $CH(CH_3)_2$ | H | $OCH_3$ | $CH(OCH_3)_2$ | |
| H | $CH_2CH_3$ | H | $CH_3$ | $CH(OCH_3)_2$ | |
| H | F | H | $OCH_3$ | $CH(OCH_3)_2$ | |
| H | Cl | H | $OCH_3$ | $CH(OCH_3)_2$ | |
| 5-Cl | Cl | H | $CH_3$ | $CH(OCH_3)_2$ | |
| H | Br | H | $OCH_3$ | $CH(OCH_3)_2$ | |
| H | $NO_2$ | H | $CH_3$ | $CH(OCH_3)_2$ | |
| H | $SO_2N(CH_3)CH_2CH_3$ | H | $CH_3$ | $CH(OCH_3)_2$ | |
| H | $SO_2N(CH_3)_2$ | H | $OCH_3$ | $CH(OCH_3)_2$ | |
| H | $SO_2N(OCH_3)CH_3$ | H | $OCH_3$ | $CH(OCH_3)_2$ | |
| H | $OCH_3$ | $CH_3$ | $CH_3$ | $CH(OCH_3)_2$ | |
| 5-$OCH_3$ | $OCH_3$ | H | $OCH_3$ | $CH(OCH_3)_2$ | |
| 5-F | $O(CH_2)_3CH_3$ | H | $OCH_3$ | $CH(OCH_3)_2$ | |
| H | $SO_2CH_2CH_2CH_3$ | H | $OCH_3$ | $CH(OCH_3)_2$ | |
| H | $SO_2CH_3$ | H | $CH_3$ | $CH(OCH_3)_2$ | |
| 4-Br | $SO_2CH_3$ | H | $CH_3$ | $CH(OCH_3)_2$ | |
| H | $CO_2CH_3$ | H | Cl | $CH(OCH_3)_2$ | |
| H | $NO_2$ | H | Cl | $CH(OCH_3)_2$ | |
| H | $CH_3$ | H | $CH_3$ | $C(CH_3)(OCH_3)_2$ | |
| H | $CH_3$ | H | $OCH_3$ | $C(CH_3)(OCH_3)_2$ | |
| H | $SCH_3$ | H | $CH_3$ | $C(CH_3)(OCH_3)_2$ | |
| H | Br | H | $OCH_3$ | $C(CH_3)(OCH_3)_2$ | |

TABLE 8a-continued

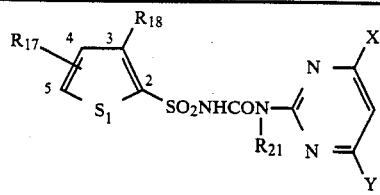

| R17 | R18 | R21 | X | Y | m.p. (°C.) |
|---|---|---|---|---|---|
| H | SO2CH2CH2CH3 | H | Cl | CH(OCH3)2 | |
| H | SO2CH3 | H | Cl | CH(OCH3)2 | |
| H | SCH3 | H | Cl | CH(OCH3)2 | |
| H | SO2—n-C3H7 | H | CH3 | CH(OCH3)2 | 121–124° d |

TABLE 8b

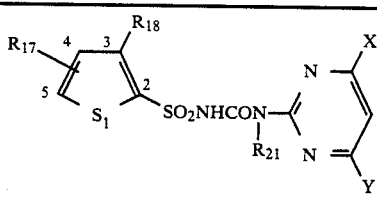

| R17 | R18 | R21 | X | Y | m.p. (°C.) |
|---|---|---|---|---|---|
| H | CO2CH3 | H | CH3 | CH2OTHP | |
| 4-CH3 | CO2CH3 | H | CH3 | CH2OTHP | |
| H | CO2CH2CH3 | H | OCH3 | CH2OTHP | |
| H | CO2CH2CH=CH2 | H | CH3 | CH2OTHP | |
| H | H | H | CH3 | CH2OTHP | |
| H | SCH2CH2CH3 | H | OCH3 | CH2OTHP | |
| H | SCH3 | H | CH3 | CH2OTHP | |
| H | CH(CH3)2 | H | OCH3 | CH2OTHP | |
| H | CH2CH3 | H | CH3 | CH2OTHP | |
| H | F | H | OCH3 | CH2OTHP | |
| H | Cl | H | OCH3 | CH2OTHP | |
| 5-Cl | Cl | H | CH3 | CH2OTHP | |
| H | Br | H | OCH3 | CH2OTHP | |
| H | NO2 | CH3 | CH3 | CH2OTHP | |
| H | SO2N(CH3)CH2CH3 | H | CH3 | CH2OTHP | |
| H | SO2N(CH3)2 | H | OCH3 | CH2OTHP | |
| H | SO2N(OCH3)CH3 | H | OCH3 | CH2OTHP | |
| H | OCH3 | H | CH3 | CH2OTHP | |
| 5-OCH3 | OCH3 | H | CH3 | CH2OTHP | |
| 5-F | O(CH2)3CH3 | H | OCH3 | CH2OTHP | |
| H | SO2CH2CH2CH3 | H | OCH2CH3 | CH2OTHP | |
| H | SO2CH3 | H | CH2CH3 | CH2OTHP | |
| 4-Br | SO2CH3 | H | CH3 | CH2OTHP | |

TABLE 8c

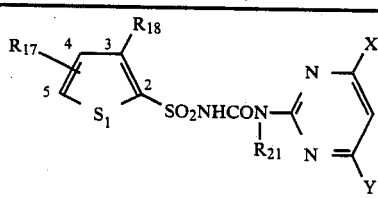

| R17 | R18 | R21 | X | Y | m.p. (°C.) |
|---|---|---|---|---|---|
| H | CO2CH3 | H | CH3 | CH2OH | |
| 4-CH3 | CO2CH3 | H | CH2CH3 | CH2OH | |
| H | CO2CH2CH3 | H | OCH2CH3 | CH2OH | |
| H | CO2CH2CH=CH2 | H | CH3 | CH2OH | |
| H | H | H | CH3 | CH2OH | |
| H | SCH2CH2CH3 | H | OCH3 | CH2OH | |
| H | SCH3 | CH3 | CH3 | CH2OH | |
| H | CH(CH3)2 | H | OCH3 | CH2OH | |
| H | CH2CH3 | H | CH3 | CH2OH | |
| H | F | H | OCH3 | CH2OH | |
| H | Cl | H | OCH3 | CH2OH | |
| 5-Cl | Cl | H | CH3 | CH2OH | |
| H | Br | H | OCH3 | CH2OH | |

TABLE 8c-continued

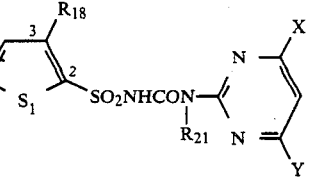

| R17 | R18 | R21 | X | Y | m.p. (°C.) |
|---|---|---|---|---|---|
| H | NO2 | H | CH3 | CH2OH | |
| H | SO2N(CH3)CH2CH3 | H | CH3 | CH2OH | |
| H | SO2N(CH3)2 | H | OCH3 | CH2OH | |
| H | SO2N(OCH3)CH3 | H | OCH3 | CH2OH | |
| H | OCH3 | H | CH3 | CH2OH | |
| 5-OCH3 | OCH3 | H | CH3 | CH2OH | |
| 5-F | O(CH2)3CH3 | H | OCH3 | CH2OH | |
| H | SO2CH2CH2CH3 | H | OCH3 | CH2OH | |
| H | SO2CH3 | H | CH3 | CH2OH | |
| 4-Br | SO2CH3 | H | CH3 | CH2OH | |

TABLE 8d

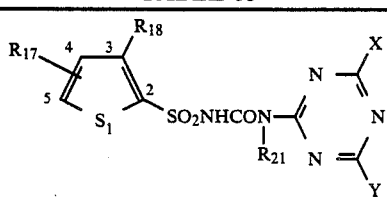

| R17 | R18 | R21 | X | Y | m.p. (°C.) |
|---|---|---|---|---|---|
| H | CO2CH3 | H | CH3 | CH(OC2H5)2 | |
| 4-CH3 | CO2CH3 | H | CH3 | CH2OCOCH3 | |
| H | CO2CH3 | H | OCH3 | CH2SCH3 | |
| H | CO2CH2CH=CH2 | H | CH3 | CH2OCONHCH3 | |
| H | H | H | CH3 | CH2OCO2CH3 | |
| H | SCH2CH2CH3 | H | OCH2CH3 | CH2SC2H5 | |
| H | SCH3 | H | CH2CH3 | CH(OCH2CH2O) | |
| H | CH(CH3)2 | H | OCH3 | CH2OCOC2H5 | |
| H | CH2CH3 | H | CH3 | CH(OCH(CH3)CH2O) | |
| H | F | H | OCH3 | CH(OCH2CH2CH2O) | |
| H | Cl | H | OCH3 | CH2SCH3 | |
| 5-Cl | Cl | H | CH3 | CH2OCOCH3 | |
| H | Br | H | OCH3 | CH2OCON(CH3)2 | |
| H | NO2 | H | CH3 | CH(OCH2CH2O) | |
| H | SO2N(CH3)C2H5 | H | CH3 | CH2OCOCH3 | |
| H | SO2N(CH3)2 | H | OCH3 | CH2SCH2CH3 | |
| H | SO2N(OCH3)CH3 | H | CH3 | CH(OC2H5)2 | |
| H | OCH3 | CH3 | CH3 | CH2OCO2C2H5 | |
| 5-OCH3 | OCH3 | H | CH3 | CH2OCON(C2H5)2 | |
| 5-F | O(CH2)3CH3 | H | OCH3 | CH2OCON(C2H5)2 | |
| H | SO2CH2CH2CH3 | H | CH3 | CH2OCO(i-C3H7) | |
| H | SO2CH3 | H | CH3 | CH2OCONH(n-C3H7) | |
| H | Cl | H | CH3 | CH2SO2CH3 | |
| H | Br | H | CH3 | CH(SCH3)2 | |
| H | F | H | CH3 | CH2SO2CH2CH3 | |
| H | SO2N(CH3)2 | H | OCH3 | C(CH3)(OCH2CH3)2 | |

TABLE 8e

| R17 | R18 | R21 | X | Y | m.p. (°C.) |
|---|---|---|---|---|---|
| H | CO2CH3 | H | CH3 | CH(OCH3)2 | |
| 4-CH3 | CO2CH3 | H | CH3 | CH(OCH3)2 | |
| H | CO2CH3 | H | OCH3 | CH(OCH3)2 | |
| H | CO2CH2CH=CH2 | H | CH3 | CH(OCH3)2 | |

TABLE 8e-continued

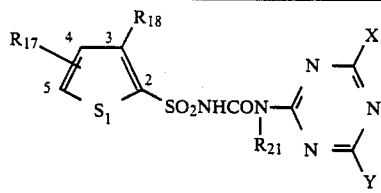

| R17 | R18 | R21 | X | Y | m.p. (°C.) |
|---|---|---|---|---|---|
| H | H | H | CH3 | CH(OCH3)2 | |
| H | SCH2CH2CH3 | H | OCH3 | CH(OCH3)2 | |
| H | SCH3 | H | CH3 | CH(OCH3)2 | |
| H | CH(CH3)2 | H | OCH3 | CH(OCH3)2 | |
| H | CH2CH3 | H | CH3 | CH(OCH3)2 | |
| H | F | H | OCH3 | CH(OCH3)2 | |
| H | Cl | H | OCH3 | CH(OCH3)2 | |
| 5-Cl | Cl | H | CH3 | CH(OCH3)2 | |
| H | Br | H | OCH3 | CH(OCH3)2 | |
| H | NO2 | H | CH3 | CH(OCH3)2 | |
| H | SO2N(CH3)CH2CH3 | H | CH2CH3 | CH(OCH3)2 | |
| H | SO2N(CH3)2 | H | OCH2CH3 | CH(OCH3)2 | |
| H | SO2N(OCH3)CH3 | CH3 | OCH3 | CH(OCH3)2 | |
| H | OCH3 | H | CH3 | CH(OCH3)2 | |
| 5-OCH3 | OCH3 | H | CH3 | CH(OCH3)2 | |
| 5-F | O(CH2)3CH3 | H | OCH3 | CH(OCH3)2 | |
| H | SO2CH2CH2CH3 | H | OCH3 | CH(OCH3)2 | |
| H | SO2CH3 | H | CH3 | CH(OCH3)2 | |
| 4-Br | SO2CH3 | H | CH3 | CH(OCH3)2 | |
| H | OCH3 | H | CH2CH3 | C(CH2CH3)(OCH3)2 | |
| H | SCH3 | H | CH3 | C(CH3)(OCH3)2 | |
| H | CH2CH3 | H | OCH3 | C(CH3)(OCH3)2 | |
| H | CH3 | H | OCH3 | C(CH3)(OCH3)2 | |

TABLE 8f

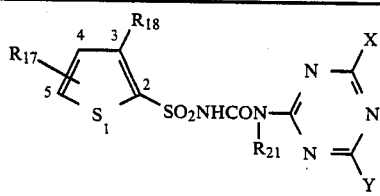

| R17 | R18 | R21 | X | Y | m.p. (°C.) |
|---|---|---|---|---|---|
| H | CO2CH3 | H | CH3 | CH2OTHP | |
| 4-CH3 | CO2CH3 | H | CH3 | CH2OTHP | |
| H | CO2CH2CH3 | H | OCH3 | CH2OTHP | |
| H | CO2CH2CH=CH2 | H | CH3 | CH2OTHP | |
| H | H | H | CH3 | CH2OTHP | |
| H | SCH2CH2CH3 | H | OCH3 | CH2OTHP | |
| H | SCH3 | H | CH3 | CH2OTHP | |
| H | CH(CH3)2 | H | OCH3 | CH2OTHP | |
| H | CH2CH3 | H | CH3 | CH2OTHP | |
| H | F | H | OCH3 | CH2OTHP | |
| H | Cl | CH3 | OCH3 | CH2OTHP | |
| 5-Cl | Cl | H | CH3 | CH2OTHP | |
| H | Br | H | OCH2CH3 | CH2OTHP | |
| H | NO2 | H | CH2CH3 | CH2OTHP | |
| H | SO2N(CH3)CH2CH3 | H | CH3 | CH2OTHP | |
| H | SO2N(CH3)2 | H | OCH3 | CH2OTHP | |
| H | SO2N(OCH3)CH3 | H | OCH3 | CH2OTHP | |
| H | OCH3 | H | CH3 | CH2OTHP | |
| 5-OCH3 | OCH3 | H | CH3 | CH2OTHP | |
| 5-F | O(CH2)3CH3 | H | OCH3 | CH2OTHP | |
| H | SO2CH2CH2CH3 | H | OCH3 | CH2OTHP | |
| H | SO2CH3 | H | CH3 | CH2OTHP | |
| 4-Br | SO2CH3 | H | CH3 | CH2OTHP | |

TABLE 8g

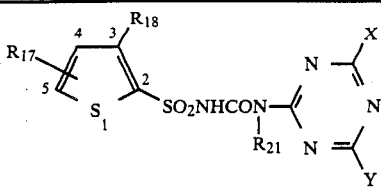

| $R_{17}$ | $R_{18}$ | $R_{21}$ | X | Y | m.p. (°C.) |
|---|---|---|---|---|---|
| H | $CO_2CH_3$ | H | $CH_3$ | $CH_2OH$ | |
| 4-$CH_3$ | $CO_2CH_3$ | H | $CH_2CH_3$ | $CH_2OH$ | |
| H | $CO_2CH_2CH_3$ | H | $OCH_2CH_3$ | $CH_2OH$ | |
| H | $CO_2CH_2CH=CH_2$ | H | $CH_3$ | $CH_2OH$ | |
| H | H | H | $CH_3$ | $CH_2OH$ | |
| H | $SCH_2CH_2CH_3$ | H | $OCH_3$ | $CH_2OH$ | |
| H | $SCH_3$ | H | $CH_3$ | $CH_2OH$ | |
| H | $CH(CH_3)_2$ | H | $OCH_3$ | $CH_2OH$ | |
| H | $CH_2CH_3$ | H | $CH_3$ | $CH_2OH$ | |
| H | F | H | $OCH_3$ | $CH_2OH$ | |
| H | Cl | H | $OCH_3$ | $CH_2OH$ | |
| 5-Cl | Cl | H | $CH_3$ | $CH_2OH$ | |
| H | Br | H | $OCH_3$ | $CH_2OH$ | |
| H | $NO_2$ | H | $CH_3$ | $CH_2OH$ | |
| H | $SO_2N(CH_3)CH_2CH_3$ | H | $CH_3$ | $CH_2OH$ | |
| H | $SO_2N(CH_3)_2$ | H | $OCH_3$ | $CH_2OH$ | |
| H | $SO_2N(OCH_3)CH_3$ | H | $OCH_3$ | $CH_2OH$ | |
| H | $OCH_3$ | H | $CH_3$ | $CH_2OH$ | |
| 5-$OCH_3$ | $OCH_3$ | H | $CH_3$ | $CH_2OH$ | |
| 5-F | $O(CH_2)_3CH_3$ | H | $OCH_3$ | $CH_2OH$ | |
| H | $SO_2CH_2CH_2CH_3$ | $CH_3$ | $OCH_3$ | $CH_2OH$ | |
| H | $SO_2CH_3$ | $CH_3$ | $CH_3$ | $CH_2OH$ | |
| 4-Br | $SO_2CH_3$ | H | $CH_3$ | $CH_2OH$ | |

TABLE 8h

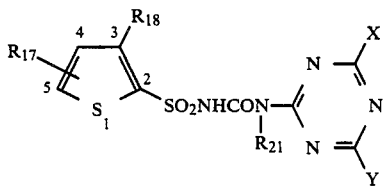

| $R_{17}$ | $R_{18}$ | $R_{21}$ | X | Y | m.p. (°C.) |
|---|---|---|---|---|---|
| H | $CO_2CH_3$ | H | $CH_3$ | $CH(OC_2H_5)_2$ | |
| 4-$CH_3$ | $CO_2CH_3$ | H | $CH_3$ | $CH_2OCOCH_3$ | |
| H | $CO_2CH_3$ | $CH_3$ | $OCH_3$ | $CH_2SCH_3$ | |
| H | $CO_2CH_2CH=CH_2$ | $CH_3$ | $CH_3$ | $CH_2OCONHCH_3$ | |
| H | H | H | $CH_3$ | $CH_2OCO_2CH_3$ | |
| H | $SCH_2CH_2CH_3$ | H | $OCH_3$ | $CH_2SC_2H_5$ | |
| H | $SCH_3$ | H | $CH_3$ | $CH(OCH_2CH_2O)$ | |
| H | $CH(CH_3)_2$ | H | $OCH_3$ | $CH_2OCOC_2H_5$ | |
| H | $CH_2CH_3$ | H | $CH_3$ | $CH(OCH(CH_3)CH_2O)$ | |
| H | F | H | $OCH_3$ | $CH(OCH_2CH_2CH_2O)$ | |
| H | Cl | H | $OCH_2CH_3$ | $CH_2SCH_3$ | |
| 5-Cl | Cl | H | $CH_2CH_3$ | $CH_2OCOCH_3$ | |
| H | Br | H | $OCH_3$ | $CH_2OCON(CH_3)_2$ | |
| H | $NO_2$ | H | $CH_3$ | $CH(OCH_2CH_2O)$ | |
| H | $SO_2N(CH_3)C_2H_5$ | H | $CH_3$ | $CH_2OCOCH_3$ | |
| H | $SO_2N(CH_3)_2$ | H | $OCH_3$ | $CH_2SCH_2CH_3$ | |
| H | $SO_2N(OCH_3)CH_3$ | H | $CH_3$ | $CH(OC_2H_5)_2$ | |
| H | $OCH_3$ | H | $CH_3$ | $CH_2OCO_2C_2H_5$ | |
| 5-$OCH_3$ | $OCH_3$ | H | $CH_3$ | $CH_2OCON(C_2H_5)_2$ | |
| 5-F | $O(CH_2)_3CH_3$ | H | $OCH_3$ | $CH_2OCON(C_2H_5)_2$ | |
| H | $SO_2CH_2CH_2CH_3$ | H | $CH_3$ | $CH_2OCO(i-C_3H_7)$ | |
| H | $SO_2CH_3$ | H | $CH_3$ | $CH_2OCONH(n-C_3H_7)$ | |
| H | Br | H | $OCH_3$ | $C(CH_3)(SCH_3)_2$ | |
| H | $NO_2$ | H | $OCH_3$ | $CH_2SO_2CH_3$ | |
| H | $SO_2CH_2CH_3$ | H | $OCH_3$ | $CH(CH_3)SCH_3$ | |
| H | $CO_2CH_3$ | H | $CH_3$ | $C(CH_2CH_3)(OCH_2CH_2O)$ | |

TABLE 9a

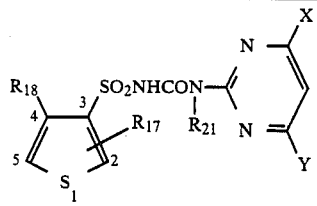

| R17 | R18 | R21 | X | Y | m.p. (°C.) |
|---|---|---|---|---|---|
| H | CO2CH3 | H | CH3 | CH(OCH3)2 | |
| H | CO2CH3 | H | OCH3 | CH(OCH3)2 | |
| H | CO2CH2CH=CH2 | H | CH3 | CH(OCH3)2 | |
| H | H | H | CH3 | CH(OCH3)2 | |
| H | SCH2CH2CH3 | H | OCH3 | CH(OCH3)2 | |
| H | SCH3 | H | CH3 | CH(OCH3)2 | |
| H | CH(CH3)2 | H | OCH3 | CH(OCH3)2 | |
| H | CH2CH3 | H | CH3 | CH(OCH3)2 | |
| H | F | CH3 | OCH3 | CH(OCH3)2 | |
| H | Cl | H | OCH3 | CH(OCH3)2 | |
| 5-Cl | Cl | CH3 | CH3 | CH(OCH3)2 | |
| H | Br | H | OCH2CH3 | CH(OCH3)2 | |
| H | NO2 | H | CH2CH3 | CH(OCH3)2 | |
| H | SO2N(CH3)CH2CH3 | H | CH3 | CH(OCH3)2 | |
| H | SO2N(CH3)2 | H | OCH3 | CH(OCH3)2 | |
| H | SO2N(OCH3)CH3 | H | OCH3 | CH(OCH3)2 | |
| H | OCH3 | H | CH3 | CH(OCH3)2 | |
| 5-OCH3 | OCH3 | H | CH3 | CH(OCH3)2 | |
| 5-F | O(CH2)3CH3 | H | OCH3 | CH(OCH3)2 | |
| H | SO2CH2CH2CH3 | H | OCH3 | CH(OCH3)2 | |
| H | SO2CH3 | H | CH3 | CH(OCH3)2 | |
| H | CO2CH3 | H | Cl | CH(OCH3)2 | |
| H | NO2 | H | Cl | CH(OCH3)2 | |
| H | SO2CH2CH2CH3 | H | Cl | CH(OCH3)2 | |
| H | SO2CH3 | H | Cl | CH(OCH3)2 | |
| H | SCH3 | H | Cl | CH(OCH3)2 | |
| H | CO2CH3 | H | OCH3 | C(CH3)(OCH3)2 | |
| H | SO2CH3 | H | OC2H5 | C(CH3)(OCH3)2 | |
| H | Br | H | CH3 | C(CH3)(OCH3)2 | |
| H | F | CH3 | OCH3 | C(CH3)(OCH3)2 | |

TABLE 9b

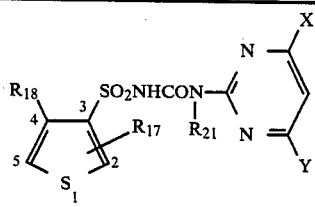

| R17 | R18 | R21 | X | Y | m.p. (°C.) |
|---|---|---|---|---|---|
| H | CO2CH3 | H | CH3 | CH2OTHP | |
| H | CO2CH2CH3 | H | OCH3 | CH2OTHP | |
| H | CO2CH2CH=CH2 | H | CH3 | CH2OTHP | |
| H | H | H | CH3 | CH2OTHP | |
| H | SCH2CH2CH3 | H | OCH3 | CH2OTHP | |
| H | SCH3 | H | CH3 | CH2OTHP | |
| H | CH(CH3)2 | H | OCH3 | CH2OTHP | |
| H | CH2CH3 | H | CH3 | CH2OTHP | |
| H | F | H | OCH3 | CH2OTHP | |
| H | Cl | H | OCH2CH3 | CH2OTHP | |
| 5-Cl | Cl | H | CH2CH3 | CH2OTHP | |
| H | Br | H | OCH3 | CH2OTHP | |
| H | NO2 | H | CH3 | CH2OTHP | |
| H | SO2N(CH3)CH2CH3 | H | CH3 | CH2OTHP | |
| H | SO2N(CH3)2 | H | OCH3 | CH2OTHP | |
| H | SO2N(OCH3)CH3 | H | OCH3 | CH2OTHP | |
| H | OCH3 | CH3 | CH3 | CH2OTHP | |
| 5-OCH3 | OCH3 | H | CH3 | CH2OTHP | |
| 5-F | O(CH2)3CH3 | H | OCH3 | CH2OTHP | |
| H | SO2CH2CH2CH3 | H | OCH3 | CH2OTHP | |
| H | SO2CH3 | H | CH3 | CH2OTHP | |

TABLE 9c

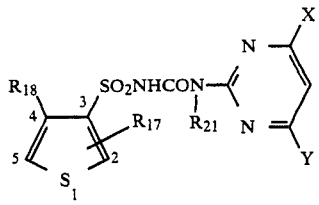

| R₁₇ | R₁₈ | R₂₁ | X | Y | m.p. (°C.) |
|---|---|---|---|---|---|
| H | CO$_2$CH$_3$ | H | CH$_3$ | CH$_2$OH | |
| H | CO$_2$CH$_2$CH$_3$ | H | OCH$_3$ | CH$_2$OH | |
| H | CO$_2$CH$_2$CH=CH$_2$ | H | CH$_3$ | CH$_2$OH | |
| H | H | H | CH$_3$ | CH$_2$OH | |
| H | SCH$_2$CH$_2$CH$_3$ | H | OCH$_3$ | CH$_2$OH | |
| H | SCH$_3$ | CH$_3$ | CH$_3$ | CH$_2$OH | |
| H | CH(CH$_3$)$_2$ | H | OCH$_3$ | CH$_2$OH | |
| H | CH$_2$CH$_3$ | H | CH$_3$ | CH$_2$OH | |
| H | F | H | OCH$_3$ | CH$_2$OH | |
| H | Cl | H | OCH$_2$CH$_3$ | CH$_2$OH | |
| 5-Cl | Cl | H | CH$_2$CH$_3$ | CH$_2$OH | |
| H | Br | H | OCH$_3$ | CH$_2$OH | |
| H | NO$_2$ | H | CH$_3$ | CH$_2$OH | |
| H | SO$_2$N(CH$_3$)CH$_2$CH$_3$ | H | CH$_3$ | CH$_2$OH | |
| H | SO$_2$N(CH$_3$)$_2$ | H | OCH$_3$ | CH$_2$OH | |
| H | SO$_2$N(OCH$_3$)CH$_3$ | H | OCH$_3$ | CH$_2$OH | |
| H | OCH$_3$ | H | CH$_3$ | CH$_2$OH | |
| 5-OCH$_3$ | OCH$_3$ | H | CH$_3$ | CH$_2$OH | |
| 5-F | O(CH$_2$)$_3$CH$_3$ | H | OCH$_3$ | CH$_2$OH | |
| H | SO$_2$CH$_2$CH$_2$CH$_3$ | H | OCH$_3$ | CH$_2$OH | |
| H | SO$_2$CH$_3$ | H | CH$_3$ | CH$_2$OH | |

TABLE 9d

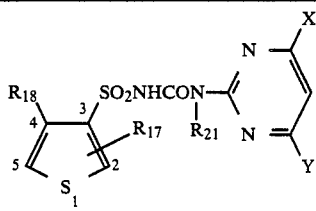

| R₁₇ | R₁₈ | R₂₁ | X | Y | m.p. (°C.) |
|---|---|---|---|---|---|
| H | CO$_2$CH$_3$ | H | CH$_3$ | CH(OC$_2$H$_5$)$_2$ | |
| H | CO$_2$CH$_3$ | H | OCH$_3$ | CH$_2$SCH$_3$ | |
| H | CO$_2$CH$_2$CH=CH$_2$ | H | CH$_3$ | CH$_2$OCONHCH$_3$ | |
| H | H | H | CH$_3$ | CH$_2$OCO$_2$CH$_3$ | |
| H | SCH$_2$CH$_2$CH$_3$ | H | OCH$_3$ | CH$_2$SC$_2$H$_5$ | |
| H | SCH$_3$ | H | CH$_3$ | CH(OCH$_2$CH$_2$O) | |
| H | CH(CH$_3$)$_2$ | H | OCH$_3$ | CH$_2$OCOC$_2$H$_5$ | |
| H | CH$_2$CH$_3$ | H | CH$_3$ | CH(OCH(CH$_3$)CH$_2$O) | |
| H | F | H | OCH$_3$ | CH(OCH$_2$CH$_2$CH$_2$O) | |
| H | Cl | H | OCH$_2$CH$_3$ | CH$_2$SCH$_3$ | |
| 5-Cl | Cl | H | CH$_2$CH$_3$ | CH$_2$OCOCH$_3$ | |
| H | Br | CH$_3$ | OCH$_3$ | CH$_2$OCON(CH$_3$)$_2$ | |
| H | NO$_2$ | H | CH$_3$ | CH(OCH$_2$CH$_2$O) | |
| H | SO$_2$N(CH$_3$)C$_2$H$_5$ | H | CH$_3$ | CH$_2$OCOCH$_3$ | |
| H | SO$_2$N(CH$_3$)$_2$ | H | OCH$_3$ | CH$_2$SCH$_2$CH$_3$ | |
| H | SO$_2$N(OCH$_3$)CH$_3$ | H | CH$_3$ | CH(OC$_2$H$_5$)$_2$ | |
| H | OCH$_3$ | H | CH$_3$ | CH$_2$OCO$_2$C$_2$H$_5$ | |
| 5-OCH$_3$ | OCH$_3$ | H | CH$_3$ | CH$_2$OCON(C$_2$H$_5$)$_2$ | |
| 5-F | O(CH$_2$)$_3$CH$_3$ | H | CH$_3$ | CH$_2$OCON(C$_2$H$_5$)$_2$ | |
| H | SO$_2$CH$_2$CH$_2$CH$_3$ | H | CH$_3$ | CH$_2$OCO(i-C$_3$H$_7$) | |
| H | SO$_2$CH$_3$ | H | CH$_3$ | CH$_2$OCONH(n-C$_3$H$_7$) | |
| H | Cl | CH$_3$ | CH$_3$ | CH$_2$SO$_2$CH$_3$ | |
| H | CH$_3$ | H | CH$_3$ | CH$_2$SO$_2$CH$_3$ | |
| H | Br | H | CH$_3$ | CH$_2$SO$_2$CH$_3$ | |
| H | SCH$_3$ | H | OCH$_3$ | C(CH$_3$)(OEt)$_2$ | |
| H | CO$_2$CH$_3$ | H | OCH$_3$ | C(CH$_2$CH$_3$)(OCH$_2$CH$_2$CH$_2$O) | |

TABLE 9e

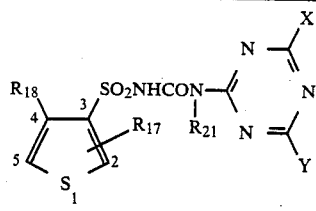

| R17 | R18 | R21 | X | Y | m.p. (°C.) |
|---|---|---|---|---|---|
| H | CO2CH3 | H | CH3 | CH(OCH3)2 | |
| H | CO2CH3 | H | OCH3 | CH(OCH3)2 | |
| H | CO2CH2CH=CH2 | H | CH3 | CH(OCH3)2 | |
| H | H | H | CH3 | CH(OCH3)2 | |
| H | SCH2CH2CH3 | CH3 | OCH3 | CH(OCH3)2 | |
| H | SCH3 | H | CH3 | CH(OCH3)2 | |
| H | CH(CH3)2 | H | OCH2CH3 | CH(OCH3)2 | |
| H | CH2CH3 | H | CH2CH3 | CH(OCH3)2 | |
| H | F | H | OCH3 | CH(OCH3)2 | |
| H | Cl | H | OCH3 | CH(OCH3)2 | |
| 5-Cl | Cl | H | CH3 | CH(OCH3)2 | |
| H | Br | H | OCH3 | CH(OCH3)2 | |
| H | NO2 | H | CH3 | CH(OCH3)2 | |
| H | SO2N(CH3)CH2CH3 | H | CH3 | CH(OCH3)2 | |
| H | SO2N(CH3)2 | H | OCH3 | CH(OCH3)2 | |
| H | SO2N(OCH3)CH3 | H | OCH3 | CH(OCH3)2 | |
| H | OCH3 | H | CH3 | CH(OCH3)2 | |
| 5-OCH3 | OCH3 | H | CH3 | CH(OCH3)2 | |
| 5-F | O(CH2)3CH3 | H | OCH3 | CH(OCH3)2 | |
| H | SO2CH2CH2CH3 | H | OCH3 | CH(OCH3)2 | |
| H | SO2CH3 | H | CH3 | CH(OCH3)2 | |
| H | SO2CH2CH3 | H | CH3 | C(CH3)(OCH3)2 | |
| H | NO2 | H | OCH3 | C(CH3)(OCH3)2 | |
| H | SO2N(CH3)2 | H | OCH3 | C(CH3)(OCH3)2 | |
| H | SCH2CH3 | H | OCH3 | C(CH3)(OCH3)2 | |
| H | Br | CH3 | CH3 | C(CH3)(OCH3)2 | |

TABLE 9f

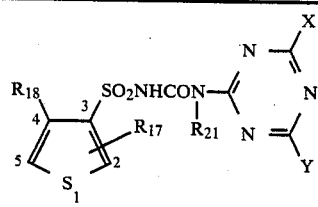

| R17 | R18 | R21 | X | Y | m.p. (°C.) |
|---|---|---|---|---|---|
| H | CO2CH3 | H | CH3 | CH2OTHP | |
| H | CO2CH2CH3 | H | OCH3 | CH2OTHP | |
| H | CO2CH2CH=CH2 | H | CH3 | CH2OTHP | |
| H | H | H | CH3 | CH2OTHP | |
| H | SCH2CH2CH3 | H | OCH2CH3 | CH2OTHP | |
| H | SCH3 | H | CH2CH3 | CH2OTHP | |
| H | CH(CH3)2 | H | OCH3 | CH2OTHP | |
| H | CH2CH3 | H | CH3 | CH2OTHP | |
| H | F | H | OCH3 | CH2OTHP | |
| H | Cl | H | OCH3 | CH2OTHP | |
| 5-Cl | Cl | H | CH3 | CH2OTHP | |
| H | Br | H | OCH3 | CH2OTHP | |
| H | NO2 | CH3 | CH3 | CH2OTHP | |
| H | SO2N(CH3)CH2CH3 | H | CH3 | CH2OTHP | |
| H | SO2N(CH3)2 | H | OCH3 | CH2OTHP | |
| H | SO2N(OCH3)CH3 | H | OCH3 | CH2OTHP | |
| H | OCH3 | H | CH3 | CH2OTHP | |
| 5-OCH3 | OCH3 | H | CH3 | CH2OTHP | |
| 5-F | O(CH2)3CH3 | H | OCH3 | CH2OTHP | |
| H | SO2CH2CH2CH3 | H | OCH3 | CH2OTHP | |
| H | SO2CH3 | H | CH3 | CH2OTHP | |

TABLE 9g

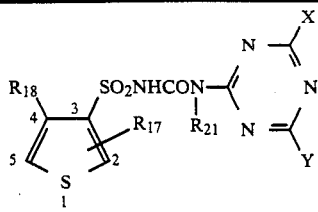

| $R_{17}$ | $R_{18}$ | $R_{21}$ | X | Y | m.p. (°C.) |
|---|---|---|---|---|---|
| H | $CO_2CH_3$ | H | $CH_3$ | $CH_2OH$ | |
| H | $CO_2CH_2CH_3$ | H | $OCH_3$ | $CH_2OH$ | |
| H | $CO_2CH_2CH=CH_2$ | H | $CH_3$ | $CH_2OH$ | |
| H | H | H | $CH_3$ | $CH_2OH$ | |
| H | $SCH_2CH_2CH_3$ | H | $OCH_3$ | $CH_2OH$ | |
| H | $SCH_3$ | H | $CH_3$ | $CH_2OH$ | |
| H | $CH(CH_3)_2$ | H | $OCH_3$ | $CH_2OH$ | |
| H | $CH_2CH_3$ | H | $CH_3$ | $CH_2OH$ | |
| H | F | H | $OCH_3$ | $CH_2OH$ | |
| H | Cl | H | $OCH_2CH_3$ | $CH_2OH$ | |
| 5-Cl | Cl | H | $CH_2CH_3$ | $CH_2OH$ | |

TABLE 9g-continued

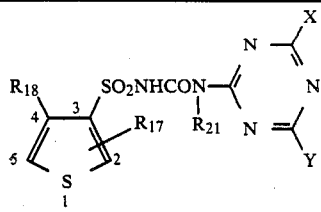

| $R_{17}$ | $R_{18}$ | $R_{21}$ | X | Y | m.p. (°C.) |
|---|---|---|---|---|---|
| H | Br | H | $OCH_3$ | $CH_2OH$ | |
| H | $NO_2$ | H | $CH_3$ | $CH_2OH$ | |
| H | $SO_2N(CH_3)CH_2CH_3$ | $CH_3$ | $CH_3$ | $CH_2OH$ | |
| H | $SO_2N(CH_3)_2$ | H | $OCH_3$ | $CH_2OH$ | |
| H | $SO_2N(OCH_3)CH_3$ | H | $OCH_3$ | $CH_2OH$ | |
| H | $OCH_3$ | H | $CH_3$ | $CH_2OH$ | |
| 5-$OCH_3$ | $OCH_3$ | H | $CH_3$ | $CH_2OH$ | |
| 5-F | $O(CH_2)_3CH_3$ | H | $OCH_3$ | $CH_2OH$ | |
| H | $SO_2CH_2CH_2CH_3$ | H | $OCH_3$ | $CH_2OH$ | |
| H | $SO_2CH_3$ | H | $CH_3$ | $CH_2OH$ | |

TABLE 9h

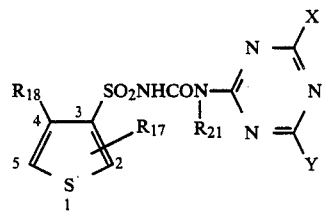

| $R_{17}$ | $R_{18}$ | $R_{21}$ | X | Y | m.p. (°C.) |
|---|---|---|---|---|---|
| H | $CO_2CH_3$ | H | $CH_3$ | $CH(OC_2H_5)_2$ | |
| H | $CO_2CH_3$ | $CH_3$ | $OCH_3$ | $CH_2SCH_3$ | |
| H | $CO_2CH_2CH=CH_2$ | H | $CH_3$ | $CH_2OCONHCH_3$ | |
| H | H | H | $CH_3$ | $CH_2OCO_2CH_3$ | |
| H | $SCH_2CH_2CH_3$ | H | $OCH_2CH_3$ | $CH_2SC_2H_5$ | |
| H | $SCH_3$ | H | $CH_2CH_3$ | $CH(OCH_2CH_2O)$ | |
| H | $CH(CH_3)_2$ | H | $OCH_3$ | $CH_2OCOC_2H_5$ | |
| H | $CH_2CH_3$ | H | $CH_3$ | $CH(OCH(CH_3)CH_2O)$ | |
| H | F | H | $OCH_3$ | $CH(SCH_2CH_2CH_2S)$ | |
| H | Cl | H | $OCH_3$ | $CH_2SCH_3$ | |
| 5-Cl | Cl | H | $CH_3$ | $CH_2OCOCH_3$ | |
| H | Br | H | $OCH_3$ | $CH_2OCON(CH_3)_2$ | |
| H | $NO_2$ | H | $CH_3$ | $CH(OCH_2CH_2O)$ | |
| H | $SO_2N(CH_3)C_2H_5$ | H | $CH_3$ | $CH_2OCOCH_3$ | |
| H | $SO_2N(CH_3)_2$ | H | $OCH_3$ | $CH_2SCH_2CH_3$ | |
| H | $SO_2N(OCH_3)CH_3$ | H | $CH_3$ | $CH(OC_2H_5)_2$ | |
| H | $OCH_3$ | H | $CH_3$ | $CH_2OCO_2C_2H_5$ | |
| 5-$OCH_3$ | $OCH_3$ | H | $CH_3$ | $CH_2OCON(C_2H_5)_2$ | |
| 5-F | $O(CH_2)_3CH_3$ | H | $OCH_3$ | $CH_2OCON(C_2H_5)_2$ | |
| H | $SO_2CH_2CH_2CH_3$ | H | $CH_3$ | $CH_2OCO(\underline{i}-C_3H_7)$ | |
| H | $SO_2CH_3$ | H | $CH_3$ | $CH_2OCONH(\underline{n}-C_3H_7)$ | |
| H | Br | H | $CH_3$ | $CH_2SO_2CH_3$ | |
| H | $NO_2$ | H | $CH_3$ | $CH(SCH_3)_2$ | |
| H | $SO_2N(CH_3)C_2H_5$ | H | $CH_3$ | $CH(CH_3)SCH_2CH_3$ | |
| H | $OCH_3$ | H | $OCH_3$ | $CH_2SO_2CH_2CH_3$ | |
| H | $CO_2CH_2CH_3$ | H | $OCH_3$ | $CH(SCH_2CH_2S)$ | |

TABLE 10a

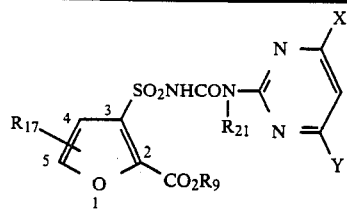

| R17 | R9 | R21 | X | Y | m.p. (°C.) |
|---|---|---|---|---|---|
| H | CH2CH=CH2 | H | CH3 | CH(OCH3)2 | |
| H | CH3 | H | CH3 | CH(OC2H5)2 | |
| H | CH3 | H | OCH3 | CH2SCH3 | |
| H | CH3 | H | CH2CH3 | CH2OH | |
| H | CH3 | H | OCH2CH3 | CH2OCOCH3 | |
| H | CH3 | H | CH3 | CH2OCONHC2H5 | |
| 5-F | C2H5 | H | OCH3 | CH(OCH3)2 | |
| 4-Br | CH3 | H | OCH3 | CH2OTHP | |
| 4-Br | CH3 | H | OCH3 | CH2OH | |
| 5-OCH3 | CH3 | H | CH3 | CH(OCH3)2 | |
| 5-Cl | CH3 | H | OCH3 | CH2OH | |
| 5-Cl | CH3 | H | CH3 | CH(OC2H5)2 | |
| 5-CH3 | CH3 | H | CH3 | CH(OCH3)2 | |
| 5-CH3 | CH3 | H | CH3 | CH2OTHP | |
| H | i-C3H7 | H | OCH3 | CH2OH | |
| H | CH2CH2OCH3 | CH3 | CH3 | CH2OH | |
| H | (CH2)3CH3 | H | CH3 | CH(OCH3)2 | |
| H | CH3 | H | OCH3 | CH(OCH3)2 | |
| H | CH3 | H | OCH3 | CH2OH | |
| H | CH2CH2Cl | H | CH3 | CH2OH | |
| H | CH3 | H | CH3 | CH2OCOC2H5 | |
| H | n-C3H7 | H | CH3 | CH(OCH3)2 | |
| H | CH3 | H | OCH3 | CH(OCH2CH2O) | |
| H | CH3 | H | CH3 | CH2OCO2CH3 | |
| H | C2H5 | H | CH3 | CH(OCH3)2 | |
| H | CH3 | H | OCH3 | CH(OC2H5)2 | |
| H | CH3 | H | OCH3 | CH2SO2CH3 | |
| H | CH3 | H | OCH3 | C(CH3)(OCH3)2 | |
| H | CH3 | H | OCH3 | CH(SCH3)2 | |

TABLE 10b

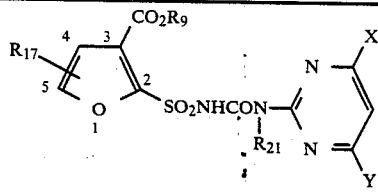

| R17 | R9 | R21 | X | Y | m.p. (°C.) |
|---|---|---|---|---|---|
| H | CH2CH=CH2 | H | CH3 | CH(OCH3)2 | |
| H | CH3 | CH3 | CH3 | CH(OC2H5)2 | |
| H | CH3 | H | OCH3 | CH2SCH3 | |
| H | CH3 | H | CH2CH3 | CH2OH | |
| H | CH3 | H | OCH2CH3 | CH2OCOCH3 | |
| H | CH3 | H | CH3 | CH2OCONHC2H5 | |
| 5-F | C2H5 | H | OCH3 | CH(OCH3)2 | |
| 4-Br | CH3 | H | OCH3 | CH2OTHP | |
| 4-Br | CH3 | H | OCH3 | CH2OH | |
| 5-OCH3 | CH3 | H | CH3 | CH(OCH3)2 | |
| 5-Cl | CH3 | H | OCH3 | CH2OH | |
| 5-Cl | CH3 | H | CH3 | CH(OC2H5)2 | |
| 5-CH3 | CH3 | H | CH3 | CH(OCH3)2 | |
| 5-CH3 | CH3 | H | CH3 | CH2OTHP | |
| H | i-C3H7 | H | OCH3 | CH2OH | |
| H | CH2CH2OCH3 | H | CH3 | CH2OH | |
| H | (CH2)3CH3 | H | CH3 | CH(OCH3)2 | |
| H | CH3 | H | OCH3 | CH(OCH3)2 | |
| H | CH3 | H | OCH3 | CH2OH | |
| H | CH2CH2Cl | H | CH3 | CH2OH | |
| H | CH3 | H | CH3 | CH2OCOC2H5 | |
| H | n-C3H7 | H | CH3 | CH(OCH3)2 | |
| H | CH3 | H | OCH3 | CH(OCH2CH2O) | |
| H | CH3 | H | CH3 | CH2OCO2CH3 | |
| H | C2H5 | H | CH3 | CH(OCH3)2 | |
| H | CH3 | H | OCH3 | CH(OC2H5)2 | |

TABLE 10b-continued

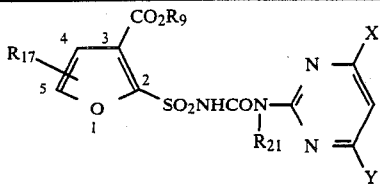

| R17 | R9 | R21 | X | Y | m.p. (°C.) |
|---|---|---|---|---|---|
| H | CH2CH3 | H | CH3 | CH(SCH2CH3)2 | |
| H | CH3 | H | OCH3 | C(CH3)(OCH2CH2O) | |
| H | CH3 | H | CH3 | CH2SO2CH3 | |

TABLE 10c

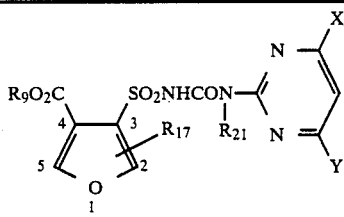

| R17 | R9 | R21 | X | Y | m.p. (°C.) |
|---|---|---|---|---|---|
| H | CH2CH=CH2 | H | CH3 | CH(OCH3)2 | |
| H | CH3 | H | CH3 | CH(OC2H5)2 | |
| H | CH3 | H | OCH3 | CH2SCH3 | |
| H | CH3 | H | CH3 | CH2OH | |
| H | CH3 | H | OCH3 | CH2OCOCH3 | |
| H | CH3 | H | CH3 | CH2OCONHC2H5 | |
| 2-F | C2H5 | H | OCH3 | CH(OCH3)2 | |
| 5-Br | CH3 | H | OCH3 | CH2OTHP | |
| 5-Br | CH3 | H | OCH3 | CH2OH | |
| 2-OCH3 | CH3 | H | CH3 | CH(OCH3)2 | |
| 2-Cl | CH3 | H | OCH2CH3 | CH2OH | |
| 2-Cl | CH3 | H | CH2CH3 | CH(OC2H5)2 | |
| 5-CH3 | CH3 | H | CH3 | CH(OCH3)2 | |
| 5-CH3 | CH3 | H | CH3 | CH2OTHP | |
| H | i-C3H7 | H | OCH3 | CH2OH | |
| H | CH2CH2OCH3 | CH3 | CH3 | CH2OH | |
| H | (CH2)3CH3 | H | CH3 | CH(OCH3)2 | |
| H | CH3 | H | OCH3 | CH(OCH3)2 | |
| H | CH3 | H | OCH3 | CH2OH | |
| H | CH2CH2Cl | H | CH3 | CH2OH | |
| H | CH3 | H | CH3 | CH2OCOC2H5 | |
| H | n-C3H7 | H | CH3 | CH(OCH3)2 | |
| H | CH3 | H | OCH3 | CH(OCH2CH2O) | |
| H | CH3 | H | CH3 | CH2OCO2CH3 | |
| H | C2H5 | H | CH3 | CH(OCH3)2 | |
| H | CH3 | H | OCH3 | CH(OC2H5)2 | |
| H | CH2CH3 | H | OCH3 | CH2SO2CH3 | |
| H | CH3 | CH3 | OCH3 | C(CH3)(OCH3)2 | |
| H | CH3 | H | OCH3 | C(CH2CH3)(OCH2CH2O) | |

TABLE 10d

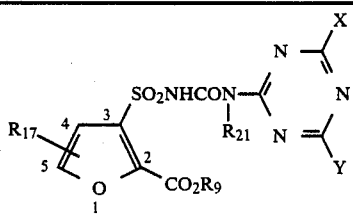

| R17 | R9 | R21 | X | Y | m.p. (°C.) |
|---|---|---|---|---|---|
| H | CH2CH=CH2 | H | CH3 | CH(OCH3)2 | |
| H | CH3 | H | CH3 | CH(OC2H5)2 | |
| H | CH3 | H | OCH3 | CH2SCH3 | |
| H | CH3 | H | CH3 | CH2OH | |
| H | CH3 | H | OCH3 | CH2OCOCH3 | |
| H | CH3 | H | CH3 | CH2OCONHC2H5 | |

TABLE 10d-continued

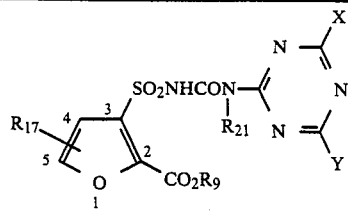

| $R_{17}$ | $R_9$ | $R_{21}$ | X | Y | m.p. (°C.) |
|---|---|---|---|---|---|
| 5-F | $C_2H_5$ | H | $OCH_3$ | $CH(OCH_3)_2$ | |
| 4-Br | $CH_3$ | H | $OCH_3$ | $CH_2OTHP$ | |
| 4-Br | $CH_3$ | H | $OCH_3$ | $CH_2OH$ | |
| 5-$OCH_3$ | $CH_3$ | H | $CH_3$ | $CH(OCH_3)_2$ | |
| 5-Cl | $CH_3$ | H | $OCH_3$ | $CH_2OH$ | |
| 5-Cl | $CH_3$ | H | $CH_3$ | $CH(OC_2H_5)_2$ | |
| 5-$CH_3$ | $CH_3$ | H | $CH_3$ | $CH(OCH_3)_2$ | |
| 5-$CH_3$ | $CH_3$ | H | $CH_3$ | $CH_2OTHP$ | |
| H | i-$C_3H_7$ | H | $OCH_3$ | $CH_2OH$ | |
| H | $CH_2CH_2OCH_3$ | H | $CH_2CH_3$ | $CH_2OH$ | |
| H | $(CH_2)_3CH_3$ | H | $CH_3$ | $CH(OCH_3)_2$ | |
| H | $CH_3$ | $CH_3$ | $OCH_3$ | $CH(OCH_3)_2$ | |
| H | $CH_3$ | H | $OCH_3$ | $CH_2OH$ | |
| H | $CH_2CH_2Cl$ | H | $CH_3$ | $CH_2OH$ | |
| H | $CH_3$ | H | $CH_3$ | $CH_2OCOC_2H_5$ | |
| H | n-$C_3H_7$ | H | $CH_3$ | $CH(OCH_3)_2$ | |
| H | $CH_3$ | H | $OCH_3$ | $CH(OCH_2CH_2O)$ | |
| H | $CH_3$ | H | $CH_3$ | $CH_2OCO_2CH_3$ | |
| H | $C_2H_5$ | H | $CH_3$ | $CH(OCH_3)_2$ | |
| H | $CH_3$ | H | $OCH_2CH_3$ | $CH(OC_2H_5)_2$ | |
| H | $CH_2CH_3$ | H | $OCH_3$ | $CH(SCH_2CH_3)_2$ | |
| H | $CH_3$ | H | $OC_2H_5$ | $CH_2SO_2CH_2CH_3$ | |
| H | $CH_3$ | H | $CH_3$ | $CH(CH_3)(SCH_3)$ | |

TABLE 10e

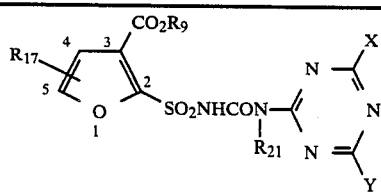

| $R_{17}$ | $R_9$ | $R_{21}$ | X | Y | m.p. (°C.) |
|---|---|---|---|---|---|
| H | $CH_2CH=CH_2$ | H | $CH_3$ | $CH(OCH_3)_2$ | |
| H | $CH_3$ | $CH_3$ | $CH_3$ | $CH(OC_2H_5)_2$ | |
| H | $CH_3$ | $CH_3$ | $OCH_3$ | $CH_2SCH_3$ | |
| H | $CH_3$ | H | $CH_3$ | $CH_2OH$ | |
| H | $CH_3$ | H | $OCH_3$ | $CH_2OCOCH_3$ | |
| H | $CH_3$ | H | $CH_3$ | $CH_2OCONHC_2H_5$ | |
| 5-F | $C_2H_5$ | H | $OCH_3$ | $CH(OCH_3)_2$ | |
| 4-Br | $CH_3$ | H | $OCH_3$ | $CH_2OTHP$ | |
| 4-Br | $CH_3$ | H | $OCH_3$ | $CH_2OH$ | |
| 5-$OCH_3$ | $CH_3$ | H | $CH_3$ | $CH(OCH_3)_2$ | |
| 5-Cl | $CH_3$ | H | $OCH_3$ | $CH_2OH$ | |
| 5-Cl | $CH_3$ | H | $CH_3$ | $CH(OC_2H_5)_2$ | |
| 5-$CH_3$ | $CH_3$ | H | $CH_2CH_3$ | $CH(OCH_3)_2$ | |
| 5-$CH_3$ | $CH_3$ | H | $CH_3$ | $CH_2OTHP$ | |
| H | i-$C_3H_7$ | H | $OCH_2CH_3$ | $CH_2OH$ | |
| H | $CH_2CH_2OCH_3$ | H | $CH_3$ | $CH_2OH$ | |
| H | $(CH_2)_3CH_3$ | H | $CH_3$ | $CH(OCH_3)_2$ | |
| H | $CH_3$ | H | $OCH_3$ | $CH(OCH_3)_2$ | |
| H | $CH_3$ | H | $OCH_3$ | $CH_2OH$ | |
| H | $CH_2CH_2Cl$ | H | $CH_3$ | $CH_2OH$ | |
| H | $CH_3$ | H | $CH_3$ | $CH_2OCOC_2H_5$ | |
| H | n-$C_3H_7$ | H | $CH_3$ | $CH(OCH_3)_2$ | |
| H | $CH_3$ | H | $OCH_3$ | $CH(OCH_2CH_2O)$ | |
| H | $CH_3$ | H | $CH_3$ | $CH_2OCO_2CH_3$ | |
| H | $C_2H_5$ | H | $CH_3$ | $CH(OCH_3)_2$ | |
| H | $CH_3$ | H | $OCH_3$ | $CH(OC_2H_5)_2$ | |
| H | $CH_3$ | H | $CH_3$ | $CH_2SCH_2CH_3$ | |
| H | $CH_3$ | H | $OCH_3$ | $CH(CH_3)SCH_3$ | |
| H | $CH_3$ | H | $CH_3$ | $CH_2SO_2CH_3$ | |

TABLE 10f

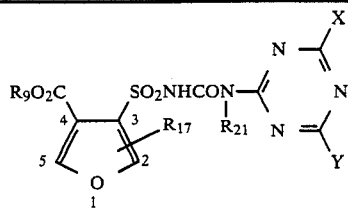

| R17 | R9 | R21 | X | Y | m.p. (°C.) |
|---|---|---|---|---|---|
| H | CH2CH=CH2 | H | CH3 | CH(OCH3)2 | |
| H | CH3 | H | CH2CH3 | CH(OC2H5)2 | |
| H | CH3 | H | OCH2CH3 | CH2SCH3 | |
| H | CH3 | H | CH3 | CH2OH | |
| H | CH3 | H | OCH3 | CH2OCOCH3 | |
| H | CH3 | H | CH3 | CH2OCONHC2H5 | |
| 2-F | C2H5 | H | OCH3 | CH(OCH3)2 | |
| 5-Br | CH3 | H | OCH3 | CH2OTHP | |
| 5-Br | CH3 | H | OCH3 | CH2OH | |
| 2-OCH3 | CH3 | H | CH3 | CH(OCH3)2 | |
| 2-Cl | CH3 | H | OCH3 | CH2OH | |
| 2-Cl | CH3 | CH3 | CH3 | CH(OC2H5)2 | |
| 5-CH3 | CH3 | H | CH3 | CH(OCH3)2 | |
| 5-CH3 | CH3 | H | CH3 | CH2OTHP | |
| H | i-C3H7 | H | OCH3 | CH2OH | |
| H | CH2CH2OCH3 | H | CH3 | CH2OH | |
| H | (CH2)3CH3 | H | CH3 | CH(OCH3)2 | |
| H | CH3 | H | OCH3 | CH(OCH3)2 | |
| H | CH3 | H | OCH3 | CH2OH | |
| H | CH2CH2Cl | H | CH3 | CH2OH | |
| H | CH3 | H | CH3 | CH2OCOC2H5 | |
| H | n-C3H7 | H | CH3 | CH(OCH3)2 | |
| H | CH3 | H | OCH3 | CH(OCH2CH2O) | |
| H | CH3 | H | CH3 | CH2OCO2CH3 | |
| H | C2H5 | H | CH3 | CH(OCH3)2 | |
| H | CH3 | H | OCH3 | CH(OC2H5)2 | |
| H | CH3 | H | OCH3 | CH(SCH2CH2S) | |
| H | CH3 | H | OCH3 | CH(OCH(CH3)CH2O) | |
| H | CH3 | H | OCH3 | C(CH3)(OCH3)2 | |

TABLE 11a

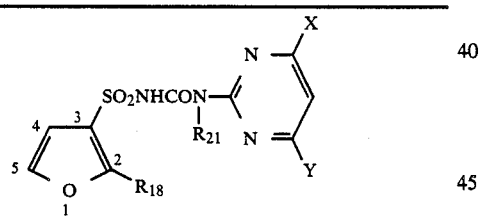

| R18 | R21 | X | Y | m.p. (°C.) |
|---|---|---|---|---|
| H | H | CH3 | CH(OCH3)2 | |
| H | H | CH3 | CH2OTHP | |
| H | H | OCH2CH3 | CH2OH | |
| H | H | OCH3 | CH(OCH2CH2O) | |
| Cl | H | CH3 | CH(OCH3)2 | |
| Cl | H | CH2CH3 | CH(OC2H5)2 | |
| Cl | H | CH3 | CH2OH | |
| Cl | H | CH3 | CH2OTHP | |
| Cl | CH3 | OCH3 | CH(OCH3)2 | |
| Cl | H | OCH3 | CH2OCOCH3 | |
| Cl | H | OCH3 | CH2OH | |
| Br | H | CH3 | CH(OCH3)2 | |
| Br | H | CH3 | CH(OC2H5)2 | |
| Br | H | CH3 | CH2OH | |
| Br | H | OCH3 | CH2OH | |
| Br | H | OCH3 | CH2OCO2CH3 | |
| CH3 | H | CH3 | CH(OCH3)2 | |
| CH3 | H | CH3 | CH(OCH2CH2CH2O) | |
| CH3 | H | CH3 | CH2OH | |
| CH3 | H | CH3 | CH2OCONHC2H5 | |
| CH3 | H | OCH3 | CH(OCH3)2 | |
| CH3 | H | OCH3 | CH2OTHP | |
| CH3 | H | OCH3 | CH2OCOCH3 | |
| CH3 | H | OCH3 | CH2OH | |
| Cl | H | CH3 | CH2SO2CH3 | |

TABLE 11a-continued

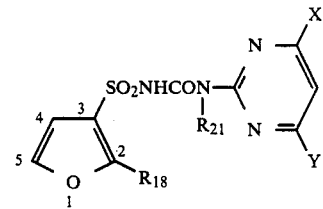

| R18 | R21 | X | Y | m.p. (°C.) |
|---|---|---|---|---|
| Br | H | OCH3 | CH(SCH3)2 | |
| CH3 | H | OCH3 | C(CH3)(OCH3)2 | |

TABLE 11b

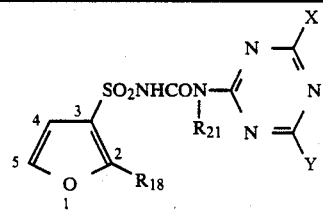

| R18 | R21 | X | Y | m.p. (°C.) |
|---|---|---|---|---|
| H | H | CH3 | CH(OCH3)2 | |
| H | H | CH3 | CH2OTHP | |
| H | H | OCH3 | CH2OH | |
| H | H | OCH3 | CH(OCH2CH2O) | |
| Cl | H | CH2CH3 | CH(OCH3)2 | |
| Cl | H | CH3 | CH(OC2H5)2 | |

TABLE 11b-continued

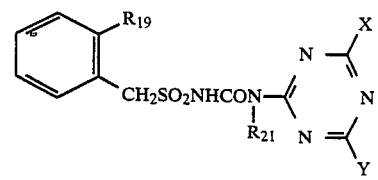

| R$_{18}$ | R$_{21}$ | X | Y | m.p. (°C.) |
|---|---|---|---|---|
| Cl | CH$_3$ | CH$_3$ | CH$_2$OH | |
| Cl | H | CH$_3$ | CH$_2$OTHP | |
| Cl | H | OCH$_3$ | CH(OCH$_3$)$_2$ | |
| Cl | H | OCH$_3$ | CH$_2$OCOCH$_3$ | |
| Cl | H | OCH$_3$ | CH$_2$OH | |
| Br | H | CH$_3$ | CH(OCH$_3$)$_2$ | |
| Br | H | CH$_3$ | CH(OC$_2$H$_5$)$_2$ | |
| Br | H | CH$_3$ | CH$_2$OH | |
| Br | H | OCH$_3$ | CH$_2$OH | |
| Br | H | OCH$_2$CH$_3$ | CH$_2$OCO$_2$CH$_3$ | |
| CH$_3$ | H | CH$_3$ | CH(OCH$_3$)$_2$ | |
| CH$_3$ | H | CH$_3$ | CH(SCH$_2$CH$_2$S) | |
| CH$_3$ | H | CH$_3$ | CH$_2$OH | |
| CH$_3$ | H | CH$_3$ | CH$_2$OCONHC$_2$H$_5$ | |
| CH$_3$ | H | OCH$_3$ | CH(OCH$_3$)$_2$ | |
| CH$_3$ | H | OCH$_3$ | CH$_2$OTHP | |
| CH$_3$ | H | OCH$_3$ | CH$_2$OCOCH$_3$ | |
| CH$_3$ | H | OCH$_3$ | CH$_2$OH | |
| Cl | H | CH$_3$ | CH$_2$SO$_2$CH$_3$ | |
| Br | H | CH$_3$ | CH(SCH$_3$)$_2$ | |
| CH$_3$ | H | CH$_3$ | CH(SCH$_2$CH$_3$)$_2$ | |

TABLE 12

| R$_{19}$ | R$_{21}$ | X | Y | Z | m.p. (°C.) |
|---|---|---|---|---|---|
| Cl | H | CH$_3$ | CH(OCH$_3$)$_2$ | CH | |
| Cl | CH$_3$ | CH$_3$ | CH$_2$OCOCH$_3$ | CH | |
| Cl | H | CH$_3$ | CH(OCH$_2$CH$_2$O) | Z | |
| Cl | H | OCH$_3$ | CH$_2$SCH$_3$ | Z | |
| Cl | H | OCH$_3$ | CH(OEt)$_2$ | CH | |
| NO$_2$ | H | C$_2$H$_5$ | CH(SCH$_2$CH$_2$S) | CH | |
| NO$_2$ | H | CH$_3$ | CH(OCH$_2$CH$_2$O) | CH | |
| NO$_2$ | H | Cl | CH(OCH$_3$)$_2$ | CH | |
| NO$_2$ | H | CH$_3$ | CH(OCH(CH$_3$)CH$_2$O) | Z | |
| NO$_2$ | H | OCH$_3$ | CH$_2$SEt | CH | |
| NO$_2$ | H | OCH$_3$ | CH$_2$OH | CH | |
| CF$_3$ | H | OC$_2$H$_5$ | CH$_2$OTHP | CH | |
| CF$_3$ | H | CH$_3$ | CH$_2$OCON(CH$_3$)$_2$ | CH | |
| CF$_3$ | H | CH$_3$ | CH(OCH$_3$)$_2$ | CH | |
| CF$_3$ | H | CH$_3$ | CH(OEt)$_2$ | Z | |
| CF$_3$ | H | OCH$_3$ | CH(SCH$_2$CH$_2$S) | CH | |
| OCH$_3$ | CH$_3$ | OCH$_3$ | CH(OCH(CH$_3$)CH$_2$O) | CH | |
| OCH$_3$ | H | OCH$_3$ | CH(OCH$_2$CH$_2$O) | CH | |
| OCH$_3$ | H | OCH$_3$ | CH(OCH$_3$)$_2$ | CH | |
| OCH$_3$ | H | CH$_3$ | CH(OEt)$_2$ | Z | |
| OCH$_3$ | H | CH$_3$ | CH$_2$SCH$_3$ | CH | |
| OCH$_3$ | H | CH$_3$ | CH$_2$SEt | CH | |
| OCH$_3$ | H | CH$_3$ | CH$_2$OCONHCH$_3$ | CH | |
| CO$_2$CH$_3$ | H | CH$_3$ | CH$_2$SEt | CH | |
| CO$_2$CH$_3$ | CH$_3$ | CH$_3$ | CH(OEt)$_2$ | Z | |
| CO$_2$CH$_3$ | CH$_3$ | CH$_3$ | CH(SCH$_2$CH$_2$S) | CH | |
| Cl | H | OCH$_3$ | CH(SCH$_3$)$_2$ | CH | |
| NO$_2$ | H | CH$_3$ | CH$_2$SO$_2$CH$_3$ | CH | |
| CO$_2$CH$_3$ | H | OCH$_3$ | C(CH$_3$)(OCH$_3$)$_2$ | CH | |
| CO$_2$CH$_3$ | CH$_3$ | OCH$_3$ | CH(OCH$_2$CH$_2$O) | CH | |
| CO$_2$CH$_3$ | CH$_3$ | OCH$_3$ | CH(OCH$_3$)$_2$ | CH | |
| CO$_2$CH$_3$ | CH$_3$ | OCH$_3$ | CH(OCH$_2$CH$_2$O) | Z | |
| CO$_2$CH$_2$CH$_3$ | CH$_3$ | C$_2$H$_5$ | CH(OCH$_3$)$_2$ | CH | |
| CO$_2$CH$_2$CH$_3$ | CH$_3$ | OC$_2$H$_5$ | CH(OCH$_3$)$_2$ | CH | |
| CO$_2$CH$_2$CH$_3$ | CH$_3$ | OCH$_3$ | CH(OCH$_3$)$_2$ | CH | |
| CO$_2$—n-C$_4$H$_9$ | CH$_3$ | OCH$_3$ | CH$_2$OH | CH | |
| CO$_2$—i-C$_3$H$_7$ | CH$_3$ | OCH$_3$ | CH$_2$OH | Z | |
| SO$_2$N(OCH$_3$)CH$_3$ | CH$_3$ | OCH$_3$ | CH$_2$OH | CH | |
| SO$_2$N(CH$_3$)$_2$ | H | CH$_3$ | CH(OCH$_2$CH$_2$O) | CH | |
| SO$_2$N(CH$_3$)$_2$ | CH$_3$ | CH$_3$ | CH(OCH$_2$CH$_2$O) | CH | |
| SO$_2$N(CH$_3$)$_2$ | H | CH$_3$ | CH(OCH$_2$CH$_2$O) | Z | |
| SO$_2$N(CH$_3$)$_2$ | H | CH$_3$ | CH$_2$OCOCH$_3$ | CH | |
| SO$_2$N(CH$_3$)$_2$ | H | OCH$_3$ | CH$_2$OCO$_2$CH$_3$ | CH | |
| SO$_2$N(CH$_3$)$_2$ | H | OCH$_3$ | CH$_2$SCH$_3$ | CH | |

TABLE 12-continued

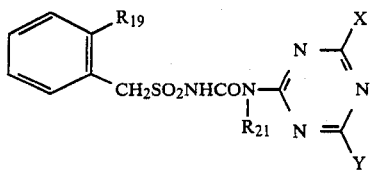

| R19 | R21 | X | Y | Z | m.p. (°C.) |
|---|---|---|---|---|---|
| SO2N(CH3)2 | H | OCH3 | CH2OTHP | CH | |
| SO2(CH2CH3)CH3 | H | OCH3 | CH2OH | Z | |
| SO2(CH2CH3)CH3 | H | CH3 | CH2OH | CH | |
| OSO2CH3 | H | CH3 | CH2OH | CH | |
| OSO2CH3 | H | CH3 | CH(OCH2CH3)2 | CH | |
| OSO2CH3 | H | CH3 | CH(OCH3)2 | CH | |
| OSO2CH3 | H | OCH3 | CH(OCH3)2 | CH | |
| OSO2CH2CH2OCH3 | H | OCH3 | CH(OCH3)2 | Z | |
| OSO2CH2CF3 | H | OCH3 | CH(OCH2CH2O) | CH | |
| SCH3 | H | CH3 | CH(OCH3)2 | CH | |
| SCH3 | CH3 | CH3 | CH2OCOC2H5 | Z | |
| SCH3 | H | OCH3 | CH(OCH2CH2O) | Z | |
| SCH2CH3 | H | OCH3 | CH2SCH3 | CH | |
| SCH2CH3 | H | Cl | CH(OEt)2 | CH | |
| SO2CH3 | CH3 | OCH3 | CH(SCH2CH2S) | Z | |
| SO2CH3 | H | CH3 | CH(OCH2CH2CH2O) | CH | |
| SO2CH3 | H | CH3 | CH(OCH3)2 | CH | |
| SO2—n-C3H7 | H | C2H5 | CH(OCH(CH3)CH2O) | CH | |
| SO2—n-C3H7 | H | OCH3 | CH2SEt | Z | |
| SO2—n-C3H7 | H | OCH3 | CH2OH | CH | |
| SO2CH2CH=CH2 | H | OCH3 | CH2OTHP | CH | |
| SO2—n-C4H9 | H | OCH3 | CH2OH | CH | |
| S—t-C4H9 | H | CH3 | CH(OCH3)2 | CH | |
| OCH2CH2Cl | H | CH3 | CH2OCON(CH3)2 | CH | |
| OCHFCHF2 | H | OC2H5 | CH2OCO2Et | Z | |
| OCH2CF3 | H | OCH3 | CH2OCO2CH3 | CH | |
| O—n-C3H7 | H | OCH3 | CH(SCH2CH2S) | CH | |
| O—n-C3H7 | H | OCH3 | CH(OCH2CH2CH2O) | CH | |
| O—n-C3H7 | H | Cl | CH(OCH2CH2CH2O) | CH | |
| O—n-C4H9 | H | OCH3 | CH(OCH2CH2CH2O) | Z | |
| O—n-C4H9 | H | CH3 | CH(OCH3)2 | CH | |
| OCH2CH3 | H | CH3 | CH(OCH2CH3)2 | CH | |
| OCH2CH3 | H | CH3 | CH2OH | CH | |
| OCF3 | CH3 | OCH3 | CH(OCH2CH2O) | CH | |
| OCF3 | H | OCH3 | CH2SCH3 | Z | |
| OCF3 | H | OCH3 | CH2OH | CH | |
| CH2Cl | H | CH3 | CH(OCH3)2 | CH | |
| CH2Cl | H | OCH3 | CH(OCH3)2 | N | |

TABLE 13

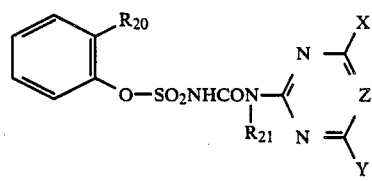

| R20 | R21 | X | Y | Z | m.p. (°C.) |
|---|---|---|---|---|---|
| Cl | H | CH3 | CH(OCH3)2 | CH | |
| Cl | CH3 | CH3 | CH2OCOCH3 | CH | |
| Cl | H | CH3 | CH(OCH2CH2O) | Z | |
| Cl | H | OCH3 | CH2SCH3 | Z | |
| Cl | H | OCH3 | CH(OEt)2 | CH | |
| NO2 | H | C2H5 | CH(SCH2CH2S) | CH | |
| NO2 | H | CH3 | CH(OCH2CH2CH2O) | CH | |
| NO2 | H | Cl | CH(OCH3)2 | CH | |
| NO2 | H | CH3 | CH(OCH(CH3)CH2O) | Z | |
| NO2 | H | OCH3 | CH2SEt | CH | |
| NO2 | H | OCH3 | CH2OH | CH | |
| CF3 | H | OC2H5 | CH2OTHP | CH | |
| CF3 | H | CH3 | CH2OCON(CH3)2 | CH | |
| CF3 | H | CH3 | CH(OCH3)2 | CH | |
| CF3 | H | CH3 | CH(OEt)2 | Z | |
| CF3 | H | OCH3 | CH(SCH2CH2S) | CH | |
| OCH3 | CH3 | OCH3 | CH(OCH(CH3)CH2O) | CH | |

TABLE 13-continued

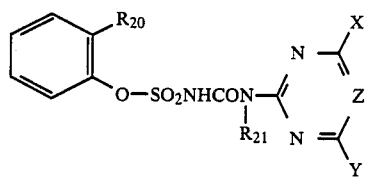

| $R_{20}$ | $R_{21}$ | X | Y | Z | m.p. (°C.) |
|---|---|---|---|---|---|
| $OCH_3$ | H | $OCH_3$ | $CH(OCH_2CH_2O)$ | CH | |
| $OCH_3$ | H | $OCH_3$ | $CH(OCH_3)_2$ | CH | |
| $OCH_3$ | H | $CH_3$ | $CH(OEt)_2$ | Z | |
| $OCH_3$ | H | $CH_3$ | $CH_2SCH_3$ | CH | |
| $OCH_3$ | H | $CH_3$ | $CH_2SEt$ | CH | |
| $OCH_3$ | H | $CH_3$ | $CH_2OCONHCH_3$ | CH | |
| $CO_2CH_3$ | H | $CH_3$ | $CH_2SEt$ | CH | |
| $CO_2CH_3$ | $CH_3$ | $CH_3$ | $CH(OEt)_2$ | Z | |
| $CO_2CH_3$ | $CH_3$ | $CH_3$ | $CH(SCH_2CH_2S)$ | CH | |
| $CO_2CH_3$ | $CH_3$ | $OCH_3$ | $CH(OCH_2CH_2O)$ | CH | |
| $CO_2CH_3$ | $CH_3$ | $OCH_3$ | $CH(OCH_3)_2$ | CH | |
| $CO_2CH_3$ | $CH_3$ | $OCH_3$ | $CH(OCH_2CH_2CH_2O)$ | Z | |
| $CO_2CH_2CH_3$ | $CH_3$ | $C_2H_5$ | $CH(OCH_3)_2$ | CH | |
| $CO_2CH_2CH_3$ | $CH_3$ | $OC_2H_5$ | $CH(OCH_3)_2$ | CH | |
| $CO_2CH_2CH_3$ | $CH_3$ | $OCH_3$ | $CH(OCH_3)_2$ | CH | |
| $CO_2-n-C_4H_9$ | $CH_3$ | $OCH_3$ | $CH_2OH$ | CH | |
| $CO_2-i-C_3H_7$ | $CH_3$ | $OCH_3$ | $CH_2OH$ | Z | |
| $SO_2N(OCH_3)CH_3$ | $CH_3$ | $OCH_3$ | $CH_2OH$ | CH | |
| $SO_2N(CH_3)_2$ | H | $CH_3$ | $CH(OCH_2CH_2O)$ | CH | |
| $SO_2N(CH_3)_2$ | $CH_3$ | $CH_3$ | $CH(OCH_2CH_2O)$ | CH | |
| $SO_2N(CH_3)_2$ | H | $CH_3$ | $CH(OCH_2CH_2O)$ | Z | |
| $SO_2N(CH_3)_2$ | H | $CH_3$ | $CH_2OCOCH_3$ | CH | |
| $SO_2N(CH_3)_2$ | H | $OCH_3$ | $CH_2OCO_2CH_3$ | CH | |
| $SO_2N(CH_3)_2$ | H | $OCH_3$ | $CH_2SCH_3$ | CH | |
| $SO_2N(CH_3)_2$ | H | $OCH_3$ | $CH_2OTHP$ | CH | |
| $OSO_2CH_3$ | H | $CH_3$ | $CH_2OH$ | CH | |
| $OSO_2CH_3$ | H | $CH_3$ | $CH(OCH_2CH_3)_2$ | CH | |
| $OSO_2CH_3$ | H | $CH_3$ | $CH(OCH_3)_2$ | CH | |
| $OSO_2CH_3$ | H | $OCH_3$ | $CH(OCH_3)_2$ | CH | |
| $OSO_2CH_2CH_2OCH_3$ | H | $OCH_3$ | $CH(OCH_3)_2$ | Z | |
| $OSO_2CH_2CF_3$ | H | $OCH_3$ | $CH(OCH_2CH_2O)$ | CH | |
| $CH_3$ | H | $CH_3$ | $CH(OCH_3)_2$ | CH | |
| $CH_3$ | $CH_3$ | $CH_3$ | $CH_2OCOC_2H_5$ | Z | |
| $CH_3$ | H | $OCH_3$ | $CH(OCH_2CH_2O)$ | Z | |
| $CH_2CH_3$ | H | $OCH_3$ | $CH_2SCH_3$ | CH | |
| $CH_2CH_3$ | H | Cl | $CH(OEt)_2$ | CH | |
| $CH_3$ | H | $CH_3$ | $CH(OCH_3)_2$ | CH | |
| $n-C_3H_7$ | H | $C_2H_5$ | $CH(OCH(CH_3)CH_2O)$ | CH | |
| $n-C_3H_7$ | H | $OCH_3$ | $CH_2SEt$ | Z | |
| $n-C_3H_7$ | H | $OCH_3$ | $CH_2OH$ | CH | |
| $n-C_4H_9$ | H | $OCH_3$ | $CH_2OH$ | CH | |
| $C_4H_9$ | H | $CH_3$ | $CH(OCH_3)_2$ | CH | |
| $OCH_2CH_2Cl$ | H | $CH_3$ | $CH_2OCON(CH_3)_2$ | CH | |
| $OCHFCHF_2$ | H | $OC_2H_5$ | $CH_2OCO_2Et$ | Z | |
| $OCH_2CF_3$ | H | $OCH_3$ | $CH_2OCO_2CH_3$ | CH | |
| $O-n-C_3H_7$ | H | $OCH_3$ | $CH(SCH_2CH_2S)$ | CH | |
| $O-n-C_3H_7$ | H | $OCH_3$ | $CH(OCH_2CH_2CH_2O)$ | CH | |
| $O-n-C_3H_7$ | H | Cl | $CH(OCH_2CH_2CH_2O)$ | CH | |
| $O-n-C_4H_9$ | H | $OCH_3$ | $CH(OCH_2CH_2CH_2O)$ | Z | |
| $O-n-C_4H_9$ | H | $CH_3$ | $CH(OCH_3)_2$ | CH | |
| $OCH_2CH_3$ | H | $CH_3$ | $CH(OCH_2CH_3)_2$ | CH | |
| $OCH_2CH_3$ | H | $CH_3$ | $CH_2OH$ | CH | |
| $OCF_3$ | $CH_3$ | $OCH_3$ | $CH(OCH_2CH_2O)$ | CH | |
| $OCF_3$ | H | $OCH_3$ | $CH_2SCH_3$ | Z | |
| $OCF_3$ | H | $OCH_3$ | $CH_2OH$ | CH | |
| $CH_2Cl$ | H | $CH_3$ | $CH(OCH_3)_2$ | CH | |
| $CH_2Cl$ | H | $OCH_3$ | $CH(OCH_3)_2$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, can contain from about 0.1% to 99% by weight ot active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 14

|  | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 7

| Wettable Powder | |
|---|---|
| 3-[[(4-dimethoxymethyl-6-methylpyrimidin-2-yl)-aminocarbonyl]aminosulfonyl]-2-thiophene-carboxylic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 8

| Wettable Powder | |
|---|---|
| N—[(4-dimethoxymethyl-6-methylpyrimidin-2-yl)-aminocarbonyl]-2-(methylsulfonyl)benzene-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
|---|---|
| Wettable Powder of Example 8 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 10

| Extruded Pellet | |
|---|---|
| N—[(4-dimethoxymethyl-6-methylpyrimidin-2-yl)amino-carbonyl]-2-nitrobenzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

| Oil Suspension | |
|---|---|
| 5-chloro-2-[[(4-dimethoxymethyl-6-methoxypyrimidin-2-yl)aminocarbonyl]aminosulfonyl]benzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 12

| Wettable Powder | |
|---|---|
| 2-[[(4-dimethoxymethyl-6-methoxypyrimidin-2-yl)aminocarbonyl]aminosulfonyl]benzoic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 13

| Low Strength Granule | |
|---|---|
| 2-[[[4-methyl-6-(tetrahydropyran-2-yloxymethyl)-pyrimidin-2-yl]aminocarbonyl]aminosulfonyl]-benzoic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

| Aqueous Suspension | |
|---|---|
| 2-[[[4-(acetyloxymethyl)-6-methylpyrimidin-2-yl]-aminocarbonyl]aminosulfonyl]benzoic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

| Solution | |
|---|---|
| 5-chloro-2-[[(4-dimethoxymethyl-6-methylpyrimidin-2-yl)aminocarbonyl]aminosulfonyl]benzoic acid, methyl ester, sodium salt | 5% |
| water | 95% |

The salt is added directly to the water with stirring to produce the solution, which may then be packaged for use.

EXAMPLE 16

| Low Strength Granule | |
|---|---|
| 2-[[[4-(dimethoxymethyl)-6-methylpyrimidin-2-yl]-aminocarbonyl]aminosulfonyl]benzoic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 17

| Granule | |
|---|---|
| 2-[[(4-(1,3-dioxan-2-yl)-6-methoxypyrimidin-2-yl)-aminocarbonyl]aminosulfonyl]benzoic acid, methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 18

| High Strength Concentrate | |
|---|---|
| 2-[[(4-(1,3-dioxolan-2-yl)-6-methoxypyrimidin-2-yl)-aminocarbonyl]aminosulfonyl]benzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
|---|---|
| 2-[[(4-(1,3-dioxan-2-yl)-6-methoxypyrimidin-2-yl)-aminocarbonyl]aminosulfonyl]benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 20

| Wettable Powder | |
|---|---|
| 2-chloro-N—[[4-(dimethoxymethyl)-6-methylpyrimidin-2-yl]aminocarbonyl]benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

| Oil Suspension | |
|---|---|
| 2-[[[4-(dimethoxymethyl)-6-methylpyrimidin-2-yl]6-methylpyrimidin-2-yl]amino-carbonyl]aminosulfonyl]benzoic acid, 2-propyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

The compounds of the present invention are highly active herbicides. They have utility for broadspectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for selective pre- or post-emergence weed control in crops, such as cotton, soybeans and wheat.

The rates of application for the compounds of the invention are influenced by a number of factors, including their use whether as selective or general herbicides, the crop species involved, the types of weeds to be controlled, weather and climate, formulation ingredients, mode of application, amount of foliage present, etc. In general terms, the subject compounds should be applied at levels of around 0.01 to 5 kg/ha, the lower rates being suggested for use on lighter soils and/or those having a low organic matter content, for selective weed control or for situations where only short-term persistence is required.

The compounds of the invention may be used in combination with any other commercial herbicides, such as, for example those listed below.

The compounds of this invention may be used in combination with other commercial herbicides such as:

| Common Name | Chemical Name |
|---|---|
| acifluorfen | 5-[2-chloro-4-(trifluoromethyl)phenoxy]-2-nitrobenzoic acid |
| alachlor | 2-chloro-2',6'-diethyl-N—(methoxymethyl)-acetanilide |
| amitrole | 3-amino-s-triazole |
| atrazine | 2-chloro-4-(ethylamino)-6-(isopropyl-amino)-s-triazine |
| barban | 4-chloro-2-butynyl m-chlorocarbanilate |
| bentazon | 3-isopropyl-1H—2,1,3-benzothiadiazin-4(3H)—one 2,2-dioxide |
| benzoylprop | N—benzoyl-N—(3,4-dichlorophenyl)-DL-alaine |
| bromacil | 5-bromo-3-sec-butyl-6-methyluracil |
| bromoxynil | 3,5-dibromo-4-hydroxybenzonitrile |
| butylate | S—ethyl-diisobutylthiocarbamate |
| CGA 82725 | 2-(4-(3,5-dichloropyridin-2-yloxy)phenoxy-propanoic acid, propynyl ester |
| chlortoluron | N'—(3-chloro-4-methylphenyl-N',N'—dimethylurea |
| cyanazine | 2-[[4-chloro-6-(ethylamino)-s-triazin-2-yl]amino]-2-methylpropionitrile |
| diallate | S—(2,3-dichloroallyl)diisopropylthio-carbamate |
| dicamba | 3,6-dichloro-o-anisic acid |
| dichloroprop | 2-(2,4-dichlorophenoxy)propionic acid |
| diclofop | 2-[4-(2,4-dichlorophenoxy)phenoxy]-propanoic acid |
| difenzoquat | 1,2-dimethyl-3,5-diphenyl-1H—pyrazolium |
| dinoseb | 2-sec-butyl-4,6-dinitrophenol |
| diuron | 3-(3,4-dichlorophenyl)-1,1-dimethylurea |
| DOWCO 453 ME | 2-(4-(3-chloro-5-trifluoromethylpyridin-2-yloxy)phenoxy)propanoic acid, methyl ester |
| EPTC | S—ethyl-dipropylthiocarbamate |
| fenoxaprop ethyl | ethyl 2-(4-(6-chloro-2-benzoxazolyloxy)-phenoxy)propanoate |
| flamprop | N—benzoyl-N—(3-chloro-4-fluorophenyl)-DL-alanine |
| fluazifop-butyl | butyl 2-[4-[5-(trifluoromethyl)-2-pyridinyloxy]phenoxy]propanoate |
| fluchloralin | N—(2-chloroethyl)-2,6-dinitro-N—propyl-4-trifluoromethyl)aniline |
| fluometuron | 1,1-dimethyl-3-(α,α,α-trifluoro-m-tolyl)-urea |
| FMC 57020 | 2-(2'-chlorophenyl)methyl-4,4-dimethyl-3-isoxazolidinone |
| fomesafen | 5-(2-chloro-4-trifluoromethylphenoxy)-N—methylsulfonyl-2-nitrobenzamide |
| fosamine | ethyl hydrogen (aminocarbonyl)phosphonate |
| glyphosate | N—(phosphonomethyl)glycine |
| hexazinone | 3-cyclohexyl-6-(dimethylamino)-1-methyl-1,3,5-triazine-2,4(1H,3H)—dione |
| ioxynil | 4-hydroxy-3,5-diiodobenzonitrile |
| isoproturon | N—(4-isopropylphenyl)-N',N'—dimethylurea |
| lenacil | 3-cyclohexyl-6,7-dihydro-1H—cyclopenta-pyrimidine-2,4(3H,5H)—dione |
| MCPA | [(4-chloro-o-tolyl)oxy]acetic acid |
| MCPB | 4-[(4-chloro-o-tolyl oxy]propionic acid |
| mefluidide | N—[2,4-dimethyl-5-[[(trifluoromethyl)-sulfonyl]amino]phenyl]acetamide |
| methabenz-thiazuron | 1,3-dimethyl-3-(2-benzothiazolyl)urea |
| methoxuron | N'—(3-chloro-4-methoxyphenyl)N,N—dimethylurea |
| metolachlor | 2-chloro-N—(2-ethyl-6-methylphenyl)-N—(2-methoxy-1-methylethyl)acetamide |
| MSMA | monosodium methanearsonate |
| neburon | 1-butyl-3-(3,4-dichlorophenyl)-1-methyl-urea |
| oryzalin | 3,4-dinitro-N,N—dipropylsulfanilamide |
| paraquat | 1,1'-dimethyl-4,4'-bipyridinium ion |
| pendimethalin | N—(1-ethylpropyl)-3,4-dimethyl-2,6-di-nitrobenzeneamine |

-continued

| Common Name | Chemical Name |
|---|---|
| profluralin | N—(cyclopropylmethyl)-α,α,α-trifluoro-2,6-dinitro-N—propyl-p-toluidine |
| propanil | 3',4'-dichloropropionalide |
| sethoxydim | 2-[1-(ethoxyimino)butyl]-5-[2-(ethylthio)propyl]-3-hydroxy-2-cyclohexene-1-one |
| siduron | 1-(2-methylcyclohexyl)-3-phenylurea |
| supriox | 2-[1-(2,5-dimethylphenyl)ethylsulfonyl]-pyridine-N—oxide |
| terbacil | 3-tert-butyl-5-chloro-6-methyluracil |
| triallate | S—(2,3,3-trichloroallyl)diisopropylthiocarbamate |
| trifluralin | α,α,α-trifluoro-2,6-dinitro-N,N—dipropyl-p-toluidine |
| 2,4-D | (2,4-dichlorophenoxy)acetic acid |
| 2,4-DB | 4-(2,4-dichlorophenoxy)butyric acid |
| | 3,4-diaryl-4-cyanobutyrates |
| | 4-(6-chloroquinoxalinyl-2-oxy)phenoxypropionate $C_1$-$C_5$ alkyl esters, such as methyl ester, butyl ester, ethyl ester, pentyl ester |
| | ethoxyethoxyethyl 4-(6-chloroquinoxalin-yl-2-oxy)phenoxypropionate |
| | propargyl 2-[4-(3,5-dichloropyridin-2-yloxy)phenoxy]propanoate |
| | methyl 2-[4-(3-chloro-5-trifluoromethyl-pyridin-2-yloxy)phenoxy]propanoate |
| oxyfluorfen | 2-chloro-1-(3-ethoxy-4-nitrophenoxy)-4-(trifluoromethyl)benzene |
| norflurazon | 4-chloro-5-(methylamino)-2-[(3-(tri-fluoro)phenyl]-3(2H)—pyridazinone |
| vernolate | S—propyl dipropylthiocarbamate |
| | ethyl 5-[2-chloro-4-(trifluoromethyl)-phenoxy]-2-nitrobenzoic acid |

The compounds of this invention may particularly be useful in combination with the following herbicides for use as pre-emergent treatments for control of weeds in soybeans:

| Common Name | Tradename | Chemical Name |
|---|---|---|
| chloramben | Amiben ® | 3-amino-2,5-dichlorobenzoic acid |
| linuron | Lorox ® | 3-(3,4-dichlorophenyl)-1-methoxy-1-methylurea |
| metribuzin | Lexone ® | 4-amino-6-tert-butyl-3-(methylthio)-as-triazin-5(4H)one |
| AC 252,214 | — | 2-(4,5-dihydro-4-methyl-4-(1-methylethyl)-5-oxo-1H—imidazol-2-yl)-3-quinolinecarboxylic acid |
| fomesafen | Flex ® | 5-(2-chloro-4-trifluoromethylphenoxy)-N—methylsulfonyl-2-nitrobenzamide |
| lactofen | — | 1'-(carboethoxy)ethyl-5-(2-chloro-4-(trifluoromethyl)phenoxy)-2-nitrobenzoate |

Also preferred are mixtures of some of the compounds of this invention with other sulfonylurea herbicides which may be useful for controlling weeds in soybeans. An example of such a sulfonylurea herbicide is: 2-hydroxy-N-[(4-methoxy-6-methyl-1,3,5-triazin-2-yl)aminocarbonyl]benzenesulfonamide, 1-propanesulfonate.

The herbicidal properties of the subject compounds were discovered in a number of greenhouse tests. The test procedures and results are shown below.

Test A

Seeds of crabgrass (Digitaria sp.), barnyardgrass (Echinochloa crusgalli), wild oats (Avena fatua), sicklepod (Cassia obtusifolia), morningglory (Ipomoea sp.), cocklebur (Xanthium sp.), sorghum, corn, soybean, rice, wheat and nutsedge tubers (Cyperus rotundus) were planted in a growth medium and treated pre-emergence with the chemicals dissolved in a non-phytotoxic solvent. At the same time, cotton having five leaves (including cotyledonary ones), bush beans with the third trifoliolate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

C=chlorosis or necrosis;
D=defoliation;
E=emergence inhibition;
G=growth retardation;
H=formative effects;
S=albinism;
U=unusual pigmentation;
X=axillary stimulation; and
6Y=abscised buds or flowers.

The ratings for the compounds tested by this procedure are presented in Table A.

TABLE A

Structures m.p. (°C.)

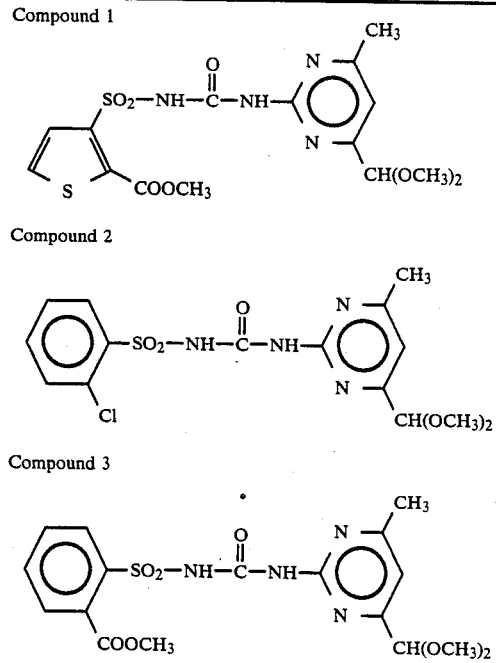

TABLE A-continued

Structures — m.p. (°C.)

Compound 4: 2-(SO2CH3)-phenyl-SO2-NH-C(=O)-NH-[4-methyl-6-CH(OCH3)2-pyrimidin-2-yl]

Compound 5: 2-NO2-phenyl-SO2-NH-C(=O)-NH-[4-methyl-6-CH(OCH3)2-pyrimidin-2-yl]

Compound 6: 2-COOCH(CH3)2-phenyl-SO2-NH-C(=O)-NH-[4-methyl-6-CH(OCH3)2-pyrimidin-2-yl]

Compound 7: 2-COOCH3-phenyl-SO2-NH-C(=O)-NH-[4-methyl-6-(CH2O-tetrahydropyran-2-yl)-pyrimidin-2-yl]

Compound 8: 2-NO2-phenyl-SO2-NH-C(=O)-NH-[4-methyl-6-(CH2O-tetrahydropyran-2-yl)-pyrimidin-2-yl]

Compound 9: 2-SO2CH3-phenyl-SO2-NH-C(=O)-NH-[4-methyl-6-(CH2O-tetrahydropyran-2-yl)-pyrimidin-2-yl]

Compound 10: 2-Cl-phenyl-SO2-NH-C(=O)-NH-[4-methyl-6-CH2OH-pyrimidin-2-yl]

Compound 11: 2-Cl-phenyl-SO2-NH-C(=O)-NH-[4-methyl-6-(CH2O-tetrahydropyran-2-yl)-pyrimidin-2-yl]

Compound 12: 2-NO2-phenyl-SO2-NH-C(=O)-NH-[4-methyl-6-CH2OH-pyrimidin-2-yl]

Compound 13: 2-SO2CH3-phenyl-SO2-NH-C(=O)-NH-[4-methyl-6-CH2OH-pyrimidin-2-yl]

Compound 14: 2-COOCH3-phenyl-SO2-NH-C(=O)-NH-[4-methyl-6-CH2OH-pyrimidin-2-yl]

Compound 15: 2-COOCH3-phenyl-SO2-NH-C(=O)-NH-[4-methyl-6-CH2OC(=O)CH3-pyrimidin-2-yl]

Compound 16: 2-Cl-phenyl-SO2NHC(=O)NH-[4-OCH3-6-(1,3-dioxolan-2-yl)-pyrimidin-2-yl]

TABLE A-continued

Structures m.p. (°C.)

Compound 17

Phenyl with CO₂CH₃ and SO₂NHCNH— linked to pyrimidine bearing OCH₃ and CH(OCH₂CH₂O) (1,3-dioxolane)

Compound 18

Phenyl with SO₂CH₂CH₂CH₃ and SO₂NHCNH— linked to pyrimidine bearing CH₃ and CH(OCH₃)₂

Compound 19

Phenyl with SO₂CH₂CH₂CH₃ and SO₂NHCNH— linked to pyrimidine bearing OCH₃ and CH(OCH₃)₂

Compound 20

Phenyl with SO₂CH₂CH₂CH₃ and SO₂NHCNH— linked to pyrimidine bearing CH₃ and CH(OCH₂CH₂O) (1,3-dioxolane)

Compound 21

Phenyl with SO₂CH₃ and SO₂NHCNH— linked to pyrimidine bearing OCH₃ and CH(OCH₃)₂

Compound 22

Phenyl with SO₂CH₃ and SO₂NHCNH— linked to pyrimidine bearing CH₃ and CH(OCH₂CH₂O) (1,3-dioxolane)

Compound 23

Phenyl with SO₂CH₃ and SO₂NHCNH— linked to pyrimidine bearing OCH₃ and CH(OCH₃)₂

Compound 24

Phenyl with CO₂CH₃ and SO₂NHCNH— linked to pyrimidine bearing OCH₃ and CH₂OH

Compound 25

Phenyl with SO₂CH₂CH₂CH₃ and SO₂NHCNH— linked to pyrimidine bearing OCH₃ and CH₂OH

Compound 26

Phenyl with NO₂ and SO₂NHCNH— linked to pyrimidine bearing OCH₃ and CH(OCH₃)₂

Compound 27

Phenyl with SO₂CH₂CH₂CH₃ and SO₂NHCNH— linked to pyrimidine bearing CH₃ and CH₂OH

Compound 28

Phenyl with CO₂CH₃ and SO₂NHCNH— linked to pyrimidine bearing Cl and CH(OCH₃)₂

Compound 29

Phenyl with Cl and SO₂NHCNH— linked to pyrimidine bearing Cl and CH(OCH₃)₂

TABLE A-continued

Structures

Compound 30

2-(methoxycarbonyl)phenylsulfonyl group linked via -SO₂NHC(O)NH- to a pyrimidine bearing OCH₃ and CH(OCH₃)₂ substituents.

Compound 31

2-chlorophenylsulfonyl group linked via -SO₂NHC(O)NH- to a pyrimidine bearing OCH₃ and CH(OCH₃)₂ substituents.

Compound 32

2-(methoxycarbonyl)phenylsulfonyl group linked via -SO₂NHC(O)NH- to a pyrimidine bearing CH₃ and a 1,3-dioxolan-2-yl substituent.

Compound 33

2-chlorophenylsulfonyl group linked via -SO₂NHC(O)NH- to a pyrimidine bearing CH₃ and a 1,3-dioxolan-2-yl substituent.

Compound 34

2-(methylsulfonyl)phenylsulfonyl group linked via -SO₂NHC(O)NH- to a pyrimidine bearing OCH₃ and CH₂OH substituents.

Compound 35

2-nitrophenylsulfonyl group linked via -SO₂NHC(O)NH- to a pyrimidine bearing CH₃ and a 1,3-dioxolan-2-yl substituent.

Compound 36

2-(methoxycarbonyl)phenylsulfonyl group linked via -SO₂NHC(O)NH- to a triazine bearing OCH₃ and CH(OCH₃)₂ substituents.

Compound 37

2-(methoxycarbonyl)phenylsulfonyl group linked via -SO₂NHC(O)NH- to a triazine bearing CH₃ and CH(OCH₃)₂ substituents.

Compound 38

2-chlorophenylsulfonyl group linked via -SO₂NHC(O)NH- to a triazine bearing OCH₃ and CH₂O-(tetrahydropyran-2-yl) substituents.

Compound 39

2-chlorophenylsulfonyl group linked via -SO₂NHC(O)NH- to a triazine bearing OCH₃ and CH₂OH substituents.

Compound 40

2-chlorophenylsulfonyl group linked via -SO₂NHC(O)NH- to a triazine bearing OCH₃ and CH(OCH₃)₂ substituents.

Compound 41

3-(methoxycarbonyl)thiophen-2-yl-sulfonyl group linked via -SO₂NHC(O)NH- to a pyrimidine bearing CH₃ and CH₂O-(tetrahydropyran-2-yl) substituents.

Compound 42

2-(N,N-dimethylsulfamoyl)phenylsulfonyl group linked via -SO₂NHC(O)NH- to a pyrimidine bearing CH₃ and CH₂O-(tetrahydropyran-2-yl) substituents.

TABLE A-continued

Structures

| Compound | Structure description | m.p. (°C.) |
|---|---|---|
| Compound 43 | Phenyl with SO$_2$N(CH$_3$)$_2$ and SO$_2$NHCNH-pyrimidine (CH$_3$, CH$_2$OH) | |
| Compound 44 | Thiophene with CO$_2$CH$_3$ and SO$_2$NHCNH-pyrimidine (CH$_3$, CH$_2$OH) | |
| Compound 45 | Phenyl with CO$_2$CH(CH$_3$)$_2$ and SO$_2$NHCNH-pyrimidine (CH$_3$, CH$_2$OH) | |
| Compound 46 | Phenyl with SO$_2$N(CH$_3$)$_2$ and SO$_2$NHCNH-pyrimidine (CH$_3$, 1,3-dioxolane) | |
| Compound 47 | Phenyl with SO$_2$N(CH$_3$)$_2$ and SO$_2$NHCNH-pyrimidine (CH$_3$, CH(OCH$_3$)$_2$) | |
| Compound 48 | Phenyl with SO$_2$N(CH$_3$)$_2$ and SO$_2$NHCNH-pyrimidine (OCH$_3$, CH(OCH$_3$)$_2$) | |
| Compound 49 | Phenyl with SO$_2$N(CH$_3$)$_2$ and SO$_2$NHCNH-pyrimidine (OCH$_3$, 1,3-dioxane) | |
| Compound 50 | Phenyl with SO$_2$CH$_3$ and SO$_2$NHCNH-pyrimidine (OCH$_3$, 1,3-dioxane) | 182–189(d) |
| Compound 51 | Phenyl with Cl and SO$_2$NHCNH-pyrimidine (OCH$_3$, 1,3-dioxane) | 186–190 |
| Compound 52 | Phenyl with CO$_2$CH$_3$ and SO$_2$NHCNH-pyrimidine (OCH$_3$, 1,3-dioxane) | 150–153 |
| Compound 53 | Phenyl with SO$_2$N(CH$_3$)$_2$ and SO$_2$NHCNH-pyrimidine (OCH$_3$, 1,3-dioxane) | 130(d) |
| Compound 54 | Phenyl with Cl and SO$_2$NHCNH-pyrimidine (OCH$_3$, CH$_2$SCH$_3$) | 149–152 |
| Compound 55 | Phenyl with CO$_2$CH$_2$CH$_3$ and SO$_2$NHCNH-pyrimidine (OCH$_3$, CH$_2$SCH$_3$) | 146–149 |

TABLE A-continued
Structures
| Compound | m.p. (°C.) |
|---|---|
| Compound 56 | 146–149 |
| Compound 57 | 136–146 |
| Compound 58 | 152–156 |
| Compound 59 | 185–188 |
| Compound 60 | 83–85 |
| Compound 61 | 95–100 |
| Compound 62 | 181–183 |
| Compound 63 | 135–138 |
| Compound 64 | 135–138 |
| Compound 65 | 158–163 |
| Compound 66 | 156–158 |
| Compound 67 | 118–119 |
| Compound 68 | 141–143 |
| Compound 69 | 144–146 |
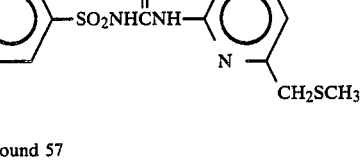
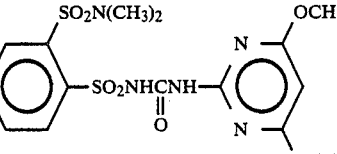
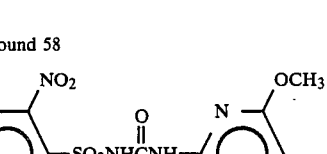
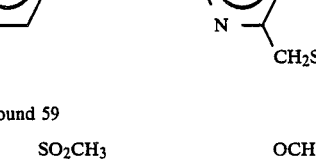
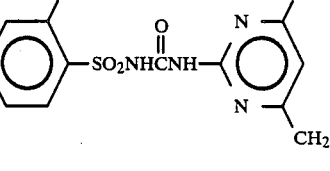
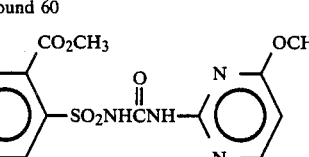
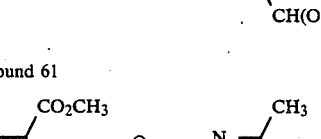
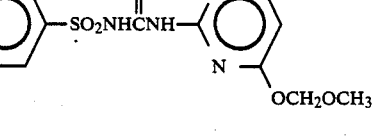

TABLE A-continued

Structures

| Compound | Structure description | m.p. (°C.) |
|---|---|---|
| Compound 70 | 4-Cl, 2-(CO₂CH₃) phenyl-SO₂NHC(O)NH-[4-CH₃, 6-CH(OCH₃)₂ pyrimidin-2-yl] | 85–90 |
| Compound 71 | 4-Cl, 2-(CO₂CH₃) phenyl-SO₂NHC(O)NH-[4-OCH₃, 6-CH(OCH₃)₂ pyrimidin-2-yl] | 90–95 |
| Compound 72 | 4-Cl, 2-(OSO₂CH₃) phenyl-SO₂NHC(O)NH-[4-CH₃, 6-CH(OCH₃)₂ pyrimidin-2-yl] | 120–128 |
| Compound 73 | 2-(CO₂CH₃) phenyl-SO₂NHC(O)NH-[4-CH₃, 6-CH₂SCH₃ pyrimidin-2-yl] | 133–138 |
| Compound 74 | 2-Cl phenyl-SO₂NHC(O)NH-[4-CH₃, 6-CH₂SCH₃ pyrimidin-2-yl] | 133–138 |
| Compound 75 | 2-SO₂N(CH₃)₂ phenyl-SO₂NHC(O)NH-[4-CH₃, 6-CH₂SCH₃ pyrimidin-2-yl] | 127–133 |
| Compound 76 | 2-NO₂ phenyl-SO₂NHC(O)NH-[4-CH₃, 6-CH₂SCH₃ pyrimidin-2-yl] | 148–154 |
| Compound 77 | 2-SO₂CH₂CH₂CH₃ phenyl-SO₂NHC(O)NH-[4-CH₃, 6-CH₂SCH₃ pyrimidin-2-yl] | 179–185 |
| Compound 78 | 2-Cl phenyl-SO₂NHC(O)NH-[4-OCH₃, 6-CH₂SO₂CH₃ pyrimidin-2-yl] | |
| Compound 79 | 2-(CO₂CH₃) phenyl-SO₂NHC(O)NH-[4-OCH₃, 6-CH₂SO₂CH₃ pyrimidin-2-yl] | |

TABLE A

| Rate kg/ha | Cmpd. 1 .05 | Cmpd. 2 .05 | Cmpd. 3 .05 | Cmpd. 4 .05 | Cmpd. 5 .05 | Cmpd. 6 .05 | Cmpd. 7 0.4 | Cmpd. 8 0.4 | Cmpd. 9 0.4 | Cmpd. 10 0.4 | Cmpd. 11 0.4 | Cmpd. 12 0.4 | Cmpd. 13 0.4 | Cmpd. 14 .05 | Cmpd. 15 .05 | Cmpd. 16 .05 |
|---|---|---|---|---|---|---|---|---|---|---|---|---|---|---|---|---|
| | | | | | | | POST-EMERGENCE | | | | | | | | | |
| Bush bean | 4C,9G,6Y | 5C,9G,6Y | 5C,9G,6Y | 3C,9G,6Y | 9C | 9C | 9C | 9C | 9C | 9C | 9C | 9C | 9C | 9C | 9C | 4C,9G,6Y |
| Cotton | 2C,2H,5G | 2C,3H,6G | 3C,5G | 4C,9H | 3C,2H | 2C,8H | 6C,9G | 6C,9G | 4C,9H | 4C,9G | 4C,9G | 5C,9G | 6C,9G | 6C,9G | 8C | 2C,3H,8G |
| Morningglory | 1C,3G | 1C,5G | 2C,5G | 3C,7H | 2C,8H | 2C,8H | 4C,9G | 4C,9G | 3C,7G | 3C,8H | 3C,8H | 5C,8G | 2C,8H | 2C,8G | 3C,7G | 3C,9G |
| Cocklebur | 2C,9G | 2C,8G | 9C | 3C,9H | 5C,9G | 5C,9G | 9C | 10C | 5C,9G | 10C | 10C | 6C,9G | 10C | 10C | 10C | 1C,9G |
| Sicklepod | 1C | 2C,5G | 5C,9G | 3C,6G | 3C,7G | 5C,9G | 9C | 3C,5G | 4C,7G | 3C,5H | 2C,5G | 5C,9G | 5C,9G | 5C,9G | 5C,9G | 3C,8G |
| Nutsedge | 0 | 1C,3G | 3C,9G | 2C,6G | 5C,9G | 10C | 10C | 10C | 2C,8G | 1C,8G | 9C | 9C | 4C,9G | 10C | 10C | 5G |
| Crabgrass | 1C,5G | 5G | 4C,9G | 5C,9H | 1C,2H | 1C,2H | 9C | 9C | 2C,7G | 9C | 9C | 9C | 9C | 9C | 9C | 7G |
| Barnyardgrass | 2C,9H | 2C,9H | 9C | 5C,9H | 3C,9H | 3C,9G | 10C | 5C,9G | 6C,9H | 3C,9G | 3C,9G | 3C,8G | 4C,9G | 4C,9G | 9C | 2C,9H |
| Wild Oats | 1C,3G | 2C,8H | 3U,9G | 2C,8H | 2C,8G | 2C,8G | 5U,9G | 2C,9G | 3C,9G | 3C,9G | 2C,9G | 10C | 2C,8H | 4C,9G | 4C,9G | 2C,9G |
| Wheat | 7G,5X | 5U,9G | 9C | 5U,9C | 3U,9G | 3U,9G | 10C | 10C | 2C,9G | 7U,9G | 7U,9G | 10C | 9C | 10C | 10C | 3C,9G |
| Corn | 2U,9H | 2C,7G | 6C,9G | 5C,8H,5X | 2C,9G | 2C,9G | 9C | 9C | 6U,9C | 5C,9G | 5C,9G | 9C | 5C,9G | 9C | 9C | 2C,9G |
| Soybean | 1G | 6C,9G | 5U,9G | 5C,9G | 4C,9G | 4C,9G | 6C,9G | 6C,9G | 6U,9G | 9C | 9C | 10C | 6C,9G | 6C,9G | 5C,9G | 5C,9G |
| Rice | 7G | 4U,9C | 5U,9C | 3U,9G | 3U,9C | 3U,9C | 9C | 9C | 6U,9G | 5C,9G | 9C | 10C | 10C | 10C | 4C,9G | 4C,9G |
| Sorghum | 9G | | | | | | | | | 10C | 10C | 9C | 9C | 9C | 9C | 4C,9G |
| Sugar beet | | | | | | | | | | | | | | | | |
| | | | | | | | PRE-EMERGENCE | | | | | | | | | |
| Morningglory | 6G | 3C,5G | 8H | 3C,5H | 1C | 1C | 2C,9H | 8G | 8G | 7G | 9H | 8H | 8G | 8G | 8G | 9G |
| Cocklebur | 9H | 9H | 9H | 1H | 9H | 9H | — | 9H | 9H | 9H | 9H | 9H | 9H | 9H | 9H | 7H |
| Sicklepod | 0 | 7G | 2C,7G | 1C | 8G | 8G | 5C,9G | 5G | 3C,9G | 2C,7G | 2C,8G | 2C,8G | 1C,3G | 4C,9G | 3C,8G | 7H |
| Nutsedge | 0 | 2C,8G | 10E | 2C,8G | 8G | 8G | 10E | 3C,9G | 1C,4G | 2C,8G | 10E | 10E | 10E | 10E | 10E | 4G |
| Crabgrass | 1C,4G | 2C | 3C,9G | 1C | 2C,5G | 1C,7G | 3C,9H | 1C,4G | 5C,9G | 3C,5G | 2C,9H | 2C,9H | 3C,6G | 3C,8G | 3C,8H | 2G |
| Barnyardgrass | 4C,7H | 3C,9H | 6C,9H | 2C,9H | 5C,8H | 2C,6H | 4C,9H | 5C,9G | 2C,9G | 3C,9H | 2C,9H | 5C,9G | 5C,9G | 5C,9H | 3C,8H | 8H |
| Wild Oats | 2C,7G | 2C,9G | 5C,9H | 2C,9G | 2C,8G | 2C,6H | 4C,9H | 9H | 3C,9H | 9G | 3C,9G | 3C,9G | 4C,9H | 4C,9H | 5C,9H | 8G |
| Wheat | 2C,8G | 2C,9G | 9H | 9G | 1C,8G | 1C,7G | 9H | 5C,9G | 9H | 9G | 2C,8G | 2C,8G | 2C,9G | 2C,9H | 9H | 8G |
| Corn | 0 | 1H | 10E | 2U,9G | 2C,9H | 2C,8H | 10E | 3C,8H | 5C,9G | 6C,9G | 10H | 10H | 10E | 10E | 10H | 9H |
| Soybean | 8H | 9H | 2C,7G | 6G | 1H | 1H | 9H | 9H | 3C,8H | 3C,7H | 9H | 6H | 2C,8H | 2C,8H | 9H | 1C,1H |
| Rice | 2C,8H | 5C,9G | 10E | 2C,8H | 9H | 3C,6G | 10E | 9H | 10E | 9H | 10E | 5C,9H | 5C,9H | 9H | 10E | 9H |
| Sorghum | | | 10H | 2C,9G | 2C,9H | 2C,9H | 7C,9H | 10E | 6U,9G | 4C,9H | 5C,9H | 2C,9G | 3C,9H | 5C,9H | 5C,9H | 9H |
| Sugar beet | | | | | | | | | | | | | | | | 8G |
| Cotton | | | | | | | | | | | | | | | | |

| Rate kg/ha | Cmpd. 17 0.05 | Cmpd. 18 0.05 | Cmpd. 19 0.05 | Cmpd. 20 0.05 | Cmpd. 21 0.05 | Cmpd. 22 0.05 | Cmpd. 23 0.05 | Cmpd. 24 0.4 | Cmpd. 25 0.05 | Cmpd. 26 0.05 | Cmpd. 27 0.05 | Cmpd. 28 0.05 | Cmpd. 29 0.05 | Cmpd. 30 0.05 | Cmpd. 31 0.05 | Cmpd. 32 0.05 |
|---|---|---|---|---|---|---|---|---|---|---|---|---|---|---|---|---|
| | | | | | | | POST-EMERGENCE | | | | | | | | | |
| Bush bean | 9C | 4S,7G,6Y | 4S,2H,6Y | 5C,9G,6Y | 5C,9G,6Y | 4C,9G,6Y | 4C,9G,6Y | 6C,9G,6Y | 5C,6G,6Y | 5C,9G,6Y | 4C,9G,6Y | 1C | 9C | 9C | 9C | 9C |
| Cotton | 5C,9G | 2C,4G | 3C | 3C,5G | 2C,4G | 1C,6G | 5C,8H | 4C,7G | 2C,3G | 4C,5G | 2C | 0 | 5C,9G | 3C,5G | 3C,5G | 5C,9G |
| Morningglory | 5C,9G | 3C,6G | 3C,8H | 3C,5G | 5C,8H | 5C,9G | 5C,9G | 4C,9G | 4C,8G | 5C,8G | 2C,2H | 0 | 9C | 3C,5G | 3C,5G | 5C,9G |
| Cocklebur | 9C | 4C,8G | 2C,2G | 1C,9G | 4C,9G | 5C,9G | 5C,9G | 4C,9G | 2C,5G | 5C,9G | 3C,8H | 3H | 10C | 9H | 9H | 10C |
| Sicklepod | 6C,9G | 2C,3H | 2C | 3C,5G | 5C,9G | 4C,9G | 4C,9H | 3C | 2C | 3C | 2C | 0 | 4C,7G | 1C,3G | 1C,3G | 2C,9G |
| Nutsedge | 5C,9G | 5G | 0 | 2C,9G | 3C,8G | 9G | 9G | 0 | 0 | 9G | 0 | 0 | 3C,9G | 3C,7G | 2C,5G | 6C,9G |
| Crabgrass | 5C,9G | 2G | 1C | 6G | 5C,9H | 5C,9H | 9C | 3C,7G | 2C,9H | 2C,8G | 2C,4H | 0 | 9C | 2C,5G | 2C,5G | 9C |
| Barnyardgrass | 9C | 2C,8H | 2C,6H | 5C,9H | 5C,9H | 4C,9H | 5C,9H | 9C | 3G | 9C | 0 | 2H | 5C,9G | 3C,9G | 3C,9G | 9C |
| Wild Oats | 5C,9G | 4G | 4G | 2C,9G | 5C,9H | 4C,9G | 4C,9H | 7G | 3G,5X | 2C,9G | 2C,4H | 0 | 5C,9G | 2C,9G | 2C,9G | 9C |
| Wheat | 4C,9G | 2G | 3G | 2C,9G | 3C,9G | 9C | 9C | 5G,5X | 2C,7H | 5U,9G | 0 | 0 | 4C,9G | 2C,9G | 3C,9G | 9C |
| Corn | 9C | 2G | 9G | 2C,8H | 2C,8G,5X | 3C,8H | 3C,8H | 7U,9G | 1C,1H | 4C,8G | 4G | 0 | 9C | 2C,8H | 9C | 9C |
| Soybean | 5C,9G | 2C | 1C | 2C,9G | 5C,9G | 3C,9G | 3C,9G | 5C,9G | 2C,8G | 5U,9G | 4G | 2H | 4C,9H | 4C,9H | 2C,8H | 5C,9G |
| Rice | 6C,9G | 2C,4G | 2C,7H | 2C,9G | 5C,9G | 3C,9G | 3C,9G | 6C,9G | 9G | 4C,8G | 2C,7H | 0 | 5C,9G | 5C,9G | 5C,9G | 9C |
| Sorghum | 9C | 2C,6G | 2C,8G | 3C,9G | 5C,9G | 3C,9G | 3C,9G | 4C,9G | 9G | 3U,9G | 0 | 6G | 10C | 10C | 10C | 9C |
| Sugar beet | 9C | 2C,2H | 1C,9G | 2C,7G | 5C,9H | 4C,9G | 4C,9G | 3C,7H | 1C,4H | 9C | — | — | — | — | 9C | — |

TABLE A-continued

PRE-EMERGENCE

| | Cmpd. 33 | Cmpd. 34 | Cmpd. 35 | Cmpd. 36 | Cmpd. 37 | Cmpd. 38 | Cmpd. 39 | Cmpd. 40 | Cmpd. 41 | Cmpd. 42 | Cmpd. 43 | Cmpd. 44 | Cmpd. 45 | Cmpd. 46 | Cmpd. 47 |
|---|---|---|---|---|---|---|---|---|---|---|---|---|---|---|---|
| Morningglory | 9C | 2C,5H | 1C,2H | 9G | 8H,2C | 9G | 9G | 2C,5H | 3C,9G,6Y | 10D,9G,6Y | 2C,4G | 0 | 3C,9G,6Y | 5G | 9G |
| Cocklebur | 9H | — | 0 | 9H | 9H | 9H | 9H | 7H | 3C,2H | 4C,8G | 8H | 8H | 9H | — | 9H |
| Sicklepod | 9G | 2C | 0 | 5G | 2C | 8G | 5G | 2C | 2C,5G | 9C | 1C | 2H | 3C,8G | 2C,7G | 9G |
| Nutsedge | 10E | 0 | 0 | 1C | 1C | 6G | 8G | 0 | 3C,5H | 8H | 0 | 0 | 2C,9G | 2C | 10E |
| Crabgrass | 5G | 2C | 0 | 1C | 1C,4G | 10E | 5G | 2C,5G | 2G | 10E | 1C | 2G | 3C,8H | 2C,5G | 3C,9G |
| Barnyardgrass | 9H | 1C | 1C | 5C,9H | 5C,9H | 2C,8G | 2C,8G | 1C,5G | 3G | 3C | 3C,5G | 2G | 5C,9H | 5C,9H | 3C,9H |
| Wild Oats | 2C,9G | 1C,4G | 4G | 5C,9H | 3C,8G | 4C,9H | 8G | 1C,5G | 1C,5G | 2C,6G | 2C,5G | 0 | 5C,9G | 5C,9H | 3C,9H |
| Wheat | 5C,9H | 3G | 2C,9H | 2C,8G | 2C,7G | 3C,8G | 7G | 2C,8H | 9H | 3C,9H | 5G | 2C,6G | 1H | 9H | 5C,9H |
| Corn | 10H | 2C | 1C,7G | 9H | 3C,9G | 5C,9H | 9G | 2G | 2G | 9G | 0 | 2C,8H | 4G | 9H | 9H |
| Soybean | 9H | 2G | 2C,9H | 0 | 0 | 3C,5H | 3C,8H | 2G | 4G | 3C,8H | 2C,4G | 2C,5G | 5G | 3C,6G | 9H |
| Rice | 10E | 5G | — | 5G | 5G | 10E | 9H | 1C,4G | 2C,8H | 3C,9H | 0 | 1C,5G | 1C,9G | 5C,9G | 10E |
| Sorghum | 10H | 1C,3G | 2C,8G | 2C,8G | 3C,9H | 5C,9H | 3C,9H | 1C,4G | 2C,9G | 5C,9G | 3C | 1U,9G | 2C,9G | 5C,9H | 3C,9H |
| Sugar beet | 5C,9H | 1C,3H | 8G | 3C,9H | 0 | 10E | 5G | 4C,9H | 9G | 5C,9G | 2C,5G | 4G | 2C,8G | — | 5C,9H |
| Cotton | — | — | — | — | — | — | — | 0 | — | 9G | 3C,6G | 3C,9G | 2C,9H | — | — |
| Rate kg/ha | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |

POST-EMERGENCE

| | Cmpd. 48 | Cmpd. 49 | Cmpd. 50 | Cmpd. 51 | Cmpd. 52 | Cmpd. 53 | Cmpd. 54 | Cmpd. 55 | Cmpd. 56 | Cmpd. 57 | Cmpd. 58 | Cmpd. 59 | Cmpd. 60 | Compound 61 | Cmpd. 62 |
|---|---|---|---|---|---|---|---|---|---|---|---|---|---|---|---|
| Bush bean | | 5C,9G,6Y | 9C | 3C,9G,6Y | 5C,9G,6Y | 4S,8G,6Y | 5C,9G,6Y | 5S,8G,6Y | 3C,9G,6Y | 10D,9G,6Y | 9D,9G,6Y | 5C,9G,6Y | 3C,9G,6Y | 9C | 5C,9G,6Y |
| Cotton | | 4C,9G | 4C,9G | 3C,3H,9G | 4C,9G | 3C,8G | 3C,3H,6G | 2C | 3C,2H | 4C,8G | 3C,5G | 3C,7G | 2C,4G | 10C | |
| Morningglory | | 3C,5G | 9C | 3C,7H | 5C,9G | 3C,7H | 3C,8H | 2C,5G | 2C,5G | 9C | 3C,8H | 1H | 1C | 10C | 10C |
| Cocklebur | | 3C,9G | 2C,9G | 2C,2H | 5C,9G | 2C,3G | 3C,6G | 2C | 3C,5H | 9C | 6C,9G | 5C,9G | 4C,9G | 10C | 10C |
| Sicklepod | | 2C | 2C,7G | 2C | 4C,8G | 2C | 3C,5G | 3C,5G | 2G | 3C | 3C,6H | 5G | 3C,4H | 9C | 4C,8H |
| Crabgrass | | 2C,9G | 9G | 0 | 0 | 0 | 0 | 4G | 3G | 1C,9G | 9G | 0 | 2C,8G | 2C | 3C,8G |
| Barnyardgrass | | 1C,5G | 9C | 1C,3G | 2C,5G | 1C | 1C | 3C,5G | 1C,5G | 2C,6G | 2C,8G | 2C,6G | 3G | 9C | 4C,9G |
| Wild Oats | | 5C,9H | 3C,9G | 1C,3G | 9C | 2G | 5C,9H | 4C,9H | 9H | 3C,9H | 4C,9H | 2C,8H | 1H | 9C | 5C,9G |
| Wheat | | 1C,8G | 3G | 5G | 1C | 5G | 1C,8G | 0 | 2G | 9G | 2C,9G | 2C,5G | 4G | 6C | 4C,9H |
| Corn | | 4C,9H | 9C | 3C,9H | 3G | 3G | 0 | 0 | 4G | 3C,8H | 3C | 1C,5G | 5G | 5C | 2C,7G |
| Soybean | | 3C,9G,7X | 5C,9G | 3C,7G,5X | 4C,9G | 2C,8H | 2C,8H | 3U,9C | 2C,8H | 5C,9H | 9C | 1U,9G | 1C,9G | 10C | 9G |
| Rice | | 6C,9G | 5C,9G | 2C,7G | 3C,8G | 1C,3G | 1C,3G | 2C,5H | 0 | 5C,9G | 6C,9G | 4G | 2C,9G | 5C | 3C,8H |
| Sorghum | | 4C,9G | 5C,9G | 2C,7G | 2C,9G | 2C,9G | 2C,7G | 2C,6G | 2C,9G | 5C,9G | 2C,8G | 3C,9G | 2C,8G | 6C | 6C,9G |
| Sugar beet | | 2C,7G | 2C,9G | 2C,9G | 2C,9G | 2C,9G | 2C,9G | 2C,8G | 9G | 9G | 2C,9G | 9G | 2C,9H | 6C | 4C,9G |

PRE-EMERGENCE

| | Cmpd. 48 | Cmpd. 49 | Cmpd. 50 | Cmpd. 51 | Cmpd. 52 | Cmpd. 53 | Cmpd. 54 | Cmpd. 55 | Cmpd. 56 | Cmpd. 57 | Cmpd. 58 | Cmpd. 59 | Cmpd. 60 | Compound 61 | Cmpd. 62 |
|---|---|---|---|---|---|---|---|---|---|---|---|---|---|---|---|
| Morningglory | 8G | 1C,4H | 9G | 0 | 8G | 7G | 7G | 9G | 1H | 8G | 9G | 5G | 0 | | 8H |
| Cocklebur | — | 9H | 9H | 0 | 7H | 0 | 0 | 0 | 8H | 8H | 8H | 9H | 8H | 9H | 9H |
| Sicklepod | 8G | 9H | 7G | 1C | 5G | 0 | 0 | 0 | 0 | 9C | 9G | 7G | 6G | 4C,9G | 5H |
| Nutsedge | 10E | 2C,8G | 10E | 0 | 0 | 0 | 0 | 1C | 1C | 7G | 9G | 5G | 0 | 10E | 10E |
| Crabgrass | 4C,6G | 1C,3G | 3C,9G | 4G,2C | 1C,3G | 2C,8G | 2C,8G | 1C | 3C | 5C,8G | 4C,8G | 2C,8G | 1C | 5C,9G | 3C,5G |
| Barnyardgrass | 5C,9H | 3C,8H | 9H | 2C | 9G,4C | 9G | 2C,7G | 1C,7G | 3C | 3C,8G | 5C,9G | 2C,9G | 2C | 5C,9H | 4C,9H |
| Wild Oats | 2C,8G | 2C,8H | 2C,7G | 1C,3G | 1C,5G | 1C | 1C | 1C | 1C | 6G | 2C,6G | 0 | 2C | 4C,8H | 4C,8H |
| Wheat | 2C,9G | 3C,9H | 1C,5G | 0 | 4G | 3G | 3G | 3G | 6G | 8G | 8G | 8G | 5G | 3C,9H | 3C,8H |
| Corn | 2C,9G | 3C,9H | 2C,9G | 2C,9G | 2C,9G | 2C,9G | 4C,9G | 2C,9G | 2C,4G | 2C,7G | 8G | 3C,7G | 2C,8G | 3C,9H | 9H |
| Soybean | 9H | 1C,1H | 9H | 1C | 1C,2G | 1C,2H | 1C | 1H | 1C | 6H | 8G | 1H | 2H | 8H | 4C,9H |
| Rice | 10E | 3C,8H | 10E | 1C,3G | 4C,9H | 3C,6G | 3C,7H | 3C,6G | 3C,8H | 8H | 9H | 9H | 5G | 1H | 1H |
| Sorghum | 5C,9H | 3C,9H | 9G | 2G | 5C,9H | 3C,9H | 5C,9H | 5C,9H | 3C,9H | 2C,9H | 5C,9H | 2C,6G | 10E | 10E | 4C,7H |
| Sugar beet | — | 8H | — | 2C | — | — | — | — | — | — | — | — | — | 10H | 5C,9H |
| Cotton | | | | | | | | | | | | | | | — |
| Rate kg/ha | 0.05 | 50 | 50 | 50 | 50 | 50 | 50 | 50 | 50 | 50 | 50 | 50 | 50 | 400 | 50 |

TABLE A-continued

POST-EMERGENCE

| | | | | | | | | | | | | | | | | |
|---|---|---|---|---|---|---|---|---|---|---|---|---|---|---|---|---|
| | | | | | | | | | | | | | | | | |
| | 5C,9G,6Y | 5C,9G,6Y | 4C,9G,6Y | 4C,7G,6Y | | | | 5C,9G,6Y | | | | | | 6C,9G,6Y | | |
| Bush bean | — | — | — | — | — | — | — | — | — | — | — | — | — | — | — | — |
| Cotton | 5C,9H | 5C,9G | 4C,5H,9G | 3C,8G | 2C,9G | 3C,8G | 3C,9G | 5C,9G | 4C,9G | 9H | 4C,8H | 3C,9G | 2C,5H | 3C,8H | 4C,5H | 4C,8H |
| Morningglory | 5C,9H | 5C,9G | 4C,9G | 3C,8G | 3C,7H | 4G | 6C,9G | 5C,9G | 5C,5G | 9H | 3C,6H | 4C,9G | 4G | 4C,9G | 3C,4G | 4C,8H |
| Cocklebur | 3C | 4C,9G | 9C | 5C,9G | 4C,8G | 9C | 5C,9G | 9C | 10C | 9G | 4C,9H | 9C | 5G | 3C,9H | 5C,9G | 5C,9G |
| Sicklepod | 3C,9G | 3C,9G | 3C,7G | 2C,9G | 3C,6H | 3C,4G | 2C,5G | 3C | 5C,9G | 8G | 9C | 5C,8G | 3G | 3C,8G | 2C,5G | 4C,8H |
| Nutsedge | 2C,8G | 2C,9G | 6C,9G | 1C,3G | 3G | 5C,9G | 2C,4G | 4C,9G | 2C,6G | 5G | 4C,8H | 10C | 2G | 3C,8G | 0 | 2C,4G |
| Crabgrass | 4C,9G | 3C,9G | 2C,8G | 3G | 0 | 3H | 2C,7G | 6H | 3C,5G | 2C,7G | 3G | 3G | 2G | 2C,5G | 0 | 3C |
| Barnyardgrass | 5C,9H | 5C,9G | 3C,9G | 2C,7G | 3C,8H | 5C,9G | 3C,7G | 9C | 5C,9H | 3C,5G | 1C,3G | 6C,9G | 9H | 9C | 3C,9H | 5C,9H |
| Wild Oats | 2C,9H | 2C,9G | 3C,9G | 3C,9H | 3G | 3C,9G | 3C,9H | 6C,9G | 2C,9H | 3C,4G | 2H | 9C | 0 | 5C,9G | 1C | 4C,9G |
| Wheat | 4C,9G | 9C | 9G | 3G | 3C,8H | 5C,9G | 5G | 6C,9G | 5C,9H | 9C | 0 | 9G | 9H | 5C,9G | 4C,9G | 3C |
| Corn | 2C,9H | 3C,9H | 4C,9G | 5G | 3C,8H | 3G | 3C,9G | 5C,9G | 4C,9G | 5U,9G | 3G | 3C | 0 | 2C,5G | 4C,9G | 9G,7X |
| Soybean | 5C,9G | 4C,9G | 3C,8G | 5C,9G | 3C,8G | 5C,9G | 3C,9G | 4C,9G | 5C,9G | 4C,9G | 3C | 2C,9G | 3G | 3C,9G | 5C,9G | 5C,9G |
| Rice | 5C,9G | 6C,9G | 4C,9G | 3C,9G | 2C,9G | 6C,9G | 5C,9G | 5C,9G | 6C,9G | 5C,9G | 3C,8H | 2C,6G | 2H | 3C,7H | 3C,9G | 5C,9G |
| Sorghum | 3C,9G | 9C | 4C,9G | 5C,9G | 6C,9G | 3C,9G | 4C,9G | 6C,9G | 4C,9G | 6C,9G | 2C,7G | 3C,9G | 2C,9G | 4C,9G | 2C,8H | 3C,9G |
| Sugar beet | — | 5C,9G | 2C,8G | 5C,9G | 3C,8H | 9C | 5C,9G | 4C,8H | 4C,9G | 5C,9G | 3C,7G | 3C,8G | 2C,5G | 4C,9G | 2H | 5C,9G |

| | Cmpd. 63 | Cmpd. 64 | Cmpd. 65 | Cmpd. 66 | Cmpd. 67 | Cmpd. 68 | Cmpd. 69 | Cmpd. 70 | Cmpd. 71 | Cmpd. 72 | Cmpd. 73 | Cmpd. 74 | Cmpd. 75 | Cmpd. 76 | Cmpd. 77 | Cmpd. 78 |
|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 50 | 50 | 50 |

PRE-EMERGENCE

| | | | | | | | | | | | | | | | | |
|---|---|---|---|---|---|---|---|---|---|---|---|---|---|---|---|---|
| Morningglory | 8H | 9G | 8G | 3C,8G | 9C | 8G | 4C,8H | 2C,9G | 6G | 9G | 3C,9H | 9G | 9H | 0 | 0 | 0 |
| Cocklebur | 9H | 9H | — | 2C,3G | — | 2C,6H | — | 9H | 9H | 9H | 9H | 9H | 9H | 2C,6H | 0 | 0 |
| Sicklepod | 2C | 9G | 2C,3G | — | — | 2C | 2C | 9G | 9G | 9G | 2C | 9G | 4C,8H | 2C | 0 | 0 |
| Nutsedge | 10E | 10E | 9G | 3C,5G | — | 5C,9G | 5C,9G | 4G | 5G | 8G | 5G | 9G | 0 | 2C,6G | 0 | 0 |
| Crabgrass | 4C,7G | 2C,5G | 2C,5G | 2C,5G | 9C | 2C,5G | 4C,8G | 3C,8G | 2C,7G | 2C,7G | 2C,4G | 2C,7G | 2C,6G | 1C | 0 | 0 |
| Barnyardgrass | 5C,9H | 5C,9H | 3C,8H | 2C,4G | — | 2C,6G | 5C,9G | 3C,9H | 3C,9H | 3C,9H | 3C,7H | 4C,8G | 2C,7G | 2C,6H | 0 | 0 |
| Wild Oats | 2C,8G | 3C,9G | 3C,9G | 3C,9G | — | 4C,9G | 4C,8G | 4C,9G | 5C,9H | 5C,9H | 3C,3G | 2C,5G | 3C,8H | 2C,6H | 0 | 0 |
| Wheat | 2C,9H | 3C,9G | 3C,9G | 2C,8G | — | 4C,6G | 4C,9G | 2C,4G | 2C,8G | 2C,9H | 7G | 6G | 8G | 8G | 0 | 2C,8H |
| Corn | 2H | 3C,8G,7X | 2C,2H | 2C,9G | — | 9G | 4C,9H | 4C,9H | 2C,8G | 2H | 2C,7H | 2C,9G | 3C,5G | 5C,9H | 0 | 0 |
| Soybean | 3C,6H | 10E | 10E | 5C,9H | 9C | 4C,9G | 3C,5H | 3C,4H | 3C,6H | 0 | 2C,8H | 3C,5G | 3C,9H | 0 | 0 | 2G |
| Rice | 3C,9H | 3C,9H | 6C,9H | 3C,6G | — | 5C,9H | 3C,8H | 4C,9G | 3C,8H | 3G | 3C,8H | 3C,9H | 3C,9H | 2C,6G | 0 | 2C,7H |
| Sugar beet | — | 5C,9G | 9C | 3C,9G | — | 5C,9G | 4C,8G | 5C,9G | 4C,9H | 3C | 4C,8G | 10E | 3C,8G | 5C,9H | 0 | 3H |
| Cotton | — | — | — | — | — | — | — | 9G | 9G | 9G | 2C,6G | 9G | 3C,5G | — | — | 0 |

| | Cmpd. 79 |
|---|---|
| | 50 |

POST-EMERGENCE

| | Cmpd. 63 | Cmpd. 64 | Cmpd. 65 | Cmpd. 66 | Cmpd. 67 | Cmpd. 68 | Cmpd. 69 | Cmpd. 70 | Cmpd. 71 | Cmpd. 72 | Cmpd. 73 | Cmpd. 74 | Cmpd. 75 | Cmpd. 76 | Cmpd. 77 | Cmpd. 78 |
|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 50 | 50 | 50 |
| Bush bean | — | 5C,9G | 3C,8H | 3C,8G | — | 3C,9G | 5C,9G | 5C,9G | 9C | 2G | 3C,9G | 2C,5H | 3C,8H | 1C | — | 4C,9G |
| Cotton | 9G | 2C,8G | 2C,3G | 2C,9G | 4G | 4G | 5C,9G | 2C,5G | 3C,7H | 1H | 2C,5G | 4G | 4C,9G | 1C,4G | 2C,5G | 4C,8H |
| Morningglory | 3C,6G | 3C,9H | 4C,8G | 5C,9G | 9C | 9C | 9C | 10C | 10C | 4C,8H | 9C | 5G | 3C,9H | 2C,8H | 2C,3H | 4C,8H |
| Cocklebur | 4C,9H | 2C,7H | 3C,6H | 3C,4G | 3C,4G | 3C,4G | 3C | 2C,4G | 5C,8G | 4C,6H | 3C,8G | 3G | 3C,8G | 1C | 1H | 4C,5H |
| Sicklepod | 2C,3G | 2C,5G | 3G | 2C,7G | 3C,4G | 5C,9G | 4C,9G | 10C | 10C | 3G | 2C,5G | 2G | 2C,5G | 0 | 2C,3H | 2C,4G |
| Nutsedge | 2C,7G | 2G | 0 | 3H | 0 | 4C,6G | 6H | 8G | 9C | 1C,3G | 6C,9G | 2G | 2H | 0 | 0 | 3C |
| Crabgrass | 0 | 4G | 0 | 5C,9H | 5C,9G | 9G | 9C | 4C,9H | 2C,8G | 2H | 9C | 9H | 9C | 3C,9H | 2G | 5C,9H |
| Barnyardgrass | 9H | 2C,9H | 3C,8H | 3C,9G | 4C,6G | 9G | 6C,9G | 3C,9G | 3C,8H | 0 | 9C | 0 | 5C,9H | 1C | 2G | 4C,9H |
| Wild Oats | 6G | 0 | 3G | 3G | 9G | 4C,9G | 6C,9G | 9G | 6C,9G | 3G | 9C | 6G | 5C,9G | 1C | 3G | 4C,8H |
| Wheat | 0 | 2C,9H | 3G | 5C,9H | 4C,9G | 4C,9G | 10C | 9G | 9G | 0 | 9C | 0 | 5C,9H | 3G | 9G,7X | 8G |
| Corn | 3C,9H | 3C,9H | 3C,8H | 3C,8H | 10C | 10C | 10C | 5C,9G | 5U,9C | 3G | 9C | 2C,8H | 3C,9H | 1C | 2H | 5C,9G |
| Soybean | 4C,9G | 4C,9G | 3C,8G | 5C,9G | 4C,9G | 4C,9G | 4C,9G | 3C,9G | 3C,9G | 3C,8H | 4C,9G | 3C,6H | 3C,9G | 3C,7H | 2C,9G | 4C,9G |
| Rice | 7G | 2C,8G | 9G | 3C,8H | 4C,6G | 3U,9C | 5C,9G | 5C,9G | 5C,9G | 2C,7G | 5C,9G | 2C,8G | 6C,9G | 4C,9G | 2C,8H | 5C,9G |
| Sorghum | 3C,9H | 3C,9G | 3C,9H | 2C,8G | 4C,9G | 9C | 3U,9G | 3U,9G | 10C | 3C,7G | 9C | 2C,9G | 10C | 3C,9H | 2C,9G | 3C,9G |
| Sugar beet | 3C,6H | 2C,3G | 2C,6G | 3C,9G | 4C,6G | 4C,8G | 9C | 5C,9G | 9C | 3C,8G | 5C,9G | 2C,5G | 4C,9G | 4C,9G | 2H | 5C,9G |

| | Cmpd. 79 |
|---|---|
| | 50 |
| Morningglory | 2C,5H | 2C,5H |

TABLE A-continued

| | | | | | | | | | | | | | | | |
|---|---|---|---|---|---|---|---|---|---|---|---|---|---|---|---|
| Cocklebur | 2C,4H | 2C,8H | 2H | 3C,5H | 2C,5H | 5C,9H | 9H | 9H | 9C | 9H | 3C,8H | 9H | 9H | 8H | 9H |
| Sicklepod | 0 | 3C,6G | 0 | 2C | 2G | 4C,7G | 5C,2C | 7G | 8G | 1C | 4G | 5G | 8G | 3G | 2C |
| Nutsedge | 8G | 8G | 5G | 0 | 0 | 10E | 10E | 10E | 10E | 0 | 7G | 0 | 0 | 0 | 0 |
| Crabgrass | 0 | 2G | 2G | 0 | 0 | 3G | 5G | 2C,4G | 3C,5G | 0 | 2G | 0 | 0 | 1C | 0 |
| Barnyardgrass | 2C,7G | 3C,8H | 3H | 0 | 3C,8H | 9H | 3C,9H | 3C,8H | 3C,5G | 2C | 1H | 3C,7G | 2G | 3C,5H | 2C,7G |
| Wild Oats | 3C,8H | 3C,8G | 2C,4G | 0 | 3C,8G | 3C,9G | 3C,9H | 3C,8G | 4C,9G | 3C,7G | 0 | 2C,8G | 2C,7G | 4C,8G | 2C,4G |
| Wheat | 5G | 3C,8H | 2G | 0 | 8G | 2C,9G | 3C,9G | 6G | 4C,9G | 3G | 0 | 3C,8G | 2G | 2C,8G | 6G |
| Corn | 3C,9H | 3C,9G | 2C,8H | 3C,9H | 9G | 5C,9H | 3C,9H | 3C,9H | 3C,8G | 2C,6H | 2C,8H | 3C,9H | 9G | 2C,9G | 3C,8G |
| Soybean | 0 | 2C,6H | 1C | 0 | 9H | 2C,8G | 5C,9H | 3C,8G | 10E | 1C,1H | 0 | 3C,7H | 8G | 2C,5G | 2C,6G |
| Rice | 3C,5G | 3C,8H | 2C,3G | 2C,3G | 4C,5G | 3C,5G | 3C,8G | 3C,6H | 3G | 2C,3H | 2C,4G | 3C,8H | 2C,5G | 2C,7H | 2C,6G |
| Sorghum | 9H | 4C,9H | 3C,8H | 3C,8G | 4C,9G | 6C,9H | 4C,7G | 3C,6H | 3C,8H | 3C,8H | 2C,4G | 3C,8H | 2C,9G | 3C,9G | 2C,8H |
| Sugar beet | 6G | 9G | 8G | 0 | 2C,4G | 5C,9G | 6C,9H | 5C,9H | 5C,9H | 3C,8H | 3G | 7G | 8G | 3C,9G | 3C,8G |
| Cotton | 5G | 8G | 6G | 0 | 6H | 8G | 9G | 9G | 9G | 2C,8G | 0 | 4H | 7G | 2C,3G | 5G,2C |

Test B

Two plastic bulb pans were filled with fertilized and limed Fallsington silt loam soil. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass, (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. At least one compound exhibits utility for pre-emergence weed control in soybeans and cotton.

TABLE B
PRE-EMERGENCE ON FALLSINGTON SILT LOAM

| | Compound 2 | | Compound 3 | | Compound 4 | | Compound 20 | | Compound 21 | | Cmpd. 22 | Compound 23 | | | Compound 24 | | Compound 26 | | Compound 30 |
|---|---|---|---|---|---|---|---|---|---|---|---|---|---|---|---|---|---|---|---|
| Rate kg/ha | 0.03 | 0.12 | 0.03 | 0.12 | 0.03 | 0.12 | 0.25 | 0.063 | 0.031 | 0.125 | 0.125 | 0.062 | 0.031 | 0.015 | 0.125 | 0.031 | 0.062 | 0.031 | 0.031 |
| Crabgrass | 0 | 3G | 6G,3C | 9G,9C | 0 | 0 | 9G | 6G | 0 | 9G | 9G | 3G | 0 | 0 | 0 | 0 | 8G | 5G | 7G |
| Barnyardgrass | 3G | 6G,3H | 8G,3H | 10C | 0 | 0 | 9G,9C | 8G | 4G | 8G,8C | 5G | 2G | 2G | 0 | 0 | 0 | 9G | 5G | 9G,5H |
| Sorghum | 10C | 10C | 10E | 10E | 3G | 9G,9C | 9G,9C | 8G | 4G | 10C | 10C | 10C | 10C | 9G | 3G | 2G | 9G,9C | 9G | 10E |
| Wild Oats | 5G | 7G | 8G,8C | 8G,8C | 0 | 6G | 8G | 6G | 2G | 9G | 8G | 7G | 5G | 4G | 0 | 0 | 8G | 5G | 7G |
| Johnsongrass | 8G,7C | 9G,9C | 9G,8C | 10C | 0 | 7G,3H | 8G | 7G | 0 | 8G | 8G | 8G | 7G | 7G | 0 | 0 | 9G,9C | 8G | 8G,7C |
| Dalligrass | 4G | 6G,3H | 8G,3H | 10C | 0 | 3G | 9G | 6G | 2G | 8G | 8G | 8G | 5G | 3G | 2G | 0 | 9G | 5G | 8G,5H |
| Giant foxtail | 0 | 8G,5H | 7G,3H | 10C | 0 | 3G | 9G | 8G | 0 | 9G,9C | 5G | 5G | 7G | 3G | 0 | 0 | 9G | 7G | 9G,3H |
| Ky. bluegrass | 6G | 8G,8C | 8G,8C | 10C | 4G | 6G,3C | 9C,9G | 8G | 2G | 9G,9C | 2G | 8G | 3G | 3G | 0 | 0 | 9G | 8G | 10C |
| Cheatgrass | 9G,9C | 9G,9C | 10C | 10C | 0 | 0 | 9G | 9G | 4G | 9G,9C | 9G | 5G | 6G | 4G | 0 | 0 | 9G,9C | 5G | 7G |
| Sugar beets | 3G | 3G | 4G | 10C | 0 | 0 | 8G | 6G | 2G | 10C | 3G | 5G | 5G | 4G | 2G | 0 | 9G,9C | 9G | 7G,5H |
| Corn | 3G | 8G,8C | 10C | 10C | 0 | 6G,3H | 8G,7H | 5G | 6G,5H | 8G,7H | 6G,5H | 6G,5H | 2G | 2G | 0 | 0 | 8G,8C | 8G | 3H,8G |
| Mustard | 7G,3H | 9G,8C | 10C | 10C | 0 | 9G | 9G | 9G | 0 | 9G | 9G | 9G | 5G | 5G | 0 | 0 | 10C | 9G | 9G,9C |
| Cocklebur | 5G | 5G | 9G,8C | 9G,9C | 0 | 6G,3H | 5G | 2G | 7G | 6G | 9G | 6G | 3G | 2G | 0 | 0 | 8G,8C | 3G | 7G,5H |
| Pigweed | 0 | 0 | 10C | 10C | 5G,5C | 10C | — | — | 0 | — | — | — | — | — | — | — | — | — | — |
| Nutsedge | 0 | 3G | 7G | 10E | 0 | 0 | 9G | 4G | 2G | 10C | 10C | 10C | 7G | 8G | 0 | 0 | 10E | 9G | 9G |
| Cotton | 0 | 2G | 5G,3H | 7G,5H | 0 | 0 | 5G | 2G | 0 | 6G | 6G | 6G | 2G | 2G | 0 | 0 | 8G,5H | 0 | 6G,3H |
| Morningglory | 0 | 4G | 3G | 3G | 0 | 0 | 8G | 5G | 0 | 4G | 4G | 4G | 3G | 0 | 0 | 0 | 9G,7C | 4G | 6G,5H |
| Sicklepod | 0 | 4G | 3G | 3G | 2G | 2G | 5G | 2G | 2G | 4G | 4G | 0 | 0 | 0 | 0 | 0 | 7G,4C | 2G | 3G |
| Teaweed | 0 | 0 | 4G,3H | 6G,5H | 0 | 0 | 9G | 0 | 0 | 2G | 0 | 0 | 0 | 0 | 0 | 0 | 7G,3H | 0 | 4G |
| Velvetleaf | 0 | 0 | 3G,5H | 7G,5H | 0 | 0 | 7G | 2G | 0 | 0 | 4G | 2G | 0 | 0 | 0 | 0 | 8G,9C | 5G | 3G |
| Jimsonweed | 0 | 0 | 3G | 7G | 0 | 2G | 3G | 2G | 0 | 0 | 8G | 9G | 2G | 4G | 0 | 0 | 9G,8C | 3G | 3G |
| Soybean | 0 | 0 | 3G,3H | 6G,5H | 0 | 0 | 3G,3H | 5G,2H | 0 | 2G | 0 | 2G | 0 | 0 | 0 | 0 | 6G,5H | 2G | 2C |
| Rice | 7G,4C | 10C | 9G,9C | 10C | 4G | 6G,3H | 10C | 8G | 4G | 10C | 10C | 9G | 6G | 6G | 0 | 0 | 10E | 10E | 10E |
| Wheat | 5G | 7G,3C | 8G,5C | 10C | 0 | 6G,3C | 8G | 7G | 2G | 9G | 9G | 3G | 4G | 3G | 0 | 0 | 9G,9C | 3G | 7G |

| | Compound 31 | Compound 32 | | Compound 33 | | Compound 35 | | Compound 38 | | Compound 39 | | Compound 42 |
|---|---|---|---|---|---|---|---|---|---|---|---|---|
| Rate kg/ha | 0.125 0.031 | 0.031 0.008 | 0.003 | 0.125 0.031 | 0.0015 | 0.031 0.008 | 0.003 | 0.125 0.062 | 0.015 | 0.125 0.062 | 0.031 | 0.125 0.031 |
| Crabgrass | 4G 3G | 8G 7G | 7G | 6G 8G | 2G | 8G 6G | 2G | 2G 3G | 2G | 2G 2G | 0 | 2G 2G |
| Barnyardgrass | 9G,5H 7G,3H | 7G 6G,3C | 3G | 3H,6G 5H,7G | 2G | 5H,7G 3G | 2G | 6G 8G,5H | 6G | 2G 0 | 0 | 0 2G |
| Sorghum | 10E 10C | 10C 10C | 10C | 3H,10C 10C | 10C | 10C 8G | 4G | 8G,8C 8G,5H | 8G,8C | 5G 10C | 0 | 10C 2G |
| Wild Oats | 7G 7G | 7G 6G | 6G | 2G 2G | 0 | 2G 3G | 2G | 0 5G | 0 | 2G 2G | 0 | 0 0 |
| Johnsongrass | 8G,3H 6G,3H | 8G 6G | 6G | 8G 9G | 5G | 9G 4G | 7G | 5G 4G | 5G | 0 0 | 0 | 0 0 |
| Dalligrass | 8G,3H 7G,3H | 9G,9C 8G | 6G | 4G 8G | 6G | 8G 2G | 2G | 3G 0 | 0 | 0 0 | 0 | 0 0 |
| Giant foxtail | 9G,9C 8G,5H | 9G 6G,2H | 7G | 9G,9C 9G,9C | 6G | 9G 7G | 3G | 4G 2G | 4G | 4G 4G | 0 | 0 0 |
| Ky. bluegrass | 10C 7G,3H | 10C 10C | — | 10C 10C | 5G,8G | 10C 2G | 2G | 3G 5G | 3G | 2G 2G | 0 | — — |
| Cheatgrass | 8G,9C 6G | 9G,9C 9G,5C | 9G | 9G,9C 9G,9C | 8G,8C | 9G,9C 8G | 3G | 4G 4G | 4G | 4G 2G | 4G | 0 0 |
| Sugar beets | 7G,5H 4G | 9G,9C 10C | 9G | 10C 7G | 6G,3H | 9G,9C 3G | 2G | 4G 3G | 3G | 2G 3G | 2G | 0 2G |
| Corn | 9G,9C 5H,7G | 9G,9C 9G,7C | 7H | 7G 8G | 0 | 10C 9G | 9G | 8G,8C 8G,8C | 8G,8C | 3G 3G | 3G | 3G 3G |
| Mustard | 9G,9C 10C | 9G,9C 9G,9C | 9G | 5G 6G | — | 6G 7G | 3G | 0 0 | 4G | 7G 2G | 2G | 7G 2G |
| Cocklebur | 2G 0 | 7G — | — | 7G,7C 4G | 5G,2H | 4G 6G | 2G | 4G 0 | 0 | 0 0 | 0 | 0 0 |
| Pigweed | — — | — — | — | — — | — | — — | — | — — | — | — — | — | — — |
| Nutsedge | 10E 7G | 10C 10C | 10C | 3G 10C | 10C | 10C 10C | 2G | — — | 5G | — 0 | — | — 0 |
| Cotton | 4G 0 | 7G 8G | 8G | 6G,3H 7G | 6G,3H | 7G 6G | 2G | 0 0 | 0 | 0 0 | 0 | 0 0 |
| Morningglory | 8G,3H 8G | 3G,2C 3C | 3C | 0 4G | 0 | 4G 8G | 3G | 2G 2G | 4G | 0 0 | 0 | 0 0 |
| Sicklepod | 7G 4G | 3G,5C 8G,5C | 3G | 7G,7C 7G | 6G,3H | 7G 3G | 3G | 4G 5G | 8G,8C | 0 0 | 0 | 0 2G |
| Teaweed | 8G,3H 3G | 8G,5C 8G,3C | 8G | 7G 8G | 8G,8C | 8G 9G | 2G | 0 0 | 0 | 0 0 | 0 | 0 0 |
| Velvetleaf | 4G,3H 3G | 8G 8G | 8G | 6G 7G | 5G,2H | 10C 2G | 2G | 2G 2G | 4G | 2G 7G | 0 | 0 0 |
| Jimsonweed | 5G,5C 3G | 9G,9C 7G,7H | 4G | 3G 5G | 3G | 7G 3G | 3G | 3G 5G | 0 | 2G 0 | 0 | 2G 0 |

TABLE B-continued
PRE-EMERGENCE ON FALLSINGTON SILT LOAM

| | Compound 43 | | Compound 44 | | | Compound 46 | | | Compound 47 | | | Compound 48 | | |
|---|---|---|---|---|---|---|---|---|---|---|---|---|---|---|
| Rate kg/ha | 0.125 | 0.031 | 0.125 | 0.031 | 0.015 | 0.125 | 0.031 | 0.015 | 0.125 | 0.031 | 0.015 | 0.125 | 0.031 | 0.015 |
| Crabgrass | 3G | 2G | 5G | 2G | 0 | 9G,7C | 8G,7C | 7G,7C | 5G,3C | 2C,2G | 0 | 4G | 2G | 0 |
| Barnyardgrass | 0 | 0 | 0 | 0 | 0 | 9G,7C | 8G,7C | 5G,3C | 6G,3C | 2G,2C | 0 | 6G,5C | 4G,3C | 2G |
| Sorghum | 7G,3H | 2G | 0 | 0 | 0 | 10C | 10C | 10C | 9G,9C | 7G,5H | 3G,3H | 9G,9C | 9G,9C | 8G,8C |
| Wild Oats | 0 | 0 | 0 | 0 | 0 | 7G,3C | 7G,3C | 5G,3C | 6G | 3G | 2G | 6G | 5G | 4G |
| Johnsongrass | 0 | 0 | 0 | 0 | 0 | 9G,5C | 8G,5C | 2G | 8G,7C | 2G | 0 | 8G | 8G | 0 |
| Dallisgrass | 3G | 2G | 2G | 0 | 0 | 9G | 9G | 8G | 8G | 5G | 0 | 7G | 5G | 3G,3H |
| Giant foxtail | 0 | 0 | 0 | 0 | 0 | 9G,9C | 9G,9C | 7G | 8G,8C | 2G,3C | 0 | 8G,8C | 4G,3C | 0 |
| Ky. bluegrass | 2G | — | — | — | — | — | — | — | — | — | — | — | — | — |
| Cheatgrass | 4G | 2G | — | 0 | 0 | 8G | 8G | 2G | 8G | 5G | 0 | 8G | 6G | 0 |
| Sugar beets | — | — | — | — | — | 8G | 8G,5C | 7G | 8G | 4G,3H | 3G | 6G | 4G | 3G |
| Corn | 2G | — | — | — | — | 9G,5C | 7G,7H | 2G,2C | 7G,7H | 3G,3C | 2G,2H | 7G,5C | 2G,2C | 0 |
| Mustard | 7G | 5G | 5G | 0 | 0 | 8G,8C | 8G,8C | 8G,8C | 9G,8C | 7G | 6G | 9G,9C | 8G,5C | 7G |
| Cocklebur | 2G | 0 | 0 | 0 | — | 6G,3C | — | 2G | 6G,7C | 0 | 0 | 5G,5C | 3C,2G | 0 |
| Pigweed | — | — | — | — | — | — | — | — | — | — | — | — | — | — |
| Nutsedge | 0 | 0 | 0 | 0 | 0 | 10C | 9G | 6G | — | — | 0 | — | 2G | 2G |
| Cotton | 5G | 2G | 3G | 0 | 0 | 4G,7H | 3G,5H | 3G | 7G,3C | 3G | 3G | 3G,3H | 2G | 2G |
| Morningglory | 2G | 0 | 0 | 0 | 0 | 7G | 5G,5H | 3G,3H | 5G,3H | 0 | 0 | 5G | 3G | 0 |
| Sicklepod | 0 | 0 | 0 | 0 | — | — | 5G,5H | 3G,3H | 2G,3C | 0 | 0 | 2G | 0 | 0 |
| Teaweed | — | — | — | — | — | — | — | — | — | — | — | — | — | — |
| Velvetleaf | 0 | 0 | 0 | 0 | 0 | — | 2G,2H | 2G | 5G,3H | 0 | 0 | 7G,5C | 0 | 0 |
| Jimsonweed | 0 | 0 | 0 | 0 | 0 | 7H | 4G | 2G | 2G,2C | 0 | 0 | 2G,2C | 0 | 0 |
| Soybean | 5G | 2G | 3G | 0 | 0 | 10C | 5G,5H | 5G,5H | 10C | 4G | 2G | 2G,3C | 5G | 3G |
| Rice | 0 | 0 | 0 | 0 | 0 | 10C | 10C | 10C | 7G | 4G | 2G | 9G | 5G | 3G |
| Wheat | — | — | — | — | — | 7G | 3G | 0 | — | — | — | 5G | 4G | 4G |

Test C

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), *Galium aparine*, tumble mustard (*Sisymbrium altissium*) kochia (*Kochia scoparia*), shepherd's purse (*Capsella bursapastoris*), *Matricaria inodora*, black nightshade (*Solanum nigrum*), yellow rocket (*Barbarea vulgaris*), wild mustard (*Brassica kaber*) and wild buckwheat (*Polygonum convolulus*). In certain tests, rapeseed was substituted for wild mustard and *Veronica persica* was included. The above two pans were treated pre-emergence. At the same time two pans in which the above plant species were growing were treated post-emergence. Plant height at the time of treatment ranged from 1-15 cm depending on plant species.

The test compounds were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table C. Several of the compounds tested exhibit utility for post-emergence weed control in wheat.

TABLE C

|  | Compound 1 | | | | Compound 35 | | | | | | | |
|---|---|---|---|---|---|---|---|---|---|---|---|---|
|  | Pre-Emergence | | Post-Emergence | | Pre-Emergence | | | | Post-Emergence | | | |
| Rate kg/ha | 0.015 | 0.06 | 0.015 | 0.06 | 0.25 | 0.06 | 0.015 | 0.004 | 0.25 | 0.06 | 0.015 | 0.004 |
| wheat | 0 | 0 | 2G | 1C,3G | 7G | 5G | 1G | 0 | 7G | 3G | 1G | 0 |
| barley | 0 | 0 | 4G | 6G | 8G | — | 3G | 0 | 8G | 5G | 1G | 0 |
| wild oats | 0 | 0 | 2G | 1G | 6G | 5G | 2G | 0 | 7G | 5G | 2G | 0 |
| downy brome | 0 | 2G | 2G | 3G | 2C,9G | 2C,8G | 7G | 5G | 3C,9G | 7G | 7G | 5G |
| cheatgrass | 0 | 1C,2G | 6G | 2C,8G | 10E | 10C | 1C,8G | 5G | 2C,9G | 8G | 7G | 5G |
| blackgrass | 0 | 0 | 3G | 2C,6G | 4C,9G | 2C,8G | 3C,7G | 5G | 9C,9G | 5C,9G | 7C,8G | 1C,5G |
| annual bluegrass | 0 | 2G | 1C,4G | 8C,9G | 3C,9G | 2C,8G | 8G | 4G | 2C,8G | 3C,8G | 7G | 3G |
| green foxtail | 0 | 0 | 3G | 5G | 9G | 5C,8G | 2C,7G | 3C,6G | 2C,8G | 2C,8G | 1C,6G | 3G |
| quackgrass | 0 | 0 | 0 | 5G | 2C,9G | 2C,8G | 8G | 5G | 1C,6G | 1C,7G | 6G | 3G |
| Italian ryegrass | 0 | 1G | 3G | 9C,9G | 10E | 1C,8G | 7G | 1C,4G | 2C,7G | 8G | 5G | 2G |
| ripgut brome | 0 | 0 | 2G | 2C,6G | 3C,9G | 1C,8G | 7G | 4G | 2C,8G | 7G | 5G | 5G |
| Russian thistle | 0 | 0 | 3C,3G | 4G | 5C,7G | 2C,6G | 1C,3G | 1C,3G | 9C,9G | 10C | 7C,8G | 5C,7G |
| tansy mustard | 0 | — | 9G | 5G | 9C,9G | 7C,9G | 2C,9G | 9G | 10C | 10C | 7C,8G | 5C,7G |
| *Galium aparine* | 0 | 0 | 2G | 2G | 3C,9G | 7G | 7G | 6G | 2C,7G | 7G | 4G | — |
| tumble mustard | 0 | 0 | 5G | 10C | 10C | 5C,9G | 9G | 8G | 10C | 10C | 10C | 5C,8G |
| kochia | 0 | 0 | 2G | 4G | 2C,9G | 9G | 8G | 6G | 10C | 9C,9G | 2C,7G | 2C,2G |
| shepherd's purse | 0 | 0 | 10C | 2C,2G | 10C | 10C | 2C,9G | 9G | 10C | 10C | 9C,9G | 7C,9G |
| *Matricaria inodora* | 0 | 0 | 3G | 8C,8G | 9G | 9G | 8G | 7G | 7C,9G | 7C,8G | 5C,9G | 3C,8G |
| black nightshade | 0 | 0 | 0 | 0 | 3C,9G | 8G | 6G | 4G | 5C,8G | 2C,7G | 2C,7G | 2G |
| yellow rocket | 0 | 0 | 0 | 0 | 3C,9G | 9G | 8G | 8G | 5C,9G | 1C,7G | 2G | 0 |
| wild mustard | 0 | 0 | 10C | 9G | 2C,9G | 9G | 1C,9G | 7G | 7C,8G | 5C,9G | 2C,7G | 6G |
| wild buckwheat | 0 | 0 | 1G | 0 | 2C,8G | 8G | 5G | 2G | 10C | 6G | 3G | — |

|  | Compound 43 | | | | Compound 46 | | | |
|---|---|---|---|---|---|---|---|---|
|  | Pre-Emergence | | Post-Emergence | | Pre-Emergence | | Post-Emergence | |
| Rate kg/ha | 0.25 | 0.06 | 0.25 | 0.06 | 0.015 | 0.004 | 0.015 | 0.004 |
| wheat | 8G | 0 | 7G | 2G | 4G | 1G | 6G | 4G |
| barley | 2G | 2G | 3C,5G | 5G | 8G | 5G | 8G | 6G |
| wild oats | 5G | 2G | 2C,4G | 2G | 8G | 5G | 3C,8G | 6G |
| downy brome | 8G | 4G | 4G | 4G | 9G | 7G | 3C,8G | 8G |
| cheatgrass | 3C,8G | 2G | 4G | 2G | 2C,8G | 6G | 3C,8G | 7G |
| blackgrass | 3C,8G | 2H | 8G | 2C,5G | 3C,9G | 2C,8G | 10C | 3C,8G |
| annual bluegrass | 2C,8G | 4G | 4G | 2G | 4C,9G | 2C,9G | 9C,9G | 3C,8G |
| green foxtail | 2C,5G | 1C,2G | 2C,7G | 2C,4G | 3C,9G | 7G | — | — |
| quackgrass | 5G | 2G | — | — | 9G | 7G | 6G | 8G |
| Italian ryegrass | 2C,8G | 1C,2G | 1C,2G | 5G | 4C,9G | 7G | 3C,8G | 7G |
| ripgut brome | 2C,7G | 2G | 5G | 2G | 2C,8G | 6G | 2C,8G | 6G |
| Russian thistle | 1C | 0 | 0 | 0 | 3G | 0 | 0 | 0 |
| tansy mustard | 9C | 9C | 2C | 1C,2G | — | — | 10C | 10C |
| *Galium aparine* | 7C | 3C | 3C | 3G | 5G | 5G | 6G | 3G |
| tumble mustard | 8G | 4G | 10C | 6G | 10C | 9G | 10C | 10C |
| kochia | 0 | 0 | — | — | 8G | 0 | 0 | — |
| shepherd's purse | 9G | 8G | 2C,2G | 5G | 10C | 9G | 10C | 8G |
| *Matricaria inodora* | 9G | 6G | 5G | 1C,3G | 9G | 8G | 2C,6G | 3G |
| black nightshade | 5G | 0 | 3C,8G | 7G | 9G | 5G | 2C,8G | 6G |
| yellow rocket | 9G | 8G | 7G | 2G | 9G | 8G | 8G | 4G |
| rapeseed | 9G | 7G | 8G | 3G | 9G | 8G | 6G | 5G |
| wild buckwheat | 2G | 0 | 5G | 0 | 7G | 5G | 10C | 2G |
| *Veronica persica* | — | — | 6G | 4G |  |  |  |  |

Test D

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table D.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and mustard. All plants were sprayed approximately 14 days after planting. Additional plant species such as johnsongrass, rape and bindweed are sometimes added to this standard test in order to evaluate unusual selectivity.

Several of the compounds tested by this procedure exhibit post-emergence control of weeds in wheat, cotton and soybeans.

TABLE D

| | Compound 30 | | Compound 31 | | | Compound 32 | | | Compound 33 | | Compound 35 | | |
|---|---|---|---|---|---|---|---|---|---|---|---|---|---|
| Rate kg/ha | 0.015 | 0.003 | 0.062 | 0.015 | 0.003 | 0.062 | 0.015 | 0.003 | 0.015 | 0.003 | 0.062 | 0.015 | 0.003 |
| Soybeans | 10G | 7G,4C | 7G | 2G | 0 | 8G | 5G,4C | 4C,4G | 9C | 8C | 9C | 9C | 9C |
| Velvetleaf | 7G,6C | 0 | 9G | 5G | 0 | 9G | 5G,5C | 3G | 2C,8G | 2G | 9C | 8G | 6G |
| Sesbania | 9G | 2G | 9G | 4G | 2G | 10C | 9C | 3C,4G | 10C | 8G,6C | 10C | 9G | 8G |
| Sicklepod | 6G,3C | 5G | 2G | 0 | 0 | 2C,5G | 3G,2C | 1C | 1G | 0 | 6G | 0 | 0 |
| Cotton | 9G | 8G | 5G | 4G | 0 | 4G,1C | 4C,5G | 3G,3C | 2C | 1C | 10G | 9G | 9G |
| Morningglory | 0 | 6G | 3G | 2G | 0 | 4G | 4G | 2G | 0 | 0 | 9G | 9G | 8G |
| Alfalfa | 8G | 9G | 8G,2C | 3G | 8G | 4G,3C | 5G,3C | 4G,2C | 3G | 2G | 9G | 9G | 7G |
| Jimsonweed | 8G | 0 | 3G | 2G | 0 | 3G | 4G,3C | 2G | 2G | 1C | 9G | 9G | 7G |
| Cocklebur | 8G,3C | 3C | 6G | 0 | 0 | 6G | 4G | 3G | — | 5G | 9G | 8G | 7G |
| Corn | 9G,8C | 9G,8C | 10G | 10C | 6G | 10C | 9C | 6G,3C | 1C,3G | 2H,3G | 10C | 9G | 8G |
| Crabgrass | 7G | 0 | 3G | 2G | 0 | 4G | 3G | 1G | 1G | 0 | 9C | 8G | 4G |
| Rice | 9G,6C | 3C,9G | 8G,6C | 8G,4C | 8G | 4G,4C | 7G,5C | 5G,3C | 8C | 6G,2C | 9G | 8G | 8G |
| Nutsedge | 0 | 0 | 3G | 2G | 0 | 5G | 3C,3G | 1C,3G | 3C,2G | 0 | 9C | 6C | 2G |
| Barnyardgrass | 8G,6C | 8G | 7G,2C | 6G | 2G | 10C | 6G,3C | 4G | 3G | 0 | 10C | 9G | 4G |
| Wheat | 5G | 3G | 6G | 4G | 2G | 5G,4C | 5G | 3G | 2G | 0 | 6G | 0 | 0 |
| Giant foxtail | 9G,9C | 9G | 9G,6C | 7G | 4G | 10C | 8G | 3G | 7G | 2G | 10C | 8G | 6G |
| Wild Oats | 7G | 5G | 8G | 4G | 0 | 6G,3C | 5G | 4G | 0 | 0 | 9G | 5G | 0 |
| Sorghum | 8G | 8G | 10C | 9G | 5G | 8C | 9C | 7G | 7G | 6G | 9G | 9G | 6G |
| Sunflower | 10G | 7G,3C | 5G | 0 | 0 | 10C | 3G | 3G | 0 | 0 | 10C | 8G | 3G |
| Rape | — | — | — | — | — | 8C | 4C,7G | 3C,5G | 2G | 1G | — | — | — |
| Johnsongrass | 10C | 9G | 9G,6U | 7G | 3G | 10C | 10C | 4C,5G | 4G,4C | 0 | 9U | 7G | 0 |
| Sugar beets | 8G | 10C | — | — | — | 10C | 8C | 7G,2C | 2G,3C | 1G,1C | 9G | 9G | 7G |
| Bindweed | 0 | 0 | 0 | 0 | 0 | 8G | 5G | 2C,5G | 0 | 1C | 8G | 4G | 0 |
| Mustard | 10C | 7G,2C | 10C | 10C | 9G | — | — | — | — | — | 9G | 8G | 3G |

| | Compound 36 | | Compound 37 | | Compound 39 | | Compound 44 | | | Compound 47 | | |
|---|---|---|---|---|---|---|---|---|---|---|---|---|
| Rate kg/ha | 0.062 | 0.015 | 0.062 | 0.015 | 0.062 | 0.015 | 0.062 | 0.015 | 0.003 | 0.062 | 0.015 | 0.003 |
| Soybeans | 3C,5G | 2C,5G | 2C,1G | 1G | 6G,3C | 6G | 0 | 0 | 0 | 10G,7C | 9G,4C | 5G,4C |
| Velvetleaf | 1C | 1G | 0 | 1C | 5G,2C | 2G | 6G | 0 | 0 | 8C | 6G | 4G |
| Sesbania | 0 | 1G | 0 | 0 | 9G | 7G | 6G | 0 | 0 | 8G | 5C | 3C |
| Sicklepod | 2C | 2C | 2C,1G | 1G | 2G | 2G | 0 | 0 | 0 | 6C | 5C | 2C |
| Cotton | 5G,3C | 4G,3C | 2G | 0 | 2G | 0 | 9G | 9G | 2G | 9G | 9G | 6G |
| Morningglory | 6G | 5G | 3C | 0 | 6C,9G | 7G,6C | 3G | 0 | 0 | 10G | 8G | 5G |
| Alfalfa | 3C | 2G | 2C | 0 | 5G | 0 | 2G | 6G | 0 | 8C,8G | 4G | 2C |
| Jimsonweed | 7G | 6G | 3G,2C | 1C | 3G | 3G | 0 | 0 | 0 | 7G | 6G | 2G |
| Cocklebur | 5C,8G | 5G | 3G | 0 | — | 4G | 9G | 7G | 0 | 10G | 7G | 3G |
| Corn | 8G | 7G | 1C,4G | 1C,3G | 9C,9G | 3C,9G | 8G,2H | 5G | 2G | 8G,1H | 6G,3H | 0 |
| Crabgrass | 0 | 0 | 1G | 0 | 6G | 2G | 8G | 5G | 2G | 6G | 3G | 0 |
| Rice | 6G | 5G | 4G | 4G | 5G,2C | 5G,4C | 5G | 2G | 2G | 9C | 9G | 4G |
| Nutsedge | 2G | 0 | 2G | 0 | 9G,5C | 2G | 0 | 0 | 0 | 8G | 5G | 0 |
| Barnyardgrass | 0 | 0 | 0 | 0 | 9G,8C | 7G | 8G | 8G | 7G | 9G | 1H,9G | 2G |
| Wheat | 0 | 0 | 2G | 0 | 0 | 0 | 0 | 0 | 0 | 9G | 9G | 3G |
| Giant foxtail | 2G | 1G | 3G | 0 | 6G | 3G | 4G | 4G | 4G | 9C,9G | 8G | 4G |
| Wild Oats | 4G | 1G | 2G | 0 | 0 | 0 | 4G | 3G | 0 | 9G | 9G | 2G |
| Sorghum | 8G | 7G | 8G | 3G | 7G | 3G | 8G | 7G | 3G | 9G,4U | 9G | 9G |
| Sunflower | 6C,8G | 4G | 2C | 0 | 7G,2C | 7G,3C | 8G | 8G | 0 | 10C | 9G | 5G |
| Rape | 5C,6G | 4G,3C | 4G,2C | 2G | — | — | — | — | — | — | — | — |
| Johnsongrass | 3G | 2G | 2G,1C | 1G | 3G | 0 | 8G | 8G | 8G | 10U | 10C | 6G |
| Sugar beets | 2C,6G | 1C,4G | 1G | 0 | 4G | 4G | 8G | 8G | 7G | 9G | 7G | 0 |
| Bindweed | 6G | 3G | 3C,2G | 0 | 7G | 9G | 3G | 3G | 3G | 8G | 2G | 0 |
| Mustard | — | — | — | — | 3G | 3G | 10C | 7G | 0 | 9G | 8G | 2G |

Test E

For a greenhouse test, a set of 25-cm diameter plastic pots filled with Woodstown sandy loam were planted to Williams soybeans. Similar pots were used to plant the following weed species, three different species per pot: cocklebur (*Xanthium pensylvanicum*), sicklepod (*Cassia obtusifolia*), pitted morningglory (*Ipomoea lacunosa*), johnsongrass (*Sorghum halepense*), barnyardgrass (*Echinochloa crusgalli*) and giant foxtail (*Setaria faberi*). Immediately after planting, the pots were treated pre-emergence with Compound No. 30, dissolved in a nonphytotoxic solvent. The rates of application extended from 4 to 125 g/ha. The treated pots were held in the greenhouse for 27 days and the plants were then rated for response to the chemical treatments. The data are summarized in Table E. Note that Compound No. 30 has potential utility for weed control—particularly grass control—in soybeans.

TABLE E

Pre-emergence on Woodstown Sandy Loam
Compound No. 30

| Rate (g/ha) | Percent Injury | | | | | | |
|---|---|---|---|---|---|---|---|
| | 4 | 8 | 16 | 31 | 62 | 125 | — |
| Cocklebur | 10 | 40 | 70 | 90 | | | 0 |
| Sicklepod | 0 | 20 | 20 | 10 | | | 0 |
| Pitted morningglory | 0 | 20 | 50 | 60 | | | 0 |
| Johnsongrass | 90 | 90 | 90 | 95 | | | 0 |
| Barnyardgrass | 0 | 20 | 60 | 95 | | | 0 |
| Giant foxtail | 75 | 95 | 95 | 100 | | | 0 |
| Williams soybeans | | | | | 30 | 60 | |
| Untreated Control | 0 | 0 | 0 | 0 | 0 | 0 | 0 |

What is claimed is:

1. A compound of the formula:

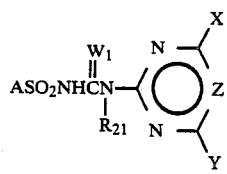

wherein
X is $CH_3$, $OCH_3$, Cl, $C_2H_5$ or $OC_2H_5$;
Z is CH;
Y is $CH_2S(O)_mR_1$, or $R_1CHS(O)_mR_1$;
$R_1$ is $C_1-C_2$ alkyl;
m is 0, 1 or 2;
A is

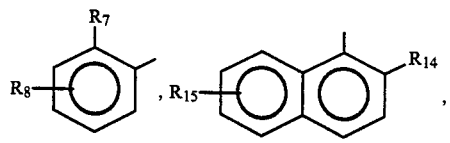

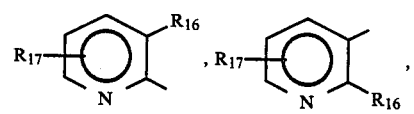

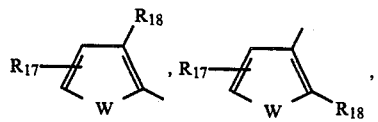

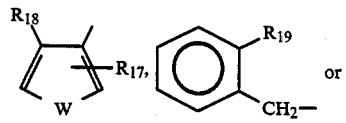

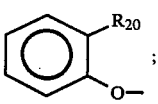

$R_7$ is H, $C_1-C_4$ alkyl, $C_1-C_4$ alkoxy, F, Cl, I, Br, $NO_2$, $CF_3$, $CO_2R_9$, $SO_2NR_{10}R_{11}$, $SO_2N(OCH_3)CH_3$, $OSO_2R_{12}$, $S(O)_nR_{13}$, $LCF_3$, $LCHF_2$, $LCF_2CF_2H$, $CH_2Cl$, $CHCl_2$, $CH_2OCH_3$ or $CH_2OCH_2CH_3$;
$R_8$ is H, F, Cl, Br, $CF_3$, $NO_2$, $C_1-C_3$ alkyl $C_1-C_3$ alkoxy, $OCF_2H$ or $SCF_2H$;
$R_9$ is $C_1-C_4$ alkyl, $CH_2CH_2OCH_3$, $CH_2CH_2Cl$ or $CH_2CH=CH_2$;
$R_{10}$ and $R_{11}$ are independently $C_1-C_3$ alkyl;
$R_{12}$ is $C_1-C_4$ alkyl, $CH_2CH_2OCH_3$, $CH_2CH_2CH_2OCH_3$ or $C_1-C_4$ alkyl substituted with 1–3 atoms of F, Cl or Br;
$R_{13}$ is $C_1-C_4$ alkyl or $CH_2CH=CH_2$;
n is 0 or 2;
L is O, S or $SO_2$;
$R_{14}$ is H, $CH_3$, $OCH_3$, F, Cl, Br, $NO_2$, $SO_2N(CH_3)_2$, $OSO_2R_1$ or $S(O)_nR_1$;
$R_{15}$ is H, Cl, Br, $CH_3$, $OCH_3$ or $NO_2$;
$R_{16}$ is H, $C_1-C_4$ alkyl, $C_1-C_4$ alkoxy, F, Cl, Br, $CF_3$, $CO_2R_9$, $SO_2NR_{10}R_{11}$, $SO_2N(OCH_3)CH_3$ or $S(O)_nR_{13}$;
$R_{17}$ is H, F, Cl, Br, $CH_3$ or $OCH_3$;
W is O or S;
$W_1$ is O or S;
$R_{18}$ is H, $C_1-C_4$ alkyl, $C_1-C_4$ alkoxy, F, Cl, Br, $NO_2$, $CO_2R_9$, $SO_2NR_{10}R_{11}$, $SO_2N(OCH_3)CH_3$ or $S(O)_nR_{13}$;
$R_{19}$ is Cl, $NO_2$, $CF_3$, $CO_2R_9$, $SO_2N(OCH_3)CH_3$, $SO_2NR_{10}R_{11}$, $OSO_2R_{12}$, $S(O)_nR_{13}$, $C_1-C_3$ alkyl, or $C_1-C_3$ alkoxy optionally substituted with 1–5 atoms of Cl or F;
$R_{20}$ is Cl, $NO_2$, $CF_3$, $CO_2R_9$, $SO_2N(OCH_3)CH_3$, $C_1-C_3$ alkyl, $OSO_2R_{12}$ or $C_1-C_3$ alkoxy optionally substituted with 1–5 atoms of Cl or F;
$R_{21}$ is H or $CH_3$;
and their agriculturally suitable salts; provided that
(1) the total number of carbon atoms of $R_{10}$ and $R_{11}$ is less than or equal to 4;
(2) when X is Cl, then Z is CH;
(3) when W is O, then $R_{18}$ is H, Cl, Br, $CH_3$ or $CO_2R_9$;
(4) when W is O and $R_{18}$ is H, Cl, Br, or $CH_3$, then A is

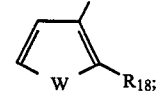

and
(5) when $W_1$ is S, then $R_{21}$ is H and A is

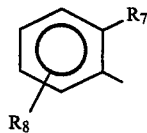

2. A composition suitable for controlling the growth of undesired vegetation which comprises an effective amount of a compound of claim 1 and at least one of the following: surfactant, solid or liquid-inert diluent.

3. A method for controlling the growth of undesired vegetation which comprises applying to the locus to be protected an effective amount of a compound of claim 1.